United States Patent
Fujimoto et al.

(10) Patent No.: US 10,898,737 B2
(45) Date of Patent: *Jan. 26, 2021

(54) SUBSTITUTED PIPERIDINE COMPOUND AND USE THEREOF

(71) Applicant: Takeda Pharmaceutical Company Limited, Osaka (JP)

(72) Inventors: Tatsuhiko Fujimoto, Kanagawa (JP); Kentaro Rikimaru, Kanagawa (JP); Hiromichi Sugimoto, Tokyo (JP); Takahiro Matsumoto, Kanagawa (JP)

(73) Assignee: Takeda Pharmaceutical Company Limited, Osaka (JP)

( * ) Notice: Subject to any disclaimer, the term of this patent is extended or adjusted under 35 U.S.C. 154(b) by 0 days.

This patent is subject to a terminal disclaimer.

(21) Appl. No.: 16/410,463

(22) Filed: May 13, 2019

(65) Prior Publication Data

US 2019/0263843 A1    Aug. 29, 2019

Related U.S. Application Data

(62) Division of application No. 15/421,702, filed on Feb. 1, 2017, now Pat. No. 10,287,305.

(30) Foreign Application Priority Data

Feb. 4, 2016 (JP) ................. 2016-019834

(51) Int. Cl.
| | |
|---|---|
| *C07D 401/12* | (2006.01) |
| *A61P 25/00* | (2006.01) |
| *C07D 215/44* | (2006.01) |
| *C07D 211/36* | (2006.01) |
| *C07D 211/24* | (2006.01) |
| *C07D 211/56* | (2006.01) |
| *C07D 401/06* | (2006.01) |
| *C07D 401/14* | (2006.01) |
| *C07D 405/06* | (2006.01) |
| *C07D 405/12* | (2006.01) |
| *C07D 405/14* | (2006.01) |
| *C07D 409/06* | (2006.01) |
| *C07D 409/12* | (2006.01) |
| *C07D 413/06* | (2006.01) |
| *C07D 417/06* | (2006.01) |
| *C07D 417/14* | (2006.01) |

(52) U.S. Cl.
CPC .......... *A61P 25/00* (2018.01); *C07D 211/24* (2013.01); *C07D 211/36* (2013.01); *C07D 211/56* (2013.01); *C07D 215/44* (2013.01); *C07D 401/06* (2013.01); *C07D 401/12* (2013.01); *C07D 401/14* (2013.01); *C07D 405/06* (2013.01); *C07D 405/12* (2013.01); *C07D 405/14* (2013.01); *C07D 409/06* (2013.01); *C07D 409/12* (2013.01); *C07D 413/06* (2013.01); *C07D 417/06* (2013.01); *C07D 417/14* (2013.01)

(58) Field of Classification Search
CPC .. C07D 211/24; C07D 211/36; C07D 215/44; C07D 401/12; A61P 25/00
USPC ........................................................ 514/315
See application file for complete search history.

(56) References Cited

U.S. PATENT DOCUMENTS

| | | | |
|---|---|---|---|
| 4,822,792 A | 4/1989 | Carlier et al. | |
| 6,051,577 A | 4/2000 | Altmann | |
| 8,258,163 B2 | 9/2012 | Yanagisawa | |
| 9,527,807 B2 * | 12/2016 | Fukumoto | C07C 311/07 |
| 10,100,047 B2 | 10/2018 | He et al. | |
| 2010/0150840 A1 | 6/2010 | Yanagisawa | |
| 2016/0362376 A1 | 12/2016 | Nagase et al. | |
| 2017/0233385 A1 | 8/2017 | He et al. | |
| 2019/0031611 A1 | 1/2019 | Fujimoto et al. | |

FOREIGN PATENT DOCUMENTS

| | | |
|---|---|---|
| EP | 0893498 A2 | 1/1999 |
| WO | WO 92/08724 A1 | 5/1992 |
| WO | WO 99/12034 A1 | 3/1999 |
| WO | WO 00/18733 A1 | 4/2000 |
| WO | WO 00/18735 A1 | 4/2000 |

(Continued)

OTHER PUBLICATIONS

Shin et al. "Orexin-A increases cell surface expression of AMPA receptors in the striatum" Biochemical and Biophysical Research Communications. (Year: 2009).*

Nagahara et al "Design and Synthesis of Non-Peptide, Selective Orexin Receptor 2 Agonists" J. Med. Chem 58:7931-7937 (Year: 2015).*

Busquets et al., "Decreased Plasma Levels of Orexin-A in Sleep Apnea," Respiration, 2004, 71:575-579.

Scientific Dictionary, 2005, second edition, p. 14, with English translation of indicated portion.

(Continued)

*Primary Examiner* — Rita J Desai
(74) *Attorney, Agent, or Firm* — Foley & Lardner LLP

(57) ABSTRACT

Provided is a substituted piperidine compound having an orexin type 2 receptor agonist activity. A compound represented by the formula (I):

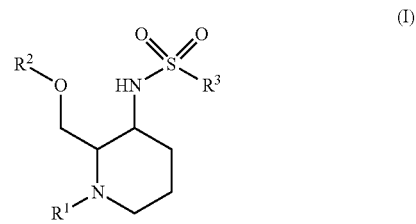

wherein each symbol is as described in the DESCRIPTION, or a salt thereof has an orexin type 2 receptor agonist activity, and is useful as a prophylactic or therapeutic agent for narcolepsy.

1 Claim, 1 Drawing Sheet

(56) References Cited

FOREIGN PATENT DOCUMENTS

| | | | |
|---|---|---|---|
| WO | WO 2001/008720 A2 | 2/2001 | |
| WO | WO 2001/074162 A1 | 10/2001 | |
| WO | WO 2004/040000 A2 | 5/2004 | |
| WO | WO 2004/054510 A2 | 7/2004 | |
| WO | WO 2009/049215 A1 | 4/2009 | |
| WO | WO 2012/137982 A2 | 10/2012 | |
| WO | WO-2012137982 A2 * | 10/2012 | ........... C07C 323/26 |
| WO | WO 2013/011098 A1 | 1/2013 | |
| WO | WO 2014/006402 A1 | 1/2014 | |
| WO | WO 2014/170343 A1 | 10/2014 | |
| WO | WO 2014/198880 A1 | 12/2014 | |
| WO | WO 2015/048091 A1 | 4/2015 | |
| WO | WO 2015/073707 A1 | 5/2015 | |
| WO | WO 2015/088000 A1 | 6/2015 | |
| WO | WO 2015/147240 A1 | 10/2015 | |
| WO | WO 2016/133160 A1 | 8/2016 | |

OTHER PUBLICATIONS

Busquets et al., "Decreased Plasma Levels of Orexin-A in Sleep Apnea," Clinical Investigations, 2004, 71:575-579.
Chemelli et al., "Narcolepsy in orexin Knockout Mice: Molecular Genetics of Sleep Regulation," Cell, Aug. 20, 1999, 98:437-451.
Claesson et al., "Competitive NMDA Antagonists that Base Their Activity on a Unique Conformational Effect," Biorganic & Medicinal Chemistry Letters, 1992, 2(10):1247-1250.
El Hadri et al., "Syntheses, Activity and Modeling Studies of 3- and 4-(Sulfo- and Sulfonamidoalkyl)pyridine and Piperidine-2-carboxylic Acid Derivatives as Analogs of NMDA Receptor Antagonists," Bioorganic & Medicinal Chemistry, 1995, 3(9):1183-1201.
Funato et al., "Enhanced Orexin Receptor-2 Signaling Prevents Diet-Induced Obesity and Improves Leptin Sensitivity," Cell Metabolism, Jan. 7, 2009, 9:64-76.
Jaeger et al., "Effects of orexin-A on memory processing," Peptides, 2002, 23:1683-1688.
Kushikata et al., "Orexinergic Neurons and Barbiturate Anesthesia," Neuroscience, 2003, 121:855-863.
Lin et al., "The Sleep Disorder Canine Narcolepsy is Caused by a Mutation in the Hypocretin (Orexin) Receptor 2 Gene," Cell, Aug. 6, 1999, 98:365-376.
Mieda et al., "Orexin (Hypocretin) Receptor Agonists and Antagonists for Treatment of Sleep Disorders," CNS Drugs, 2013, 27:83-90.
Mieda et al., "Orexin peptides prevent cataplexy and improve wakefulness in an orexin neuron-ablated model of narcolepsy in mice," PNAS, Mar. 30, 2004, 101(13):4649-4654.
Moss et al., "Ureido-Based Peptidomimetic Inhibitors of Herpes Simplex Virus Ribonucleotide Reductase: An Investigation of Inhibitor Bioactive Conformation," J. Med. Chem., 1996, 39:2178-2187.
Nagahara et al. "Design and Synthesis of Non-Peptide, Selective Orexin Receptor 2 Agonists," J. Med. Chem., 2015, 58:7931-7937.
Perez et al., "Systems Genomics Identifies a Key Role for Hypocretin/Orexin Receptor-2 in Human Heart Failure," Journal of the American College of Cardiology, 2015, 66(22):2522-2533.
Sakurai et al., "Orexins and Orexin Receptors: A Family of Hypothalamic Neuropeptides and G Protein-Coupled Receptors that Regulate Feeding Behavior," Cell, Feb. 20, 1998, 92:573-585.
Shin et al., "Orexin-A increases cell surface expression of AMPA receptors in the striatum," Biochemical and Biophysical Research Communications, 2009, 378:409-413.
Thannickal et al., "Hypocretin (orexin) cell loss in Parkinson's disease," Brain, 2007, 130:1586-1595.
Willie et al., "Distinct Narcolepsy Syndromes in Orexin Receptor-2 and Orexin Null Mice: Molecular Genetic Dissection of Non-REM and REM Sleep Regulatory Processes," Neuron, Jun. 5, 2003, 38:715-730.
Desseilles et al., "Neuroimaging Insights into the Pathophysiology of Sleep Disorders," Sleep, Jun. 1, 2008, 31(6):777-794.

* cited by examiner

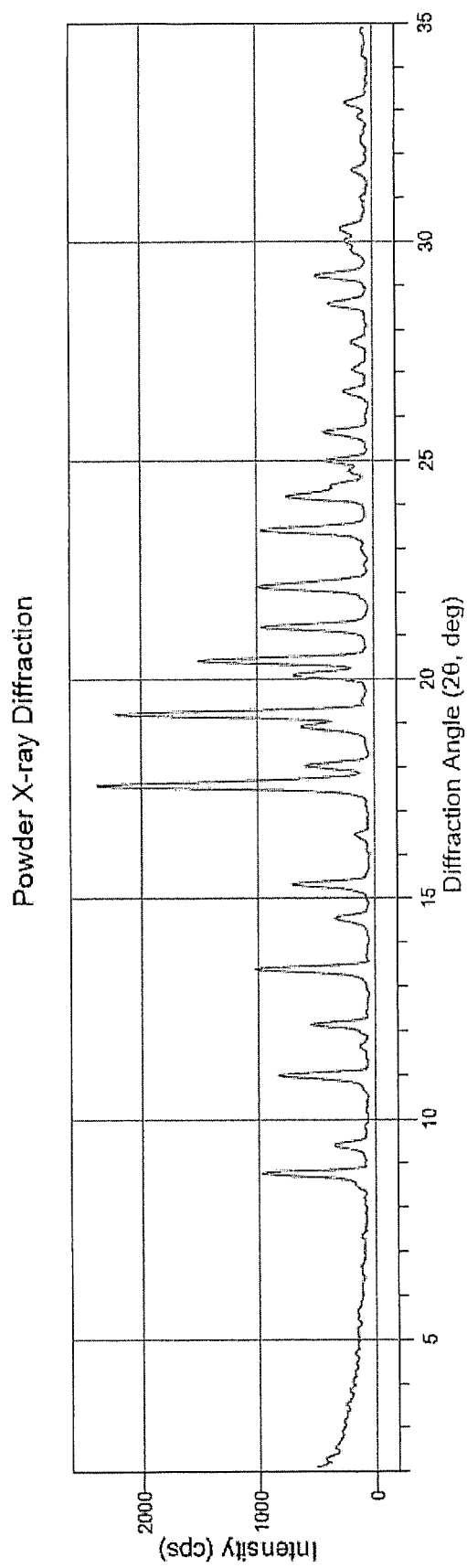

SUBSTITUTED PIPERIDINE COMPOUND AND USE THEREOF

CROSS-REFERENCE TO RELATED APPLICATIONS

This application is a Divisional of U.S. application Ser. No. 15/421,702, filed Feb. 1, 2017, which claims priority to JP 2016-019834, filed Feb. 4, 2016.

TECHNICAL FIELD

The present invention relates to a substituted piperidine compound, particularly, a substituted piperidine compound having an orexin type 2 receptor agonist activity.

BACKGROUND OF THE INVENTION

Orexin is a neuropeptide specifically produced in particular neurons located sparsely in the lateral hypothalamus and its surrounding area, and consists of two subtypes, orexin A and orexin B. Both orexin A and orexin B are endogenous ligands of the orexin receptors, which are G protein-coupled receptors mainly present in the brain, and two types of subtypes, type 1 and type 2, are known for the orexin receptors (non-patent document 1).

Since orexin-producing neurons (orexin neurons) are localized in the vicinity of the feeding center, and intraventricular administration of orexin peptide results in an increase in food intake, orexin initially attracted attention as a neuropeptide having a feeding behavioral regulation. Thereafter, however, it was reported that the cause of dog narcolepsy is genetic variation of orexin type 2 receptor (non-patent document 2), and the role of orexin in controlling sleep and wakefulness has been also attracted.

From the studies using a transgenic mouse having denatured orexin neurons and a double transgenic mouse obtained by crossing this mouse with orexin overexpressing transgenic mouse, it was clarified that narcolepsy-like symptoms that appear by degeneration of orexin neurons disappear due to sustained expression of orexin. Similarly, when orexin peptide was intraventricularly administered to a transgenic mouse having denatured orexin neuron, improvement of narcolepsy-like symptoms was also observed (non-patent document 3). Studies of orexin type 2 receptor knockout mice have suggested that orexin type 2 receptor is important for maintaining arousal (non-patent document 4, non-patent document 5). Such background suggests that orexin type 2 receptor agonists become therapeutic drugs for narcolepsy or therapeutic drugs for other sleep disorders exhibiting excessive sleepiness (non-patent document 6).

In addition, it is suggested that a peptidic agonist that selectively acts on the orexin type 2 receptor improves obesity due to high fat diet load in mice (non-patent document 7).

In addition, it is suggested that intraventricular administration of orexin peptide shortens the systemic anesthetic time of rat (non-patent document 8).

In addition, it is suggested that patients with sleep apnea syndrome show low orexin A concentration levels in plasma (non-patent document 9).

In addition, it is suggested that intraventricular administration of orexin peptide improves memory retention of senescence-accelerated model mouse (SAMP8) with cognitive dysfunction (non-patent document 10).

In addition, it is suggested that Orexin type 2 receptor agonist will be a therapeutic drug for cardiac failure (patent document 1, non-patent document 11).

In addition, it is suggested that the daytime sleepiness of Parkinson's disease patients is caused by orexin nerve fallout (non-patent document 12).

In addition, it is suggested that orexin regulates bone formation and bone loss, and orexin type 2 receptor agonist will be a therapeutic drug for diseases related to bone loss such as osteoporosis, rheumatoid arthritis and the like (patent document 2).

In addition, it is suggested that orexin receptor agonist is useful for the prophylaxis or treatment of sepsis, severe sepsis and septic shock, since the mortality was significantly improved by mere continuous administration of orexin from the periphery in septic shock model mouse (patent document 3).

Therefore, a compound having an orexin type 2 receptor agonist activity is expected to be useful as a novel therapeutic drug for narcolepsy, idiopathic hypersomnia, hypersomnia, sleep apnea syndrome, disturbance of consciousness such as coma and the like, narcolepsy syndrome accompanied by narcolepsy-like symptoms, hypersomnia syndrome accompanied by daytime hypersomnia (e.g., Parkinson's disease, Guillain-Barre syndrome and Kleine Levin syndrome), Alzheimer, obesity, insulin resistance syndrome, cardiac failure, diseases related to bone loss, sepsis and the like, further, anesthetic antagonist, a prophylactic or therapeutic drug for side effects and complications due to anesthesia.

Some of such compounds have been reported (patent document 4, patent document 5, patent document 6, non-patent document 13).

For example, such compounds include a compound represented by the formula

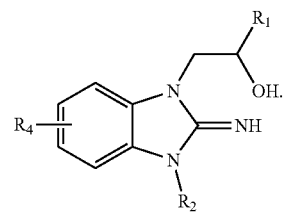

In addition, for example, such compounds include a compound represented by the formula

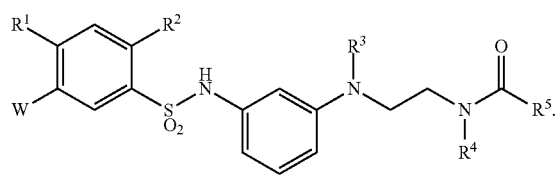

Also, for example, such compounds include a compound represented by the formula

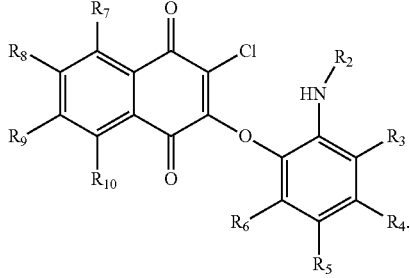

(I)

However, it is considered that these compounds are not satisfactory in terms of activity, pharmacokinetics or safety, and the development of a compound having an orexin type 2 receptor agonist activity is still desired.

DOCUMENT LIST

Patent Documents patent document 1: WO 2015/073707 A1
patent document 2: WO 2015/048091 A1
patent document 3: WO 2015/147240 A1
patent document 4: U.S. Pat. No. 8,258,163 B2
patent document 5: WO 2015/088000 A1
patent document 6: WO 2014/198880 A1

Non-Patent Document non-patent document 1: Cell, Vol. 92, 573-585, 1998
non-patent document 2: Cell, Vol. 98, 365-376, 1999
non-patent document 3: Proc. Natl. Acad. Sci. USA, Vol. 101, 4649-4654, 2004
non-patent document 4: Cell, Vol. 98, 437-451, 1999
non-patent document 5: Neuron, Vol. 38, 715-730, 2003
non-patent document 6: CNS Drugs, Vol. 27, 83-90, 2013
non-patent document 7: Cell Metabolism, Vol. 9, 64-76, 2009
non-patent document 8: Neuroscience, Vol. 121, 855-863, 2003
non-patent document 9: Respiration, Vol. 71, 575-579, 2004
non-patent document 10: Peptides, Vol. 23, 1683-1688, 2002
non-patent document 11: Journal of the American College of Cardiology. Vol. 66, 2015, pages 2522-2533
non-patent document 12: Brain, Vol. 130, 2007, pages 1586-1595
non-patent document 13: Journal of Medicinal Chemistry. Vol. 58, pages 7931-7937

SUMMARY OF THE INVENTION

Problems to be Solved by the Invention

The present invention aims to provide a substituted piperidine compound having an orexin type 2 receptor agonist activity.

Means of Solving the Problems

The present inventors have found that a compound represented by the following formula (I) or a salt thereof (sometimes to be referred to as compound (I) in the present specification) has an orexin type 2 receptor agonist activity. As a result of further studies, they have completed the present invention.

Accordingly, the present invention relates to
[1] a compound represented by the formula:

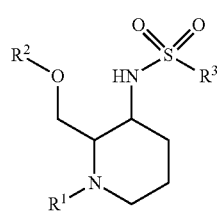

(I)

wherein
R$^1$ is an acyl group, or a hydrogen atom;
R$^2$ is an optionally substituted 3- to 6-membered saturated cyclic group; and
R$^3$ is an optionally substituted $C_{1-6}$ alkyl group, a mono- or di-$C_{1-6}$ alkylamino group or a $C_{3-6}$ cycloalkyl group, or a salt thereof;
[2] the compound of [1], wherein R$^3$ is an optionally substituted $C_{1-6}$ alkyl group or a mono- or di-$C_{1-6}$ alkylamino group, or a salt thereof;
[3] the compound of [1] or [2], which is represented by the formula:

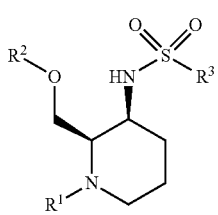

(II)

wherein R$^1$, R$^2$ and R$^3$ are as defined in [1], or a salt thereof;
[4] the compound of [1], [2] or [3], wherein R$^1$ is an acyl group, or a salt thereof;
[5] the compound of [1], [2], [3] or [4], wherein R$^2$ is a $C_{3-6}$ cycloalkyl group substituted by one optionally substituted phenyl group, or a salt thereof;
[6] the compound of [1], [2], [3], [4] or [5], wherein R$^3$ is an optionally substituted $C_{1-6}$ alkyl group, or a salt thereof;
[7] the compound of [1], [2] or [3], wherein R$^1$ is
(1) a hydrogen atom,
(2) an optionally substituted $C_{1-6}$ alkyl-carbonyl group,
(3) an optionally substituted $C_{3-10}$ cycloalkyl-carbonyl group,
(4) an optionally substituted $C_{1-6}$ alkoxy-carbonyl group,
(5) an optionally substituted $C_{3-10}$ cycloalkyloxy-carbonyl group,
(6) an optionally substituted $C_{6-14}$ aryl-carbonyl group,
(7) an optionally substituted $C_{6-14}$ aryloxy-carbonyl group,
(8) an optionally substituted 5- to 14-membered aromatic heterocyclylcarbonyl group,
(9) an optionally substituted 3- to 14-membered non-aromatic heterocyclylcarbonyl group,
(10) an optionally substituted mono- or di-$C_{1-6}$ alkyl-carbamoyl group,

(11) an optionally substituted mono- or di-$C_{3-10}$ cycloalkyl-carbamoyl group,
(12) an optionally substituted mono- or di-$C_{6-14}$ aryl-carbamoyl group,
(13) an optionally substituted $C_{1-6}$ alkylsulfonyl group,
(14) an optionally substituted $C_{3-10}$ cycloalkylsulfonyl group,
(15) an optionally substituted $C_{6-14}$ arylsulfonyl group,
(16) an optionally substituted heterocyclyl-sulfonyl group,
(17) an optionally substituted mono- or di-$C_{1-6}$ alkyl-sulfamoyl group or
(18) an optionally substituted $C_{1-6}$ alkyl-carbonyl-carbonyl group;
$R^2$ is a $C_{3-6}$ cycloalkyl group or a 3- to 6-membered saturated monocyclic non-aromatic heterocyclic group, each of which is optionally substituted by 1 to 3 substituents selected from
(1) deuterium,
(2) a halogen atom,
(3) a hydroxy group,
(4) an optionally substituted $C_{1-6}$ alkyl group,
(5) a $C_{3-10}$ cycloalkyl group,
(6) an optionally substituted $C_{1-6}$ alkoxy group,
(7) an optionally substituted $C_{6-14}$ aryl group,
(8) a $C_{6-14}$ aryloxy group,
(9) a tri-$C_{1-6}$ alkylsilyloxy group,
(10) an optionally substituted 5- to 14-membered aromatic heterocyclic group and
(11) an optionally substituted $C_{6-14}$ aryl-carbonyl group; and
$R^3$ is a $C_{1-6}$ alkyl group optionally substituted by 1 to 3 substituents selected from a halogen atom and a $C_{6-14}$ aryl group, or a mono- or di-$C_{1-6}$ alkylamino group, or a salt thereof;
[8] the compound of [1], [2] or [3], wherein $R^1$ is
(1) a hydrogen atom,
(2) a $C_{1-6}$ alkyl-carbonyl group optionally substituted by 1 to 7 substituents selected from
(i) a halogen atom, (ii) a cyano group, (iii) a hydroxy group, (iv) a $C_{3-10}$ cycloalkyl group, (v) a $C_{1-6}$ alkoxy group, (vi) a $C_{6-14}$ aryl group, (vii) a $C_{6-14}$ aryloxy group, (viii) a pyrazolyl group, a thiazolyl group, a pyrimidinyl group or a pyridazinyl group, each of which is optionally substituted by an oxo group, (ix) a pyrazolyloxy group optionally substituted by 1 to 3 $C_{1-6}$ alkyl groups, (x) a $C_{1-6}$ alkyl-carbonyl group, (xi) a $C_{1-6}$ alkoxy-carbonyl group, (xii) a $C_{1-6}$ alkyl-carbonyloxy group, (xiii) a $C_{1-6}$ alkylsulfonyl group, (xiv) a mono- or di-$C_{1-6}$ alkylamino group, (xv) a $C_{1-6}$ alkyl-carbonylamino group and (xvi) a ($C_{1-6}$ alkyl) ($C_{1-6}$ alkyl-carbonyl) amino group,
(3) a $C_{3-10}$ cycloalkyl-carbonyl group optionally substituted by 1 to 3 substituents selected from a halogen atom, a cyano group, a hydroxy group, an oxo group and a $C_{1-6}$ alkyl group,
(4) a $C_{1-6}$ alkoxy-carbonyl group optionally substituted by 1 to 6 substituents selected from deuterium, a halogen atom and a $C_{6-14}$ aryl group,
(5) a $C_{3-10}$ cycloalkyloxy-carbonyl group optionally substituted by 1 to 3 substituents selected from a $C_{1-6}$ alkyl group,
(6) a $C_{6-14}$ aryl-carbonyl group optionally substituted by 1 to 3 substituents selected from a halogen atom and a $C_{6-14}$ aryl group,
(7) a $C_{6-14}$ aryloxy-carbonyl group,
(8) a furylcarbonyl group, a thienylcarbonyl group, a pyrazolylcarbonyl group, an isoxazolylcarbonyl group or a pyridylcarbonyl group, each of which is optionally substituted by 1 to 3 substituents selected from a $C_{1-6}$ alkyl group,
(9) an azetidinylcarbonyl group, an oxetanylcarbonyl group, a pyrrolidinylcarbonyl group, a tetrahydrofuranylcarbonyl group, a tetrahydropyranylcarbonyl group or a morpholinyl-carbonyl group, each of which is optionally substituted by 1 to 3 substituents selected from an oxo group, a $C_{1-6}$ alkyl-carbonyl group, a $C_{1-6}$ alkoxy-carbonyl group and a $C_{1-6}$ alkylsulfonyl group,
(10) a mono- or di-$C_{1-6}$ alkyl-carbamoyl group optionally substituted by 1 to 3 substituents selected from a halogen atom, a cyano group, a hydroxy group and a $C_{1-6}$ alkoxy group,
(11) a mono- or di-$C_{3-10}$ cycloalkyl-carbamoyl group,
(12) a mono- or di-$C_{6-14}$ aryl-carbamoyl group,
(13) a $C_{1-6}$ alkylsulfonyl group,
(14) a $C_{3-10}$ cycloalkylsulfonyl group,
(15) a $C_{6-14}$ arylsulfonyl group optionally substituted by 1 to 3 halogen atoms,
(16) a thienylsulfonyl group, a pyrazolylsulfonyl group, an imidazolylsulfonyl group, a pyridylsulfonyl group or a dihydrochromenylsulfonyl group, each of which is optionally substituted by 1 to 3 substituents selected from a $C_{1-6}$ alkyl group,
(17) a mono- or di-$C_{1-6}$ alkyl-sulfamoyl group or
(18) a $C_{1-6}$ alkyl-carbonyl-carbonyl group;
$R^2$ is a $C_{3-6}$ cycloalkyl group, a pyrrolidinyl group, a piperidinyl group or a dioxanyl group, each of which is optionally substituted by 1 to 3 substituents selected from
(1) deuterium,
(2) a halogen atom,
(3) a hydroxy group,
(4) a $C_{1-6}$ alkyl group optionally substituted by 1 to 3 substituents selected from a halogen atom and a $C_{6-14}$ aryl group,
(5) a $C_{3-10}$ cycloalkyl group,
(6) a $C_{1-6}$ alkoxy group optionally substituted by a $C_{3-10}$ cycloalkyl group,
(7) a $C_{6-14}$ aryl group optionally substituted by 1 to 3 substituents selected from a halogen atom, a cyano group, a $C_{1-6}$ alkyl group optionally substituted by 1 to 3 halogen atoms, a $C_{1-6}$ alkoxy group optionally substituted by 1 to 3 halogen atoms and a hydroxy group,
(8) a $C_{6-14}$ aryloxy group,
(9) a tri-$C_{1-6}$ alkylsilyloxy group,
(10) a pyrazolyl group, a thiazolyl group, a pyridyl group, a pyrimidinyl group, a quinazolinyl group, a benzothiazolyl group or an isoquinolinyl group, each of which is optionally substituted by 1 to 3 substituents selected from a halogen atom, a $C_{1-6}$ alkyl group and a $C_{1-6}$ alkoxy group, and
(11) a $C_{6-14}$ aryl-carbonyl group; and
$R^3$ is a $C_{1-6}$ alkyl group, or a mono- or di-$C_{1-6}$ alkylamino group, or a salt thereof;
[9] the compound of [1], [2] or [3], wherein $R^1$ is
(1) a hydrogen atom,
(2) a $C_{1-6}$ alkyl-carbonyl group optionally substituted by a hydroxy group,
(3) a cyclopropanecarbonyl group,
(4) a $C_{1-6}$ alkoxy-carbonyl group or
(5) a mono- or di-$C_{1-6}$ alkyl-carbamoyl group;
$R^2$ is
(A) a cyclohexyl group optionally substituted by 1 to 3 substituents selected from
(1) a $C_{1-6}$ alkyl group and
(2) a phenyl group optionally substituted by 1 to 3 substituents selected from a halogen atom, a $C_{1-6}$ alkyl group optionally substituted by 1 to 3 halogen atoms and a $C_{1-6}$ alkoxy group or (B) a piperidinyl group optionally substituted by 1 to 3 pyrimidinyl groups; and $R^3$ is a $C_{1-6}$ alkyl group or a di-$C_{1-6}$ alkylamino group, or a salt thereof;

[10] the compound of [1], [2] or [3], wherein $R^1$ is (1) a $C_{1-6}$ alkyl-carbonyl group optionally substituted by a hydroxy group, (2) a $C_{1-6}$ alkoxy-carbonyl group or (3) a mono- or di-$C_{1-6}$ alkyl-carbamoyl group;

$R^2$ is a cyclohexyl group optionally substituted by 1 to 3 substituents selected from (1) a $C_{1-6}$ alkyl group and (2) a phenyl group optionally substituted by 1 to 3 halogen atoms; and $R^3$ is a $C_{1-6}$ alkyl group, or a salt thereof;

[11] methyl (2R,3S)-3-((methylsulfonyl)amino)-2-(((cis-4-phenylcyclohexyl)oxy)methyl)piperidine-1-carboxylate or a salt thereof;

[12] N-((2R,3S)-1-glycoloyl-2-(((cis-4-(2,3,6-trifluorophenyl)cyclohexyl)oxy)methyl)piperidin-3-yl)methanesulfonamide or a salt thereof;

[13] (2R,3S)—N-ethyl-2-(((cis-4-isopropylcyclohexyl)oxy)methyl)-3-((methylsulfonyl)amino)piperidine-1-carboxamide or a salt thereof;

[14] a medicament comprising the compound of [1]-[13] or a salt thereof;

[15] the medicament of [14], which is an orexin type 2 receptor agonist;

[16] the medicament of [14], which is a prophylactic or therapeutic agent for narcolepsy;

[17] the compound of [1]-[13] or a salt thereof for use in the prophylaxis or treatment of narcolepsy;

[18] a method of activating an orexin type 2 receptor in a mammal, comprising administering an effective amount of the compound of [1]-[13] or a salt thereof to the mammal;

[19] a method for the prophylaxis or treatment of narcolepsy in a mammal, comprising administering an effective amount of the compound of [1]-[13] or a salt thereof to the mammal; and

[20] use of the compound of [1]-[13] or a salt thereof for the manufacture of a prophylactic or therapeutic agent for narcolepsy.

Effect of the Invention

The compound of the present invention has an orexin type 2 receptor agonist activity, and is useful as a prophylactic or therapeutic agent for narcolepsy.

BRIEF DESCRIPTION OF THE DRAWINGS

FIG. 1 is a powder X-ray diffraction chart of the crystals obtained in Example 5A.

DETAILED DESCRIPTION OF THE INVENTION

The definition of each substituent used in the present specification is described in detail in the following. Unless otherwise specified, each substituent has the following definition.

In the present specification, examples of the "halogen atom" include fluorine, chlorine, bromine and iodine.

In the present specification, examples of the "$C_{1-6}$ alkyl group" include methyl, ethyl, propyl, isopropyl, butyl, isobutyl, sec-butyl, tert-butyl, pentyl, isopentyl, neopentyl, 1-ethylpropyl, hexyl, isohexyl, 1,1-dimethylbutyl, 2,2-dimethylbutyl, 3,3-dimethylbutyl and 2-ethylbutyl.

In the present specification, examples of the "optionally halogenated $C_{1-6}$ alkyl group" include a $C_{1-6}$ alkyl group optionally having 1 to 7, preferably 1 to 5, a halogen atoms. Specific examples thereof include methyl, chloromethyl, difluoromethyl, trichloromethyl, trifluoromethyl, ethyl, 2-bromoethyl, 2,2,2-trifluoroethyl, tetrafluoroethyl, pentafluoroethyl, propyl, 2,2-difluoropropyl, 3,3,3-trifluoropropyl, isopropyl, butyl, 4,4,4-trifluorobutyl, isobutyl, sec-butyl, tert-butyl, pentyl, isopentyl, neopentyl, 5,5,5-trifluoropentyl, hexyl and 6,6,6-trifluorohexyl.

In the present specification, examples of the "$C_{2-6}$ alkenyl group" include ethenyl, 1-propenyl, 2-propenyl, 2-methyl-1-propenyl, 1-butenyl, 2-butenyl, 3-butenyl, 3-methyl-2-butenyl, 1-pentenyl, 2-pentenyl, 3-pentenyl, 4-pentenyl, 4-methyl-3-pentenyl, 1-hexenyl, 3-hexenyl and 5-hexenyl.

In the present specification, examples of the "$C_{2-6}$ alkynyl group" include ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, 5-hexynyl and 4-methyl-2-pentynyl.

In the present specification, examples of the "$C_{3-10}$ cycloalkyl group" include cyclopropyl, cyclobutyl, cyclopentyl, cyclohexyl, cycloheptyl, cyclooctyl, bicyclo[2.2.1]heptyl, bicyclo[2.2.2]octyl, bicyclo[3.2.1]octyl and adamantyl.

In the present specification, examples of the "optionally halogenated $C_{3-10}$ cycloalkyl group" include a $C_{3-10}$ cycloalkyl group optionally having 1 to 7, preferably 1 to 5, a halogen atoms. Specific examples thereof include cyclopropyl, 2,2-difluorocyclopropyl, 2,3-difluorocyclopropyl, cyclobutyl, difluorocyclobutyl, cyclopentyl, cyclohexyl, cycloheptyl and cyclooctyl.

In the present specification, examples of the "$C_{3-10}$ cycloalkenyl group" include cyclopropenyl, cyclobutenyl, cyclopentenyl, cyclohexenyl, cycloheptenyl and cyclooctenyl.

In the present specification, examples of the "$C_{6-14}$ aryl group" include phenyl, 1-naphthyl, 2-naphthyl, 1-anthryl, 2-anthryl and 9-anthryl.

In the present specification, examples of the "$C_{7-16}$ aralkyl group" include benzyl, phenethyl, naphthylmethyl and phenylpropyl.

In the present specification, examples of the "$C_{1-6}$ alkoxy group" include methoxy, ethoxy, propoxy, isopropoxy, butoxy, isobutoxy, sec-butoxy, tert-butoxy, pentyloxy and hexyloxy.

In the present specification, examples of the "optionally halogenated $C_{1-6}$ alkoxy group" include a $C_{1-6}$ alkoxy group optionally having 1 to 7, preferably 1 to 5, a halogen atoms. Specific examples thereof include methoxy, difluoromethoxy, trifluoromethoxy, ethoxy, 2,2,2-trifluoroethoxy, propoxy, isopropoxy, butoxy, 4,4,4-trifluorobutoxy, isobutoxy, sec-butoxy, pentyloxy and hexyloxy.

In the present specification, examples of the "$C_{3-10}$ cycloalkyloxy group" include cyclopropyloxy, cyclobutyloxy, cyclopentyloxy, cyclohexyloxy, cycloheptyloxy and cyclooctyloxy.

In the present specification, examples of the "$C_{1-6}$ alkylthio group" include methylthio, ethylthio, propylthio, isopropylthio, butylthio, sec-butylthio, tert-butylthio, pentylthio and hexylthio.

In the present specification, examples of the "optionally halogenated $C_{1-6}$ alkylthio group" include a $C_{1-6}$ alkylthio group optionally having 1 to 7, preferably 1 to 5, a halogen atoms. Specific examples thereof include methylthio, difluoromethylthio, trifluoromethylthio, ethylthio, propylthio, isopropylthio, butylthio, 4,4,4-trifluorobutylthio, pentylthio and hexylthio.

In the present specification, examples of the "$C_{1-6}$ alkyl-carbonyl group" include acetyl, propanoyl, butanoyl, 2-methylpropanoyl, pentanoyl, 3-methylbutanoyl, 2-methylbutanoyl, 2,2-dimethylpropanoyl, hexanoyl and heptanoyl.

In the present specification, examples of the "optionally halogenated $C_{1-6}$ alkyl-carbonyl group" include a $C_{1-6}$ alkyl-carbonyl group optionally having 1 to 7, preferably 1 to 5, a halogen atoms. Specific examples thereof include acetyl, chloroacetyl, trifluoroacetyl, trichloroacetyl, propanoyl, butanoyl, pentanoyl and hexanoyl.

In the present specification, examples of the "$C_{1-6}$ alkoxy-carbonyl group" include methoxycarbonyl, ethoxycarbonyl, propoxycarbonyl, isopropoxycarbonyl, butoxycarbonyl, isobutoxycarbonyl, sec-butoxycarbonyl, tert-butoxycarbonyl, pentyloxycarbonyl and hexyloxycarbonyl.

In the present specification, examples of the "$C_{6-14}$ aryl-carbonyl group" include benzoyl, 1-naphthoyl and 2-naphthoyl.

In the present specification, examples of the "$C_{7-16}$ aralkyl-carbonyl group" include phenylacetyl and phenylpropionyl.

In the present specification, examples of the "5- to 14-membered aromatic heterocyclylcarbonyl group" include nicotinoyl, isonicotinoyl, thenoyl and furoyl.

In the present specification, examples of the "3- to 14-membered non-aromatic heterocyclylcarbonyl group" include morpholinylcarbonyl, piperidinylcarbonyl and pyrrolidinylcarbonyl.

In the present specification, examples of the "mono- or di-$C_{1-6}$ alkyl-carbamoyl group" include methylcarbamoyl, ethylcarbamoyl, dimethylcarbamoyl, diethylcarbamoyl and N-ethyl-N-methylcarbamoyl.

In the present specification, examples of the "mono- or di-$C_{7-16}$ aralkyl-carbamoyl group" include benzylcarbamoyl and phenethylcarbamoyl.

In the present specification, examples of the "$C_{1-6}$ alkylsulfonyl group" include methylsulfonyl, ethylsulfonyl, propylsulfonyl, isopropylsulfonyl, butylsulfonyl, sec-butylsulfonyl and tert-butylsulfonyl.

In the present specification, examples of the "optionally halogenated $C_{1-6}$ alkylsulfonyl group" include a $C_{1-6}$ alkylsulfonyl group optionally having 1 to 7, preferably 1 to 5, a halogen atoms. Specific examples thereof include methylsulfonyl, difluoromethylsulfonyl, trifluoromethylsulfonyl, ethylsulfonyl, propylsulfonyl, isopropylsulfonyl, butylsulfonyl, 4,4,4-trifluorobutylsulfonyl, pentylsulfonyl and hexylsulfonyl.

In the present specification, examples of the "$C_{6-14}$ arylsulfonyl group" include phenylsulfonyl, 1-naphthylsulfonyl and 2-naphthylsulfonyl.

In the present specification, examples of the "substituent" include a halogen atom, a cyano group, a nitro group, an optionally substituted hydrocarbon group, an optionally substituted heterocyclic group, an acyl group, an optionally substituted amino group, an optionally substituted carbamoyl group, an optionally substituted thiocarbamoyl group, an optionally substituted sulfamoyl group, an optionally substituted hydroxy group, an optionally substituted sulfanyl (SH) group and an optionally substituted silyl group.

In the present specification, examples of the "hydrocarbon group" (including "hydrocarbon group" of "optionally substituted hydrocarbon group") include a $C_{1-6}$ alkyl group, a $C_{2-6}$ alkenyl group, a $C_{2-6}$ alkynyl group, a $C_{3-10}$ cycloalkyl group, a $C_{3-10}$ cycloalkenyl group, a $C_{6-14}$ aryl group and a $C_{7-16}$ aralkyl group.

In the present specification, examples of the "optionally substituted hydrocarbon group" include a hydrocarbon group optionally having substituent(s) selected from the following substituent group A.

[Substituent Group A]
(1) a halogen atom,
(2) a nitro group,
(3) a cyano group,
(4) an oxo group,
(5) a hydroxy group,
(6) an optionally halogenated $C_{1-6}$ alkoxy group,
(7) a $C_{6-14}$ aryloxy group (e.g., phenoxy, naphthoxy),
(8) a $C_{7-16}$ aralkyloxy group (e.g., benzyloxy),
(9) a 5- to 14-membered aromatic heterocyclyloxy group (e.g., pyridyloxy),
(10) a 3- to 14-membered non-aromatic heterocyclyloxy group (e.g., morpholinyloxy, piperidinyloxy),
(11) a $C_{1-6}$ alkyl-carbonyloxy group (e.g., acetoxy, propanoyloxy),
(12) a $C_{6-14}$ aryl-carbonyloxy group (e.g., benzoyloxy, 1-naphthoyloxy, 2-naphthoyloxy),
(13) a $C_{1-6}$ alkoxy-carbonyloxy group (e.g., methoxycarbonyloxy, ethoxycarbonyloxy, propoxycarbonyloxy, butoxycarbonyloxy),
(14) a mono- or di-$C_{1-6}$ alkyl-carbamoyloxy group (e.g., methylcarbamoyloxy, ethylcarbamoyloxy, dimethylcarbamoyloxy, diethylcarbamoyloxy),
(15) a $C_{6-14}$ aryl-carbamoyloxy group (e.g., phenylcarbamoyloxy, naphthylcarbamoyloxy),
(16) a 5- to 14-membered aromatic heterocyclylcarbonyloxy group (e.g., nicotinoyloxy),
(17) a 3- to 14-membered non-aromatic heterocyclylcarbonyloxy group (e.g., morpholinylcarbonyloxy, piperidinylcarbonyloxy),
(18) an optionally halogenated $C_{1-6}$ alkylsulfonyloxy group (e.g., methylsulfonyloxy, trifluoromethylsulfonyloxy),
(19) a $C_{6-14}$ arylsulfonyloxy group optionally substituted by a $C_{1-6}$ alkyl group (e.g., phenylsulfonyloxy, toluenesulfonyloxy),
(20) an optionally halogenated $C_{1-6}$ alkylthio group,
(21) a 5- to 14-membered aromatic heterocyclic group,
(22) a 3- to 14-membered non-aromatic heterocyclic group,
(23) a formyl group,
(24) a carboxy group,
(25) an optionally halogenated $C_{1-6}$ alkyl-carbonyl group,
(26) a $C_{6-14}$ aryl-carbonyl group,
(27) a 5- to 14-membered aromatic heterocyclylcarbonyl group,
(28) a 3- to 14-membered non-aromatic heterocyclylcarbonyl group,
(29) a $C_{1-6}$ alkoxy-carbonyl group,
(30) a $C_{6-14}$ aryloxy-carbonyl group (e.g., phenyloxycarbonyl, 1-naphthyloxycarbonyl, 2-naphthyloxycarbonyl),
(31) a $C_{7-16}$ aralkyloxy-carbonyl group (e.g., benzyloxycarbonyl, phenethyloxycarbonyl),
(32) a carbamoyl group,
(33) a thiocarbamoyl group,
(34) a mono- or di-$C_{1-6}$ alkyl-carbamoyl group,
(35) a $C_{6-14}$ aryl-carbamoyl group (e.g., phenylcarbamoyl),
(36) a 5- to 14-membered aromatic heterocyclylcarbamoyl group (e.g., pyridylcarbamoyl, thienylcarbamoyl),
(37) a 3- to 14-membered non-aromatic heterocyclylcarbamoyl group (e.g., morpholinylcarbamoyl, piperidinylcarbamoyl),

(38) an optionally halogenated $C_{1-6}$ alkylsulfonyl group,
(39) a $C_{6-14}$ arylsulfonyl group,
(40) a 5- to 14-membered aromatic heterocyclylsulfonyl group (e.g., pyridylsulfonyl, thienylsulfonyl),
(41) an optionally halogenated $C_{1-6}$ alkylsulfinyl group,
(42) a $C_{6-14}$ arylsulfinyl group (e.g., phenylsulfinyl, 1-naphthylsulfinyl, 2-naphthylsulfinyl),
(43) a 5- to 14-membered aromatic heterocyclylsulfinyl group (e.g., pyridylsulfinyl, thienylsulfinyl),
(44) an amino group,
(45) a mono- or di-$C_{1-6}$ alkylamino group (e.g., methylamino, ethylamino, propylamino, isopropylamino, butylamino, dimethylamino, diethylamino, dipropylamino, dibutylamino, N-ethyl-N-methylamino),
(46) a mono- or di-$C_{6-14}$ arylamino group (e.g., phenylamino),
(47) a 5- to 14-membered aromatic heterocyclylamino group (e.g., pyridylamino),
(48) a $C_{7-16}$ aralkylamino group (e.g., benzylamino),
(49) a formylamino group,
(50) a $C_{1-6}$ alkyl-carbonylamino group (e.g., acetylamino, propanoylamino, butanoylamino),
(51) a ($C_{1-6}$ alkyl) ($C_{1-6}$ alkyl-carbonyl)amino group (e.g., N-acetyl-N-methylamino),
(52) a $C_{6-14}$ aryl-carbonylamino group (e.g., phenylcarbonylamino, naphthylcarbonylamino),
(53) a $C_{1-6}$ alkoxy-carbonylamino group (e.g., methoxycarbonylamino, ethoxycarbonylamino, propoxycarbonylamino, butoxycarbonylamino, tert-butoxycarbonylamino),
(54) a $C_{7-16}$ aralkyloxy-carbonylamino group (e.g., benzyloxycarbonylamino),
(55) a $C_{1-6}$ alkylsulfonylamino group (e.g., methylsulfonylamino, ethylsulfonylamino),
(56) a $C_{6-14}$ arylsulfonylamino group optionally substituted by a $C_{1-6}$ alkyl group (e.g., phenylsulfonylamino, toluenesulfonylamino),
(57) an optionally halogenated $C_{1-6}$ alkyl group,
(58) a $C_{2-6}$ alkenyl group,
(59) a $C_{2-6}$ alkynyl group,
(60) a $C_{3-10}$ cycloalkyl group,
(61) a $C_{3-10}$ cycloalkenyl group and
(62) a $C_{6-14}$ aryl group.

The number of the above-mentioned substituents in the "optionally substituted hydrocarbon group" is, for example, 1 to 5, preferably 1 to 3. When the number of the substituents is two or more, the respective substituents may be the same or different.

In the present specification, examples of the "heterocyclic group" (including "heterocyclic group" of "optionally substituted heterocyclic group") include (i) an aromatic heterocyclic group, (ii) a non-aromatic heterocyclic group and (iii) a 7- to 10-membered bridged heterocyclic group, each containing, as a ring-constituting atom besides carbon atom, 1 to 4 hetero atoms selected from a nitrogen atom, a sulfur atom and an oxygen atom.

In the present specification, examples of the "aromatic heterocyclic group" (including "5- to 14-membered aromatic heterocyclic group") include a 5- to 14-membered (preferably 5- to 10-membered) aromatic heterocyclic group containing, as a ring-constituting atom besides carbon atom, 1 to 4 hetero atoms selected from a nitrogen atom, a sulfur atom and an oxygen atom.

Preferable examples of the "aromatic heterocyclic group" include 5- or 6-membered monocyclic aromatic heterocyclic groups such as thienyl, furyl, pyrrolyl, imidazolyl, pyrazolyl, thiazolyl, isothiazolyl, oxazolyl, isoxazolyl, pyridyl, pyrazinyl, pyrimidinyl, pyridazinyl, 1,2,4-oxadiazolyl, 1,3,4-oxadiazolyl, 1,2,4-thiadiazolyl, 1,3,4-thiadiazolyl, triazolyl, tetrazolyl, triazinyl and the like; and 8- to 14-membered fused polycyclic (preferably bi or tricyclic) aromatic heterocyclic groups such as benzothiophenyl, benzofuranyl, benzimidazolyl, benzoxazolyl, benzisoxazolyl, benzothiazolyl, benzisothiazolyl, benzotriazolyl, imidazopyridinyl, thienopyridinyl, furopyridinyl, pyrrolopyridinyl, pyrazolopyridinyl, oxazolopyridinyl, thiazolopyridinyl, imidazopyrazinyl, imidazopyrimidinyl, thienopyrimidinyl, furopyrimidinyl, pyrrolopyrimidinyl, pyrazolopyrimidinyl, oxazolopyrimidinyl, thiazolopyrimidinyl, pyrazolotriazinyl, naphtho[2,3-b]thienyl, phenoxathiinyl, indolyl, isoindolyl, 1H-indazolyl, purinyl, isoquinolyl, quinolyl, phthalazinyl, naphthyridinyl, quinoxalinyl, quinazolinyl, cinnolinyl, carbazolyl, β-carbolinyl, phenanthridinyl, acridinyl, phenazinyl, phenothiazinyl, phenoxazinyl and the like.

In the present specification, examples of the "non-aromatic heterocyclic group" (including "3- to 14-membered non-aromatic heterocyclic group") include a 3- to 14-membered (preferably 4- to 10-membered) non-aromatic heterocyclic group containing, as a ring-constituting atom besides carbon atom, 1 to 4 hetero atoms selected from a nitrogen atom, a sulfur atom and an oxygen atom.

Preferable examples of the "non-aromatic heterocyclic group" include 3- to 8-membered monocyclic non-aromatic heterocyclic groups such as aziridinyl, oxiranyl, thiiranyl, azetidinyl, oxetanyl, thietanyl, tetrahydrothienyl, tetrahydrofuranyl, pyrrolinyl, pyrrolidinyl, imidazolinyl, imidazolidinyl, oxazolinyl, oxazolidinyl, pyrazolinyl, pyrazolidinyl, thiazolinyl, thiazolidinyl, tetrahydroisothiazolyl, tetrahydrooxazolyl, tetrahydroisoxazolyl, piperidinyl, piperazinyl, tetrahydropyridinyl, dihydropyridinyl, dihydrothiopyranyl, tetrahydropyrimidinyl, tetrahydropyridazinyl, dihydropyranyl, tetrahydropyranyl, tetrahydrothiopyranyl, morpholinyl, thiomorpholinyl, azepanyl, diazepanyl, azepinyl, oxepanyl, azocanyl, diazocanyl and the like; and 9- to 14-membered fused polycyclic (preferably bi or tricyclic) non-aromatic heterocyclic groups such as dihydrobenzofuranyl, dihydrobenzimidazolyl, dihydrobenzoxazolyl, dihydrobenzothiazolyl, dihydrobenzisothiazolyl, dihydronaphtho[2,3-b]thienyl, tetrahydroisoquinolyl, tetrahydroquinolyl, 4H-quinolizinyl, indolinyl, isoindolinyl, tetrahydrothieno[2,3-c]pyridinyl, tetrahydrobenzazepinyl, tetrahydroquinoxalinyl, tetrahydrophenanthridinyl, hexahydrophenothiazinyl, hexahydrophenoxazinyl, tetrahydrophthalazinyl, tetrahydronaphthyridinyl, tetrahydroquinazolinyl, tetrahydrocinnolinyl, tetrahydrocarbazolyl, tetrahydro-β-carbolinyl, tetrahydroacrydinyl, tetrahydrophenazinyl, tetrahydrothioxanthenyl, octahydroisoquinolyl and the like.

In the present specification, preferable examples of the "7- to 10-membered bridged heterocyclic group" include quinuclidinyl and 7-azabicyclo[2.2.1]heptanyl.

In the present specification, examples of the "nitrogen-containing heterocyclic group" include the "heterocyclic group" containing at least one nitrogen atom as a ring-constituting atom.

In the present specification, examples of the "optionally substituted heterocyclic group" include a heterocyclic group optionally having substituent(s) selected from the aforementioned substituent group A.

The number of the substituents in the "optionally substituted heterocyclic group" is, for example, 1 to 3. When the number of the substituents is two or more, the respective substituents may be the same or different.

In the present specification, examples of the "acyl group" include a formyl group, a carboxy group, a carbamoyl group, a thiocarbamoyl group, a sulfino group, a sulfo group, a sulfamoyl group and a phosphono group, each optionally having "1 or 2 substituents selected from a $C_{1-6}$ alkyl group, a $C_{2-6}$ alkenyl group, a $C_{3-10}$ cycloalkyl group, a $C_{3-10}$ cycloalkenyl group, a $C_{6-14}$ aryl group, a $C_{7-16}$ aralkyl group, a 5- to 14-membered aromatic heterocyclic group and a 3- to 14-membered non-aromatic heterocyclic group, each of which optionally has 1 to 3 substituents selected from a halogen atom, an optionally halogenated $C_{1-6}$ alkoxy group, a hydroxy group, a nitro group, a cyano group, an amino group and a carbamoyl group".

Examples of the "acyl group" also include a hydrocarbon-sulfonyl group, a heterocyclylsulfonyl group, a hydrocarbon-sulfinyl group and a heterocyclylsulfinyl group.

Here, the hydrocarbon-sulfonyl group means a hydrocarbon group-bonded sulfonyl group, the heterocyclylsulfonyl group means a heterocyclic group-bonded sulfonyl group, the hydrocarbon-sulfinyl group means a hydrocarbon group-bonded sulfinyl group and the heterocyclylsulfinyl group means a heterocyclic group-bonded sulfinyl group.

Preferable examples of the "acyl group" include a formyl group, a carboxy group, a $C_{1-6}$ alkyl-carbonyl group, a $C_{2-6}$ alkenyl-carbonyl group (e.g., crotonoyl), a $C_{3-10}$ cycloalkyl-carbonyl group (e.g., cyclobutanecarbonyl, cyclopentanecarbonyl, cyclohexanecarbonyl, cycloheptanecarbonyl), a $C_{3-10}$ cycloalkenyl-carbonyl group (e.g., 2-cyclohexenecarbonyl), a $C_{6-14}$ aryl-carbonyl group, a $C_{7-16}$ aralkyl-carbonyl group, a 5- to 14-membered aromatic heterocyclylcarbonyl group, a 3- to 14-membered non-aromatic heterocyclylcarbonyl group, a $C_{1-6}$ alkoxy-carbonyl group, a $C_{6-14}$ aryloxy-carbonyl group (e.g., phenyloxycarbonyl, naphthyloxycarbonyl), a $C_{7-16}$ aralkyloxy-carbonyl group (e.g., benzyloxycarbonyl, phenethyloxycarbonyl), a carbamoyl group, a mono- or di-$C_{1-6}$ alkyl-carbamoyl group, a mono- or di-$C_{2-6}$ alkenyl-carbamoyl group (e.g., diallylcarbamoyl), a mono- or di-$C_{3-10}$ cycloalkyl-carbamoyl group (e.g., cyclopropylcarbamoyl), a mono- or di-$C_{6-14}$ aryl-carbamoyl group (e.g., phenylcarbamoyl), a mono- or di-$C_{7-16}$ aralkyl-carbamoyl group, a 5- to 14-membered aromatic heterocyclylcarbamoyl group (e.g., pyridylcarbamoyl), a thiocarbamoyl group, a mono- or di-$C_{1-6}$ alkyl-thiocarbamoyl group (e.g., methylthiocarbamoyl, N-ethyl-N-methylthiocarbamoyl), a mono- or di-$C_{2-6}$ alkenyl-thiocarbamoyl group (e.g., diallylthiocarbamoyl), a mono- or di-$C_{3-10}$ cycloalkyl-thiocarbamoyl group (e.g., cyclopropylthiocarbamoyl, cyclohexylthiocarbamoyl), a mono- or di-$C_{6-14}$ aryl-thiocarbamoyl group (e.g., phenylthiocarbamoyl), a mono- or di-$C_{7-16}$ aralkyl-thiocarbamoyl group (e.g., benzylthiocarbamoyl, phenethylthiocarbamoyl), a 5- to 14-membered aromatic heterocyclylthiocarbamoyl group (e.g., pyridylthiocarbamoyl), a sulfino group, a $C_{1-6}$ alkylsulfinyl group (e.g., methylsulfinyl, ethylsulfinyl), a sulfo group, a $C_{1-6}$ alkylsulfonyl group, a $C_{6-14}$ arylsulfonyl group, a phosphono group and a mono- or di-$C_{1-6}$ alkylphosphono group (e.g., dimethylphosphono, diethylphosphono, diisopropylphosphono, dibutylphosphono).

In the present specification, examples of the "optionally substituted amino group" include an amino group optionally having "1 or 2 substituents selected from a $C_{1-6}$ alkyl group, a $C_{2-6}$ alkenyl group, a $C_{3-10}$ cycloalkyl group, a $C_{6-14}$ aryl group, a $C_{7-16}$ aralkyl group, a $C_{1-6}$ alkyl-carbonyl group, a $C_{6-14}$ aryl-carbonyl group, a $C_{7-16}$ aralkyl-carbonyl group, a 5- to 14-membered aromatic heterocyclylcarbonyl group, a 3- to 14-membered non-aromatic heterocyclylcarbonyl group, a $C_{1-6}$ alkoxy-carbonyl group, a 5- to 14-membered aromatic heterocyclic group, a carbamoyl group, a mono- or di-$C_{1-6}$ alkyl-carbamoyl group, a mono- or di-$C_{7-16}$ aralkyl-carbamoyl group, a $C_{1-6}$ alkylsulfonyl group and a $C_{6-14}$ arylsulfonyl group, each of which optionally has 1 to 3 substituents selected from substituent group A".

Preferable examples of the optionally substituted amino group include an amino group, a mono- or di-(optionally halogenated $C_{1-6}$ alkyl)amino group (e.g., methylamino, trifluoromethylamino, dimethylamino, ethylamino, diethylamino, propylamino, dibutylamino), a mono- or di-$C_{2-6}$ alkenylamino group (e.g., diallylamino), a mono- or di-$C_{3-10}$ cycloalkylamino group (e.g., cyclopropylamino, cyclohexylamino), a mono- or di-$C_{6-14}$ arylamino group (e.g., phenylamino), a mono- or di-$C_{7-16}$ aralkylamino group (e.g., benzylamino, dibenzylamino), a mono- or di-(optionally halogenated $C_{1-6}$ alkyl)-carbonylamino group (e.g., acetylamino, propionylamino), a mono- or di-$C_{6-14}$ aryl-carbonylamino group (e.g., benzoylamino), a mono- or di-$C_{7-16}$ aralkyl-carbonylamino group (e.g., benzylcarbonylamino), a mono- or di-5- to 14-membered aromatic heterocyclylcarbonylamino group (e.g., nicotinoylamino, isonicotinoylamino), a mono- or di-3- to 14-membered non-aromatic heterocyclylcarbonylamino group (e.g., piperidinylcarbonylamino), a mono- or di-$C_{1-6}$ alkoxy-carbonylamino group (e.g., tert-butoxycarbonylamino), a 5- to 14-membered aromatic heterocyclylamino group (e.g., pyridylamino), a carbamoylamino group, a (mono- or di-$C_{1-6}$ alkyl-carbamoyl) amino group (e.g., methylcarbamoylamino), a (mono- or di-$C_{7-16}$ aralkyl-carbamoylamino group (e.g., benzylcarbamoylamino), a $C_{1-6}$ alkylsulfonylamino group (e.g., methylsulfonylamino, ethylsulfonylamino), a $C_{6-14}$ arylsulfonylamino group (e.g., phenylsulfonylamino), a ($C_{1-6}$ alkyl) ($C_{1-6}$ alkyl-carbonyl)amino group (e.g., N-acetyl-N-methylamino) and a ($C_{1-6}$ alkyl) ($C_{6-14}$ aryl-carbonyl)amino group (e.g., N-benzoyl-N-methylamino).

In the present specification, examples of the "optionally substituted carbamoyl group" include a carbamoyl group optionally having "1 or 2 substituents selected from a $C_{1-6}$ alkyl group, a $C_{2-6}$ alkenyl group, a $C_{3-10}$ cycloalkyl group, a $C_{6-14}$ aryl group, a $C_{7-16}$ aralkyl group, a $C_{1-6}$ alkyl-carbonyl group, a $C_{6-14}$ aryl-carbonyl group, a $C_{7-16}$ aralkyl-carbonyl group, a 5- to 14-membered aromatic heterocyclylcarbonyl group, a 3- to 14-membered non-aromatic heterocyclylcarbonyl group, a $C_{1-6}$ alkoxy-carbonyl group, a 5- to 14-membered aromatic heterocyclic group, a carbamoyl group, a mono- or di-$C_{1-6}$ alkyl-carbamoyl group and a mono- or di-$C_{7-16}$ aralkyl-carbamoyl group, each of which optionally has 1 to 3 substituents selected from substituent group A".

Preferable examples of the optionally substituted carbamoyl group include a carbamoyl group, a mono- or di-$C_{1-6}$ alkyl-carbamoyl group, a mono- or di-$C_{2-6}$ alkenyl-carbamoyl group (e.g., diallylcarbamoyl), a mono- or di-$C_{3-10}$ cycloalkyl-carbamoyl group (e.g., cyclopropylcarbamoyl, cyclohexylcarbamoyl), a mono- or di-$C_{6-14}$ aryl-carbamoyl group (e.g., phenylcarbamoyl), a mono- or di-$C_{7-16}$ aralkyl-carbamoyl group, a mono- or di-$C_{1-6}$ alkyl-carbonyl-carbamoyl group (e.g., acetylcarbamoyl, propionylcarbamoyl), a mono- or di-$C_{6-14}$ aryl-carbonyl-carbamoyl group (e.g., benzoylcarbamoyl) and a 5- to 14-membered aromatic heterocyclylcarbamoyl group (e.g., pyridylcarbamoyl).

In the present specification, examples of the "optionally substituted thiocarbamoyl group" include a thiocarbamoyl group optionally having "1 or 2 substituents selected from a $C_{1-6}$ alkyl group, a $C_{2-6}$ alkenyl group, a $C_{3-10}$ cycloalkyl group, a $C_{6-14}$ aryl group, a $C_{7-16}$ aralkyl group, a $C_{1-6}$ alkyl-carbonyl group, a $C_{6-14}$ aryl-carbonyl group, a $C_{7-16}$ aralkyl-carbonyl group, a 5- to 14-membered aromatic heterocyclylcarbonyl group, a 3- to 14-membered non-aromatic heterocyclylcarbonyl group, a $C_{1-6}$ alkoxy-carbonyl group, a 5- to 14-membered aromatic heterocyclic group, a carbamoyl group, a mono- or di-$C_{1-6}$ alkyl-carbamoyl group and a mono- or di-$C_{7-16}$ aralkyl-carbamoyl group, each of which optionally has 1 to 3 substituents selected from substituent group A".

Preferable examples of the optionally substituted thiocarbamoyl group include a thiocarbamoyl group, a mono- or di-$C_{1-6}$ alkyl-thiocarbamoyl group (e.g., methylthiocarbamoyl, ethylthiocarbamoyl, dimethylthiocarbamoyl, diethylthiocarbamoyl, N-ethyl-N-methylthiocarbamoyl), a mono- or di-$C_{2-6}$ alkenyl-thiocarbamoyl group (e.g., diallylthiocarbamoyl), a mono- or di-$C_{3-10}$ cycloalkyl-thiocarbamoyl group (e.g., cyclopropylthiocarbamoyl, cyclohexylthiocarbamoyl), a mono- or di-$C_{6-14}$ aryl-thiocarbamoyl group (e.g., phenylthiocarbamoyl), a mono- or di-$C_{7-16}$ aralkyl-thiocarbamoyl group (e.g., benzylthiocarbamoyl, phenethylthiocarbamoyl), a mono- or di-$C_{1-6}$ alkyl-carbonyl-thiocarbamoyl group (e.g., acetylthiocarbamoyl, propionylthiocarbamoyl), a mono- or di-$C_{6-14}$ aryl-carbonyl-thiocarbamoyl group (e.g., benzoylthiocarbamoyl) and a 5- to 14-membered aromatic heterocyclylthiocarbamoyl group (e.g., pyridylthiocarbamoyl).

In the present specification, examples of the "optionally substituted sulfamoyl group" include a sulfamoyl group optionally having "1 or 2 substituents selected from a $C_{1-6}$ alkyl group, a $C_{2-6}$ alkenyl group, a $C_{3-10}$ cycloalkyl group, a $C_{6-14}$ aryl group, a $C_{7-16}$ aralkyl group, a $C_{1-6}$ alkyl-carbonyl group, a $C_{6-14}$ aryl-carbonyl group, a $C_{7-16}$ aralkyl-carbonyl group, a 5- to 14-membered aromatic heterocyclylcarbonyl group, a 3- to 14-membered non-aromatic heterocyclylcarbonyl group, a $C_{1-6}$ alkoxy-carbonyl group, a 5- to 14-membered aromatic heterocyclic group, a carbamoyl group, a mono- or di-$C_{1-6}$ alkyl-carbamoyl group and a mono- or di-$C_{7-16}$ aralkyl-carbamoyl group, each of which optionally has 1 to 3 substituents selected from substituent group A".

Preferable examples of the optionally substituted sulfamoyl group include a sulfamoyl group, a mono- or di-$C_{1-6}$ alkyl-sulfamoyl group (e.g., methylsulfamoyl, ethylsulfamoyl, dimethylsulfamoyl, diethylsulfamoyl, N-ethyl-N-methylsulfamoyl), a mono- or di-$C_{2-6}$ alkenyl-sulfamoyl group (e.g., diallylsulfamoyl), a mono- or di-$C_{3-10}$ cycloalkyl-sulfamoyl group (e.g., cyclopropylsulfamoyl, cyclohexylsulfamoyl), a mono- or di-$C_{6-14}$ aryl-sulfamoyl group (e.g., phenylsulfamoyl), a mono- or di-$C_{7-16}$ aralkyl-sulfamoyl group (e.g., benzylsulfamoyl, phenethylsulfamoyl), a mono- or di-$C_{1-6}$ alkyl-carbonyl-sulfamoyl group (e.g., acetylsulfamoyl, propionylsulfamoyl), a mono- or di-$C_{6-14}$ aryl-carbonyl-sulfamoyl group (e.g., benzoylsulfamoyl) and a 5- to 14-membered aromatic heterocyclylsulfamoyl group (e.g., pyridylsulfamoyl).

In the present specification, examples of the "optionally substituted hydroxy group" include a hydroxyl group optionally having "a substituent selected from a $C_{1-6}$ alkyl group, a $C_{2-6}$ alkenyl group, a $C_{3-10}$ cycloalkyl group, a $C_{6-14}$ aryl group, a $C_{7-16}$ aralkyl group, a $C_{1-6}$ alkyl-carbonyl group, a $C_{6-14}$ aryl-carbonyl group, a $C_{7-16}$ aralkyl-carbonyl group, a 5- to 14-membered aromatic heterocyclylcarbonyl group, a 3- to 14-membered non-aromatic heterocyclylcarbonyl group, a $C_{1-6}$ alkoxy-carbonyl group, a 5- to 14-membered aromatic heterocyclic group, a carbamoyl group, a mono- or di-$C_{1-6}$ alkyl-carbamoyl group, a mono- or di-$C_{7-16}$ aralkyl-carbamoyl group, a $C_{1-6}$ alkylsulfonyl group and a $C_{6-14}$ arylsulfonyl group, each of which optionally has 1 to 3 substituents selected from substituent group A".

Preferable examples of the optionally substituted hydroxy group include a hydroxy group, a $C_{1-6}$ alkoxy group, a $C_{2-6}$ alkenyloxy group (e.g., allyloxy, 2-butenyloxy, 2-pentenyloxy, 3-hexenyloxy), a $C_{3-10}$ cycloalkyloxy group (e.g., cyclohexyloxy), a $C_{6-14}$ aryloxy group (e.g., phenoxy, naphthyloxy), a $C_{7-16}$ aralkyloxy group (e.g., benzyloxy, phenethyloxy), a $C_{1-6}$ alkyl-carbonyloxy group (e.g., acetyloxy, propionyloxy, butyryloxy, isobutyryloxy, pivaloyloxy), a $C_{6-14}$ aryl-carbonyloxy group (e.g., benzoyloxy), a $C_{7-16}$ aralkyl-carbonyloxy group (e.g., benzylcarbonyloxy), a 5- to 14-membered aromatic heterocyclylcarbonyloxy group (e.g., nicotinoyloxy), a 3- to 14-membered non-aromatic heterocyclylcarbonyloxy group (e.g., piperidinylcarbonyloxy), a $C_{1-6}$ alkoxy-carbonyloxy group (e.g., tert-butoxycarbonyloxy), a 5- to 14-membered aromatic heterocyclyloxy group (e.g., pyridyloxy), a carbamoyloxy group, a $C_{1-6}$ alkyl-carbamoyloxy group (e.g., methylcarbamoyloxy), a $C_{7-16}$ aralkyl-carbamoyloxy group (e.g., benzylcarbamoyloxy), a $C_{1-6}$ alkylsulfonyloxy group (e.g., methylsulfonyloxy, ethylsulfonyloxy) and a $C_{6-14}$ arylsulfonyloxy group (e.g., phenylsulfonyloxy).

In the present specification, examples of the "optionally substituted sulfanyl group" include a sulfanyl group optionally having "a substituent selected from a $C_{1-6}$ alkyl group, a $C_{2-6}$ alkenyl group, a $C_{3-10}$ cycloalkyl group, a $C_{6-14}$ aryl group, a $C_{7-16}$ aralkyl group, a $C_{1-6}$ alkyl-carbonyl group, a $C_{6-14}$ aryl-carbonyl group and a 5- to 14-membered aromatic heterocyclic group, each of which optionally has 1 to 3 substituents selected from substituent group A" and a halogenated sulfanyl group.

Preferable examples of the optionally substituted sulfanyl group include a sulfanyl (—SH) group, a $C_{1-6}$ alkylthio group, a $C_{2-6}$ alkenylthio group (e.g., allylthio, 2-butenylthio, 2-pentenylthio, 3-hexenylthio), a $C_{3-10}$ cycloalkylthio group (e.g., cyclohexylthio), a $C_{6-14}$ arylthio group (e.g., phenylthio, naphthylthio), a $C_{7-16}$ aralkylthio group (e.g., benzylthio, phenethylthio), a $C_{1-6}$ alkyl-carbonylthio group (e.g., acetylthio, propionylthio, butyrylthio, isobutyrylthio, pivaloylthio), a $C_{6-14}$ aryl-carbonylthio group (e.g., benzoylthio), a 5- to 14-membered aromatic heterocyclylthio group (e.g., pyridylthio) and a halogenated thio group (e.g., pentafluorothio).

In the present specification, examples of the "optionally substituted silyl group" include a silyl group optionally having "1 to 3 substituents selected from a $C_{1-6}$ alkyl group, a $C_{2-6}$ alkenyl group, a $C_{3-10}$ cycloalkyl group, a $C_{6-14}$ aryl group and a $C_{7-16}$ aralkyl group, each of which optionally has 1 to 3 substituents selected from substituent group A".

Preferable examples of the optionally substituted silyl group include a tri-$C_{1-6}$ alkylsilyl group (e.g., trimethylsilyl, tert-butyl(dimethyl)silyl).

In the present specification, examples of the "$C_{3-6}$ cycloalkyl group" include the above-mentioned "$C_{3-10}$ cycloalkyl group" wherein the carbon number is 3 to 6.

In the present specification, examples of the "3- to 6-membered saturated cyclic group" include the above-mentioned "$C_{3-10}$ cycloalkyl group" wherein the carbon number is 3 to 6 ($C_{3-6}$ cycloalkyl group), the above-mentioned "3- to 8-membered monocyclic non-aromatic heterocyclic group" which is 3- to 6-membered and saturated (3- to 6-membered saturated monocyclic non-aromatic heterocyclic group).

In the present specification, examples of the "mono- or di-$C_{1-6}$ alkylamino group" include an amino group mono- or di-substituted by the above-mentioned "$C_{1-6}$ alkyl group". When it is a di-$C_{1-6}$ alkylamino group, two $C_{1-6}$ alkyl groups may be the same or different (e.g., N-ethyl-N-methylamino etc.).

The definition of each symbol in the formula (I) is described in detail below.

$R^1$ is an acyl group, or a hydrogen atom.

As the "acyl group" for $R^1$, the above-mentioned "acyl group" can be mentioned.

$R^1$ is preferably (1) a hydrogen atom, (2) an optionally substituted $C_{1-6}$ alkyl-carbonyl group (e.g., methylcarbonyl, ethylcarbonyl, propylcarbonyl, isopropylcarbonyl, isobutylcarbonyl, tert-butylcarbonyl, neopentylcarbonyl), (3) an optionally substituted $C_{3-10}$ (preferably $C_{3-6}$) cycloalkyl-carbonyl group (e.g., cyclopropanecarbonyl, cyclobutanecarbonyl, cyclopentanecarbonyl, cyclohexanecarbonyl), (4) an optionally substituted $C_{1-6}$ alkoxy-carbonyl group (e.g., methoxycarbonyl, ethoxycarbonyl, isopropoxycarbonyl, tert-butoxycarbonyl), (5) an optionally substituted $C_{3-10}$ cycloalkyloxy-carbonyl group (e.g., cyclopropyloxycarbonyl), (6) an optionally substituted $C_{6-14}$ aryl-carbonyl group (e.g., phenylcarbonyl), (7) an optionally substituted $C_{6-14}$ aryloxy-carbonyl group (e.g., phenyloxycarbonyl), (8) an optionally substituted 5- to 14-membered aromatic heterocyclylcarbonyl group (e.g., furylcarbonyl, thienylcarbonyl, pyrazolylcarbonyl, isoxazolylcarbonyl, pyridylcarbonyl), (9) an optionally substituted 3- to 14-membered non-aromatic heterocyclylcarbonyl group (e.g., azetidinylcarbonyl, oxetanylcarbonyl, pyrrolidinylcarbonyl, tetrahydrofuranylcarbonyl, tetrahydropyranylcarbonyl, morpholinylcarbonyl), (10) an optionally substituted mono- or di-$C_{1-6}$ alkyl-carbamoyl group (e.g., methylcarbamoyl, ethylcarbamoyl, propylcarbamoyl, isopropylcarbamoyl, dimethylcarbamoyl), (11) an optionally substituted mono- or di-$C_{3-10}$ cycloalkyl-carbamoyl group (e.g., cyclopropylcarbamoyl), (12) an optionally substituted mono- or di-$C_{6-14}$ aryl-carbamoyl group (e.g., phenylcarbamoyl), (13) an optionally substituted $C_{1-6}$ alkylsulfonyl group (e.g., methylsulfonyl), (14) an optionally substituted $C_{3-10}$ cycloalkylsulfonyl group (e.g., cyclopropylsulfonyl), (15) an optionally substituted $C_{6-14}$ arylsulfonyl group (e.g., phenylsulfonyl), (16) an optionally substituted heterocyclyl-sulfonyl group (e.g., thienylsulfonyl, pyrazolylsulfonyl, imidazolylsulfonyl, pyridylsulfonyl, dihydrochromenylsulfonyl), (17) an optionally substituted mono- or di-$C_{1-6}$ alkyl-sulfamoyl group (e.g., dimethylsulfamoyl) and (18) an optionally substituted $C_{1-6}$ alkyl-carbonyl-carbonyl group (e.g., methylcarbonyl-carbonyl).

$R^1$ is more preferably (1) a hydrogen atom, (2) a $C_{1-6}$ alkyl-carbonyl group (e.g., methylcarbonyl, ethylcarbonyl, propylcarbonyl, isopropylcarbonyl, isobutylcarbonyl, tert-butylcarbonyl, neopentylcarbonyl) optionally substituted by 1 to 7 substituents selected from a halogen atom (e.g., fluorine atom), a cyano group, a hydroxy group, a $C_{3-10}$ cycloalkyl group (e.g., cyclopropyl), a $C_{1-6}$ alkoxy group (e.g., methoxy), a $C_{6-14}$ aryl group (e.g., phenyl), a $C_{6-14}$ aryloxy group (e.g., phenoxy), a 5- to 14-membered aromatic heterocyclic group (e.g., pyrazolyl, thiazolyl, pyrimidinyl, pyridazinyl) optionally substituted by an oxo group, a 5- to 14-membered aromatic heterocyclyloxy group (e.g., pyrazolyloxy) optionally substituted by 1 to 3 substituents selected from a $C_{1-6}$ alkyl group (e.g., methyl), a $C_{1-6}$ alkyl-carbonyl group (e.g., methylcarbonyl), a $C_{1-6}$ alkoxy-carbonyl group (e.g., methoxycarbonyl), a $C_{1-6}$ alkyl-carbonyloxy group (e.g., methylcarbonyloxy), a $C_{1-6}$ alkylsulfonyl group (e.g., methylsulfonyl), a mono- or di-$C_{1-6}$ alkylamino group (e.g., dimethylamino), a $C_{1-6}$ alkyl-carbonylamino group (e.g., acetylamino) and a ($C_{1-6}$ alkyl) ($C_{1-6}$ alkyl-carbonyl)amino group (e.g., N-acetyl-N-methylamino), (3) a $C_{3-10}$ (preferably $C_{3-6}$) cycloalkyl-carbonyl group (e.g., cyclopropanecarbonyl, cyclobutanecarbonyl, cyclopentanecarbonyl, cyclohexanecarbonyl) optionally substituted by 1 to 3 substituents selected from a halogen atom (e.g., fluorine atom), a cyano group, a hydroxy group, an oxo group and a $C_{1-6}$ alkyl group (e.g., methyl), (4) a $C_{1-6}$ alkoxy-carbonyl group (e.g., methoxycarbonyl, ethoxycarbonyl, isopropoxycarbonyl, tert-butoxycarbonyl) optionally substituted by 1 to 6 substituents selected from deuterium, a halogen atom (e.g., fluorine atom) and a $C_{6-14}$ aryl group (e.g., phenyl), (5) a $C_{3-10}$ cycloalkyloxy-carbonyl group (e.g., cyclopropyloxycarbonyl) optionally substituted by 1 to 3 substituents selected from a $C_{1-6}$ alkyl group (e.g., methyl), (6) a $C_{6-14}$ aryl-carbonyl group (e.g., phenylcarbonyl) optionally substituted by 1 to 3 substituents selected from a halogen atom (e.g., fluorine atom, chlorine atom) and a $C_{6-14}$ aryl group (e.g., phenyl), (7) a $C_{6-14}$ aryloxy-carbonyl group (e.g., phenyloxycarbonyl), (8) a 5- to 14-membered aromatic heterocyclylcarbonyl group (e.g., furylcarbonyl, thienylcarbonyl, pyrazolylcarbonyl, isoxazolylcarbonyl, pyridylcarbonyl) optionally substituted by 1 to 3 substituents selected from a $C_{1-6}$ alkyl group (e.g., methyl), (9) a 3- to 14-membered non-aromatic heterocyclylcarbonyl group (e.g., azetidinylcarbonyl, oxetanylcarbonyl, pyrrolidinylcarbonyl, tetrahydrofuranylcarbonyl, tetrahydropyranylcarbonyl, morpholinylcarbonyl) optionally substituted by 1 to 3 substituents selected from an oxo group, a $C_{1-6}$ alkyl-carbonyl group (e.g., methylcarbonyl), a $C_{1-6}$ alkoxy-carbonyl group (e.g., tert-butoxycarbonyl) and a $C_{1-6}$ alkylsulfonyl group (e.g., methylsulfonyl), (10) a mono- or di-$C_{1-6}$ alkyl-carbamoyl group (e.g., methylcarbamoyl, ethylcarbamoyl, propylcarbamoyl, isopropylcarbamoyl, dimethylcarbamoyl) optionally substituted by 1 to 3 substituents selected from a halogen atom (e.g., fluorine atom), a cyano group, a hydroxy group and a $C_{1-6}$ alkoxy group (e.g., methoxy), (11) a mono- or di-$C_{3-10}$ cycloalkyl-carbamoyl group (e.g., cyclopropylcarbamoyl), (12) a mono- or di-$C_{6-14}$ aryl-carbamoyl group (e.g., phenylcarbamoyl), (13) a $C_{1-6}$ alkylsulfonyl group (e.g., methylsulfonyl), (14) a $C_{3-10}$ cycloalkylsulfonyl group (e.g., cyclopropylsulfonyl), (15) a $C_{6-14}$ arylsulfonyl group (e.g., phenylsulfonyl) optionally substituted by 1 to 3 halogen atoms (e.g., chlorine atom), (16) a heterocyclyl-sulfonyl group (e.g., thienylsulfonyl, pyrazolylsulfonyl, imidazolylsulfonyl, pyridylsulfonyl, dihydrochromenylsulfonyl) optionally substituted by 1 to 3 substituents selected from a $C_{1-6}$ alkyl group (e.g., methyl), (17) a mono- or di-$C_{1-6}$ alkyl-sulfamoyl group (e.g., dimethylsulfamoyl) or (18) a $C_{1-6}$ alkyl-carbonyl-carbonyl group (e.g., methylcarbonyl-carbonyl).

In another embodiment of the present invention, $R^1$ is preferably an acyl group.

In a still another embodiment of the present invention, $R^1$ is preferably a $C_{1-6}$ alkyl-carbonyl group optionally substituted by one hydroxy group, a $C_{1-6}$ alkoxy-carbonyl group, a $C_{3-6}$ cycloalkyl-carbonyl group or a mono- or di-$C_{1-6}$ alkyl-carbamoyl group.

In yet another embodiment of the present invention, $R^1$ is preferably a hydrogen atom.

In another embodiment of the present invention, $R^1$ is preferably (1) a hydrogen atom, (2) a $C_{1-6}$ alkyl-carbonyl group optionally substituted by a hydroxy group, (3) a cyclopropanecarbonyl group, (4) a $C_{1-6}$ alkoxy-carbonyl group or (5) a mono- or di-$C_{1-6}$ alkyl-carbamoyl group.

In another embodiment of the present invention, $R^1$ is preferably (1) a $C_{1-6}$ alkyl-carbonyl group optionally substituted by a hydroxy group, (2) a $C_{1-6}$ alkoxy-carbonyl group or (3) a mono- or di-$C_{1-6}$ alkyl-carbamoyl group.

In another embodiment of the present invention, $R^1$ is preferably a $C_{1-6}$ alkoxy-carbonyl group (preferably methoxycarbonyl).

In another embodiment of the present invention, $R^1$ is preferably a $C_{1-6}$ alkyl-carbonyl group optionally substituted by a hydroxy group.

In another embodiment of the present invention, $R^1$ is preferably a mono- or di-$C_{1-6}$ alkyl-carbamoyl group.

$R^2$ is an optionally substituted 3- to 6-membered saturated cyclic group.

As the "3- to 6-membered saturated cyclic group" of the "optionally substituted 3- to 6-membered saturated cyclic group" for $R^2$, a $C_{3-6}$ cycloalkyl group (e.g., cyclobutyl, cyclopentyl, cyclohexyl) or a 3- to 6-membered saturated monocyclic non-aromatic heterocyclic group (e.g., pyrrolidinyl, piperidinyl, dioxanyl) can be mentioned.

As the substituent of the "optionally substituted 3- to 6-membered saturated cyclic group" for $R^2$, the above-mentioned "substituent" can be mentioned, and (1) deuterium, (2) a halogen atom (e.g., fluorine atom), (3) a hydroxy group, (4) an optionally substituted $C_{1-6}$ alkyl group (e.g., methyl, isopropyl), (5) a $C_{3-10}$ cycloalkyl group (e.g., cyclohexyl), (6) an optionally substituted $C_{1-6}$ alkoxy group (e.g., methoxy), (7) an optionally substituted $C_{6-14}$ aryl group (e.g., phenyl), (8) a $C_{6-14}$ aryloxy group (e.g., phenoxy), (9) a tri-$C_{1-6}$ alkylsilyloxy group (e.g., tert-butyl(dimethyl)silyloxy), (10) an optionally substituted 5- to 14-membered aromatic heterocyclic group (e.g., pyrazolyl, thiazolyl, pyridyl, pyrimidinyl, quinazolinyl, benzothiazolyl, isoquinolinyl) or (11) an optionally substituted $C_{6-14}$ aryl-carbonyl group (e.g., benzoyl) is preferable, (1) deuterium, (2) a halogen atom (e.g., fluorine atom), (3) a hydroxy group, (4) a $C_{1-6}$ alkyl group (e.g., methyl, isopropyl) optionally substituted by 1 to 3 substituents selected from a halogen atom (e.g., fluorine atom) and a $C_{6-14}$ aryl group (e.g., phenyl), (5) a $C_{3-10}$ cycloalkyl group (e.g., cyclohexyl), (6) a $C_{1-6}$ alkoxy group (e.g., methoxy) optionally substituted by a $C_{3-10}$ cycloalkyl group (e.g., cyclopropyl), (7) a $C_{6-14}$ aryl group (e.g., phenyl) optionally substituted by 1 to 3 substituents selected from a halogen atom (e.g., fluorine atom, chlorine atom), a cyano group, a $C_{1-6}$ alkyl group (e.g., methyl, ethyl) optionally substituted by 1 to 3 halogen atoms (e.g., fluorine atom), a $C_{1-6}$ alkoxy group (e.g., methoxy) optionally substituted by 1 to 3 halogen atoms (e.g., fluorine atom) and a hydroxy group, (8) a $C_{6-14}$ aryloxy group (e.g., phenoxy), (9) a tri-$C_{1-6}$ alkylsilyloxy group (e.g., tert-butyl(dimethyl)silyloxy), (10) a 5- to 14-membered aromatic heterocyclic group (e.g., pyrazolyl, thiazolyl, pyridyl, pyrimidinyl, quinazolinyl, benzothiazolyl, isoquinolinyl) optionally substituted by 1 to 3 substituents selected from a halogen atom (e.g., fluorine atom, chlorine atom), a $C_{1-6}$ alkyl group (e.g., methyl) and a $C_{1-6}$ alkoxy group (e.g., methoxy) or (11) a $C_{6-14}$ aryl-carbonyl group (e.g., benzoyl) is more preferable.

In the present specification, when the "optionally substituted 3- to 6-membered saturated cyclic group" for $R^2$ has two substituents on one carbon constituting the "3- to 6-membered saturated cyclic group", it includes an embodiment wherein said two substituents are bonded to each other to form a spiro ring system (e.g., 3H-spiro[2-benzofuran-1,1'-cyclohexane]-4'-yl, 1,4-dioxaspiro[4.5]dec-8-yl) together with the "3- to 6-membered saturated cyclic group".

$R^2$ is preferably a $C_{3-6}$ cycloalkyl group (e.g., cyclobutyl, cyclopentyl, cyclohexyl) or a 3- to 6-membered saturated monocyclic non-aromatic heterocyclic group (e.g., pyrrolidinyl, piperidinyl, dioxanyl), each of which is optionally substituted by 1 to 3 substituents selected from (1) deuterium, (2) a halogen atom (e.g., fluorine atom), (3) a hydroxy group, (4) an optionally substituted $C_{1-6}$ alkyl group (e.g., methyl, isopropyl), (5) a $C_{3-10}$ cycloalkyl group (e.g., cyclohexyl), (6) an optionally substituted $C_{1-6}$ alkoxy group (e.g., methoxy), (7) an optionally substituted $C_{6-14}$ aryl group (e.g., phenyl), (8) a $C_{6-14}$ aryloxy group (e.g., phenoxy), (9) a tri-$C_{1-6}$ alkylsilyloxy group (e.g., tert-butyl(dimethyl)silyloxy), (10) an optionally substituted 5- to 14-membered aromatic heterocyclic group (e.g., pyrazolyl, thiazolyl, pyridyl, pyrimidinyl, quinazolinyl, benzothiazolyl, isoquinolinyl) and (11) an optionally substituted $C_{6-14}$ aryl-carbonyl group (e.g., benzoyl), more preferably a $C_{3-6}$ cycloalkyl group (e.g., cyclobutyl, cyclopentyl, cyclohexyl) or a 3- to 6-membered saturated monocyclic non-aromatic heterocyclic group (e.g., pyrrolidinyl, piperidinyl, dioxanyl), each of which is optionally substituted by 1 to 3 substituents selected from (1) deuterium, (2) a halogen atom (e.g., fluorine atom), (3) a hydroxy group, (4) a $C_{1-6}$ alkyl group (e.g., methyl, isopropyl) optionally substituted by 1 to 3 substituents selected from a halogen atom (e.g., fluorine atom) and a $C_{6-14}$ aryl group (e.g., phenyl), (5) a $C_{3-10}$ cycloalkyl group (e.g., cyclohexyl), (6) a $C_{1-6}$ alkoxy group (e.g., methoxy) optionally substituted by a $C_{3-10}$ cycloalkyl group (e.g., cyclopropyl), (7) a $C_{6-14}$ aryl group (e.g., phenyl) optionally substituted by 1 to 3 substituents selected from a halogen atom (e.g., fluorine atom, chlorine atom), a cyano group, a $C_{1-6}$ alkyl group (e.g., methyl, ethyl) optionally substituted by 1 to 3 halogen atoms (e.g., fluorine atom), a $C_{1-6}$ alkoxy group (e.g., methoxy) optionally substituted by 1 to 3 halogen atoms (e.g., fluorine atom) and a hydroxy group, (8) a $C_{6-14}$ aryloxy group (e.g., phenoxy), (9) a tri-$C_{1-6}$ alkylsilyloxy group (e.g., tert-butyl(dimethyl)silyloxy), (10) a 5- to 14-membered aromatic heterocyclic group (e.g., pyrazolyl, thiazolyl, pyridyl, pyrimidinyl, quinazolinyl, benzothiazolyl, isoquinolinyl) optionally substituted by 1 to 3 substituents selected from a halogen atom, a $C_{1-6}$ alkyl group (e.g., methyl) and a $C_{1-6}$ alkoxy group (e.g., methoxy) and (11) a $C_{6-14}$ aryl-carbonyl group (e.g., benzoyl).

$R^2$ is further more preferably, (A) a $C_{3-6}$ cycloalkyl group (e.g., cyclobutyl, cyclopentyl, cyclohexyl) optionally substituted by 1 to 3 substituents selected from (1) deuterium, (2) a halogen atom (e.g., fluorine atom), (3) a hydroxy group, (4) a $C_{1-6}$ alkyl group (e.g., methyl, isopropyl) optionally substituted by 1 to 3 substituents selected from a halogen atom (e.g., fluorine atom) and a $C_{6-14}$ aryl group (e.g., phenyl), (5) a $C_{3-10}$ cycloalkyl group (e.g., cyclohexyl), (6) a $C_{1-6}$ alkoxy group (e.g., methoxy) optionally substituted by a $C_{3-10}$ cycloalkyl group (e.g., cyclopropyl), (7) a $C_{6-14}$ aryl group (e.g., phenyl) optionally substituted by 1 to 3 substituents selected from a halogen atom (e.g., fluorine atom, chlorine atom), a cyano group, a $C_{1-6}$ alkyl group (e.g., methyl, ethyl) optionally substituted by 1 to 3 halogen atoms (e.g., fluorine atom), a $C_{1-6}$ alkoxy group (e.g., methoxy) optionally substituted by 1 to 3 halogen atoms (e.g., fluorine atom) and a hydroxy group, (8) a $C_{6-14}$ aryloxy group (e.g., phenoxy), (9) a tri-$C_{1-6}$ alkylsilyloxy group (e.g., tert-butyl(dimethyl)silyloxy), (10) a 5- to 14-membered aromatic heterocyclic group (e.g., pyrazolyl, thiazolyl, pyridyl, pyrimidinyl, quinazolinyl, benzothiazolyl, isoquinolinyl) optionally substituted by 1 to 3 substituents selected from a halogen atom, a $C_{1-6}$ alkyl group (e.g., methyl) and a $C_{1-6}$ alkoxy group (e.g., methoxy) and (11) a $C_{6-14}$ aryl-carbonyl group (e.g., benzoyl) or (B) a 3- to 6-membered saturated monocyclic non-aromatic heterocyclic group (e.g., pyrrolidinyl, piperidinyl, dioxanyl) optionally substituted by 1 to 3 substituents selected from (1) a halogen atom (e.g., fluorine atom), (2) a $C_{1-6}$ alkyl group (e.g., methyl), (3) a $C_{6-14}$ aryl group (e.g., phenyl) optionally substituted by 1 to 3 substituents selected from a halogen atom (e.g., fluorine atom, chlorine atom), a $C_{1-6}$ alkyl group (e.g., methyl) optionally substituted by 1 to 3 halogen atoms (e.g., fluorine atom) and a $C_{1-6}$ alkoxy group (e.g., methoxy) and (4) a 5- to 14-membered aromatic heterocyclic group (e.g., thiazolyl, pyridyl, pyrimidinyl, quinazolinyl, benzothiazolyl, isoquinolinyl) optionally substituted by 1 to 3 substituents selected from a halogen atom (e.g., fluorine atom, chlorine atom), a $C_{1-6}$ alkyl group (e.g., methyl) and a $C_{1-6}$ alkoxy group (e.g., methoxy).

In another embodiment of the present invention, $R^2$ is preferably a $C_{3-6}$ cycloalkyl group substituted by one optionally substituted phenyl group.

In a still another embodiment of the present invention, $R^2$ is preferably a $C_{3-6}$ cycloalkyl group substituted by one phenyl group optionally substituted by 1 to 3 substituents selected from a halogen atom, a $C_{1-6}$ alkyl group optionally substituted by 1 to 3 halogen atoms, and a $C_{1-6}$ alkoxy group.

In a yet another embodiment of the present invention, $R^2$ is preferably a piperidinyl group substituted by one pyrimidinyl group.

In another embodiment of the present invention, $R^2$ is preferably a $C_{3-6}$ cycloalkyl group, a pyrrolidinyl group, a piperidinyl group or a dioxanyl group, each of which is optionally substituted by 1 to 3 substituents selected from (1) deuterium, (2) a halogen atom, (3) a hydroxy group, (4) a $C_{1-6}$ alkyl group optionally substituted by 1 to 3 substituents selected from a halogen atom and a $C_{6-14}$ aryl group, (5) a $C_{3-10}$ cycloalkyl group, (6) a $C_{1-6}$ alkoxy group optionally substituted by a $C_{3-10}$ cycloalkyl group, (7) a $C_{6-14}$ aryl group optionally substituted by 1 to 3 substituents selected from a halogen atom, a cyano group, a $C_{1-6}$ alkyl group optionally substituted by 1 to 3 halogen atoms, a $C_{1-6}$ alkoxy group optionally substituted by 1 to 3 halogen atoms and a hydroxy group, (8) a $C_{6-14}$ aryloxy group, (9) a tri-$C_{1-6}$ alkylsilyloxy group, (10) a pyrazolyl group, a thiazolyl group, a pyridyl group, a pyrimidinyl group, quinazolinyl group, a benzothiazolyl group or an isoquinolinyl group, each of which is optionally substituted by 1 to 3 substituents selected from a halogen atom, a $C_{1-6}$ alkyl group and a $C_{1-6}$ alkoxy group, and (11) a $C_{6-14}$ aryl-carbonyl group.

In another embodiment of the present invention, $R^2$ is preferably a cyclobutyl group, a cyclopentyl group, a cyclohexyl group, a pyrrolidinyl group, a piperidinyl group or a dioxanyl group, each of which is optionally substituted by 1 to 3 substituents selected from (1) deuterium, (2) a halogen atom, (3) a hydroxy group, (4) a $C_{1-6}$ alkyl group optionally substituted by 1 to 3 substituents selected from a halogen atom and a phenyl group, (5) a cyclohexyl group, (6) a $C_{1-6}$ alkoxy group optionally substituted by a cyclopropyl group, (7) a phenyl group optionally substituted by 1 to 3 substituents selected from a halogen atom, a cyano group, a $C_{1-6}$ alkyl group optionally substituted by 1 to 3 halogen atoms, a $C_{1-6}$ alkoxy group optionally substituted by 1 to 3 halogen atoms and a hydroxy group, (8) a phenoxy group, (9) a tri-$C_{1-6}$ alkylsilyloxy group, (10) a pyrazolyl group, a thiazolyl group, a pyridyl group, a pyrimidinyl group, a quinazolinyl group, a benzothiazolyl group or an isoquinolinyl group, each of which is optionally substituted by 1 to 3 substituents selected from a halogen atom, a $C_{1-6}$ alkyl group and a $C_{1-6}$ alkoxy group, and (11) a benzoyl group.

In another embodiment of the present invention, $R^2$ is preferably (A) a cyclohexyl group optionally substituted by 1 to 3 substituents selected from (1) a $C_{1-6}$ alkyl group and (2) a phenyl group optionally substituted by 1 to 3 substituents selected from a halogen atom, a $C_{1-6}$ alkyl group optionally substituted by 1 to 3 halogen atoms and a $C_{1-6}$ alkoxy group or (B) a piperidinyl group optionally substituted by 1 to 3 pyrimidinyl groups.

In another embodiment of the present invention, $R^2$ is preferably a cyclohexyl group optionally substituted by 1 to 3 substituents selected from (1) a $C_{1-6}$ alkyl group and (2) a phenyl group optionally substituted by 1 to 3 halogen atoms.

In another embodiment of the present invention, $R^2$ is preferably a cyclohexyl group optionally substituted by a phenyl group.

In another embodiment of the present invention, $R^2$ is preferably a cyclohexyl group optionally substituted by a phenyl group optionally substituted by 1 to 3 halogen atoms.

In another embodiment of the present invention, $R^2$ is preferably a cyclohexyl group optionally substituted by a $C_{1-6}$ alkyl group.

$R^3$ is an optionally substituted $C_{1-6}$ alkyl group, a mono- or di-$C_{1-6}$ alkylamino group or a $C_{3-6}$ cycloalkyl group; preferably an optionally substituted $C_{1-6}$ alkyl group, or a mono- or di-$C_{1-6}$ alkylamino group.

As the substituent of the "optionally substituted $C_{1-6}$ alkyl group" for $R^3$, the above-mentioned "substituent" can be mentioned, and a halogen atom (e.g., fluorine atom) or a $C_{6-14}$ aryl group (e.g., phenyl) is preferable.

$R^3$ is preferably a $C_{1-6}$ alkyl group (e.g., methyl, ethyl, propyl, isopropyl, isobutyl) optionally substituted by 1 to 3 substituents selected from a halogen atom (e.g., fluorine atom) and a $C_{6-14}$ aryl group (e.g., phenyl), or a mono- or di-$C_{1-6}$ alkylamino group (e.g., ethylamino, dimethylamino), more preferably, a $C_{1-6}$ alkyl group (e.g., methyl), or a mono- or di-$C_{1-6}$ alkylamino group (e.g., dimethylamino).

In another embodiment of the present invention, $R^3$ is preferably an optionally substituted $C_{1-6}$ alkyl group.

In another embodiment of the present invention, $R^3$ is preferably a $C_{1-6}$ alkyl group or a di-$C_{1-6}$ alkylamino group, more preferably a $C_{1-6}$ alkyl group (preferably methyl).

In a preferable embodiment of the present invention, compound (I) is represented by the formula:

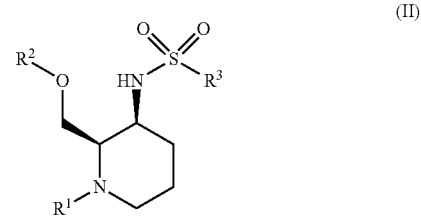

(II)

wherein $R^1$, $R^2$ and $R^3$ are as defined above.

As a preferable embodiment of compound (I), the following compounds can be mentioned.

[Compound I-1]

Compound (I) wherein $R^1$ is (1) a hydrogen atom, (2) an optionally substituted $C_{1-6}$ alkyl-carbonyl group (e.g., methylcarbonyl, ethylcarbonyl, propylcarbonyl, isopropylcarbonyl, isobutylcarbonyl, tert-butylcarbonyl, neopentylcarbonyl), (3) an optionally substituted $C_{3-10}$ (preferably $C_{3-6}$) cycloalkyl-carbonyl group (e.g., cyclopropanecarbonyl, cyclobutanecarbonyl, cyclopentanecarbonyl, cyclohexanecarbonyl), (4) an optionally substituted $C_{1-6}$ alkoxy-carbonyl group (e.g., methoxycarbonyl, ethoxycarbonyl, isopropoxycarbonyl, tert-butoxycarbonyl), (5) an optionally substituted $C_{3-10}$ cycloalkyloxy-carbonyl group (e.g., cyclopropyloxycarbonyl), (6) an optionally substituted $C_{6-14}$ aryl-carbonyl group (e.g., phenylcarbonyl), (7) an optionally substituted $C_{6-14}$ aryloxy-carbonyl group (e.g., phenyloxycarbonyl), (8) an optionally substituted 5- to 14-membered aromatic heterocyclylcarbonyl group (e.g., furylcarbonyl, thienylcarbonyl, pyrazolylcarbonyl, isoxazolylcarbonyl, pyridylcarbonyl), (9) an optionally substituted 3- to 14-membered non-aromatic heterocyclylcarbonyl group (e.g., azetidinylcarbonyl, oxetanylcarbonyl, pyrrolidinylcarbonyl, tetrahydrofuranylcarbonyl, tetrahydropyranylcarbonyl, morpholinylcarbonyl), (10) an optionally substituted mono- or di-$C_{1-6}$ alkyl-carbamoyl group (e.g., methylcarbamoyl, ethylcarbamoyl, propylcarbamoyl, isopropylcarbamoyl, dimethylcarbamoyl), (11) an optionally substituted mono- or di-$C_{3-10}$ cycloalkyl-carbamoyl group (e.g., cyclopropylcarbamoyl), (12) an optionally substituted mono- or di-$C_{6-14}$ aryl-carbamoyl group (e.g., phenylcarbamoyl), (13) an optionally substituted $C_{1-6}$ alkylsulfonyl group (e.g., methylsulfonyl), (14) an optionally substituted $C_{3-10}$ cycloalkylsulfonyl group (e.g., cyclopropylsulfonyl), (15) an optionally substituted $C_{6-14}$ arylsulfonyl group (e.g., phenylsulfonyl), (16) an optionally substituted heterocyclylsulfonyl group (e.g., thienylsulfonyl, pyrazolylsulfonyl, imidazolylsulfonyl, pyridylsulfonyl, dihydrochromenylsulfonyl), (17) an optionally substituted mono- or di-$C_{1-6}$ alkyl-sulfamoyl group (e.g., dimethylsulfamoyl) or (18) an optionally substituted $C_{1-6}$ alkyl-carbonyl-carbonyl group (e.g., methylcarbonylcarbonyl);

$R^2$ is a $C_{3-6}$ cycloalkyl group (e.g., cyclobutyl, cyclopentyl, cyclohexyl) or a 3- to 6-membered saturated monocyclic non-aromatic heterocyclic group (e.g., pyrrolidinyl, piperidinyl, dioxanyl), each of which is optionally substituted by 1 to 3 substituents selected from (1) deuterium, (2) a halogen atom (e.g., fluorine atom), (3) a hydroxy group, (4) an optionally substituted $C_{1-6}$ alkyl group (e.g., methyl, isopropyl), (5) a $C_{3-10}$ cycloalkyl group (e.g., cyclohexyl), (6) an optionally substituted $C_{1-6}$ alkoxy group (e.g., methoxy), (7) an optionally substituted $C_{6-14}$ aryl group (e.g., phenyl), (8) a $C_{6-14}$ aryloxy group (e.g., phenoxy), (9) a tri-$C_{1-6}$ alkylsilyl group (e.g., tert-butyl(dimethyl)silyl) and (10) an optionally substituted 5- to 14-membered aromatic heterocyclic group (e.g., pyrazolyl, thiazolyl, pyridyl, pyrimidinyl, quinazolinyl, benzothiazolyl, isoquinolinyl); and $R^3$ is a $C_{1-6}$ alkyl group (e.g., methyl, ethyl, propyl, isopropyl, isobutyl) optionally substituted by 1 to 3 substituents selected from a halogen atom (e.g., fluorine atom) and a $C_{6-14}$ aryl group (e.g., phenyl), or a mono- or di-$C_{1-6}$ alkylamino group (e.g., ethylamino, dimethylamino).

[Compound I-2]

Compound (I) wherein $R^1$ is (1) a hydrogen atom, (2) a $C_{1-6}$ alkyl-carbonyl group (e.g., methylcarbonyl, ethylcarbonyl, propylcarbonyl, isopropylcarbonyl, isobutylcarbonyl, tert-butylcarbonyl, neopentylcarbonyl) optionally substituted by 1 to 7 substituents selected from a halogen atom (e.g., fluorine atom), a cyano group, a hydroxy group, a $C_{3-10}$ cycloalkyl group (e.g., cyclopropyl), a $C_{1-6}$ alkoxy group (e.g., methoxy), a $C_{6-14}$ aryl group (e.g., phenyl), a $C_{6-14}$ aryloxy group (e.g., phenoxy), a 5- to 14-membered aromatic heterocyclic group (e.g., pyrazolyl, thiazolyl, pyrimidinyl, pyridazinyl) optionally substituted by an oxo group, a 5- to 14-membered aromatic heterocyclyloxy group (e.g., pyrazolyloxy) optionally substituted by 1 to 3 substituents selected from a $C_{1-6}$ alkyl group (e.g., methyl), a $C_{1-6}$ alkyl-carbonyl group (e.g., methylcarbonyl), a $C_{1-6}$ alkoxy-carbonyl group (e.g., methoxycarbonyl), a $C_{1-6}$ alkyl-carbonyloxy group (e.g., methylcarbonyloxy), a $C_{1-6}$ alkylsulfonyl group (e.g., methylsulfonyl), a mono- or di-$C_{1-6}$ alkylamino group (e.g., dimethylamino), a $C_{1-6}$ alkyl-carbonylamino group (e.g., acetylamino) and a ($C_{1-6}$ alkyl) ($C_{1-6}$ alkyl-carbonyl)amino group (e.g., N-acetyl-N-methylamino), (3) a $C_{3-10}$ (preferably $C_{3-6}$) cycloalkyl-carbonyl group (e.g., cyclopropanecarbonyl, cyclobutanecarbonyl, cyclopentanecarbonyl, cyclohexanecarbonyl) optionally substituted by 1 to 3 substituents selected from a halogen atom (e.g., fluorine atom), a cyano group, a hydroxy group, an oxo group and a $C_{1-6}$ alkyl group (e.g., methyl), (4) a $C_{1-6}$ alkoxy-carbonyl group (e.g., methoxycarbonyl, ethoxycarbonyl, isopropoxycarbonyl, tert-butoxycarbonyl) optionally substituted by 1 to 6 substituents selected from deuterium, a halogen atom (e.g., fluorine atom) and a $C_{6-14}$ aryl group (e.g., phenyl), (5) a $C_{3-10}$ cycloalkyloxy-carbonyl group (e.g., cyclopropyloxycarbonyl) optionally substituted by 1 to 3 substituents selected from a $C_{1-6}$ alkyl group (e.g., methyl), (6) a $C_{6-14}$ aryl-carbonyl group (e.g., phenylcarbonyl) optionally substituted by 1 to 3 substituents selected from a halogen atom (e.g., fluorine atom, chlorine atom) and a $C_{6-14}$ aryl group (e.g., phenyl), (7) a $C_{6-14}$ aryloxy-carbonyl group (e.g., phenyloxycarbonyl), (8) a 5- to 14-membered aromatic heterocyclylcarbonyl group (e.g., furylcarbonyl, thienylcarbonyl, pyrazolylcarbonyl, isoxazolylcarbonyl, pyridylcarbonyl) optionally substituted by 1 to 3 substituents selected from a $C_{1-6}$ alkyl group (e.g., methyl), (9) a 3- to 14-membered non-aromatic heterocyclylcarbonyl group (e.g., azetidinylcarbonyl, oxetanylcarbonyl, pyrrolidinylcarbonyl, tetrahydrofuranylcarbonyl, tetrahydropyranylcarbonyl, morpholinylcarbonyl) optionally substituted by 1 to 3 substituents selected from an oxo group, a $C_{1-6}$ alkyl-carbonyl group (e.g., methylcarbonyl), a $C_{1-6}$ alkoxy-carbonyl group (e.g., tert-butoxycarbonyl) and a $C_{1-6}$ alkylsulfonyl group (e.g., methylsulfonyl), (10) a mono- or di-$C_{1-6}$ alkyl-carbamoyl group (e.g., methylcarbamoyl, ethylcarbamoyl, propylcarbamoyl, isopropylcarbamoyl, dimethylcarbamoyl) optionally substituted by 1 to 3 substituents selected from a halogen atom (e.g., fluorine atom), a cyano group, a hydroxy group and a $C_{1-6}$ alkoxy group (e.g., methoxy), (11) a mono- or di-$C_{3-10}$ cycloalkyl-carbamoyl group (e.g., cyclopropylcarbamoyl), (12) a mono- or di-$C_{6-14}$ aryl-carbamoyl group (e.g., phenylcarbamoyl), (13) a $C_{1-6}$ alkylsulfonyl group (e.g., methylsulfonyl), (14) a $C_{3-10}$ cycloalkylsulfonyl group (e.g., cyclopropylsulfonyl), (15) a $C_{6-14}$ arylsulfonyl group (e.g., phenylsulfonyl) optionally substituted by 1 to 3 halogen atoms (e.g., chlorine atom), (16) a heterocyclyl-sulfonyl group (e.g., thienylsulfonyl, pyrazolylsulfonyl, imidazolylsulfonyl, pyridylsulfonyl, dihydrochromenylsulfonyl) optionally substituted by 1 to 3 substituents selected from a $C_{1-6}$ alkyl group (e.g., methyl), (17) a mono- or di-$C_{1-6}$ alkyl-sulfamoyl group (e.g., dimethylsulfamoyl) or (18) a $C_{1-6}$ alkyl-carbonyl-carbonyl group (e.g., methylcarbonylcarbonyl);

$R^2$ is a $C_{3-6}$ cycloalkyl group (e.g., cyclobutyl, cyclopentyl, cyclohexyl) or a 3- to 6-membered saturated monocyclic non-aromatic heterocyclic group (e.g., pyrrolidinyl, piperidinyl, dioxanyl), each of which is optionally substituted by 1 to 3 substituents selected from (1) deuterium, (2) a halogen atom (e.g., fluorine atom), (3) a hydroxy group, (4) a $C_{1-6}$ alkyl group (e.g., methyl, isopropyl) optionally substituted by 1 to 3 substituents selected from a halogen atom (e.g., fluorine atom) and a $C_{6-14}$ aryl group (e.g., phenyl), (5) a $C_{3-10}$ cycloalkyl group (e.g., cyclohexyl), (6) a $C_{1-6}$ alkoxy group (e.g., methoxy) optionally substituted by a $C_{3-10}$ cycloalkyl group (e.g., cyclopropyl), (7) a $C_{6-14}$ aryl group (e.g., phenyl) optionally substituted by 1 to 3 substituents selected from a halogen atom (e.g., fluorine atom, chlorine atom), a cyano group, a $C_{1-6}$ alkyl group (e.g., methyl, ethyl)

optionally substituted by 1 to 3 halogen atoms (e.g., fluorine atom) and a $C_{1-6}$ alkoxy group (e.g., methoxy) optionally substituted by 1 to 3 halogen atoms (e.g., fluorine atom), (8) a $C_{6-14}$ aryloxy group (e.g., phenoxy), (9) a tri-$C_{1-6}$ alkylsilyl group (e.g., tert-butyl(dimethyl)silyl) and (10) a 5- to 14-membered aromatic heterocyclic group (e.g., pyrazolyl, thiazolyl, pyridyl, pyrimidinyl, quinazolinyl, benzothiazolyl, isoquinolinyl) optionally substituted by 1 to 3 substituents selected from a halogen atom (e.g., fluorine atom, chlorine atom), $C_{1-6}$ alkyl group (e.g., methyl) and a $C_{1-6}$ alkoxy group (e.g., methoxy); and $R^3$ is a $C_{1-6}$ alkyl group (e.g., methyl), or a mono- or di-$C_{1-6}$ alkylamino group (e.g., dimethylamino).

[Compound I-3]

Compound (I), wherein $R^1$ is (1) a $C_{1-6}$ alkyl-carbonyl group (e.g., methylcarbonyl) optionally substituted by a hydroxy group, (2) a $C_{3-6}$ cycloalkyl-carbonyl group (e.g., cyclopropanecarbonyl), (3) a $C_{1-6}$ alkoxy-carbonyl group (e.g., methoxycarbonyl, isopropoxycarbonyl) or (4) a mono- or di-$C_{1-6}$ alkyl-carbamoyl group (e.g., ethylcarbamoyl);

$R^2$ is (A) a $C_{3-6}$ cycloalkyl group (e.g., cyclohexyl) optionally substituted by 1 to 3 substituents selected from (1) a $C_{1-6}$ alkyl group (e.g., isopropyl) and (2) a $C_{6-14}$ aryl group (e.g., phenyl) optionally substituted by 1 to 3 substituents selected from a halogen atom (e.g., fluorine atom), a $C_{1-6}$ alkyl group (e.g., methyl) optionally substituted by 1 to 3 halogen atoms (e.g., fluorine atom) and a $C_{1-6}$ alkoxy group (e.g., methoxy) or (B) a 3- to 6-membered saturated monocyclic non-aromatic heterocyclic group (e.g., piperidinyl) optionally substituted by 1 to 3 substituents selected from a 5- to 14-membered aromatic heterocyclic group (e.g., pyrimidinyl); and $R^3$ is a $C_{1-6}$ alkyl group (e.g., methyl) or a di-$C_{1-6}$ alkylamino group (e.g., dimethylamino).

[Compound I-4]

Compound (I), which is the compound of [7] mentioned above.

[Compound I-5]

Compound (I), wherein $R^1$ is (1) a hydrogen atom, (2) a $C_{1-6}$ alkyl-carbonyl group optionally substituted by 1 to 7 substituents selected from (i) a halogen atom, (ii) a cyano group, (iii) a hydroxy group, (iv) a $C_{3-10}$ cycloalkyl group, (v) a $C_{1-6}$ alkoxy group, (vi) a $C_{6-14}$ aryl group, (vii) a $C_{6-14}$ aryloxy group, (viii) a 5- to 14-membered aromatic heterocyclic group optionally substituted by an oxo group, (ix) a 5- to 14-membered aromatic heterocyclyloxy group optionally substituted by 1 to 3 $C_{1-6}$ alkyl groups, (x) a $C_{1-6}$ alkyl-carbonyl group, (xi) a $C_{1-6}$ alkoxy-carbonyl group, (xii) a $C_{1-6}$ alkyl-carbonyloxy group, (xiii) a $C_{1-6}$ alkylsulfonyl group, (xiv) a mono- or di-$C_{1-6}$ alkylamino group, (xv) a $C_{1-6}$ alkyl-carbonylamino group and (xvi) a ($C_{1-6}$ alkyl)($C_{1-6}$ alkyl-carbonyl)amino group, (3) a $C_{3-10}$ cycloalkyl-carbonyl group optionally substituted by 1 to 3 substituents selected from a halogen atom, a cyano group, a hydroxy group, an oxo group and a $C_{1-6}$ alkyl group, (4) a $C_{1-6}$ alkoxy-carbonyl group optionally substituted by 1 to 6 substituents selected from deuterium, a halogen atom and a $C_{6-14}$ aryl group, (5) a $C_{3-10}$ cycloalkyloxy-carbonyl group optionally substituted by 1 to 3 substituents selected from a $C_{1-6}$ alkyl group, (6) a $C_{6-14}$ aryl-carbonyl group optionally substituted by 1 to 3 substituents selected from a halogen atom and a $C_{6-14}$ aryl group, (7) a $C_{6-14}$ aryloxy-carbonyl group, (8) a 5- to 14-membered aromatic heterocyclylcarbonyl group optionally substituted by 1 to 3 substituents selected from a $C_{1-6}$ alkyl group, (9) a 3- to 14-membered non-aromatic heterocyclylcarbonyl group optionally substituted by 1 to 3 substituents selected from an oxo group, a $C_{1-6}$ alkyl-carbonyl group, a $C_{1-6}$ alkoxy-carbonyl group and a $C_{1-6}$ alkylsulfonyl group,

(10) a mono- or di-$C_{1-6}$ alkyl-carbamoyl group optionally substituted by 1 to 3 substituents selected from a halogen atom, a cyano group, a hydroxy group and a $C_{1-6}$ alkoxy group,

(11) a mono- or di-$C_{3-10}$ cycloalkyl-carbamoyl group,

(12) a mono- or di-$C_{6-14}$ aryl-carbamoyl group,

(13) a $C_{1-6}$ alkylsulfonyl group,

(14) a $C_{3-10}$ cycloalkylsulfonyl group,

(15) a $C_{6-14}$ arylsulfonyl group optionally substituted by 1 to 3 halogen atoms,

(16) a heterocyclyl-sulfonyl group optionally substituted by 1 to 3 substituents selected from a $C_{1-6}$ alkyl group,

(17) a mono- or di-$C_{1-6}$ alkyl-sulfamoyl group or

(18) a $C_{1-6}$ alkyl-carbonyl-carbonyl group;

$R^2$ is a $C_{3-6}$ cycloalkyl group or a 3- to 6-membered saturated monocyclic non-aromatic heterocyclic group, each of which is optionally substituted by 1 to 3 substituents selected from (1) deuterium, (2) a halogen atom, (3) a hydroxy group, (4) a $C_{1-6}$ alkyl group optionally substituted by 1 to 3 substituents selected from a halogen atom and a $C_{6-14}$ aryl group, (5) a $C_{3-10}$ cycloalkyl group, (6) a $C_{1-6}$ alkoxy group optionally substituted by a $C_{3-10}$ cycloalkyl group, (7) a $C_{6-14}$ aryl group optionally substituted by 1 to 3 substituents selected from a halogen atom, a cyano group, a $C_{1-6}$ alkyl group optionally substituted by 1 to 3 halogen atoms, a $C_{1-6}$ alkoxy group optionally substituted by 1 to 3 halogen atoms and a hydroxy group, (8) a $C_{6-14}$ aryloxy group, (9) a tri-$C_{1-6}$ alkylsilyloxy group,

(10) a 5- to 14-membered aromatic heterocyclic group optionally substituted by 1 to 3 substituents selected from a halogen atom, a $C_{1-6}$ alkyl group and a $C_{1-6}$ alkoxy group and

(11) a $C_{6-14}$ aryl-carbonyl group; and $R^3$ is a $C_{1-6}$ alkyl group, or a mono- or di-$C_{1-6}$ alkylamino group.

[Compound I-6]

Compound (I), which is the compound of [8] mentioned above.

[Compound I-7]

Compound (I), wherein $R^1$ is (1) a hydrogen atom, (2) a $C_{1-6}$ alkyl-carbonyl group optionally substituted by 1 to 7 substituents selected from (i) a halogen atom, (ii) a cyano group, (iii) a hydroxy group, (iv) a cyclopropyl group, (v) a $C_{1-6}$ alkoxy group, (vi) a phenyl group, (vii) a phenoxy group, (viii) a pyrazolyl group, a thiazolyl group, a pyrimidinyl group or a pyridazinyl group, each of which is optionally substituted by an oxo group, (ix) a pyrazolyloxy group optionally substituted by 1 to 3 substituents selected from a $C_{1-6}$ alkyl group, (x) a $C_{1-6}$ alkyl-carbonyl group, (xi) a $C_{1-6}$ alkoxy-carbonyl group, (xii) a $C_{1-6}$ alkyl-carbonyloxy group, (xiii) a $C_{1-6}$ alkylsulfonyl group, (xiv) a mono- or di-$C_{1-6}$ alkylamino group, (xv) a $C_{1-6}$ alkyl-carbonylamino group and (xvi) a ($C_{1-6}$ alkyl) ($C_{1-6}$ alkyl-carbonyl)amino group, (3) a cyclopropanecarbonyl group, a cyclobutanecarbonyl group, a cyclopentanecarbonyl group or a cyclohexanecarbonyl group, each of which is optionally substituted by 1 to 3 substituents selected from a halogen atom, a cyano group, a hydroxy group, an oxo group and a $C_{1-6}$ alkyl group,
(4) a $C_{1-6}$ alkoxy-carbonyl group optionally substituted by 1 to 6 substituents selected from deuterium, a halogen atom and a phenyl group,
(5) a cyclopropyloxycarbonyl group optionally substituted by 1 to 3 substituents selected from a $C_{1-6}$ alkyl group,
(6) a phenylcarbonyl group optionally substituted by 1 to 3 substituents selected from a halogen atom and a phenyl group,
(7) a phenyloxycarbonyl group,
(8) a furylcarbonyl group, a thienylcarbonyl group, a pyrazolylcarbonyl group, an isoxazolylcarbonyl group or a pyridylcarbonyl group, each of which is optionally substituted by 1 to 3 $C_{1-6}$ alkyl groups,
(9) an azetidinylcarbonyl group, an oxetanylcarbonyl group, a pyrrolidinylcarbonyl group, a tetrahydrofuranylcarbonyl group, a tetrahydropyranylcarbonyl group or a morpholinylcarbonyl group, each of which is optionally substituted by 1 to 3 substituents selected from an oxo group, a $C_{1-6}$ alkyl-carbonyl group, a $C_{1-6}$ alkoxy-carbonyl group and a $C_{1-6}$ alkylsulfonyl group,
(10) a mono- or di-$C_{1-6}$ alkyl-carbamoyl group optionally substituted by 1 to 3 substituents selected from a halogen atom, a cyano group, a hydroxy group and a $C_{1-6}$ alkoxy group,
(11) a cyclopropylcarbamoyl group,
(12) a phenylcarbamoyl group,
(13) a $C_{1-6}$ alkylsulfonyl group,
(14) a cyclopropylsulfonyl group,
(15) a phenylsulfonyl group optionally substituted by 1 to 3 halogen atoms,
(16) a thienylsulfonyl group, a pyrazolylsulfonyl group, an imidazolylsulfonyl group, a pyridylsulfonyl group or a dihydrochromenylsulfonyl group, each of which is optionally substituted by 1 to 3 $C_{1-6}$ alkyl groups,
(17) a dimethylsulfamoyl group or
(18) a $C_{1-6}$ alkyl-carbonyl-carbonyl group;
$R^2$ is a cyclobutyl group, a cyclopentyl group, a cyclohexyl group, a pyrrolidinyl group, a piperidinyl group or a dioxanyl group, each of which is optionally substituted by 1 to 3 substituents selected from
(1) deuterium,
(2) a halogen atom,
(3) a hydroxy group,
(4) a $C_{1-6}$ alkyl group optionally substituted by 1 to 3 substituents selected from a halogen atom and a phenyl group,
(5) a cyclohexyl group,
(6) a $C_{1-6}$ alkoxy group optionally substituted by a cyclopropyl group,
(7) a phenyl group optionally substituted by 1 to 3 substituents selected from a halogen atom, a cyano group, a $C_{1-6}$ alkyl group optionally substituted by 1 to 3 halogen atoms, a $C_{1-6}$ alkoxy group optionally substituted by 1 to 3 halogen atoms and a hydroxy group,
(8) a phenoxy group,
(9) a tri-$C_{1-6}$ alkylsilyloxy group,
(10) a pyrazolyl group, a thiazolyl group, a pyridyl group, a pyrimidinyl group, a quinazolinyl group, a benzothiazolyl group or an isoquinolinyl group, each of which is optionally substituted by 1 to 3 substituents selected from a halogen atom, a $C_{1-6}$ alkyl group and a $C_{1-6}$ alkoxy group, and
(11) a benzoyl group; and
$R^3$ is a $C_{1-6}$ alkyl group, or a mono- or di-$C_{1-6}$ alkylamino group.
[Compound I-8]
Compound (I), which is the compound of [9] mentioned above.
[Compound I-9]
Compound (I), which is the compound of [10] mentioned above.
[Compound I-10]
Compound (I), wherein $R^1$ is a $C_{1-6}$ alkoxy-carbonyl group;
$R^2$ is a cyclohexyl group optionally substituted by a phenyl group; and
$R^3$ is a $C_{1-6}$ alkyl group.
[Compound I-11]
Compound (I), wherein $R^1$ is a $C_{1-6}$ alkyl-carbonyl group optionally substituted by a hydroxy group;
$R^2$ is a cyclohexyl group optionally substituted by a phenyl group optionally substituted by 1 to 3 halogen atoms; and
$R^3$ is a $C_{1-6}$ alkyl group.
[Compound I-12]
Compound (I), wherein $R^1$ is a mono- or di-$C_{1-6}$ alkyl-carbamoyl group;
$R^2$ is a cyclohexyl group optionally substituted by a $C_{1-6}$ alkyl group; and
$R^3$ is a $C_{1-6}$ alkyl group.
Specific examples of compound (I) include the compounds of the below-mentioned Examples 1-372, of which
(2R,3S)—N-ethyl-2-(((cis-4-isopropylcyclohexyl)oxy)methyl)-3-((methylsulfonyl)amino)piperidine-1-carboxamide (Example 2),
N-((2R,3S)-1-acetyl-2-(((cis-4-phenylcyclohexyl)oxy)methyl)piperidin-3-yl)methanesulfonamide (Example 4),
methyl (2R,3S)-3-((methylsulfonyl)amino)-2-(((cis-4-phenylcyclohexyl)oxy)methyl)piperidine-1-carboxylate (Example 5),
N-((2R,3S)-1-acetyl-2-(((cis-4-(3,5-difluorophenyl)cyclohexyl)oxy)methyl)piperidin-3-yl)methanesulfonamide (Example 8),
methyl (2R,3S)-2-(((cis-4-(2,5-difluorophenyl)cyclohexyl)oxy)methyl)-3-((methylsulfonyl)amino)piperidine-1-carboxylate (Example 11),
N-((2R,3S)-1-acetyl-2-(((cis-4-(2,6-difluorophenyl)cyclohexyl)oxy)methyl)piperidin-3-yl)methanesulfonamide (Example 14),
N-((2R,3S)-1-(cyclopropylcarbonyl)-2-(((cis-4-(3-fluorophenyl)cyclohexyl)oxy)methyl)piperidin-3-yl)methanesulfonamide (Example 16),
N-((2R,3S)-1-acetyl-2-(((cis-4-(2,3-difluorophenyl)cyclohexyl)oxy)methyl)piperidin-3-yl)methanesulfonamide (Example 19),
methyl (2R,3S)-2-(((cis-4-(2,3-difluorophenyl)cyclohexyl)oxy)methyl)-3-((methylsulfonyl)amino)piperidine-1-carboxylate (Example 20),
N-((2R,3S)-1-acetyl-2-(((cis-4-(2,3,6-trifluorophenyl)cyclohexyl)oxy)methyl)piperidin-3-yl)methanesulfonamide (Example 22),
N-((2R,3S)-1-acetyl-2-(((cis-4-(2-(trifluoromethyl)phenyl)cyclohexyl)oxy)methyl)piperidin-3-yl)methanesulfonamide (Example 24),
N-((2R,3S)-2-(((cis-4-(2,3-difluorophenyl)cyclohexyl)oxy)methyl)-1-glycoloylpiperidin-3-yl)methanesulfonamide (Example 25), N-((2R,3S)-1-(cyclopropylcarbonyl)-2-(((cis-4-(2-methoxyphenyl)cyclohexyl)oxy)methyl)piperidin-3-yl)methanesulfonamide (Example 28), isopropyl (2R,3S)-3-((dimethylsulfamoyl)amino)-2-(((1-(pyrimidin-2-yl)piperidin-4-yl)oxy)methyl)piperidine-1-carboxylate (Example 29), (2R,3S)—N-ethyl-3-((methylsulfonyl)amino)-2-(((cis-4-phenylcyclohexyl)oxy)methyl)piperidine-1-carboxamide (Example 30), N-((2R,3S)-1-(cyclopropylcarbonyl)-2-(((cis-4-phenylcyclohexyl)oxy)methyl)piperidin-3-yl)methanesulfonamide (Example 31), methyl (2R,3S)-3-((methylsulfonyl)amino)-2-(((cis-4-(2-(trifluoromethyl)phenyl)cyclohexyl)oxy)methyl)piperidine-1-carboxylate (Example 32), N-((2R,3S)-2-(((cis-4-(3,5-difluorophenyl)cyclohexyl)oxy)methyl)piperidin-3-yl)methanesulfonamide (Example 7), N-((2R,3S)-2-(((cis-4-(2,6-difluorophenyl)cyclohexyl)oxy)methyl)piperidin-3-yl)methanesulfonamide (Example 13), N-(2-(((cis-4-(3-fluorophenyl)cyclohexyl)oxy)methyl)pyridin-3-yl)methanesulfonamide (Example 15), and N-((2R,3S)-1-glycoloyl-2-(((cis-4-(2,3,6-trifluorophenyl)cyclohexyl)oxy)methyl)piperidin-3-yl)methanesulfonamide (Example 340) are preferable.

As a salt of a compound represented by the formula (I), a pharmacologically acceptable salt is preferable, and examples of such salt include a salt with inorganic base, a salt with organic base, a salt with inorganic acid, a salt with organic acid, a salt with basic or acidic amino acid and the like.

Preferable examples of the salt with inorganic base include alkali metal salts such as sodium salt, potassium salt and the like, alkaline earth metal salts such as calcium salt, magnesium salt and the like, aluminum salt, ammonium salt and the like.

Preferable examples of the salt with organic base include salts with trimethylamine, triethylamine, pyridine, picoline, ethanolamine, diethanolamine, triethanolamine, tromethamine[tris(hydroxymethyl)methylamine], tert-butylamine, cyclohexylamine, benzylamine, dicyclohexylamine, N,N-dibenzylethylenediamine and the like.

Preferable examples of the salt with inorganic acid include salts with hydrochloric acid, hydrobromic acid, nitric acid, sulfuric acid, phosphoric acid and the like.

Preferable examples of the salt with organic acid include salts with formic acid, acetic acid, trifluoroacetic acid, phthalic acid, fumaric acid, oxalic acid, tartaric acid, maleic acid, citric acid, succinic acid, malic acid, methanesulfonic acid, benzenesulfonic acid, p-toluenesulfonic acid and the like.

Preferable examples of the salt with basic amino acid include salts with arginine, lysine, ornithine and the like.

Preferable examples of the salt with acidic amino acid include salts with aspartic acid, glutamic acid and the like.

Compound (I) may be used as a prodrug. A prodrug of the compound (I) means a compound which is converted to the compound (I) of the present invention with a reaction due to an enzyme, an gastric acid, etc. under the physiological condition in the living body, that is, a compound which is converted to the compound (I) of the present invention with oxidation, reduction, hydrolysis, etc. according to an enzyme; a compound which is converted to the compound (I) of the present invention by hydrolysis etc. due to gastric acid, etc.

A prodrug of compound (I) may be a compound obtained by subjecting an amino group in compound (I) to an acylation, alkylation or phosphorylation (e.g., a compound obtained by subjecting an amino group in compound (I) to an eicosanoylation, alanylation, pentylaminocarbonylation, (5-methyl-2-oxo-1,3-dioxolen-4-yl)methoxycarbonylation, tetrahydrofuranylation, pyrrolidylmethylation, pivaloyloxymethylation and tert-butylation, etc.); a compound obtained by subjecting a hydroxy group in compound (I) to an acylation, alkylation, phosphorylation or boration (e.g., a compound obtained by subjecting an hydroxy group in compound (I) to an acetylation, palmitoylation, propanoylation, pivaloylation, succinylation, fumarylation, alanylation, dimethylaminomethylcarbonylation, etc.); a compound obtained by subjecting a carboxyl group in compound (I) to an esterification or amidation (e.g., a compound obtained by subjecting a carboxyl group in compound (I) to an ethyl esterification, phenyl esterification, carboxymethyl esterification, dimethylaminomethyl esterification, pivaloyloxymethyl esterification, ethoxycarbonyloxyethyl esterification, phthalidyl esterification, (5-methyl-2-oxo-1,3-dioxolen-4-yl)methyl esterification, cyclohexyloxycarbonylethyl esterification and methylamidation, etc.) and the like. Any of these compounds can be produced from compound (I) by a method known per se.

A prodrug for compound (I) may also be one which is converted into compound (I) under a physiological condition, such as those described in *IYAKUHIN no KAIHATSU* (Development of Pharmaceuticals), Vol. 7, Design of Molecules, p.163-198, Published by HIROKAWA SHOTEN (1990).

In the present specification, a prodrug may form a salt, and as such salt, those exemplified as a salt of the compound represented by the aforementioned formula (I) can be mentioned.

Compound (I) may be labeled with an isotope (e.g., $^3$H, $^{13}$C, $^{14}$C, $^{18}$F, $^{35}$S, $^{125}$I) and the like.

Compound (I) labeled with or substituted by an isotope can be used, for example, as a tracer used for Positron Emission Tomography (PET) (PET tracer), and is useful in the field of medical diagnosis and the like.

Furthermore, compound (I) may be a hydrate or a non-hydrate, or a non-solvate (e.g., anhydride), or a solvate (e.g., hydrate).

Compound (I) also encompasses a deuterium conversion form wherein $^1$H is converted to $^2$H(D).

Furthermore, compound (I) may be a pharmaceutically acceptable cocrystal or cocrystal salt. The cocrystal or cocrystal salt means a crystalline substance constituted with two or more special solids at room temperature, each having different physical properties (e.g., structure, melting point, melting heat, hygroscopicity, solubility and stability). The cocrystal or cocrystal salt can be produced by a cocrystallization method known per se.

Compound (I) or a prodrug thereof (hereinafter sometimes to be simply abbreviated as the compound of the present invention) is low in its toxicity and can be used as it is or in the form of a pharmaceutical composition (also referred to as a medicament) by mixing with a pharmacologically acceptable carrier etc. to mammals (e.g., human, mouse, rat, rabbit, dog, cat, bovine, horse, swine, monkey) as an agent for the prophylaxis or treatment of various diseases mentioned below.

As pharmacologically acceptable carriers, various organic or inorganic carrier substances conventionally used as preparation materials can be used. These are incorporated as excipient, lubricant, binder and disintegrant for solid preparations; or solvent, solubilizing agent, suspending agent, isotonicity agent, buffer and soothing agent for liquid preparations; and the like; and preparation additives such as preservative, antioxidant, colorant, sweetening agent and the like can be added as necessary.

Preferable examples of the excipient include lactose, sucrose, D-mannitol, D-sorbitol, starch, gelatinated starch, dextrin, crystalline cellulose, low-substituted hydroxypropylcellulose, sodium carboxymethylcellulose, gum arabic, pullulan, light anhydrous silicic acid, synthetic aluminum silicate and magnesium alumino metasilicate.

Preferable examples of the lubricant include magnesium stearate, calcium stearate, talc and colloidal silica.

Preferable examples of the binder include gelatinated starch, sucrose, gelatin, gum arabic, methylcellulose, carboxymethylcellulose, sodium carboxymethylcellulose, crystalline cellulose, sucrose, D-mannitol, trehalose, dextrin, pullulan, hydroxypropylcellulose, hydroxypropylmethylcellulose and polyvinylpyrrolidone.

Preferable examples of the disintegrant include lactose, sucrose, starch, carboxymethylcellulose, calcium carboxymethylcellulose, croscarmellose sodium, sodium carboxymethyl starch, light anhydrous silicic acid and low-substituted hydroxypropylcellulose.

Preferable examples of the solvent include water for injection, physiological brine, Ringer's solution, alcohol, propylene glycol, polyethylene glycol, sesame oil, corn oil, olive oil and cottonseed oil.

Preferable examples of the solubilizing agent include polyethylene glycol, propylene glycol, D-mannitol, trehalose, benzyl benzoate, ethanol, trisaminomethane, cholesterol, triethanolamine, sodium carbonate, sodium citrate, sodium salicylate and sodium acetate.

Preferable examples of the suspending agent include surfactants such as stearyltriethanolamine, sodium lauryl sulfate, lauryl aminopropionate, lecithin, benzalkonium chloride, benzethonium chloride, glycerol monostearate and the like; hydrophilic polymers such as poly(vinyl alcohol), polyvinylpyrrolidone, carboxymethylcellulose sodium, methylcellulose, hydroxymethylcellulose, hydroxyethylcellulose, hydroxypropylcellulose and the like, polysorbates; and polyoxyethylene hydrogenated castor oil.

Preferable examples of the isotonicity agent include sodium chloride, glycerol, D-mannitol, D-sorbitol and glucose.

Preferable examples of the buffer include buffers of phosphate, acetate, carbonate, citrate etc.

Preferable examples of the soothing agent include benzyl alcohol.

Preferable examples of the preservative include p-oxybenzoate esters, chlorobutanol, benzyl alcohol, phenethyl alcohol, dehydroacetic acid and sorbic acid.

Preferable examples of the antioxidant include sulfite salts and ascorbate salts.

Preferable examples of the colorant include aqueous food tar colors (e.g., food colors such as Food Color Red Nos. 2 and 3, Food Color Yellow Nos. 4 and 5, Food Color Blue Nos. 1 and 2 and the like food colors), water insoluble lake dyes (e.g., aluminum salt of the aforementioned aqueous food tar color), natural dyes (e.g., β-carotene, chlorophyll, red iron oxide) and the like.

Preferable examples of the sweetening agent include saccharin sodium, dipotassium glycyrrhizinate, aspartame and stevia.

Examples of the dosage form of the aforementioned pharmaceutical composition include oral preparations such as tablet (including sugar-coated tablet, film-coated tablet, sublingual tablet, orally disintegrating tablet), capsule (including soft capsule, microcapsule), granule, powder, troche, syrup, emulsion, suspension, films (e.g., orally disintegrable films) and the like; and parenteral agents such as injection (e.g., subcutaneous injection, intravenous injection, intramuscular injection, intraperitoneal injection, drip infusion), external preparation (e.g., dermal preparation, ointment), suppository (e.g., rectal suppository, vaginal suppository), pellet, nasal preparation, pulmonary preparation (inhalant), eye drop and the like, which can be respectively safely administered orally or parenterally (e.g., topical, rectal, intravenous administration).

These preparations may be a release control preparation (e.g., sustained-release microcapsule) such as an immediate-release preparation, a sustained-release preparation and the like.

The pharmaceutical composition can be produced according to a method conventionally used in the field of pharmaceutical the formulation, for example, the method described in the Japanese Pharmacopoeia, and the like.

While the content of the compound of the present invention in the pharmaceutical composition of the present invention varies depending on the dosage form, dose of the compound of the present invention and the like, it is, for example, about 0.1 to 100 wt %.

When an oral preparation is produced, coating may be applied where necessary for the purpose of taste masking, enteric solubility or sustainability.

Examples of the coating base used for coating include sugar coating base, water-soluble film coating base, enteric film coating base, and sustained-release film coating base.

As the sugar coating base, sucrose is used, and one or more kinds selected from talc, precipitated calcium carbonate, gelatin, gum arabic, pullulan, carnauba wax and the like may be further used in combination.

Examples of the water-soluble film coating base include cellulose polymers such as hydroxypropylcellulose, hydroxypropylmethylcellulose, hydroxyethylcellulose, methylhydroxyethylcellulose and the like; synthetic polymers such as polyvinyl acetal diethylaminoacetate, aminoalkylmethacrylate copolymer E [Eudragit E (trade name)], polyvinylpyrrolidone and the like; and polysaccharides such as pullulan and the like.

Examples of the enteric film coating base include cellulose polymers such as hydroxypropylmethylcellulose phthalate, hydroxypropylmethylcellulose acetate succinate, carboxymethylethylcellulose, cellulose acetate phthalate and the like; acrylic acid polymers such as methacrylic acid copolymer L [Eudragit L (trade name)], methacrylic acid copolymer LD [Eudragit L-30D-55 (trade name)], methacrylic acid copolymer S [Eudragit S (trade name)] and the like; and naturally-occurring substances such as shellac and the like.

Examples of the sustained-release film coating base include cellulose polymers such as ethylcellulose and the like; and acrylic acid polymers such as aminoalkylmethacrylate copolymer RS [Eudragit RS (trade name)], ethyl acrylate-methyl methacrylate copolymer suspension [Eudragit NE (trade name)] and the like.

Two or more kinds of the above-mentioned coating bases may be used in a mixture at an appropriate ratio. In addition, for example, light shielding agents such as titanium oxide, red ferric oxide and the like may also be used during coating.

Since the compound of the present invention shows low toxicity (e.g., acute toxicity, chronic toxicity, genetic toxicity, reproductive toxicity, cardiotoxicity, carcinogenicity) and less side effects, it can be used as a prophylactic or therapeutic agent, or diagnostic agent for various diseases in mammals (e.g., human, bovine, horse, dog, cat, monkey, mouse, rat).

Orexin type 2 receptors have been considered to be involved in a wide range of biological functions. This suggests that this receptor plays a role in diverse disease processes in humans or other species. The compound of the present invention is useful for treating, preventing, or ameliorating the risk of one or more of the following symptoms or diseases of various neurological and psychiatric diseases associated with one or more orexin type 2 receptors. That is, narcolepsy, idiopathic hypersomnia, hypersomnia, sleep apnea syndrome, narcolepsy syndrome accompanied by narcolepsy-like symptoms, hypersomnia syndrome accompanied by daytime hypersomnia (e.g., Kleine Levin syndrome, major depression with hypersomnia, Lewy body dementia, Parkinson's disease, progressive supranuclear paralysis, Prader-Willi syndrome, Mobius syndrome, hypoventilation syndrome, Niemann-Pick disease type C, brain contusion, cerebral infarction, brain tumor, muscular dystrophy, multiple sclerosis, acute disseminated encephalomyelitis, Guillain-Barre syndrome, Rasmussen's encephalitis, Wernicke's encephalitis, limbic encephalitis, Hashimoto's encephalopathy), coma, loss of consciousness, obesity (e.g., malignant mastocytosis, exogenous obesity, hyperinsulinar obesity, hyperplasmic obesity, hypop hyseal adiposity, hypoplasmic obesity, hypothyroid obesity, hypothalamic obesity, symptomatic obesity, infantile obesity, upper body obesity, alimentary obesity, hypogonadal obesity, systemic mastocytosis, simple obesity, central obesity), insulin resistance syndrome, Alzheimer, disturbance of consciousness such as coma and the like, side effects and complications due to anesthesia, sleep disturbance, sleep problem, insomnia, Intermittent sleep, nocturnal myoclonus, REM sleep interruption, jet lag, jet lag syndrome, sleep disorder of alternating worker, sleep disorder, night terror, depression, major depression, sleepwalking disease, enuresis, sleep disorder, Alzheimer's dusk, diseases associated with circadian rhythm, fibromyalgia, condition arising from decline in the quality of sleep, overeating, obsessive compulsive eating disorder, obesity-related disease, hypertension, diabetes, elevated plasma insulin concentration and insulin resistance, hyperlipidemia, hyperlipemia, endometrial cancer, breast cancer, prostate cancer, colorectal cancer, cancer, osteoarthritis, obstructive sleep apnea, cholelithiasis, gallstones, cardiac disease, abnormal heartbeat, arrhythmia, myocardial infarction, congestive cardiac failure, cardiac failure, coronary heart disease, cardiovascular disorder, sudden death, polycysticovarian disease, craniopharingioma, Prader-Willi syndrome, Froelich's syndrome, growth hormone deficient, normal mutant short stature, Turner's syndrome, children suffering from acute lymphoblastic leukemia, syndrome X, reproductive hormone abnormality, declining fertility, infertility, male gonadal function decline, sexual and reproductive dysfunction such as female male hirsutism, fetal defects associated with pregnant women obesity, gastrointestinal motility disorders such as obesity-related gastroesophageal reflux, obesity hypoventilation syndrome (Pickwick syndrome), respiratory diseases such as dyspnea, inflammation such as systemic inflammation of the vascular system, arteriosclerosis, hypercholesterolemia, hyperuricemia, lower back pain, gall bladder disease, gout, kidney cancer, risk of secondary outcomes of obesity, such as lowering the risk of left ventricular hypertrophy, migraine pain, headache, neuropathic pain, Parkinson's disease, psychosis, schizophrenia, facial flushing, night sweats, diseases of the genital/urinary system, diseases related to sexual function or fertility, dysthymic disorder, bipolar disorder, bipolar I disorder, bipolar II disorder, cyclothymic disorder, acute stress disorder, agoraphobia, generalized anxiety disorder, obsessive disorder, panic attack, panic disorder, posttraumatic stress disorder, separation anxiety disorder, social phobia, anxiety disorder, acute neurological and psychiatric disorders such as cardiac bypass surgery and post-transplant cerebral deficit, stroke, ischemic stroke, cerebral ischemia, spinal cord trauma, head trauma, perinatal hypoxia, cardiac arrest, hypoglycemic nerve injury, Huntington's chorea, amyotrophic lateral sclerosis, multiple sclerosis, eye damage, retinopathy, cognitive impairment, muscle spasm, tremor, epilepsy, disorders associated with muscle spasticity, delirium, amnestic disorder, age-related cognitive decline, schizoaffective disorder, delusional disorder, drug addiction, dyskinesia, chronic fatigue syndrome, fatigue, medication-induced Parkinsonism syndrome, Jill-do La Tourette's syndrome, chorea, myoclonus, tic, restless legs syndrome, dystonia, dyskinesia, attention deficit hyperactivity disorder (ADHD), behavior disorder, urinary incontinence, withdrawal symptoms, trigeminal neuralgia, hearing loss, tinnitus, nerve damage, retinopathy, macular degeneration, vomiting, cerebral edema, pain, bone pain, arthralgia, toothache, cataplexy, and traumatic brain injury (TBI).

Particularly, the compound of the present invention is useful as a therapeutic or prophylactic drug for narcolepsy, idiopathic hypersomnia, hypersomnia, sleep apnea syndrome, narcolepsy syndrome accompanied by narcolepsy-like symptoms, hypersomnia syndrome accompanied by daytime hypersomnia (e.g., Parkinson's disease, Guillain-Barre syndrome and Kleine Levin syndrome), Alzheimer, obesity, insulin resistance syndrome, cardiac failure, diseases related to bone loss, sepsis, disturbance of consciousness such as coma and the like, side effects and complications due to anesthesia, and the like, or anesthetic antagonist.

While the dose of the compound of the present invention varies depending on the subject of administration, administration route, target disease, symptom and the like, for example, when the compound of the present invention is administered orally or parenterally to an adult patient, its dose is for example, about 0.01 to 100 mg/kg body weight per dose, preferably 0.1 to 50 mg/kg body weight per dose and more preferably 0.5 to 20 mg/kg body weight per dose. This amount is desirably administered in one to 3 portions daily.

The compound of the present invention can be used in combination with other drugs (hereinafter to be abbreviated as concomitant drug).

By combining the compound of the present invention and a concomitant drug, a superior effect, for example, (1) the dose can be reduced as compared to single administration of the compound of the present invention or a concomitant drug, (2) the drug to be combined with the compound of the present invention can be selected according to the condition of patients (mild case, severe case and the like), (3) the period of treatment can be set longer by selecting a concomitant drug having different action and mechanism from the compound of the present invention, (4) a sustained treatment effect can be designed by selecting a concomitant drug having different action and mechanism from the compound of the present invention, (5) a synergistic effect can be afforded by a combined use of the compound of the present invention and a concomitant drug, and the like, can be achieved.

In the present specification, the compound of the present invention and a concomitant drug used in combination are referred to as the "combination agent of the present invention".

When using the combination agent of the present invention, the administration time of the compound of the present invention and the concomitant drug is not restricted, and the compound of the present invention or a pharmaceutical composition thereof, or the concomitant drug or a pharmaceutical composition thereof can be administered to an administration subject simultaneously, or may be administered at different times. The dosage of the concomitant drug may be determined according to the dose clinically used, and can be appropriately selected depending on an administration subject, administration route, disease, combination and the like.

The administration mode of the combination agent of the present invention and the concomitant drug is not particularly limited, and the compound of the present invention and the concomitant drug only need to be combined on administration. Examples of such administration mode include the following: (1) administration of a single preparation obtained by simultaneously processing the compound of the present invention and the concomitant drug, (2) simultaneous administration of two kinds of preparations of the compound of the present invention and the concomitant drug, which have been separately produced, by the same administration route, (3) administration of two kinds of preparations of the compound of the present invention and the concomitant drug, which have been separately produced, by the same administration route in a staggered manner, (4) simultaneous administration of two kinds of preparations of the compound of the present invention and the concomitant drug, which have been separately produced, by different administration routes, (5) administration of two kinds of preparations of the compound of the present invention and the concomitant drug, which have been separately produced, by different administration routes in a staggered manner (e.g., administration in the order of the compound of the present invention and the concomitant drug, or in the reverse order) and the like.

The dose of the concomitant drug can be appropriately determined based on the dose employed in clinical situations. The mixing ratio of the compound of the present invention and a concomitant drug can be appropriately determined depending on the administration subject, administration route, target disease, symptom, combination and the like.

For example, the content of the compound of the present invention in the combination agent of the present invention differs depending on the form of a preparation, and usually from about 0.01 to about 100 wt %, preferably from about 0.1 to about 50 wt %, further preferably from about 0.5 to about 20 wt %, based on the whole preparation.

The content of the concomitant drug in the combination agent of the present invention differs depending on the form of a preparation, and usually from about 0.01 to about 100 wt %, preferably from about 0.1 to about 50 wt %, further preferably from about 0.5 to about 20 wt %, based on the whole preparation.

The content of additives such as a carrier and the like in the combination agent of the present invention differs depending on the form of a preparation, and usually from about 1 to about 99.99 wt %, preferably from about 10 to about 90 wt %, based on the preparation.

Similar contents may be employed even when the compound of the present invention and a concomitant drug are separately formulated into preparations.

Examples of the concomitant drug include, but are not limited to, the following. A therapeutic drug for narcolepsy (e.g., methylphenidate, amphetamine, pemoline, phenelzine, protriptyline, sodium oxybate, modafinil, caffeine), antiobesity drug (amphetamine, benzfetamine, bromocriptine, bupropion, diethylpropion, exenatide, fenfluramine, liothyronine, liraglutide, mazindol, methamphetamine, octreotide, octreotide, orlistat, phendimetrazine, phendimetrazine, phenmetrazine, phentermine, Qnexa (registered trade mark), phenylpropanolamine, pramlintide, propylhexedrine, recombinant leptin, sibutramine, topiramate, zimelidine, zonisamide, Lorcaserin, metformin), acetylcholine esterase inhibitor (e.g., donepezil, rivastigmine, galanthamine, zanapezil, idebenone, tacrine), antidementia agent (e.g., memantine), inhibitor of β amyloid protein production, secretion, accumulation, aggregation and/or deposition, β secretase inhibitor (e.g., 6-(4-biphenylyl)methoxy-2-[2-(N,N-dimethylamino)ethyl]tetralin, 6-(4-biphenylyl)methoxy-2-(N,N-dimethylamino)methyltetralin, 6-(4-biphenylyl)methoxy-2-(N,N-dipropylamino)methyltetralin, 2-(N,N-dimethylamino)methyl-6-(4'-methoxybiphenyl-4-yl)methoxytetralin, 6-(4-biphenylyl)methoxy-2-[2-(N,N-diethylamino)ethyl]tetralin, 2-[2-(N,N-dimethylamino)ethyl]-6-(4'-methylbiphenyl-4-yl)methoxytetralin, 2-[2-(N,N-dimethylamino)ethyl]-6-(4'-methoxybiphenyl-4-yl)methoxytetralin, 6-(2',4'-dimethoxybiphenyl-4-yl)methoxy-2-[2-(N,N-dimethylamino)ethyl]tetralin, 6-[4-(1,3-benzodioxol-5-yl)phenyl]methoxy-2-[2-(N,N-dimethylamino)ethyl]tetralin, 6-(3',4'-dimethoxybiphenyl-4-yl)methoxy-2-[2-(N,N-dimethylamino)ethyl]tetralin, an optically active form thereof, a salt thereof and a hydrate thereof, OM99-2 (WO01/00663)), γ secretase inhibitor, β amyloid protein aggregation inhibitor (e.g., PTI-00703, ALZHEMED (NC-531), PPI-368 (National Publication of International Patent Application No. 11-514333), PPI-558 (National Publication of International Patent Application No. 2001-500852), SKF-74652 (Biochem. J. (1999), 340(1), 283-289)), β amyloid vaccine, β amyloid-degrading enzyme and the like, brain function enhancer (e.g., aniracetam, nicergoline), therapeutic drug for Parkinson's disease [(e.g., dopamine receptor agonist (e.g., L-DOPA, bromocriptine, pergolide, talipexole, pramipexole, cabergoline, amantadine), monoamine oxidase inhibitor (MAO) inhibitor (e.g., deprenyl, selegiline, remacemide, riluzole), anticholinergic agent (e.g., trihexyphenidyl, biperiden), COMT inhibitor (e.g., entacapone)], therapeutic drug for amyotrophic lateral sclerosis (e.g., riluzole etc., neurotrophic factor), therapeutic drug for abnormal behavior accompanying progress of dementia, wandering and the like (e.g., sedative, anti-anxiety drug), apoptosis inhibitor (e.g., CPI-1189, IDN-6556, CEP-1347), neuronal differentiation ●regenerate promoter (e.g., leteprinim, xaliproden; SR-57746-A), SB-216763, Y-128, VX-853, prosaptide, 5,6-dimethoxy-2-[2,2,4,6,7-pentamethyl-3-(4-methylphenyl)-2,3-dihydro-1-benzofuran-5-yl]isoindoline, 5,6-dimethoxy-2-[3-(4-isopropylphenyl)-2,2,4,6,7-pentamethyl-2,3-dihydro-1-benzofuran-5-yl]isoindoline, 6-[3-(4-isopropylphenyl)-2,2,4,6,7-pentamethyl-2,3-dihydro-1-benzofuran-5-yl]-6,7-dihydro-5H-[1,3]dioxolo[4,5-f]isoindole and an optically active form, salt or hydrate thereof), non-steroidal antiinflammatory agents (meloxicam, tenoxicam, indomethacin, ibuprofen, celecoxib, rofecoxib, aspirin, indomethacin etc.), steroid drug (dexamethasone, hexestrol, cortisone acetate etc.), disease-modifying anti-rheumatic drug (DMARDs), anti-cytokine drug (e.g., TNF inhibitor, MAP kinase inhibitor), therapeutic agent for incontinence, frequent urination (e.g., flavoxate hydrochloride, oxybutynin hydrochloride, propiverine hydrochloride), phosphodiesterase inhibitor (e.g., sildenafil (citrate)), dopamine agonist (e.g., apomorphine), antiarrhythmic drugs (e.g., mexiletine), sex hormone or a derivative thereof (e.g., progesterone, estradiol, estradiol benzoate), therapeutic agent for osteoporosis (e.g., alfacalcidol, calcitriol, elcatonin, calcitonin salmon, estriol, ipriflavone, pamidronate disodium, alendronate sodium hydrate, incadronate disodium), parathyroid hormone (PTH), calcium receptor antagonists, therapeutic drug for insomnia (e.g., benzodiazepines medicament, non-benzodiazepines medicament, melatonin agonist, orexin receptor antagonists), therapeutic drug for schizophrenia (e.g., typical antipsychotic agents such as haloperidol and the like; atypical antipsychotic agents such as clozapine, olanzapine, risperidone, aripiprazole and the like; medicament acting on metabotropic glutamate receptor or ion channel conjugated-type glutamate receptor; phosphodiesterase inhibitor), benzodiazepines medicament (chlordiazepoxide, diazepam, potassium clorazepate, lorazepam, clonazepam, alprazolam etc.), L-type calcium channel inhibitor (pregabalin etc.), tricyclic or tetracyclic antidepressant (imipramine hydrochloride, amitriptyline hydrochloride, desipramine hydrochloride, clomipramine hydrochloride etc.), selective serotonin reuptake inhibitor (fluvoxamine maleate, fluoxetine hydrochloride, citalopram hydrobromide, sertraline hydrochloride, paroxetine hydrochloride, escitalopram oxalate etc.), serotonin-noradrenaline reuptake inhibitor (venlafaxine hydrochloride, duloxetine hydrochloride, desvenlafaxine hydrochloride etc.), noradrenaline reuptake inhibitor (reboxetine mesylate etc.), mirtazapine, trazodone hydrochloride, nefazodone hydrochloride, bupropion hydrochloride, setiptiline maleate, 5-$HT_{1A}$ agonist, (buspirone hydrochloride, tandospirone citrate, osemozotan hydrocloride etc.), 5-$HT_{2A}$ antagonist, 5-$HT_{2A}$ inverse agonist, 5-$HT_3$ antagonist (cyamemazine etc.), heart non-selective β inhibitor (propranolol hydrochloride, oxprenolol hydrochloride etc.), histamine $H_1$ antagonist (hydroxyzine hydrochloride etc.), CRF antagonist, other antianxiety drug (meprobamate etc.), tachykinin antagonist (MK-869, saredutant etc.), medicament that acts on metabotropic glutamate receptor, CCK antagonist, β3 adrenaline antagonist (amibegron hydrochloride etc.), GAT-1 inhibitor (tiagabine hydrochloride etc.), N-type calcium channel inhibitor, carbonic anhydrase II inhibitor, NMDA glycine moiety agonist, NMDA antagonist (memantine etc.), peripheral benzodiazepine receptor agonist, vasopressin antagonist, vasopressin V1b antagonist, vasopressin V1a antagonist, phosphodiesterase inhibitor, opioid antagonist, opioid agonist, uridine, nicotinic acid receptor agonist, thyroid hormone (T3, T4), TSH, TRH, MAO inhibitor (phenelzine sulfate, tranylcypromine sulfate, moclobemide etc.), COMT inhibitor (entacapone etc.), therapeutic drug for bipolar disorder (lithium carbonate, sodium valproate, lamotrigine, riluzole, felbamate etc.), cannabinoid CB1 antagonist (rimonabant etc.), FAAH inhibitor, sodium channel inhibitor, anti-ADHD drug (methylphenidate hydrochloride, methamphetamine hydrochloride etc.), therapeutic drug for alcoholism, therapeutic drug for autism, therapeutic drug for chronic fatigue syndrome, therapeutic drug for spasm, therapeutic drug for fibromyalgia syndrome, therapeutic drug for headache, therapeutic drug for quitting smoking, therapeutic drug for myasthenia gravis, therapeutic drug for cerebral infarction, therapeutic drug for mania, therapeutic drug for hypersomnia, therapeutic drug for pain, therapeutic drug for dysthymia, therapeutic drug for autonomic ataxia, therapeutic drug for male and female sexual dysfunction, therapeutic drug for migraine, therapeutic drug for pathological gambler, therapeutic drug for restless legs syndrome, therapeutic drug for substance addiction, therapeutic drug for alcohol-related syndrome, therapeutic drug for irritable bowel syndrome, therapeutic drug for ALS (riluzole etc., neurotrophic factor etc.), therapeutic drug for lipid abnormality such as cholesterol-lowering drug (statin series (pravastatin sodium, atorvastatin, simvastatin, rosuvastatin etc.), fibrate (clofibrate etc.), squalene synthetase inhibitor), therapeutic drug for abnormal behavior or suppressant of dromomania due to dementia (sedatives, antianxiety drug etc.), antiobesity drug, therapeutic drug for diabetes, therapeutic agent for diabetic complications, therapeutic drug for hypertension, therapeutic drug for hypotension, diuretic, chemotherapeutic agent, immunotherapeutic agent, antithrombotic agent, anti-cancer agent and the like.

Two or more kinds of the above-mentioned concomitant drug may be used in a mixture at an appropriate ratio.

When the compound of the present invention is applied to each of the above-mentioned diseases, it can also be used in combination with biologics (e.g., antibody drug, nucleic acid or nucleic acid derivative, aptamer drug, vaccine preparation), or can be combined with a gene therapy method and the like and applied as a combination therapy, or can also be used in combination with a treatment in psychiatric field without using drugs.

Examples of the antibody and vaccine preparation include vaccine preparation against angiotensin II, vaccine preparation against CETP, CETP antibody, antibody against TNFα antibody and other cytokines, amyloid β vaccine preparation, vaccine for type 1 diabetes (e.g., DIAPEP-277 of Peptor), anti-HIV antibody and HIV vaccine preparation, as well as antibodies or vaccine preparations against cytokines, renin-angiotensin type enzymes and products thereof, antibodies or vaccine preparations against enzymes or proteins involved in blood lipid metabolism, antibodies or vaccines relating to enzymes and proteins involved in blood coagulation or fibrinolysis system, antibodies or vaccine preparations against proteins involved in sugar metabolism and insulin resistance, and the like. In addition, it can be used in combination with biologics relating to growth factors such as GH, IGF and the like.

Examples of the gene therapy method include a treatment method using gene relating to cytokine, renin-angiotensin type enzyme and product thereof, G protein, G protein conjugated receptor and phosphorylating enzyme thereof, a treatment method using a DNA decoy such as NFκB decoy and the like, a treatment method using antisense, a treatment method using a gene relating to a enzyme or protein involved in blood lipid metabolism (e.g., a gene relating to metabolism, excretion and absorption of cholesterol or triglyceride or HDL-cholesterol or blood phospholipid), a treatment method using a gene relating to a enzyme or protein involved in angiogenesis therapy for peripheral vascular obstruction and the like (e.g., growth factors such as HGF, VEGF etc.), a treatment method using a gene relating to a protein involved in glucose metabolism and insulin resistance, antisense against cytokines such as TNF etc., and the like.

Examples of the treatment method in the psychiatric field without using drug include modified electroconvulsive therapy, deep brain stimulation therapy, repetitive transcranial magnetic stimulation therapy, psychotherapy including cognitive behavioral therapy and the like.

It can also be used in combination with various organ regeneration methods such as cardiac regeneration, renal regeneration, pancreatic regeneration, revascularization and the like, cell transplantation therapy utilizing bone marrow cells (bone marrow-derived mononuclear cell, myelogenic stem cell), or artificial organ utilizing tissue engineering (e.g., artificial blood vessel, cardiomyocyte sheet).

The compound of the present invention can be administered orally, parenterally (e.g., intramuscular, intraperitoneal, intravenous, intraarterial, intraventricular, intracisternal injection or infusion; subcutaneous injection; or implant), and by topical route such as inhalation spray, intratracheal, nasal, vaginal, rectal, sublingual, subdermal, transdermal and ocular instillation administration, in a suitable unit dosage form containing a pharmaceutically acceptable conventional nontoxic carrier, adjuvant and vehicle suitable for each administration route. In addition to the treatment of warm-blooded animals such as mouse, rat, horse, bovine, sheep, dog, cat, monkey and the like, the compound of the present invention is effective for use in human.

A pharmaceutical composition for the administration of the compound of the present invention may conveniently be given in a unit dosage form and may be prepared by any of the methods well known in the pharmaceutical field. All methods include a step of mixing the active ingredient and one or more carriers constituting the auxiliary components. Generally, a pharmaceutical composition is prepared by uniformly and completely admixing the active ingredient with liquid carrier or finely-divided solid carrier or both, and then molding the product into a desirable dosage form as necessary. In a pharmaceutical composition, the active compound of interest is included in an amount sufficient to produce a desired effect on the process or condition of a disease. As used herein, the term "composition" is intended to encompass a product comprising specified amounts of specified ingredients and all products obtained directly or indirectly from the combination of the specified amounts of the specified ingredients.

A pharmaceutical composition for oral use may be prepared according to any method known in the this field relating to the manufacture of pharmaceutical compositions, and such composition may contain one or more agents selected from the group consisting of sweetener, flavor, colorant and preservative to provide a preparation having pharmaceutically high quality and good taste. A tablet contains an active ingredient in admixture with a pharmaceutically acceptable non-toxic excipient suitable for the manufacture of tablets. These excipients may be, for example, inert diluents such as calcium carbonate, sodium carbonate, lactose, calcium phosphate, sodium phosphate and the like; granulating agent and disintegrant such as cornstarch, alginic acid and the like; binder such as starch, gelatin, acacia and the like; and lubricant such as magnesium stearate, stearic acid, talc and the like. Tablets may not be coated or coated by a known technique for delaying disintegration and absorption in the gastrointestinal tract, whereby a sustained action is provided over a longer period of time. A composition for oral use may also be provided as a hard gelatin capsule wherein the active ingredient is mixed with an inert solid diluent such as calcium carbonate, calcium phosphate and kaolin, or as a soft gelatin capsule wherein the active ingredient is mixed with water or an oil medium, such as peanut oil, liquid paraffin and olive oil. An aqueous suspension contains an active material in admixture with excipients suitable for the manufacture of an aqueous suspension. An oily suspension may be formulated by suspending the active ingredient in a suitable oil. An oil-in-water emulsion may also be adopted. Dispersible powders and granules suitable for the preparation of an aqueous suspension by the addition of water provide an active ingredient in admixture with a dispersing or wetting agent, a suspending agent, and one or more preservatives. The pharmaceutical composition of the present compound may be in the form of a sterile injectable aqueous or oily suspension. The compound of the invention may also be administered in the form of a suppository for rectal administration. For topical use, cream, ointment, jelly, solution, suspension and the like containing the compound of the present invention may be employed. The compound of the present invention may also be formulated for the administration by inhalation. The compound of the present invention may also be administered by a transdermal patch according to a method known in this field.

While various production methods of the compound (I) of the present invention or a salt thereof (hereinafter to be simply referred to as compound (I)) are considered, a representative example thereof is shown in the following scheme 1. In the explanation of the following production method, a compound and a reaction product thereof to be the starting materials may form a salt which does not adversely influence the reaction.

Compound (I) is produced, for example, by the method shown in the following scheme 1.

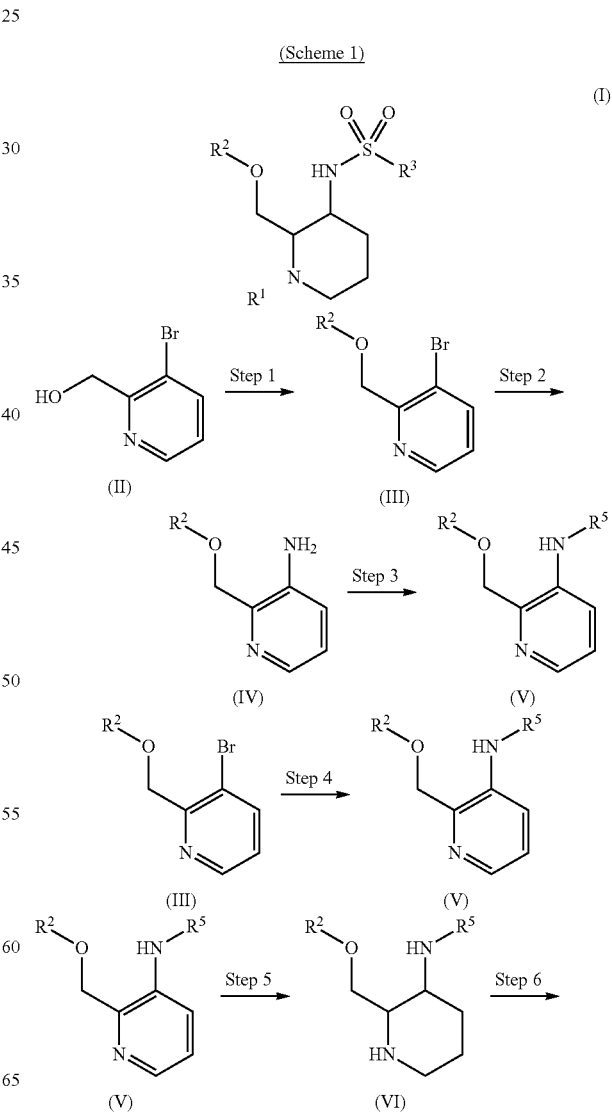

(Scheme 1)

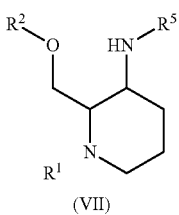

(VII)

wherein R⁵ is a carbonyl group or a sulfonyl group substituted by R³, and other symbols are as defined above.

As compound (II) to be a starting material, for example, a commercially available compound or a compound known per se or a compound produced by a method analogous to the production method thereof can be used (e.g., Organic Letters 2008, V10(13), 2701-2704) and the like).

Step 1 can be performed by a method known per se or a method analogous thereto. For example, alkylation reaction (e.g., S. R. Sandler and W. Karo, Organic Functional Group Preparations I, 2$^{nd}$ ed., Academic Press, 1983, Chapter 13) and the like) and the like can be used.

For step 2, for example, a method known per se (e.g., Journal of Organic Chemistry, 77(16), 6908-6916; 2012 and the like) and the like can be used.

Step 3 shows the production of compound (V) by reaction of compound (IV) with sulfonyl chloride, acyl chloride or isocyanate in the presence of a base.

As the base, organic bases (e.g., triethylamine, pyridine, diethylisopropylamine, sodium methoxide, sodium ethoxide and the like), inorganic bases (e.g., sodium hydroxide, potassium hydroxide, sodium carbonate, potassium carbonate, sodium hydrogen carbonate, potassium hydrogen carbonate, cesium carbonate, sodium hydride, metal sodium and the like) and the like are used. The amount of the base to be used is generally 1 to 10 mol, preferably 1 to 3 mol, per 1 mol of compound (IV). As the kind of the base, an organic base is preferable, and triethylamine, pyridine, diethylisopropylamine and the like, particularly pyridine, are preferable.

This reaction can be advantageously performed in a solvent. As the solvent, hydrocarbons (e.g., pentane, hexane, cyclohexane, benzene, toluene and the like), ethers (e.g., diethyl ether, tetrahydrofuran, dioxane and the like), amides (e.g., N,N-dimethylformamide, hexamethylphosphoric acid triamide and the like), halogenated hydrocarbons (e.g., dichloromethane, chloroform and the like), sulfoxides (e.g., dimethyl sulfoxide and the like), ureas (e.g., 1,3-dimethyl-3,4,5,6-tetrahydro-2 (1H)-pyrimidine) and the like are used. When the aforementioned organic base is a liquid (e.g., triethylamine, pyridine, diethylisopropylamine and the like), it can also be used as a solvent. These solvents may be used alone or two or more kinds thereof may be mixed at a suitable ratio and used. The amount of the solvent to be used is generally 1 to 100 ml, preferably 5 to 20 ml, per 1 g of compound (IV). The reaction temperature is generally −20° C. to the boiling point of the solvent to be used for the reaction, preferably 0° C. to 60° C. While the reaction time varies depending on the kind and amount of the base to be used and the like, it is 10 min to 3 days, preferably 1 hr to 24 hr.

Step 4 can be performed according to, for example, a method known per se (e.g., Organic Letters 2011, V13(10), 2564-2567) and the like).

Step 5 can be performed according to, for example, a method known per se (e.g., WO 2011119541 A1 and the like).

Step 6 can be performed according to a method known per se (e.g., S. R. Sandler and W. Karo, Organic Functional Group Preparations II, 2$^{nd}$ ed., Academic Press, 1989, Chapter 6) and the like).

In the thus-obtained compound (VII), an intramolecular functional group can also be converted to an object functional group by a combination of chemical reactions known per se. Examples of the chemical reaction include oxidation reaction, reduction reaction, alkylation reaction, acylation reaction, ureation reaction, hydrolysis reaction, amination reaction, esterification reaction, aryl coupling reaction, deprotection reaction and the like.

In the above-mentioned production method, when a starting compound has an amino group, a carboxyl group, a hydroxy group, a carbonyl group or a mercapto group as a substituent, a protecting group generally used in the peptide chemistry may be introduced into these groups, and the object compound can be obtained by removing the protecting group as necessary after the reaction.

Examples of the amino-protecting group include formyl group, $C_{1-6}$ alkyl-carbonyl group, $C_{1-6}$ alkoxy-carbonyl group, benzoyl group, $C_{7-10}$ aralkyl-carbonyl group (e.g., benzylcarbonyl), $C_{7-14}$ aralkyloxy-carbonyl group (e.g., benzyloxycarbonyl, 9-fluorenylmethoxycarbonyl), trityl group, phthaloyl group, N,N-dimethylaminomethylene group, substituted silyl group (e.g., trimethylsilyl, triethylsilyl, dimethylphenylsilyl, tert-butyldimethylsilyl, tert-butyldiethylsilyl), $C_{2-6}$ alkenyl group (e.g., 1-allyl) and the like. These groups may be substituted by 1 to 3 substituents selected from a halogen atom, a $C_{1-6}$ alkoxy group and a nitro group.

Examples of the carboxyl-protecting group include $C_{1-6}$ alkyl group, $C_{7-10}$ aralkyl group (e.g., benzyl), phenyl group, trityl group, substituted silyl group (e.g., trimethylsilyl, triethylsilyl, dimethylphenylsilyl, tert-butyldimethylsilyl, tert-butyldiethylsilyl), $C_{2-6}$ alkenyl group (e.g., 1-allyl) and the like. These groups may be substituted by 1 to 3 substituents selected from a halogen atom, a $C_{1-6}$ alkoxy group and a nitro group.

Examples of the hydroxy-protecting group include $C_{1-6}$ alkyl group, phenyl group, trityl group, $C_{7-10}$ aralkyl group (e.g., benzyl), formyl group, $C_{1-6}$ alkyl-carbonyl group, benzoyl group, a $C_{7-10}$ aralkyl-carbonyl group (e.g., benzylcarbonyl), 2-tetrahydropyranyl group, 2-tetrahydrofuranyl group, substituted silyl group (e.g., trimethylsilyl, triethylsilyl, dimethylphenylsilyl, tert-butyldimethylsilyl, tert-butyldiethylsilyl), $C_{2-6}$ alkenyl group (e.g., 1-allyl) and the like. These groups may be substituted by 1 to 3 substituents selected from a halogen atom, a $C_{1-6}$ alkyl group, a $C_{1-6}$ alkoxy group and a nitro group.

Examples of the carbonyl-protecting group include cyclic acetal (e.g., 1,3-dioxane), non-cyclic acetal (e.g., di-$C_{1-6}$ alkylacetal) and the like.

Examples of the mercapto-protecting group include $C_{1-6}$ alkyl group, phenyl group, trityl group, $C_{7-10}$ aralkyl group (e.g., benzyl), $C_{1-6}$ alkyl-carbonyl group, benzoyl group, $C_{7-10}$ aralkyl-carbonyl group (e.g., benzylcarbonyl), $C_{1-6}$ alkoxy-carbonyl group, $C_{6-14}$ aryloxy-carbonyl group (e.g., phenyloxycarbonyl), $C_{7-14}$ aralkyloxy-carbonyl group (e.g., benzyloxycarbonyl, 9-fluorenylmethoxycarbonyl), 2-tetrahydropyranyl group, $C_{1-6}$ alkylamino-carbonyl group (e.g., methylaminocarbonyl, ethylaminocarbonyl) and the like. These groups may be substituted by 1 to 3 substituents selected from a halogen atom, a $C_{1-6}$ alkyl group, a $C_{1-6}$ alkoxy group and a nitro group.

The above-mentioned protecting groups can be removed by a deprotection reaction known per se.

Compound (I) obtained by the above-mentioned production method can be isolated and purified by a known means, such as solvent extraction, liquid conversion, phase transfer, crystallization, recrystallization, chromatography and the like.

When compound (I) contains optical isomer, stereoisomer, regio isomer and rotamer, these compounds are also included in compound (I), and each can be obtained as a single product by a synthesis method or a separation method known per se. For example, when an optical isomer exists in compound (I), an optical isomer resolved from the compound is also encompassed in compound (I).

Here, an optical isomer can be produced by a method known per se.

Compound (I) may be a crystal.

A crystal of compound (I) (hereinafter sometimes to be abbreviated as the crystal of the present invention) can be produced by crystallizing compound (I), by applying a crystallization method known per se.

The crystal of the present invention is superior in the physicochemical properties (e.g., melting point, solubility, stability) and biological properties (e.g., pharmacokinetics (absorbability, distribution, metabolism, excretion), efficacy expression), and is extremely useful as a medicament.

EXAMPLE

The present invention is explained in detail in the following by referring to Examples, Experimental Examples and Formulation Examples. However, the examples do not limit the present invention and the present invention can be modified within the scope of the present invention.

The "room temperature" in the following Examples is generally about 10° C. to about 35° C. The ratio for a mixed solvent is, unless otherwise specified, a volume mixing ratio and % means wt % unless otherwise specified.

The elution by column chromatography in the Examples was performed under the observation by TLC (Thin Layer Chromatography) unless otherwise specified. In the observation by TLC, 60 $F_{254}$ manufactured by Merck was used as a TLC plate, the solvent used as an elution solvent in column chromatography was used as an eluent, and UV detector was used for the detection. In silica gel column chromatography, the indication of NH means use of aminopropylsilane-bonded silica gel and the indication of Diol means use of 3-(2,3-dihydroxypropoxy) propylsilane-bonded silica gel. In preparative HPLC (high performance liquid chromatography), the indication of C18 means use of octadecyl-bonded silica gel. The ratio of elution solvents is, unless otherwise specified, a volume mixing ratio.

In the following Examples, the following abbreviations are used.

THF: tetrahydrofuran, DMSO: dimethylsulfoxide, DME: 1,2-dimethoxyethane, IPE: isopropyl ether, $PdCl_2(dppf)$: 1,1'-bis(diphenylphosphino)ferrocene-palladium(II)dichloride, NMP: 1-methyl-2-pyrrolidone, MPa: megapascal, psi: psi, $CDCl_3$: deuterochloroform, DMSO-$d_6$: deuterodimethyl sulfoxide $^1$H NMR (proton nuclear magnetic resonance) was measured by Fourier transform NMR. For the analysis of $^1$H NMR, ACD/SpecManager (trade name) software and the like were used. Very mild peaks of protons of hydroxyl group, amino group and the like are not described sometimes.

MS (mass spectrum) was measured by LC/MS (liquid chromatograph mass spectrometer). As the ionization method, ESI (electrospray ionization) method, or APCI (atomspheric pressure chemical ionization) method was used. The data indicates those found. While molecular ion peak is generally observed, a fragment ion is sometimes observed. In the case of a salt, a molecular ion peak or fragment ion peak of free form is generally observed. Peaks by powder X-ray diffraction in the Examples mean peaks measured at room temperature by using Ultima IV (Rigaku Corporation, Japan) using Cu Kα radiation as a radiation source. The measurement conditions are as follows.

Electric pressure/Electric current: 40 kV/50 mA
Scan speed: 6 degrees/min
Scan range of 2 Theta: 2-35 degrees The crystallinity by powder X-ray diffraction in the Examples was calculated by the Hermans method.

Example 1

N-(cis-2-(((cis-4-isopropylcyclohexyl)oxy)methyl) piperidin-3-yl)methanesulfonamide A) 3-bromo-2-(((cis-4-isopropylcyclohexyl)oxy) methyl)pyridine To a suspension of 60% sodium hydride (7.00 g) in THF (80 ml) was added cis-4-isopropylcyclohexanol (19.91 g) at room temperature. The reaction mixture was stirred at room temperature overnight, 3-bromo-2-(bromomethyl)pyridine (17.56 g) was added to the reaction mixture, and the mixture was stirred overnight at room temperature. To the mixture was added saturated aqueous ammonium chloride solution, and the mixture was extracted with ethyl acetate. The organic layer was washed with saturated brine, dried over anhydrous sodium sulfate, and the solvent was evaporated under reduced pressure. The residue was purified by NH silica gel chromatography (ethyl acetate/hexane) to give the title compound (17.30 g).

MS, found: 312.2, 314.2.

B) N-(2-(((cis-4-isopropylcyclohexyl)oxy)methyl) pyridin-3-yl)methanesulfonamide A mixture of 3-bromo-2-(((cis-4-isopropylcyclohexyl) oxy)methyl)pyridine (3.0 g), methanesulfonamide (1.097 g), di-tert-butyl(2',4',6'-triisopropylbiphenyl-2-yl)phosphine (0.408 g), tris(dibenzylideneacetone)dipalladium(0) (0.440 g), cesium carbonate (4.70 g) and THF (40 ml) was stirred with heating under microwave radiation at 120° C. for 20 min. The reaction mixture was filtered through celite, and the filtrate was extracted with ethyl acetate. The organic layer was washed with water and saturated brine, dried over anhydrous magnesium sulfate, and the solvent was evaporated under reduced pressure. The residue was purified by silica gel chromatography (ethyl acetate/hexane) to give the title compound (2.310 g).

MS, found: 327.3.

C) N-(cis-2-(((cis-4-isopropylcyclohexyl)oxy) methyl)piperidin-3-yl)methanesulfonamide A mixture of N-(2-(((cis-4-isopropylcyclohexyl)oxy) methyl)pyridin-3-yl)methanesulfonamide (2.285 g), platinum oxide (0.079 g), methanol (15 ml) and acetic acid (15 ml) was stirred overnight under a 0.6 MPa hydrogen atmosphere at 50° C. The mixture was filtrated, and the filtrate was neutralized with saturated aqueous sodium hydrogen carbonate solution at 0° C. and extracted with ethyl acetate. The organic layer was washed with water and saturated brine, dried over anhydrous sodium sulfate, and the solvent was evaporated under reduced pressure. The residue was purified by NH silica gel chromatography (ethyl acetate/hexane) to give the title compound (1.630 g).

$^1$H NMR (300 MHz, CDCl$_3$) δ 0.78-0.90 (6H, m), 0.96-1.15 (1H, m), 1.20-1.48 (8H, m), 1.48-1.77 (9H, m), 1.79-1.90 (2H, m), 1.91-2.03 (1H, m), 2.67 (1H, td, J=11.8, 2.8 Hz), 2.86 (1H, ddd, J=7.9, 4.5, 1.9 Hz), 3.04 (1H, dt, J=11.4, 2.4 Hz), 3.33 (1H, dd, J=9.4, 7.9 Hz), 3.46 (2H, dd, J=9.4, 4.5 Hz), 3.59 (1H, brs), 5.36 (1H, d, J=8.3 Hz).

Example 2

(2R,3S)—N-ethyl-2-(((cis-4-isopropylcyclohexyl)oxy)methyl)-3-((methylsulfonyl)amino)piperidine-1-carboxamide To a solution of (2S,3S)-2,3-bis((4-methylbenzoyl)oxy)succinic acid (579 mg) in ethanol (4 ml) was added a solution of N-(cis-2-(((cis-4-isopropylcyclohexyl)oxy)methyl)piperidin-3-yl)methanesulfonamide (498 mg) in ethanol (4 ml) at room temperature, and the solution was left standing overnight. The resulting solid was collected by filtration, and washed with acetonitrile to give a solid (270 mg). To a solution of the obtained solid (100 mg) and triethylamine (0.078 ml) in THF (2 ml) was added ethylisocyanate (14.83 mg) at 0° C., and the mixture was stirred at room temperature overnight. To the reaction mixture was added water, and the mixture was extracted with ethyl acetate. The organic layer was washed with saturated brine, dried over anhydrous sodium sulfate, and the solvent was evaporated under reduced pressure. The residue was purified by silica gel chromatography (ethyl acetate/hexane) to give the title compound (54 mg).

$^1$H NMR (300 MHz, CDCl$_3$) δ 0.86 (6H, d, J=6.8 Hz), 1.20-1.25 (1H, m), 1.34-1.53 (5H, m), 1.56-1.71 (8H, m), 1.71-1.81 (1H, m), 1.89 (2H, d, J=13.4 Hz), 2.82 (1H, td, J=12.7, 2.7 Hz), 3.00 (3H, s), 3.25 (2H, qd, J=7.2, 5.4 Hz), 3.48-3.61 (3H, m), 3.66-3.79 (1H, m), 3.87 (1H, dd, J=9.3, 7.8 Hz), 4.44-4.56 (1H, m), 4.66 (1H, t, J=4.9 Hz), 5.73 (1H, d, J=7.7 Hz).

Example 3

N-((2R,3S)-2-(((cis-4-phenylcyclohexyl)oxy)methyl)piperidin-3-yl)methanesulfonamide A) 3-bromo-2-(((cis-4-phenylcyclohexyl)oxy)methyl)pyridine To a solution of cis-4-phenylcyclohexanol (50.8 g) in THF (300 ml) was added 60% sodium hydride (17.29 g) at 0° C., and the mixture was stirred for 30 min. To the reaction mixture was added 3-bromo-2-(bromomethyl)pyridine (72.3 g), and the mixture was stirred at room temperature overnight. Saturated aqueous ammonium chloride solution was added, and the mixture was extracted with ethyl acetate. The extract was washed with saturated brine, dried over anhydrous magnesium sulfate and the solvent was evaporated under reduced pressure. The residue was purified by silica gel column chromatography (ethyl acetate/hexane) to give the title compound (84.43 g).

MS, found: 346.0, 348.0.

B) N-(2-(((cis-4-phenylcyclohexyl)oxy)methyl)pyridin-3-yl)methanesulfonamide

To a mixture of 3-bromo-2-(((cis-4-phenylcyclohexyl)oxy)methyl)pyridine (38 g) in DME (450 ml) were added di-tert-butyl(2',4',6'-triisopropylbiphenyl-2-yl)phosphine (9.32 g), tris(dibenzylideneacetone)dipalladium(0) (10.05 g), cesium carbonate (53.6 g) and methanesulfonamide (12.53 g) at room temperature and the reaction mixture was stirred under a nitrogen atmosphere at 100° C. for 5 hr. Water was added to the reaction mixture at room temperature, and the mixture was extracted with ethyl acetate. The extract was washed with saturated brine, dried over anhydrous magnesium sulfate and the solvent was evaporated under reduced pressure. The residue was purified by silica gel column chromatography (ethyl acetate/hexane) to give pale orange solid, which was recrystallized from ethyl acetate/hexane to give the title compound (17.19 g).

MS, found: 361.2.

C) N-((2R,3S)-2-(((cis-4-phenylcyclohexyl)oxy)methyl)piperidin-3-yl)methanesulfonamide A mixture of N-(2-(((cis-4-phenylcyclohexyl)oxy)methyl)pyridin-3-yl)methanesulfonamide (6.48 g), 5% rhodium/carbon (7.40 g), and ethanol/acetic acid (9:1) solution (222.22 ml) was stirred under a hydrogen atmosphere for 23.5 hr. The reaction mixture was filtered through celite, and the solvent was evaporated under reduced pressure. The residue was diluted with ethyl acetate, washed successively with saturated aqueous sodium hydrogen carbonate solution, and saturated brine, dried over anhydrous sodium sulfate, and the solvent was evaporated under reduced pressure. To a solution of the obtained residue (6.80 g) in ethyl acetate (48 ml) was added a solution of (+)-mandelic acid (2.82 g) in ethyl acetate (20 ml) at 60° C., and the mixture was stirred at the same temperature for 1 hr. Seed crystal was added to the reaction mixture at 50° C., and the mixture was gradually cooled to room temperature and stirred at room temperature overnight. The salt was collected by filtration, and washed with a mixed solvent of ethyl acetate/IPE (2:3). The solid was recrystallized from a mixed solvent of ethyl acetate/acetonitrile (1:1). The obtained crystal was dissolved in ethyl acetate-10% aqueous potassium carbonate solution, and the mixture was extracted with ethyl acetate. The extract was washed with saturated brine, dried over anhydrous sodium sulfate, and the solvent was evaporated under reduced pressure to give the title compound (1.09 g).

$^1$H NMR (300 MHz, CDCl$_3$) δ 1.47-1.86 (10H, m), 1.92-2.08 (3H, m), 2.53 (1H, tt, J=11.4, 3.7 Hz), 2.69 (1H, td, J=11.6, 2.8 Hz), 2.86-2.94 (1H, m), 2.98 (3H, s), 3.02-3.12 (1H, m), 3.32-3.42 (1H, m), 3.51 (1H, dd, J=9.3, 4.4 Hz), 3.57-3.68 (2H, m), 5.38 (1H, d, J=7.2 Hz), 7.13-7.37 (5H, m).

Example 4

N-((2R,3S)-1-acetyl-2-(((cis-4-phenylcyclohexyl)oxy)methyl)piperidin-3-yl)methanesulfonamide A reaction mixture of N-((2R,3S)-2-(((cis-4-phenylcyclohexyl)oxy)methyl)piperidin-3-yl)methanesulfonamide (220 mg), pyridine (4 ml), and acetic anhydride (1 ml) was stirred at room temperature overnight. The reaction mixture was concentrated under reduced pressure, and the residue was purified by NH silica gel column chromatography (ethyl acetate/hexane) to give the title compound (249 mg).
$^1$H NMR (300 MHz, CDCl$_3$) δ 1.48-2.65 (15H, m), 2.94-3.16 (4H, m), 3.43-5.20 (7H, m), 5.31-6.22 (1H, m), 7.13-7.36 (5H, m).

Example 5

Methyl (2R,3S)-3-((methylsulfonyl)amino)-2-(((cis-4-phenylcyclohexyl)oxy)methyl)piperidine-1-carboxylate To a reaction mixture of N-((2R,3S)-2-(((cis-4-phenylcyclohexyl)oxy)methyl)piperidin-3-yl)methanesulfonamide (58 mg), triethylamine (0.044 ml) in THF (3 ml) was added methyl chloroformate (0.024 ml) at room temperature, and the mixture was stirred overnight under a calcium chloride tube dry atmosphere. To the reaction mixture was added water, and the mixture was extracted with ethyl acetate. The extract was washed with saturated brine, dried over anhydrous sodium sulfate, and the solvent was evaporated under reduced pressure. The residue was purified by silica gel column chromatography (ethyl acetate/hexane) to give the title compound (64 mg).
$^1$H NMR (300 MHz, CDCl$_3$) δ 1.48-1.58 (2H, m), 1.59-1.67 (2H, m), 1.68-1.89 (6H, m), 2.01-2.12 (3H, m), 2.47-2.61 (1H, m), 2.73-2.88 (1H, m), 2.99 (3H, s), 3.53-3.63 (2H, m), 3.64-3.69 (1H, m), 3.70-3.77 (3H, m), 4.00-4.10 (1H, m), 4.48-4.73 (1H, m), 6.00 (1H, brs), 7.14-7.26 (3H, m), 7.27-7.35 (2H, m).

Example 5A

Methyl (2R,3S)-3-((methylsulfonyl)amino)-2-(((cis-4-phenylcyclohexyl)oxy)methyl)piperidine-1-carboxylate To a solution of N-((2R,3S)-2-(((cis-4-phenylcyclohexyl)oxy)methyl)piperidin-3-yl)methanesulfonamide (1.09 g) in THF (25 ml) were added methyl chloroformate (337 mg) and triethylamine (0.622 ml) at room temperature, and the mixture was stirred over weekend. Saturated aqueous ammonium chloride solution was added, and the mixture was extracted with ethyl acetate. The extract was washed with saturated brine, dried over anhydrous sodium sulfate and the solvent was evaporated under reduced pressure. The residue was dissolved in hot ethanol (3 ml), and the solution was stirred at room temperature for 10 min. After crystals started to precipitate, water (3 ml) was added to the solution and then stirred overnight. The crystals were collected by filtration to give crystals of the title compound (1.023 g).
X-ray powder diffraction patterns of the obtained crystals were generated using Ultima IV with Cu Kα radiation.
The obtained crystal showed a powder X-ray diffraction pattern having characteristic peaks at the diffraction angle (2θ) of 8.8°, 11.0°, 13.4°, 15.3°, 17.6°, 19.2°, 20.4° and 23.4°.

Example 6

N-(cis-2-(((cis-4-(3,5-difluorophenyl)cyclohexyl)oxy)methyl)piperidin-3-yl)methanesulfonamide acetate A) 3-bromo-2-(((cis-4-(3,5-difluorophenyl)cyclohexyl)oxy)methyl)pyridine A solution of cis-4-(3,5-difluorophenyl)cyclohexanol (1.91 g) in THF (40 ml) was cooled to 0° C., 60% sodium hydride (0.720 g) was added, and the mixture was stirred at room temperature under a calcium chloride tube dry atmosphere for 2 hr. To the reaction mixture was added 3-bromo-2-(bromomethyl)pyridine (2.416 g), and the mixture was stirred at room temperature for 30 min, and at 70° C. for 3 hr. To the mixture was added water at room temperature, and the mixture was extracted with ethyl acetate. The organic layer was washed with water and saturated brine, dried over anhydrous magnesium sulfate, and the solvent was evaporated under reduced pressure. The residue was purified by silica gel chromatography (ethyl acetate/hexane) to give the title compound (3.33 g).
MS, found: 382.0, 384.0.

B) N-(2-(((cis-4-(3,5-difluorophenyl)cyclohexyl)oxy)methyl)pyridin-3-yl)methanesulfonamide A mixture of 3-bromo-2-(((cis-4-(3,5-difluorophenyl)cyclohexyl)oxy)methyl)pyridine (3.3 g), methanesulfonamide (0.985 g), di-tert-butyl(2',4',6'-triisopropylbiphenyl-2-yl)phosphine (0.440 g), tris(dibenzylideneacetone)dipalladium (0) (0.395 g), cesium carbonate (4.22 g) and DME (40 ml) was heated under reflux at 95° C. under a nitrogen atmosphere for 6 hr. To the reaction mixture was added water at room temperature, and the mixture was extracted with ethyl acetate. The organic layer was washed with saturated brine, dried over anhydrous magnesium sulfate, and the solvent was evaporated under reduced pressure. The residue was purified by silica gel chromatography (ethyl acetate/hexane) to give the title compound (3.20 g).
MS, found: 397.2.

C) N-(cis-2-(((cis-4-(3,5-difluorophenyl)cyclohexyl)oxy)methyl)piperidin-3-yl)methanesulfonamide acetate A mixture of N-(2-(((cis-4-(3,5-difluorophenyl)cyclohexyl)oxy)methyl)pyridin-3-yl)methanesulfonamide (1.95 g), 5% rhodium/carbon (2.025 g), ethanol (45 ml) and acetic acid (5.0 ml) was stirred at room temperature under a hydrogen atmosphere for 6 hr. The mixture was filtrated, toluene was added to the filtrate, and the mixture was concentrated under reduced pressure. The residue was washed with IPE to give the title compound (1.5045 g).
MS, found: 403.2.

Example 7

N-((2R,3S)-2-(((cis-4-(3,5-difluorophenyl)cyclohexyl)oxy)methyl)piperidin-3-yl)methanesulfonamide N-(cis-2-(((cis-4-(3,5-difluorophenyl)cyclohexyl)oxy)methyl)piperidin-3-yl)methanesulfonamide acetate (1.15 g) was dissolved in ethyl acetate and the mixture was basified with 1 mol/l aqueous sodium hydroxide solution. The organic layer was washed with saturated brine, dried over anhydrous sodium sulfate, and the solvent was evaporated under reduced pressure. From the residue (0.976 g) was separated 295.5 mg by HPLC (column: CHIRALPAK AD (LF001), 50 mmIDx500 mmL, manufactured by Daicel Corporation, mobile phase: hexane/2-propanol/diethylamine=700/300/1) and a fraction having a shorter retention time was obtained as the title compound (0.143 g).
$^1$H NMR (300 MHz, CDCl$_3$) δ 1.45-1.59 (3H, m), 1.60-1.77 (6H, m), 1.81-1.89 (1H, m), 1.89-2.04 (2H, m), 2.52 (1H, tt, J=11.1, 4.0 Hz), 2.64-2.76 (1H, m), 2.90 (1H, ddd, J=8.1, 4.4, 1.9 Hz), 2.94-3.01 (3H, m), 3.07 (1H, dt, J=11.5, 2.4 Hz), 3.30-3.42 (1H, m), 3.46-3.55 (1H, m), 3.56-3.67 (2H, m), 3.71-3.79 (1H, m), 5.35 (1H, d, J=8.0 Hz), 6.61 (1H, tt, J=8.9, 2.3 Hz), 6.69-6.79 (2H, m).

Example 8

N-((2R,3S)-1-acetyl-2-(((cis-4-(3,5-difluorophenyl) cyclohexyl)oxy)methyl)piperidin-3-yl)methanesulfonamide To a solution of N-((2R,3S)-2-(((cis-4-(3,5-difluorophenyl)cyclohexyl)oxy)methyl)piperidin-3-yl)methanesulfonamide (200 mg) and triethylamine (0.138 ml) in THF (5 ml) was added acetyl chloride (0.068 ml) at room temperature, and the mixture was stirred under a calcium chloride tube dry atmosphere for 30 min. To the mixture was added water at room temperature, and the mixture was extracted with ethyl acetate. The organic layer was washed with saturated brine, dried over anhydrous sodium sulfate, and the solvent was evaporated under reduced pressure. The residue was purified by silica gel chromatography (ethyl acetate/hexane) to give the title compound (218 mg).
$^1$H NMR (300 MHz, CDCl$_3$) δ 1.52 (1H, brs), 1.58-1.88 (7H, m), 1.97-2.25 (6H, m), 2.44-2.66 (1H, m), 2.92-3.14 (4H, m), 3.39-3.75 (4.5H, m), 3.84-4.08 (1H, m), 4.38 (0.5H, brs), 5.11 (1H, brs), 5.24-6.18 (1H, m), 6.62 (1H, tt, J=9.0, 2.3 Hz), 6.76 (2H, d, J=6.8 Hz).

Example 9

N-(cis-2-(((cis-4-(2,5-difluorophenyl)cyclohexyl) oxy)methyl)piperidin-3-yl)methanesulfonamide A) 8-(2,5-difluorophenyl)-1,4-dioxaspiro[4.5]dec-7-ene To a mixed solution of (2,5-difluorophenyl)boronic acid (4.11 g), 1,4-dioxaspiro[4.5]dec-7-en-8-yl trifluoromethanesulfonate (5 g), sodium carbonate (7.35 g), and lithium chloride (0.037 g) in DME (60 ml)-water (15.00 ml) was added tetrakis(triphenylphosphine)palladium(0) (1.002 g) at room temperature. The mixture was heated under reflux at 100° C. under a nitrogen atmosphere overnight. To the mixture was added water at room temperature, and the mixture was extracted with ethyl acetate. The organic layer was washed with saturated aqueous sodium hydrogen carbonate solution and saturated brine, dried over anhydrous magnesium sulfate, and the solvent was evaporated under reduced pressure. The residue was purified by silica gel chromatography (ethyl acetate/hexane) to give the title compound (3.582 g).
MS, found: 253.0.

B) 8-(2,5-difluorophenyl)-1,4-dioxaspiro[4.5]decane

To a solution of 8-(2,5-difluorophenyl)-1,4-dioxaspiro [4.5]dec-7-ene (800 mg) in ethanol (15 ml) was added 10% palladium/carbon (337 mg) at room temperature. The mixture was stirred at room temperature under a hydrogen atmosphere for 1 hr. The mixture was filtered, and the solvent was evaporated under reduced pressure. The residue was purified by silica gel chromatography (ethyl acetate/ hexane) to give the title compound (754 mg).
MS, found: 255.0.

C) 4-(2,5-difluorophenyl)cyclohexanone

To a solution of 8-(2,5-difluorophenyl)-1,4-dioxaspiro [4.5]decane (4.15 g) in acetone (30 ml) was added 2 mol/l hydrochloric acid (30 ml) at room temperature. The mixture was stirred at 60° C. for 2 hr. The reaction mixture was partitioned by adding ethyl acetate. The organic layer was washed with saturated aqueous sodium hydrogen carbonate solution and saturated brine, dried over anhydrous sodium sulfate, and the solvent was evaporated under reduced pressure. The residue was purified by silica gel chromatography (ethyl acetate/hexane) to give the title compound (3.32 g).
MS, found: 211.0.

D) cis-4-(2,5-difluorophenyl)cyclohexanol

To a solution of 4-(2,5-difluorophenyl)cyclohexanone (3.32 g) in THF (150 ml) was added lithium tri-(sec-butyl) borohydride 1 mol/l THF solution (46.0 ml) at −78° C. The mixture was stirred at 0° C. for 3 hr. To the mixture was added dropwise 30% hydrogen peroxide water at 0° C., and the mixture was stirred for 5 min. To the reaction mixture were added acetone (22 ml), water (52 ml), 30% hydrogen peroxide water (22 ml) in this order, and the mixture was stirred for 5 min and extracted with ethyl acetate. The organic layer was washed with water and saturated brine, dried over anhydrous magnesium sulfate, and the solvent was evaporated under reduced pressure. The residue was purified by silica gel chromatography (ethyl acetate/hexane) to give the title compound (2.85 g).
$^1$H NMR (300 MHz, CDCl$_3$) δ 1.31 (1H, d, J=2.3 Hz), 1.64-1.99 (8H, m), 2.75-2.98 (1H, m), 4.07-4.23 (1H, m), 6.74-7.06 (3H, m).

E) 3-bromo-2-(((cis-4-(2,5-difluorophenyl)cyclo-hexyl)oxy)methyl)pyridine

A solution of cis-4-(2,5-difluorophenyl)cyclohexanol (2.85 g) in THF (60 ml) was cooled to 0° C., 60% sodium hydride (1.074 g) was added, and the mixture was stirred under a calcium chloride tube dry atmosphere at room temperature for 2 hr. To the reaction mixture was added 3-bromo-2-(chloromethyl)pyridine (3.60 g), and the mixture was stirred at room temperature for 30 min and at 70° C. for 3 hr. Water was added to the mixture at room temperature, and the mixture was extracted with ethyl acetate. The organic layer was washed with water and saturated brine, dried over anhydrous sodium sulfate, and the solvent was evaporated under reduced pressure. The residue was purified by silica gel chromatography (ethyl acetate/hexane) to give the title compound (4.33 g).
MS, found: 382.0, 383.9.

F) N-(2-(((cis-4-(2,5-difluorophenyl)cyclohexyl) oxy)methyl)pyridin-3-yl) methanesulfonamide To a mixed solution of 3-bromo-2-(((cis-4-(2,5-difluorophenyl)cyclohexyl)oxy)methyl)pyridine (4.33 g), methanesulfonamide (1.293 g), di-tert-butyl(2',4',6'-triisopropylbiphenyl-2-yl)phosphine (0.962 g), and cesium carbonate (5.54 g) in DME (65 ml) was added tris(dibenzylideneacetone)dipalladium(0) (1.037 g) at room temperature. The mixture was heated under reflux at 100° C. under a nitrogen atmosphere for 6 hr. Water was added to the reaction mixture, and the mixture was extracted with ethyl acetate. The organic layer was washed with saturated brine, dried over anhydrous magnesium sulfate, and the solvent was evaporated under reduced pressure. The residue was purified by silica gel chromatography (ethyl acetate/hexane) to give the title compound (3.95 g).
MS, found: 397.1.

G) N-(cis-2-(((cis-4-(2,5-difluorophenyl)cyclohexyl)oxy)methyl)piperidin-3-yl)methanesulfonamide To a mixed solution of N-(2-(((cis-4-(2,5-difluorophenyl)cyclohexyl)oxy)methyl)pyridin-3-yl)methanesulfonamide (3.76 g) in ethanol (99 ml) and acetic acid (11.00 ml) was added 5% rhodium/carbon (3.90 g) at room temperature. The mixture was stirred at room temperature under a hydrogen atmosphere for 11 hr. The mixed solution was filtered, and the solvent was evaporated under reduced pressure. After washing with IPE-methanol, the residue was suspended in saturated aqueous sodium hydrogen carbonate solution, and the suspension was extracted with ethyl acetate. The organic layer was dried over anhydrous magnesium sulfate, and the solvent was evaporated under reduced pressure to give the title compound (2.015 g).

$^1$H NMR (300 MHz, CDCl$_3$) δ 1.44-1.65 (7H, m), 1.69-1.82 (3H, m), 2.02 (3H, d, J=13.3 Hz), 2.59-2.75 (1H, m), 2.80-2.94 (2H, m), 2.96-3.00 (3H, m), 3.08 (1H, dt, J=11.5, 2.4 Hz), 3.31-3.42 (1H, m), 3.51 (1H, dd, J=9.3, 4.4 Hz), 3.62 (2H, d, J=2.7 Hz), 5.37 (1H, d, J=6.1 Hz), 6.73-6.87 (1H, m), 6.89-7.02 (2H, m).

Example 10

N-((2R,3S)-2-(((cis-4-(2,5-difluorophenyl)cyclohexyl)oxy)methyl)piperidin-3-yl)methanesulfonamide N-(cis-2-(((cis-4-(2,5-difluorophenyl)cyclohexyl)oxy)methyl)piperidin-3-yl)methanesulfonamide was separated by HPLC (column: CHIRALPAK AD(LF001), 50 mmID×500 mmL, manufactured by Daicel Corporation, mobile phase: hexane/2-propanol/diethylamine=700/300/1) and a fraction having a shorter retention time was obtained as the title compound (0.718 g).

$^1$H NMR (300 MHz, CDCl$_3$) δ 1.48-1.65 (6H, m), 1.70-1.83 (4H, m), 1.93-2.12 (3H, m), 2.70 (1H, td, J=11.6, 2.8 Hz), 2.80-2.95 (2H, m), 2.98 (3H, s), 3.09 (1H, dt, J=11.5, 2.2 Hz), 3.30-3.43 (1H, m), 3.48-3.55 (1H, m), 3.59-3.70 (2H, m), 5.30-5.60 (1H, m), 6.76-6.87 (1H, m) 6.88-7.04 (2H, m).

Example 11 methyl (2R,3S)-2-(((cis-4-(2,5-difluorophenyl)cyclohexyl)oxy)methyl)-3-((methylsulfonyl)amino)piperidine-1-carboxylate To a solution of N-((2R,3S)-2-(((cis-4-(2,5-difluorophenyl)cyclohexyl)oxy)methyl)piperidin-3-yl)methanesulfonamide (300 mg) and triethylamine (0.207 ml) in THF (5 ml) was added methyl chloroformate (0.115 ml) at room temperature, and the mixture was stirred for 1 hr. Water was added to the mixture at room temperature, and the mixture was extracted with ethyl acetate. The organic layer was washed with saturated brine, dried over anhydrous sodium sulfate, and the solvent was evaporated under reduced pressure. The residue was purified by silica gel chromatography (ethyl acetate/hexane) to give the title compound (329 mg).

$^1$H NMR (300 MHz, CDCl$_3$) δ 1.50-1.56 (1H, m), 1.59-1.91 (8H, m), 2.03 (1H, brs), 2.08 (2H, brs), 2.70-2.95 (2H, m), 3.01 (3H, s), 3.53-3.71 (3H, m), 3.73 (3H, s), 3.84-4.08 (2H, m), 4.63 (1H, brs), 5.96 (1H, brs), 6.77-6.88 (1H, m), 6.89-7.06 (2H, m).

Example 12

N-(cis-2-(((cis-4-(2,6-difluorophenyl)cyclohexyl)oxy)methyl)piperidin-3-yl)methanesulfonamide A) cis-4-(2,6-difluorophenyl)cyclohexanol To a solution of 4-(2,6-difluorophenyl)cyclohexanone (2.71 g) in THF (120 ml) was added lithium tri(sec-butyl)borohydride 1 mol/l THF solution (37.0 ml) at −78° C. The mixture was warmed to 0° C. over 3 hr. To the mixture were added dropwise acetone, water and 30% hydrogen peroxide water at 0° C. and the mixture was stirred for 5 min and extracted with ethyl acetate. The organic layer was washed with water and saturated brine, dried over anhydrous magnesium sulfate, and the solvent was evaporated under reduced pressure. The residue was purified by silica gel chromatography (ethyl acetate/hexane) to give the title compound (2.69 g).

$^1$H NMR (300 MHz, CDCl$_3$) δ 1.40 (1H, d, J=4.5 Hz), 1.56-1.74 (4H, m), 1.84-2.01 (2H, m), 2.25 (2H, d, J=14.0 Hz), 3.02 (1H, tt, J=12.6, 3.3 Hz), 4.13 (1H, brs), 6.73-6.92 (2H, m), 7.01-7.20 (1H, m).

B) 3-bromo-2-(((cis-4-(2,6-difluorophenyl)cyclohexyl)oxy)methyl)pyridine

A solution of cis-4-(2,6-difluorophenyl)cyclohexanol (2.69 g) in THF (60 ml) was cooled to 0° C., 60% sodium hydride (1.014 g) was added, and the mixture was stirred under a calcium chloride tube dry atmosphere for 2 hr. To the reaction mixture was added 3-bromo-2-(chloromethyl)pyridine (3.40 g), and the mixture was stirred at room temperature for 30 min, and at 70° C. overnight. Water was added to the mixture at room temperature, and the mixture was extracted with ethyl acetate. The organic layer was washed with water and saturated brine, dried over anhydrous magnesium sulfate, and the solvent was evaporated under reduced pressure. The residue was purified by silica gel chromatography (ethyl acetate/hexane) to give the title compound (3.96 g).

MS, found: 382.0, 384.0.

C) N-(2-(((cis-4-(2,6-difluorophenyl)cyclohexyl)oxy)methyl)pyridin-3-yl) methanesulfonamide A mixture of 3-bromo-2-(((cis-4-(2,6-difluorophenyl)cyclohexyl)oxy)methyl)pyridine (3.96 g), methanesulfonamide (1.183 g), di-tert-butyl(2',4',6'-triisopropylbiphenyl-2-yl)phosphine (0.880 g), tris(dibenzylideneacetone)dipalladium(0) (0.949 g), cesium carbonate (5.06 g) and DME (60 ml) was heated under reflux at 100° C. under a nitrogen atmosphere for 6 hr. Water was added to the reaction mixture at room temperature, and the mixture was extracted with ethyl acetate. The organic layer was washed with saturated brine, dried over anhydrous magnesium sulfate, and the solvent was evaporated under reduced pressure. The residue was purified by silica gel chromatography (ethyl acetate/hexane) to give the title compound (3.76 g).

MS, found: 397.1.

D) N-(cis-2-(((cis-4-(2,6-difluorophenyl)cyclohexyl)oxy)methyl)piperidin-3-yl)methanesulfonamide A mixture of N-(2-(((cis-4-(2,6-difluorophenyl)cyclohexyl)oxy)methyl)pyridin-3-yl)methanesulfonamide (3.76 g), 5% rhodium/carbon (3.90 g), ethanol (99 ml) and acetic acid (11.0 ml) was stirred at room temperature under a hydrogen atmosphere for 9 hr. The mixture was filtered, and the solvent was evaporated under reduced pressure. The residue was washed with IPE. The obtained solid was dissolved in saturated aqueous sodium hydrogen carbonate solution and then neutralized, and extracted with ethyl acetate. The organic layer was dried over anhydrous magnesium sulfate, and the solvent was evaporated under reduced pressure. The residue was purified by NH silica gel chromatography (ethyl acetate/hexane) to give the title compound (1.84 g).

$^1$H NMR (300 MHz, CDCl$_3$) δ 1.40-1.80 (8H, m), 1.92-2.22 (5H, m), 2.71 (1H, td, J=11.7, 2.6 Hz), 2.89-3.13 (6H, m), 3.35-3.44 (1H, m), 3.45-3.53 (1H, m), 3.63 (2H, brs), 5.40 (1H, brs), 6.69-6.94 (2H, m), 7.01-7.22 (1H, m).

Example 13

N-((2R,3S)-2-(((cis-4-(2,6-difluorophenyl)cyclohexyl)oxy)methyl)piperidin-3-yl)methanesulfonamide N-(cis-2-(((cis-4-(2,6-difluorophenyl)cyclohexyl)oxy)methyl)piperidin-3-yl)methanesulfonamide (1800 mg) was separated by HPLC (column: CHIRALPAK AD(LF001), 50 mmID×500 mmL, manufactured by Daicel Corporation, mobile phase: hexane/2-propanol/diethylamine=800/200/1) and a fraction having a shorter retention time was obtained as the title compound (593.2 mg).

$^1$H NMR (300 MHz, CDCl$_3$) δ 1.51 (4H, dd, J=9.8, 4.2 Hz), 1.65-1.82 (4H, m), 1.93-2.28 (5H, m), 2.71 (1H, td, J=11.6, 2.8 Hz), 2.85-3.13 (6H, m), 3.31-3.44 (1H, m), 3.44-3.51 (1H, m), 3.63 (2H, brs), 5.40 (1H, brs), 6.70-6.94 (2H, m), 7.10 (1H, tt, J=8.3, 6.4 Hz).

Example 14

N-((2R,3S)-1-acetyl-2-(((cis-4-(2,6-difluorophenyl)cyclohexyl)oxy)methyl)piperidin-3-yl)methanesulfonamide To a solution of N-((2R,3S)-2-(((cis-4-(2,6-difluorophenyl)cyclohexyl)oxy)methyl)piperidin-3-yl)methanesulfonamide (51.9 mg) in pyridine (2.0 ml) was added acetic anhydride (0.036 ml) at room temperature, and the mixture was stirred under a calcium chloride tube dry atmosphere for 30 min. Toluene was added to the mixture, and the solvent was evaporated under reduced pressure. The residue was purified by silica gel chromatography (ethyl acetate/hexane) to give the title compound (53.1 mg).

$^1$H NMR (300 MHz, CDCl$_3$) δ 1.56-1.65 (3H, m), 1.68-2.24 (11H, m), 2.60-3.35 (5H, m), 3.44-3.81 (4H, m), 3.82-3.95 (1H, m), 4.26-4.66 (1H, m), 4.98-5.47 (1H, m), 5.72 (1H, d, J=8.3 Hz), 6.82 (2H, t, J=8.5 Hz), 7.11 (1H, tt, J=8.3, 6.3 Hz).

Example 15

N-(2-(((cis-4-(3-fluorophenyl)cyclohexyl)oxy)methyl)pyridin-3-yl)methanesulfonamide A) 8-(3-fluorophenyl)-1,4-dioxaspiro[4.5]dec-7-ene To a mixed solution of (3-fluorophenyl)boronic acid (7.28 g), 1,4-dioxaspiro[4.5]dec-7-en-8-yl trifluoromethanesulfonate (10 g), sodium carbonate (7.35 g), and lithium chloride (0.147 g) in DME (150 ml)-water (30.0 ml) was added tetrakis(triphenylphosphine)palladium(0) (2.005 g) at room temperature. The mixture was heated under reflux at 100° C. under a nitrogen atmosphere for 3 hr. Water was added to the mixture at room temperature, and the mixture was extracted with ethyl acetate. The organic layer was washed with saturated brine, dried over anhydrous sodium sulfate, and the solvent was evaporated under reduced pressure. The residue was purified by silica gel chromatography (ethyl acetate/hexane) to give the title compound (5.13 g).

MS, found: 235.0.

B) 8-(3-fluorophenyl)-1,4-dioxaspiro[4.5]decane

To a solution of 8-(3-fluorophenyl)-1,4-dioxaspiro[4.5] dec-7-ene (2.40 g) in ethanol (30 ml) was added 10% palladium/carbon (1.090 g) at room temperature. The mixture was stirred at room temperature under a hydrogen atmosphere for 2 hr. The mixed solution was filtered, and the solvent was evaporated under reduced pressure. The residue was purified by silica gel chromatography (ethyl acetate/hexane) to give the title compound (1.900 g).

MS, found: 237.0.

C) 4-(3-fluorophenyl)cyclohexanone

To a solution of 8-(3-fluorophenyl)-1,4-dioxaspiro[4.5] dec-7-ene (3.96 g) in acetone (30 ml) was added 6 mol/l hydrochloric acid (3 ml) at room temperature. The mixture was stirred at room temperature overnight. The solvent was evaporated under reduced pressure. To the mixture was added saturated brine, and the mixture was extracted with ethyl acetate. The organic layer was dried over anhydrous sodium sulfate, and the solvent was evaporated under reduced pressure. The residue was purified by silica gel chromatography (ethyl acetate/hexane) to give the title compound (3.01 g).

MS, found: 193.1.

D) cis-4-(3-fluorophenyl)cyclohexanol

To 4-(3-fluorophenyl)cyclohexanone (380 mg) in THF (15 ml) was added lithium tri(sec-butyl)borohydride 1 mol/l THF solution (3.95 ml) at −78° C. The mixture was stirred at 0° C. for 2 hr. To the reaction mixture was added saturated aqueous ammonium chloride solution, and the mixture was extracted with ethyl acetate. The organic layer was washed with water and saturated brine, dried over anhydrous sodium sulfate, and the solvent was evaporated under reduced pressure. The residue was purified by silica gel chromatography (ethyl acetate/hexane) to give the title compound (325 mg).

$^1$H NMR (300 MHz, CDCl$_3$) δ 1.31 (1H, s), 1.60-1.76 (4H, m), 1.77-1.98 (4H, m), 2.45-2.62 (1H, m), 4.10-4.18 (1H, m), 6.82-6.97 (2H, m), 7.01 (1H, d, J=7.6 Hz), 7.18-7.26 (1H, m).

E) 3-bromo-2-(((cis-4-(3-fluorophenyl)cyclohexyl)oxy)methyl)pyridine

A solution of cis-4-(3-fluorophenyl)cyclohexanol (1.0 g) in THF (20 ml) was cooled to 0° C., 60% sodium hydride (0.412 g) was added, and the mixture was stirred under a calcium chloride tube dry atmosphere for 1 hr. To the reaction mixture was added 3-bromo-2-(chloromethyl)pyridine (1.382 g), and the mixture was stirred at room temperature for 2 hr, and at 70° C. for 2.5 hr. To the mixture was added saturated aqueous ammonium chloride solution at room temperature, and the mixture was extracted with ethyl acetate. The organic layer was washed with saturated brine, dried over anhydrous sodium sulfate, and the solvent was evaporated under reduced pressure. The residue was purified by silica gel chromatography (ethyl acetate/hexane) to give the title compound (1.580 g).

MS, found: 363.9, 365.9.

F) N-(2-(((cis-4-(3-fluorophenyl)cyclohexyl)oxy) methyl)pyridin-3-yl)methanesulfonamide To a solution of 3-bromo-2-(((cis-4-(3-fluorophenyl)cyclohexyl)oxy)methyl)pyridine (1.15 g), methanesulfonamide (0.601 g), di-tert-butyl(2',4',6'-triisopropylbiphenyl-2-yl)phosphine (0.134 g), and cesium carbonate (2.057 g) in DME (20 ml) was added tris(dibenzylideneacetone)dipalladium(0) (0.289 g) at room temperature. The mixture was stirred under microwave radiation at 120° C. for 2 hr. The reaction mixture was filtered through celite, and the filtrate was washed with saturated brine, dried over anhydrous sodium sulfate, and the solvent was evaporated under reduced pressure. The residue was purified by silica gel chromatography (ethyl acetate/hexane) to give the title compound (1.100 g).

MS, found: 379.0.

G) N-((2R,3S)-2-(((cis-4-(3-fluorophenyl)cyclohexyl)oxy)methyl)piperidin-3-yl)methanesulfonamide To a mixed solution of a solution of N-(2-(((cis-4-(3-fluorophenyl)cyclohexyl)oxy)methyl)pyridin-3-yl)methanesulfonamide (2.82 g) in ethanol (40 ml) and acetic acid (2.105 ml) was added 5% rhodium/carbon (3.07 g) at room temperature. The mixture was stirred at room temperature under a hydrogen atmosphere overnight. The mixed solution was filtered, and the solvent was evaporated under reduced pressure. The residue was dissolved in saturated aqueous sodium hydrogen carbonate solution, extracted with ethyl acetate, and the solvent was evaporated under reduced pressure. The residue was separated by HPLC (column: CHIRALPAK AD(AF003), 50 mmID×500 mmL, manufactured by Daicel Corporation, mobile phase: hexane/2-propanol/diethylamine=650/350/1) and a fraction having a shorter retention time was obtained as the title compound (1.040 g).

$^1$H NMR (300 MHz, CDCl$_3$) δ 1.50-1.76 (10H, m), 1.92-2.07 (3H, m), 2.54 (1H, tt, J=11.4, 4.0 Hz), 2.69 (1H, td, J=11.7, 2.7 Hz), 2.90 (1H, ddd, J=8.0, 4.3, 2.1 Hz), 2.97 (3H, s), 3.07 (1H, dt, J=11.5, 2.4 Hz), 3.29-3.42 (1H, m), 3.49-3.54 (1H, m), 3.49-3.54 (1H, m), 3.56-3.66 (2H, m), 5.38 (1H, d, J=7.6 Hz), 6.82-6.95 (2H, m), 6.99 (1H, d, J=7.6 Hz), 7.18-7.26 (1H, m).

Example 16

N-((2R,3S)-1-(cyclopropylcarbonyl)-2-(((cis-4-(3-fluorophenyl)cyclohexyl)oxy)methyl)piperidin-3-yl) methanesulfonamide To a solution of N-((2R,3S)-2-(((cis-4-(3-fluorophenyl) cyclohexyl)oxy)methyl)piperidin-3-yl)methanesulfonamide (60 mg), triethylamine (0.043 ml) in THF (4 ml) was added cyclopropanecarbonyl chloride (0.028 ml) at room temperature, and the mixture was stirred for 1 hr. Water was added to the mixture at room temperature, and the mixture was extracted with ethyl acetate. The organic layer was washed with saturated brine, dried over anhydrous sodium sulfate, and the solvent was evaporated under reduced pressure. The residue was purified by silica gel chromatography (ethyl acetate/hexane) to give the title compound (59.3 mg).

$^1$H NMR (300 MHz, CDCl$_3$) δ 0.80 (2H, dd, J=7.8, 3.6 Hz), 0.92-1.05 (2H, m), 1.52 (1H, d, J=2.3 Hz), 1.59-2.25 (12H, m), 2.54 (1H, dt, J=15.0, 7.7 Hz), 2.92-3.20 (4H, m), 3.43-3.73 (3H, m), 4.00 (1H, t, J=9.1 Hz), 4.50 (1H, brs), 4.65-5.23 (1H, m), 5.42-6.37 (1H, m), 6.81-6.97 (2H, m), 7.01 (1H, d, J=7.6 Hz), 7.19-7.26 (1H, m).

Example 17

N-(cis-2-(((cis-4-(2,3-difluorophenyl)cyclohexyl) oxy)methyl)piperidin-3-yl)methanesulfonamide A) 8-(2,3-difluorophenyl)-1,4-dioxaspiro[4.5]dec-7-ene To a solution of 1,4-dioxaspiro[4.5]dec-7-en-8-yl trifluoromethanesulfonate (20.0 g) in DME/water (4:1) (250 ml) were added 2,3-difluorophenylboronic acid (16.45 g), lithium chloride (1.0 g), and sodium carbonate (29.8 g). Tetrakis(triphenylphosphine)palladium(0) (6.42 g) was added, and the reaction mixture was stirred with heating under reflux for 16 hr. The reaction mixture was diluted with ethyl acetate and filtered through celite. The filtrate was successively washed with water and saturated brine, dried over anhydrous sodium sulfate, and the solvent was evaporated under reduced pressure. The residue was purified by silica gel column chromatography (ethyl acetate/hexane) to give the title compound (11.0 g).

$^1$H NMR (400 MHz, DMSO-d$_6$) δ 1.80 (2H, t, J=6.4 Hz), 2.38 (2H, s), 2.50 (2H, brs), 3.93 (4H, s), 5.88 (1H, s), 7.12-7.19 (1H, m), 7.25-7.34 (1H, m), 7.41 (1H, t, J=7.6 Hz).

B) 8-(2,3-difluorophenyl)-1,4-dioxaspiro[4.5]decane

A solution of 8-(2,3-difluorophenyl)-1,4-dioxaspiro[4.5] dec-7-ene (10.0 g) in ethanol (500 ml) was deaerated with an argon stream for 15 min, and 10% palladium/carbon (1 g) was added. The reaction mixture was stirred under normal pressure hydrogen atmosphere at room temperature for 2 hr. The reaction mixture was filtered through celite, and the residue was washed with ethanol. The filtrate was concentrated under reduced pressure to give the title compound (8.0 g).

$^1$H NMR (400 MHz, DMSO-d$_6$) δ 1.61-1.78 (8H, m), 2.90-2.93 (1H, m), 3.89 (4H, s), 7.11-7.18 (1H, m), 7.21 (1H, m), 7.40 (1H, t, J=8.1 Hz).

C) 4-(2,3-difluorophenyl)cyclohexanone

To a solution of 8-(2,3-difluorophenyl)-1,4-dioxaspiro [4.5]decane (8.0 g) in THF/water (1:1) (100 ml) was added concentrated sulfuric acid (6.4 ml) at 0° C., and the mixture was stirred at room temperature for 16 hr. To the reaction mixture was added aqueous sodium carbonate solution at 0° C., and the mixture was extracted with ethyl acetate. The extract was successively washed with water and saturated brine, dried over anhydrous sodium sulfate, and the solvent was evaporated under reduced pressure. The residue was purified by silica gel column chromatography (ethyl acetate/ hexane) to give the title compound (6.0 g).

¹H NMR (400 MHz, DMSO-d₆) δ 1.87-1.98 (2H, m), 2.03-2.07 (2H, m), 2.26-2.29 (2H, m), 2.59-2.67 (2H, m), 3.35-3.44 (1H, m), 7.14-7.22 (1H, m), 7.25-7.31 (1H, m), 7.41 (1H, t, J=7.7 Hz).

D) cis-4-(2,3-difluorophenyl)cyclohexanol

To a solution of 4-(2,3-difluorophenyl)cyclohexanone (3.0 g) in THF (20 ml) was added lithium tri(sec-butyl)borohydride 1 mol/l THF solution (21.43 ml) at −78° C., and the mixture was stirred at the same temperature for 30 min. The reaction mixture was gradually warmed to 0° C., and stirred at 0° C. for 2 hr. To the reaction mixture were successively added dropwise at 0° C. water and 1 mol/l aqueous sodium hydroxide solution, and the mixture was extracted with ethyl acetate. The extract was successively washed with water and saturated brine, dried over anhydrous sodium sulfate, and the solvent was evaporated under reduced pressure. The residue was purified by silica gel column chromatography (ethyl acetate/hexane) to give the title compound (1.3 g).
¹H NMR (400 MHz, DMSO-d₆) δ 1.49-1.59 (4H, m), 1.73-1.77 (2H, m), 1.82-1.91 (2H, m), 2.80-2.86 (1H, m), 3.90-3.91 (1H, m), 4.38-4.39 (1H, m), 7.12-7.26 (3H, m).

E) 3-bromo-2-(((cis-4-(2,3-difluorophenyl)cyclohexyl)oxy)methyl)pyridine

To a solution of cis-4-(2,3-difluorophenyl)cyclohexanol (1.3 g) in THF (5 ml) was added 60% sodium hydride (610 mg) at 0° C., and the mixture was stirred with heating under reflux for 2 hr. To the reaction mixture was slowly added a solution of 3-bromo-2-(bromomethyl)pyridine (2.31 g) in THF (5 ml) at room temperature, and the reaction mixture was stirred with heating under reflux for 4 hr. To the reaction mixture was added water, and the mixture was neutralized with 1 mol/l hydrochloric acid and extracted with ethyl acetate. The extract was successively washed with water and saturated brine, dried over anhydrous sodium sulfate, and the solvent was evaporated under reduced pressure. The residue was purified by silica gel column chromatography (ethyl acetate/hexane) to give the title compound (810 mg).
¹H NMR (400 MHz, DMSO-d₆) δ 1.52-1.60 (4H, m), 1.75-1.85 (2H, m), 2.00-2.03 (2H, m), 2.86-2.92 (1H, m), 3.78 (1H, s), 4.60 (2H, s), 7.10-7.20 (2H, m), 7.22-7.26 (1H, m), 7.32-7.35 (1H, m), 8.10 (1H, dd, J=8.1, 1.1 Hz), 8.55 (1H, dd, J=4.5, 1.2 Hz).

F) N-(2-(((cis-4-(2,3-difluorophenyl)cyclohexyl)oxy)methyl)pyridin-3-yl)methanesulfonamide To a solution of 3-bromo-2-(((cis-4-(2,3-difluorophenyl)cyclohexyl)oxy)methyl)pyridine (800 mg) in dioxane (5 ml) were added methanesulfonamide (345 mg) and cesium carbonate (1.02 g). The reaction mixture was aerated with an argon stream for 20 min, di-tert-butyl(2',4',6'-triisopropylbiphenyl-2-yl)phosphine (178 mg) and tris(dibenzylideneacetone)dipalladium(0) (192 mg) were added, and the mixture was sealed and stirred under an argon atmosphere at 120° C. for 4 hr. The reaction mixture was filtered through celite, and the residue was washed with ethyl acetate. The filtrate was successively washed with water and saturated brine, dried over anhydrous sodium sulfate, and the solvent was evaporated under reduced pressure. The residue was purified by silica gel column chromatography (ethyl acetate/hexane) to give the title compound (620 mg).
¹H NMR (400 MHz, DMSO-d₆) δ 1.53-1.61 (4H, m), 1.70-1.76 (2H, m), 1.99-2.05 (2H, m), 2.87-2.93 (1H, m), 3.10 (3H, s), 3.79 (1H, brs), 4.75 (2H, s), 7.10-7.15 (2H, m), 7.22-7.24 (1H, m), 7.37-7.41 (1H, m), 7.79 (1H, d, J=8.0 Hz), 8.37-8.38 (1H, m), 9.11 (1H, brs).

G) N-(cis-2-(((cis-4-(2,3-difluorophenyl)cyclohexyl)oxy)methyl)piperidin-3-yl)methanesulfonamide To a solution of N-(2-(((cis-4-(2,3-difluorophenyl)cyclohexyl)oxy)methyl)pyridin-3-yl)methanesulfonamide (600 mg) in methanol/acetic acid (10:1) (66 ml) was added platinum oxide (60 mg). The reaction mixture was stirred under a 40 psi hydrogen atmosphere for 16 hr at room temperature. The reaction mixture was filtered through celite, and the residue was washed with methanol. The filtrate was concentrated under reduced pressure, and the residue was dissolved in ethyl acetate and the mixture was successively washed with saturated aqueous sodium hydrogen carbonate solution and saturated brine, dried over anhydrous sodium sulfate, and the solvent was evaporated under reduced pressure. The residue was purified by NH silica gel column chromatography (ethyl acetate/hexane) to give the title compound (400 mg).
¹H NMR (400 MHz, DMSO-d₆) δ 1.35-1.38 (1H, m), 1.50-1.56 (5H, m), 1.68-1.98 (7H, m), 2.54-2.57 (1H, m), 2.84-2.90 (3H, m), 2.93 (3H, s), 3.36-3.40 (2H, m), 3.51 (1H, brs), 3.59 (1H, brs), 6.72 (1H, brs), 7.11-7.18 (2H, m), 7.19-7.26 (1H, m).

Example 18

N-((2R,3S)-2-(((cis-4-(2,3-difluorophenyl)cyclohexyl)oxy)methyl)piperidin-3-yl) methanesulfonamide N-(cis-2-(((cis-4-(2,3-difluorophenyl)cyclohexyl)oxy)methyl)piperidin-3-yl)methanesulfonamide (3.5 g) was separated by HPLC (column: CHIRALPAK AD(LF001), 50 mmID×500 mmL, manufactured by Daicel Corporation, mobile phase: hexane/2-propanol/diethylamine=700/100/1), and a fraction having a shorter retention time was obtained as the title compound (1.57 g)
¹H NMR (300 MHz, CDCl₃) δ 1.48-1.64 (6H, m), 1.70-1.86 (3H, m), 2.69 (1H, td, J=11.7, 2.7 Hz), 2.85-1.96 (2H, m), 2.97-3.00 (3H, m), 3.07 (1H, dt, J=11.5, 2.4 Hz), 3.28-3.56 (3H, m), 3.63 (2H, d, J=2.7 Hz), 5.38 (1H, dt, J=8.3 Hz), 6.90-7.06 (3H, m).

Example 19

N-((2R,3S)-1-acetyl-2-(((cis-4-(2,3-difluorophenyl)cyclohexyl)oxy)methyl)piperidin-3-yl)methanesulfonamide To a solution of N-((2R,3S)-2-(((cis-4-(2,3-difluorophenyl)cyclohexyl)oxy)methyl)piperidin-3-yl)methanesulfonamide (300 mg) in THF (15 ml) were added acetyl chloride (0.079 ml) and triethylamine (0.208 ml) at room temperature, and the mixture was stirred at the same temperature for 4 hr. To the reaction mixture was added saturated aqueous ammonium chloride solution, and the mixture was extracted with ethyl acetate. The extract was successively washed with saturated aqueous ammonium chloride solution and saturated brine, dried over anhydrous sodium sulfate, and the solvent was evaporated under reduced pressure. The residue was purified by silica gel column chromatography (ethyl acetate/hexane) to give the title compound (315 mg).
$^1$H NMR (300 MHz, CDCl$_3$) δ 1.59-1.90 (8H, m), 1.95-2.24 (6H, m), 2.79-4.43 (10H, m), 4.48-6.25 (2H, m), 6.87-7.16 (3H, m).

Example 20 methyl (2R,3S)-2-(((cis-4-(2,3-difluorophenyl)cyclohexyl)oxy)methyl)-3-((methylsulfonyl)amino)piperidine-1-carboxylate To a solution of N-((2R,3S)-2-(((cis-4-(2,3-difluorophenyl)cyclohexyl)oxy)methyl)piperidin-3-yl)methanesulfonamide (50 mg) in THF (5 ml) were added methyl chloroformate (18 mg) and triethylamine (38 mg) at room temperature, and the mixture was stirred at the same temperature overnight. To the reaction mixture was added saturated aqueous ammonium chloride solution, and the mixture was extracted with ethyl acetate. The extract was washed with saturated brine, dried over anhydrous sodium sulfate, and the solvent was evaporated under reduced pressure. The residue was purified by silica gel column chromatography (ethyl acetate/hexane) to give the title compound (52 mg).
$^1$H NMR (300 MHz, CDCl$_3$) δ 1.51-2.12 (12H, m), 2.74-2.86 (1H, m), 2.87-2.98 (1H, m), 3.00 (3H, s), 3.54-3.65 (2H, m), 3.68 (1H, t, J=2.5 Hz), 3.72 (3H, s), 3.90-4.07 (2H, m), 4.64 (1H, brs), 6.02 (1H, brs), 6.86-7.16 (3H, m).

Example 21

N-((2R,3S)-2-(((cis-4-(2,3,6-trifluorophenyl)cyclohexyl)oxy)methyl)piperidin-3-yl)methanesulfonamide A) 8-(2,3,6-trifluorophenyl)-1,4-dioxaspiro[4.5]dec-7-ene To a mixed solution of 8-(4,4,5,5-tetramethyl-1,3,2-dioxaborolan-2-yl)-1,4-dioxaspiro[4.5]dec-7-ene (1 g), 2-bromo-1,3,4-trifluorobenzene (1.189 g), and sodium hydrogen carbonate (0.631 g) in DME (15 ml)-water (3.00 ml) was added PdCl$_2$(dppf) (0.275 g) at room temperature. The mixture was heated under reflux at 100° C. under a nitrogen atmosphere overnight. The mixture was filtered through celite, and the filtrate was extracted with ethyl acetate. The organic layer was washed with saturated brine, dried over anhydrous sodium sulfate, and the solvent was evaporated under reduced pressure. The residue was purified by silica gel chromatography (ethyl acetate/hexane) to give the title compound (0.970 g).
MS, found: 271.0.

B) 8-(2,3,6-trifluorophenyl)-1,4-dioxaspiro[4.5]decane

To a solution of 8-(2,3,6-trifluorophenyl)-1,4-dioxaspiro[4.5]dec-7-ene (6.94 g) in ethanol (60 ml) was added 10% palladium/carbon (2.73 g) at room temperature. The mixture was stirred at room temperature under a hydrogen atmosphere for 7 hr. The mixed solution was filtered, and the solvent was evaporated under reduced pressure. The residue was purified by silica gel chromatography (ethyl acetate/hexane) to give the title compound (4.23 g).
MS, found: 273.0.

C) 4-(2,3,6-trifluorophenyl)cyclohexanone

To a mixed solution of 8-(2,3,6-trifluorophenyl)-1,4-dioxaspiro[4.5]decane (6.49 g) in acetone (100 ml) and water (20 ml) was added 6 mol/l hydrochloric acid (7.95 ml) at room temperature. The mixture was stirred at 70° C. for 1 hr. The solvent was evaporated under reduced pressure, saturated brine was added to the mixture, and the mixture was extracted with ethyl acetate. The organic layer was dried over anhydrous sodium sulfate, and the solvent was evaporated under reduced pressure. The residue was purified by silica gel chromatography (ethyl acetate/hexane) to give the title compound (5.24 g).
MS, found: 229.1.

D) cis-4-(2,3,6-trifluorophenyl)cyclohexanol

To a solution of 4-(2,3,6-trifluorophenyl)cyclohexanone (3.98 g) in THF (50 ml) was added lithium tri(sec-butyl)borohydride 1 mol/l THF solution (22.67 ml) at −78° C. The mixture was stirred at −78° C. under a nitrogen atmosphere for 1 hr. To the mixture was added dropwise 30% hydrogen peroxide water at −78° C., and the mixture was warmed to room temperature and stirred for 5 min. To the reaction mixture was added water, and the mixture was extracted with ethyl acetate. The organic layer was washed with saturated aqueous ammonium chloride solution, dried over anhydrous sodium sulfate, and the solvent was evaporated under reduced pressure. The residue was purified by silica gel chromatography (ethyl acetate/hexane) to give the title compound (3.66 g).
$^1$H NMR (300 MHz, CDCl$_3$) δ 1.39 (1H, d, J=3.0 Hz), 1.54 (1H, d, J=2.7 Hz), 1.58-1.74 (3H, m), 1.84-1.98 (2H, m), 2.15-2.37 (2H, m), 3.02 (1H, tt, J=12.6, 3.3 Hz), 4.11-4.19 (1H, m), 6.76 (1H, tdd, J=9.5, 4.2, 2.3 Hz), 6.95 (1H, qd, J=9.1, 4.9 Hz).

E) 3-bromo-2-(((cis-4-(2,3,6-trifluorophenyl)cyclohexyl)oxy)methyl)pyridin

A solution of cis-4-(2,3,6-trifluorophenyl)cyclohexanol (3.66 g) in THF (100 ml) was cooled to 0° C., 60% sodium hydride (1.272 g) was added, and the mixture was stirred under a calcium chloride tube dry atmosphere at room temperature for 10 min. To the reaction mixture was added 3-bromo-2-(chloromethyl)pyridine (4.92 g), and the mixture was stirred at 70° C. for 3 hr. Water was added to the mixture at room temperature, and the mixture was extracted with ethyl acetate. The organic layer was washed with saturated brine, dried over anhydrous sodium sulfate, and the solvent was evaporated under reduced pressure. The residue was purified by silica gel chromatography (ethyl acetate/hexane) to give the title compound (3.73 g).
MS, found: 401.0, 403.0.

F) N-(2-(((cis-4-(2,3,6-trifluorophenyl)cyclohexyl)oxy)methyl)pyridin-3-yl)methanesulfonamide To a mixed solution of 3-bromo-2-(((cis-4-(2,3,6-trifluorophenyl)cyclohexyl)oxy)methyl)pyridine (4.0 g), methanesulfonamide (1.901 g), di-tert-butyl(2',4',6'-triisopropylbiphenyl-2-yl)phosphine (0.424 g), and cesium carbonate (6.51 g) in DME (100 ml) was added tris(dibenzylideneacetone)dipalladium(0) (0.915 g) at room temperature. The mixture was heated under reflux at 100° C. under a nitrogen atmosphere overnight. The reaction mixture was filtered through celite, and the filtrate was washed with water and saturated brine, dried over anhydrous sodium sulfate, and the solvent was evaporated under reduced pressure. The residue was purified by silica gel chromatography (ethyl acetate/hexane) to give the title compound (3.97 g).

MS, found: 415.2.

G) N-((2R,3S)-2-(((cis-4-(2,3,6-trifluorophenyl)cyclohexyl)oxy)methyl)piperidin-3-yl) methanesulfonamide To a mixed solution of N-(2-(((cis-4-(2,3,6-trifluorophenyl)cyclohexyl)oxy)methyl)pyridin-3-yl)methanesulfonamide (3.95 g) in ethanol (100 ml) and acetic acid (11.11 ml) was added 5% rhodium/carbon (3.92 g) at room temperature. The mixture was stirred at room temperature under a hydrogen atmosphere for 6 hr. The mixed solution was filtered, and the solvent was evaporated under reduced pressure. The residue was dissolved in ethyl acetate-hexane, and the resulting precipitate was collected by filtration. The obtained precipitate was dissolved in saturated aqueous sodium hydrogen carbonate solution, and the mixture was extracted with ethyl acetate. The organic layer was washed with saturated brine, dried over anhydrous sodium sulfate, and the solvent was evaporated under reduced pressure. The residue was separated by HPLC (column: CHIRALPAK AD(AF003), 50 mmID×500 mmL, manufactured by Daicel Corporation, mobile phase: hexane/2-propanol/diethylamine=700/300/1), and a fraction having a shorter retention time was obtained as the title compound (1.02 g)

$^1$H NMR (300 MHz, CDCl$_3$) δ 1.39-1.85 (12H, m), 1.89-2.04 (2H, m), 2.06-2.24 (2H, m), 2.70 (1H, td, J=11.7, 2.7 Hz), 2.92 (1H, ddd, J=8.2, 4.4, 2.1 Hz), 3.00-3.14 (2H, m), 3.33-3.43 (1H, m), 3.45-3.55 (1H, m), 3.63 (2H, d, J=2.3 Hz), 5.37 (1H, brs), 6.68-6.80 (1H, m), 6.94 (1H, qd, J=9.1, 4.9 Hz).

Example 22

N-((2R,3S)-1-acetyl-2-(((cis-4-(2,3,6-trifluorophenyl)cyclohexyl)oxy)methyl)piperidin-3-yl)methanesulfonamide To a solution of N-((2R,3S)-2-(((cis-4-(2,3,6-trifluorophenyl)cyclohexyl)oxy)methyl)piperidin-3-yl)methanesulfonamide (900 mg) and triethylamine (0.893 ml) in THF (15 ml) was added acetyl chloride (0.303 ml) at room temperature, and the mixture was stirred for 1 hr. Water was added to the mixture at room temperature, and the mixture was extracted with ethyl acetate. The organic layer was washed with saturated brine, dried over anhydrous sodium sulfate, and the solvent was evaporated under reduced pressure. The residue was purified by silica gel chromatography (ethyl acetate/hexane) to give the title compound (920 mg).

$^1$H NMR (300 MHz, CDCl$_3$) δ 1.45-1.57 (3H, m), 1.58-1.69 (3H, m), 1.74-2.10 (6H, m), 2.18 (2H, s), 2.97-3.06 (4H, m), 3.06-3.30 (1H, m), 3.51-3.79 (4H, m), 3.81-3.96 (1H, m), 4.24-4.64 (1H, m), 4.98-5.28 (1H, m), 5.67 (1H, d, J=8.7 Hz), 6.68-6.82 (1H, m), 6.88-7.03 (1H, m).

Example 23

N-((2R,3S)-2-(((cis-4-(2-(trifluoromethyl)phenyl)cyclohexyl)oxy)methyl)piperidin-3-yl)methanesulfonamide A) cis-4-(2-(trifluoromethyl)phenyl)cyclohexanol To a solution of 4-(2-(trifluoromethyl)phenyl)cyclohexanone (2.56 g) in THF (50 ml) was added dropwise over 4 min at −78° C. lithium tri(sec-butyl)borohydride 1 mol/l THF solution (13.74 ml). The mixture was stirred at −78° C. for 2 hr, and at 0° C. overnight. To the mixture were added dropwise acetone, water and 30% hydrogen peroxide water at 0° C., and the mixture was stirred at room temperature for 1 hr, and the mixture was extracted with ethyl acetate. The organic layer was washed with water and saturated brine, dried over anhydrous magnesium sulfate, and the solvent was evaporated under reduced pressure. The residue was purified by silica gel chromatography (ethyl acetate/hexane) to give the title compound (2.13 g).

$^1$H NMR (300 MHz, CDCl$_3$) δ 1.31 (1H, d, J=2.3 Hz), 1.58-1.79 (4H, m), 1.83-2.01 (4H, m), 2.95 (1H, t, J=11.2 Hz), 4.14-4.25 (1H, m), 7.22-7.31 (1H, m), 7.46-7.65 (3H, m).

B) 3-bromo-2-(((cis-4-(2-(trifluoromethyl)phenyl)cyclohexyl)oxy)methyl)pyridine

To a solution of cis-4-(2-(trifluoromethyl)phenyl)cyclohexanol (9.36 g) in THF (150 ml) was added at 0° C. potassium hexamethyl disilazide 1.0 mol/l tert-butyl methyl ether solution (57.5 ml), and the mixture was stirred for 30 min. To the reaction mixture was added 3-bromo-2-(bromomethyl)pyridine (19.26 g), and the mixture was stirred under a calcium chloride tube dry atmosphere at 60° C. for 5 hr, potassium carbonate (15.89 g) and 2-mercaptoacetic acid (5.32 ml) were added at room temperature, and the mixture was stirred overnight. Water was added to the mixture at room temperature, and the mixture was extracted with ethyl acetate. The organic layer was washed with 1 mol/l aqueous sodium hydroxide solution and saturated brine, dried over anhydrous magnesium sulfate, and the solvent was evaporated under reduced pressure. The residue was purified by NH silica gel chromatography and silica gel column chromatography (ethyl acetate/hexane) to give the title compound (3.87 g).

MS, found: 414.1, 416.1.

C) N-(2-(((cis-4-(2-(trifluoromethyl)phenyl)cyclohexyl)oxy)methyl)pyridin-3-yl) methanesulfonamide To a solution of 3-bromo-2-(((cis-4-(2-(trifluoromethyl)phenyl)cyclohexyl)oxy)methyl)pyridine (3.87 g) in DME (25 ml) were added methanesulfonamide (1.066 g), di-tert-butyl(2',4',6'-triisopropylbiphenyl-2-yl)phosphine (0.159 g), tris(dibenzylideneacetone)dipalladium(0) (0.171 g) and cesium carbonate (4.57 g) at room temperature. The mixture was stirred at 80° C. under a nitrogen atmosphere overnight. Water was added to the reaction mixture at room temperature, and the mixture was extracted with ethyl acetate. The organic layer was washed with saturated brine, dried over anhydrous magnesium sulfate, and the solvent was evaporated under reduced pressure. The residue was purified by silica gel chromatography (ethyl acetate/hexane) to give the title compound (3.85 g).

MS, found: 429.2.

D) N-((2R,3S)-2-(((cis-4-(2-(trifluoromethyl)phenyl)cyclohexyl)oxy)methyl)piperidin-3-yl)methanesulfonamide A mixture of N-(2-(((cis-4-(2-(trifluoromethyl)phenyl)cyclohexyl)oxy)methyl)pyridin-3-yl)methanesulfonamide (0.93 g), 5% rhodium/carbon (0.893 g), ethanol (27 ml) and acetic acid (3.00 ml) was stirred at room temperature under a hydrogen atmosphere for 11 hr. The mixture was filtered, and the solvent was evaporated under reduced pressure. The residue was dissolved in ethyl acetate, the organic layer was washed with 1 mol/l aqueous sodium hydroxide solution and saturated brine, dried over anhydrous sodium sulfate, and the solvent was evaporated under reduced pressure. The residue was washed with IPE, and recrystallized from ethanol/hexane to give a white solid (361 mg). The mother liquor was concentrated under reduced pressure. The residue was purified by NH silica gel chromatography (ethyl acetate/hexane) to give a white solid (208 mg). The obtained white solids (361 mg and 208 mg) were combined, and separated by HPLC (column: CHIRALPAK AD(LF001), 50 mmID× 500 mmL, manufactured by Daicel Corporation, mobile phase: hexane/2-propanol/diethylamine=900/100/1), and a fraction having a shorter retention time was obtained as the title compound (0.257 g).

$^1$H NMR (300 MHz, CDCl$_3$) δ 1.51 (2H, brs), 1.57-1.88 (8H, m), 2.03 (3H, d, J=13.0 Hz), 2.71 (1H, td, J=12.0, 2.8 Hz), 2.86-2.96 (2H, m), 2.99 (3H, s), 3.09 (1H, d, J=11.0 Hz), 3.39 (1H, dd, J=9.3, 7.8 Hz), 3.54 (1H, dd, J=9.5, 4.5 Hz), 3.60-3.69 (2H, m), 5.35 (1H, d, J=7.6 Hz), 7.27-7.33 (1H, m), 7.43-7.54 (2H, m), 7.61 (1H, s).

Example 24

N-((2R,3S)-1-acetyl-2-(((cis-4-(2-(trifluoromethyl)phenyl)cyclohexyl)oxy)methyl)piperidin-3-yl) methanesulfonamide To a solution of N-((2R,3S)-2-(((cis-4-(2-(trifluoromethyl)phenyl)cyclohexyl)oxy)methyl)piperidin-3-yl)methanesulfonamide (97.2 mg) and triethylamine (0.094 ml) in THF (5 ml) was added acetic anhydride (0.042 ml) at room temperature, and the mixture was stirred under a calcium chloride tube dry atmosphere overnight. Water was added to the mixture at room temperature, and the mixture was extracted with ethyl acetate. The organic layer was washed with water and saturated brine, dried over anhydrous magnesium sulfate, and the solvent was evaporated under reduced pressure. The residue was purified by silica gel chromatography and NH silica gel column chromatography (ethyl acetate/hexane) to give the title compound (87.8 mg).

$^1$H NMR (300 MHz, CDCl$_3$) δ 1.48-2.31 (14H, m), 2.50-3.22 (5H, m), 3.31-3.79 (3H, m), 3.84-4.06 (1H, m), 4.30-4.65 (1H, m), 5.17 (1H, dt, J=9.0, 4.4 Hz), 5.63 (1H, brs), 6.31 (1H, d, J=7.6 Hz), 7.20-7.29 (1H, m), 7.47-7.64 (3H, m).

Example 25

N-((2R,3S)-2-(((cis-4-(2,3-difluorophenyl)cyclohexyl)oxy)methyl)-1-glycoloylpiperidin-3-yl)methanesulfonamide To a solution of N-((2R,3S)-2-(((cis-4-(2,3-difluorophenyl)cyclohexyl)oxy)methyl)piperidin-3-yl)methanesulfonamide (100.2 mg) in pyridine (2 ml) was added 2-chloro-2-oxoethyl acetate (51 mg) at room temperature. The mixture was stirred under a calcium chloride tube dry atmosphere at the same temperature overnight. To the reaction mixture was added 1 mol/l hydrochloric acid at room temperature, and the mixture was extracted with ethyl acetate. The extract was successively washed with saturated aqueous sodium hydrogen carbonate solution, and saturated brine, dried over anhydrous sodium sulfate, and the solvent was evaporated under reduced pressure. The residue was dissolved in methanol (2 ml), 1 mol/l aqueous sodium hydroxide solution (1.25 ml) was added at 0° C., and the mixture was stirred at room temperature for 1 hr. To the reaction mixture was added water at room temperature, and the mixture was extracted with ethyl acetate. The extract was washed with saturated brine, dried over anhydrous sodium sulfate, and the solvent was evaporated under reduced pressure. The residue was purified by silica gel column chromatography (ethyl acetate/hexane) to give the title compound (104 mg).

$^1$H NMR (300 MHz, CDCl$_3$) δ 1.58-2.23 (11H, m), 2.70-3.00 (2H, m), 3.01 (3H, s), 3.05-3.37 (1H, m), 3.44-4.00 (5H, m), 4.01-4.62 (3H, m), 4.79-5.29 (1H, m), 5.89 (1H, d, J=7.95 Hz), 6.81-7.15 (3H, m).

Example 26

N-(cis-2-(((cis-4-(2-methoxyphenyl)cyclohexyl)oxy)methyl)piperidin-3-yl)methanesulfonamide A) 8-(2-methoxyphenyl)-1,4-dioxaspiro[4.5]dec-7-ene To a mixed solution of 1,4-dioxaspiro[4.5]dec-7-en-8-yl trifluoromethanesulfonate (3.00 g), (2-methoxyphenyl)boronic acid (2.37 g), sodium carbonate (4.41 g) and lithium chloride (22 mg) in DME (40 ml)/water (10 ml) was added tetrakis(triphenylphosphine)palladium(0) (601 mg), and the mixture was stirred under a nitrogen atmosphere at 90° C. for 2 hr. To the reaction mixture was added water, and the mixture was extracted with ethyl acetate. The obtained organic layer was washed successively with saturated aqueous sodium hydrogen carbonate solution and saturated brine, dried over anhydrous magnesium sulfate and the solvent was evaporated under reduced pressure. The residue was purified by silica gel column chromatography (ethyl acetate/hexane) to give the title compound (1.60 g).

MS, found: 247.1.

B) 4-(2-methoxyphenyl)cyclohexanone

To a solution of 8-(2-methoxyphenyl)-1,4-dioxaspiro[4.5]dec-7-ene (1.60 g) in ethanol (25 ml) was added 10% palladium/carbon (346 mg), and the mixture was stirred under a hydrogen atmosphere (normal pressure) at room temperature for 2 hr. The reaction mixture was filtered, and the filtrate was concentrated under reduced pressure. To a solution of the residue in acetone (15 ml) was added 2 mol/l hydrochloric acid (15 ml), and the mixture was stirred at 60° C. for 2 hr. The reaction mixture was extracted with ethyl acetate. The obtained organic layer was washed successively with saturated aqueous sodium hydrogen carbonate solution and saturated brine, dried over anhydrous magnesium sulfate, and the solvent was evaporated under reduced pressure. The residue was purified by silica gel column chromatography (ethyl acetate/hexane) to give the title compound (1.02 g).

MS, found: 205.1.

C) cis-4-(2-methoxyphenyl)cyclohexanol

Under a nitrogen atmosphere, to a solution of 4-(2-methoxyphenyl)cyclohexanone (1.00 g) in THF (20 ml) was added dropwise lithium tri(sec-butyl)borohydride 1 mol/l THF solution (6.4 ml) at 0° C., and the mixture was stirred at the same temperature for 1 hr. To the reaction mixture were successively added water and 30% hydrogen peroxide water at 0° C., and the mixture was stirred at the same temperature for 5 min and extracted with ethyl acetate. The obtained organic layer was washed with saturated brine, dried over anhydrous magnesium sulfate, and the solvent was evaporated under reduced pressure. The residue was purified by silica gel column chromatography (ethyl acetate/hexane) to give the title compound (893 mg).

$^1$H NMR (300 MHz, DMSO-d$_6$) δ 1.36-1.59 (4H, m), 1.66-1.87 (4H, m), 2.80-2.95 (1H, m), 3.76 (3H, s), 3.86-3.94 (1H, m), 4.22-4.39 (1H, m), 6.76-7.00 (2H, m), 7.04-7.27 (2H, m).

D) 3-bromo-2-(((cis-4-(2-methoxyphenyl)cyclohexyl)oxy)methyl)pyridine

To a solution of cis-4-(2-methoxyphenyl)cyclohexanol (889 mg) in THF (20 ml) was added 60% sodium hydride (345 mg) at 0° C., and the mixture was stirred at under a nitrogen atmosphere at room temperature for 2 hr. To the reaction mixture was added 3-bromo-2-(chloromethyl)pyridine (1.16 g), and the mixture was stirred at room temperature for 2 hr, and at 70° C. for 3 hr. To the reaction mixture was added water, and the mixture was extracted with ethyl acetate. The obtained organic layer was washed successively with water and saturated brine, dried over anhydrous magnesium sulfate, and the solvent was evaporated under reduced pressure. The residue was purified by silica gel column chromatography (ethyl acetate/hexane) to give the title compound (743 mg).

MS, found: 376.0, 378.0.

E) N-(2-(((cis-4-(2-methoxyphenyl)cyclohexyl)oxy)methyl)pyridin-3-yl)methanesulfonamide A mixture of 3-bromo-2-(((cis-4-(2-methoxyphenyl)cyclohexyl)oxy)methyl)pyridine (740 mg), methanesulfonamide (224 mg), di-tert-butyl(2',4',6'-triisopropylbiphenyl-2-yl)phosphine (100 mg), tris(dibenzylideneacetone)dipalladium(0) (90 mg), cesium carbonate (961 mg) and DME (10 ml) was heated under reflux under a nitrogen atmosphere for 6 hr. To the reaction mixture was added water, and the mixture was extracted with ethyl acetate. The obtained organic layer was washed with saturated brine, dried over anhydrous magnesium sulfate, and the solvent was evaporated under reduced pressure. The residue was purified by silica gel column chromatography (ethyl acetate/hexane) to give the title compound (723 mg).

MS, found: 391.2.

F) N-(cis-2-(((cis-4-(2-methoxyphenyl)cyclohexyl)oxy)methyl)piperidin-3-yl)methanesulfonamide To a mixed solution of N-(2-(((cis-4-(2-methoxyphenyl)cyclohexyl)oxy)methyl)pyridin-3-yl)methanesulfonamide (669 mg) in ethanol (9 ml)/acetic acid (1 ml) was added 5% rhodium/carbon (705 mg), and the mixture was stirred under a hydrogen atmosphere (normal pressure) at room temperature for 20 hr. Rhodium/carbon was filtered off, toluene was added, and the solvent was evaporated under reduced pressure. The residue was washed with diisopropyl ether, and the obtained solid was dissolved in ethyl acetate. Saturated aqueous sodium hydrogen carbonate solution was added, and the aqueous layer was extracted with ethyl acetate. The combined organic layers were washed successively with water and saturated brine, dried over anhydrous magnesium sulfate, and the solvent was evaporated under reduced pressure. The residue was purified by NH silica gel column chromatography (ethyl acetate/hexane) to give the title compound (123 mg).

$^1$H NMR (300 MHz, CDCl$_3$) δ 1.48-1.89 (9H, m), 1.94-2.11 (4H, m), 2.59-2.76 (1H, m), 2.84-3.15 (6H, m), 3.28-3.43 (1H, m), 3.45-3.54 (1H, m), 3.56-3.69 (2H, m), 3.82 (3H, s), 5.27-5.54 (1H, m), 6.81-6.88 (1H, m), 6.89-6.98 (1H, m), 7.09-7.24 (2H, m).

Example 27

N-((2R,3S)-2-(((cis-4-(2-methoxyphenyl)cyclohexyl)oxy)methyl)piperidin-3-yl)methanesulfonamide N-(cis-2-(((cis-4-(2-methoxyphenyl)cyclohexyl)oxy)methyl)piperidin-3-yl)methanesulfonamide (2.0 g) was separated by HPLC (column: CHIRALPAK AD(AF003), 50 mmID×500 mmL, manufactured by Daicel Corporation, mobile phase: hexane/2-propanol/diethylamine=700/300/1), and a fraction having a shorter retention time was obtained as the title compound (783 mg).

$^1$H NMR (300 MHz, CDCl$_3$) δ 1.45-1.83 (9H, m), 1.90-2.10 (4H, m), 2.62-2.76 (1H, m), 2.86-3.13 (6H, m), 3.32-3.42 (1H, m), 3.46-3.55 (1H, m), 3.56-3.68 (2H, m), 3.82 (3H, s), 5.30-5.51 (1H, m), 6.82-6.88 (1H, m), 6.88-6.97 (1H, m), 7.10-7.24 (2H, m).

Example 28

N-((2R,3S)-1-(cyclopropylcarbonyl)-2-(((cis-4-(2-methoxyphenyl)cyclohexyl)oxy)methyl)piperidin-3-yl)methanesulfonamide To a solution of N-((2R,3S)-2-(((cis-4-(2-methoxyphenyl)cyclohexyl)oxy)methyl)piperidin-3-yl)methanesulfonamide (200 mg) and triethylamine (102 mg) in THF (5 ml) was added cyclopropanecarbonyl chloride (79 mg) at room temperature, and the mixture was stirred at the same temperature for 30 min. To the reaction mixture was added water, and the mixture was extracted with ethyl acetate. The extract was washed with saturated brine, dried over anhydrous magnesium sulfate, and the solvent was evaporated under reduced pressure. The residue was purified by silica gel column chromatography (ethyl acetate/hexane) to give the title compound (227 mg).

$^1$H NMR (300 MHz, DMSO-d$_6$) δ 0.57-0.87 (4H, m), 1.31-1.81 (10H, m), 1.83-2.07 (3H, m), 2.56-3.07 (4H, m), 3.10-3.88 (8H, m), 3.99-5.01 (2H, m), 6.80-7.39 (5H, m).

Example 29 isopropyl cis-3-((dimethylsulfamoyl)amino)-2-(((1-(pyrimidin-2-yl)piperidin-4-yl)oxy)methyl)piperidine-1-carboxylate A) tert-butyl 4-((3-bromopyridin-2-yl)methoxy)piperidine-1-carboxylate A solution of tert-butyl 4-hydroxypiperidine-1-carboxylate (9.63 g) in THF (100 ml) was cooled to 0° C., 60% sodium hydride (3.19 g) was added, and the mixture was stirred for 20 min. To the reaction mixture was added a solution of 3-bromo-2-(bromomethyl)pyridine (10.00 g) in THF (100 ml), and the mixture was stirred at room temperature under an argon atmosphere overnight. To the mixture was added water at 0° C., and the mixture was extracted with ethyl acetate. The organic layer was washed with water and saturated brine, dried over anhydrous magnesium sulfate, and the solvent was evaporated under reduced pressure.

The residue was purified by silica gel chromatography (ethyl acetate/hexane) to give the title compound (13.12 g).
MS, found: 371.1, 373.1.

B) tert-butyl 4-((3-((dimethylsulfamoyl)amino)pyridin-2-yl)methoxy)piperidine-1-carboxylate To a mixed solution of tert-butyl 4-((3-bromopyridin-2-yl)methoxy)piperidine-1-carboxylate (5 g), N,N-dimethylsulfuric acid diamide (2.007 g), di-tert-butyl(2',4',6'-triisopropylbiphenyl-2-yl)phosphine (0.686 g), and cesium carbonate (6.58 g) in DME (50 ml) was added tris(dibenzylideneacetone)dipalladium(0) (0.617 g) at room temperature. The mixture was heated under reflux at 100° C. under an argon atmosphere for 20 hr. The reaction mixture was neutralized with 1 mol/l hydrochloric acid, and extracted with ethyl acetate. The organic layer was washed with saturated brine, and the solvent was evaporated under reduced pressure. The residue was purified by silica gel chromatography (ethyl acetate/hexane, methanol/ethyl acetate) and NH silica gel chromatography (ethyl acetate/hexane) to give the title compound (4.10 g).
MS, found: 415.2.

C) tert-butyl 4-((cis-3-((dimethylsulfamoyl)amino)piperidin-2-yl)methoxy)piperidine-1-carboxylate To a mixed solution of tert-butyl 4-((3-((dimethylsulfamoyl)amino)pyridin-2-yl)methoxy)piperidine-1-carboxylate (4.00 g) in ethanol (100 ml) and acetic acid (10.00 ml) was added 5% rhodium/carbon (3.97 g) at room temperature. The mixture was stirred at room temperature under a hydrogen atmosphere overnight. The mixed solution was filtered, and the solvent was evaporated under reduced pressure. To the residue were added ethyl acetate and hexane and the precipitated solid was collected by filtration. The obtained solid was dissolved in saturated aqueous sodium hydrogen carbonate solution, and the mixture was extracted with ethyl acetate. The organic layer was dried over anhydrous sodium sulfate, and the solvent was evaporated under reduced pressure to give the title compound (1.870 g).
MS, found: 421.2.

D) isopropyl cis-2-(((1-(tert-butoxycarbonyl)piperidin-4-yl)oxy)methyl)-3-((dimethylsulfamoyl)amino)piperidine-1-carboxylate To a solution of tert-butyl 4-((cis-3-((dimethylsulfamoyl)amino)piperidin-2-yl)methoxy)piperidine-1-carboxylate (100 mg) and N,N-diisopropylethylamine (0.164 ml) in THF (3 ml) was added isopropyl chloroformate (29.1 mg) at room temperature, and the mixture was stirred for 2 days. Water was added to the mixture at room temperature, and the mixture was extracted with ethyl acetate. The organic layer was washed with saturated brine, dried over anhydrous sodium sulfate, and the solvent was evaporated under reduced pressure. The residue was purified by silica gel chromatography (ethyl acetate/hexane) to give the title compound (120 mg).
MS, found: 407.2.

E) isopropyl cis-3-((dimethylsulfamoyl)amino)-2-((piperidin-4-yloxy) methyl) piperidine-1-carboxylate hydrochloride To isopropyl cis-2-(((1-(tert-butoxycarbonyl)piperidin-4-yl)oxy)methyl)-3-((dimethylsulfamoyl)amino)piperidine-1-carboxylate (120 mg) was added 4 mol/l hydrogen chloride ethyl acetate solution (5 ml) at room temperature, and the mixture was stirred for 2 hr. The solvent in the mixture was evaporated under reduced pressure to give the title compound (106 mg).
MS, found: 407.2.

F) isopropyl cis-3-((dimethylsulfamoyl)amino)-2-(((1-(pyrimidin-2-yl)piperidin-4-yl)oxy)methyl)piperidine-1-carboxylate To a solution of isopropyl cis-3-((dimethylsulfamoyl)amino)-2-((piperidin-4-yloxy)methyl)piperidine-1-carboxylate hydrochloride (106 mg) and cesium carbonate (235 mg) in NMP (2 ml) was added 2-chloropyrimidine (41.2 mg), and the mixture was stirred at 90° C. for 2 hr. Water was added to the mixture at room temperature, and the mixture was extracted with ethyl acetate. The organic layer was washed with saturated brine, dried over anhydrous sodium sulfate, and the solvent was evaporated under reduced pressure. The residue was purified by silica gel chromatography (ethyl acetate/hexane) to give the title compound (89 mg).
$^1$H NMR (300 MHz, CDCl$_3$) δ 1.24 (3H, s), 1.26 (3H, s), 1.42-1.58 (2H, m), 1.60-1.66 (1H, m), 1.67-1.79 (2H, m), 1.88-2.00 (2H, m), 2.00-2.11 (1H, m), 2.69-2.78 (1H, m), 2.80 (6H, s), 3.35-3.54 (3H, m), 3.62 (1H, tt, J=8.2, 3.9 Hz), 3.70 (1H, dd, J=9.7, 4.4 Hz), 3.96 (2H, dd, J=9.8, 8.3 Hz), 4.26 (2H, dt, J=13.3, 5.1 Hz), 4.46-4.69 (1H, m), 4.93 (1H, spt, J=6.2 Hz), 5.51 (1H, d, J=8.0 Hz), 6.47 (1H, t, J=4.7 Hz), 8.29 (2H, d, J=4.5 Hz).

Example 30

(2R,3S)—N-ethyl-3-((methylsulfonyl)amino)-2-(((cis-4-phenylcyclohexyl)oxy)methyl)piperidine-1-carboxamide To a solution of N-[cis-2-(4-phenyl-cyclohexyloxymethyl)-piperidin-3-yl]-methanesulfonamide (280 mg), triethylamine (0.319 ml) in THF (2 ml) was added ethylisocyanate (81 mg) at 0° C., and the mixture was stirred at room temperature overnight. To the reaction mixture was added water, and the mixture was extracted with ethyl acetate. The extract was washed with saturated brine, dried over anhydrous sodium sulfate, and the solvent was evaporated under reduced pressure. The residue was purified by silica gel column chromatography (ethyl acetate/hexane). The obtained compound was separated by HPLC (column: CHIRALPAK IC(ME001), 50 mmID×500 mmL, manufactured by Daicel Corporation, mobile phase: hexane/2-propanol=200/800), and a fraction having a longer retention time was obtained as the title compound (153 mg).
$^1$H NMR (300 MHz, CDCl$_3$) δ 1.14 (3H, t, J=7.2 Hz), 1.56-1.80 (9H, m), 1.98-2.10 (3H, m), 2.45-2.59 (1H, m), 2.84 (1H, qd, J=12.7, 2.8 Hz), 3.01 (3H, s), 3.26 (2H, qd, J=7.2, 5.3 Hz), 3.52-3.81 (4H, m), 3.93 (1H, dd, J=9.2, 7.7 Hz), 4.48-4.59 (1H, m), 4.70 (1H, t, J=5.1 Hz), 5.74 (1H, d, J=7.7 Hz), 7.14-7.35 (5H, m).

Example 31

N-((2R,3S)-1-(cyclopropylcarbonyl)-2-(((cis-4-phenylcyclohexyl)oxy)methyl)piperidin-3-yl)methanesulfonamide To a solution of N-((2R,3S)-2-(((cis-4-phenylcyclohexyl)oxy)methyl)piperidin-3-yl)methanesulfonamide (58 mg), triethylamine (0.044 ml) in THF (3 ml) was added cyclopropanecarbonyl chloride (0.022 ml) at room temperature, and the mixture was stirred under a calcium chloride tube dry atmosphere overnight. To the reaction mixture was added water, and the mixture was extracted with ethyl acetate. The extract was washed with saturated brine, dried over anhydrous sodium sulfate, and the solvent was evaporated under reduced pressure. The residue was purified by silica gel column chromatography (ethyl acetate/hexane) to give the title compound (62 mg).

$^1$H NMR (300 MHz, CDCl$_3$) δ 0.74-0.85 (2H, m), 0.94-1.05 (2H, m), 1.58-1.88 (10H, m), 2.01-2.23 (3H, m), 2.45-2.63 (1H, m), 2.92-3.18 (4H, m), 3.41-3.77 (3H, m), 3.89-4.60 (2H, m), 4.69-5.23 (1H, m), 5.46-6.39 (1H, m), 7.13-7.25 (3H, m), 7.27-7.34 (2H, m).

Example 32 methyl (2R,3S)-3-((methylsulfonyl)amino)-2-(((cis-4-(2-(trifluoromethyl)phenyl)cyclohexyl)oxy)methyl)piperidine-1-carboxylate To a solution of N-((2R,3S)-2-(((cis-4-(2-(trifluoromethyl)phenyl)cyclohexyl)oxy)methyl)piperidin-3-yl)methanesulfonamide (51.2 mg) and triethylamine (0.049 ml) in THF (2 ml) was added methyl chloroformate (0.018 ml) at room temperature, and the mixture was stirred under a calcium chloride tube dry atmosphere overnight. Water was added to the mixture at room temperature, and the mixture was extracted with ethyl acetate. The organic layer was washed with water and saturated brine, dried over anhydrous sodium sulfate, and the solvent was evaporated under reduced pressure. The residue was purified by silica gel chromatography (ethyl acetate/hexane) to give the title compound (56.3 mg).

$^1$H NMR (300 MHz, CDCl$_3$) δ 1.55-1.89 (9H, m), 1.97-2.19 (3H, m), 2.80 (1H, td, J=13.3, 3.0 Hz), 2.88-3.10 (4H, m), 3.44-3.71 (3H, m), 3.72-3.78 (3H, m), 4.02 (2H, t, J=9.1 Hz), 4.67 (1H, brs), 6.15 (1H, brs), 7.19-7.31 (1H, m), 7.47-7.67 (3H, m).

Example 340

N-((2R,3S)-1-glycoloyl-2-(((cis-4-(2,3,6-trifluorophenyl)cyclohexyl)oxy)methyl)piperidin-3-yl)methanesulfonamide To a mixture of N-((2R,3S)-2-(((cis-4-(2,3,6-trifluorophenyl)cyclohexyl)oxy)methyl)piperidin-3-yl)methanesulfonamide (100.8 mg) and pyridine (2.0 ml) was added 2-chloro-2-oxoethyl acetate (49.1 mg) at room temperature. The mixture was stirred at room temperature overnight. To the mixture was added 1 mol/l hydrochloric acid at room temperature, and the mixture was extracted with ethyl acetate. The organic layer was separated, washed with saturated aqueous sodium hydrogen carbonate solution and saturated brine, dried over anhydrous sodium sulfate, and concentrated under reduced pressure. To a mixture of the residue and methanol (2.0 ml) was added 1 mol/l aqueous sodium hydroxide solution at 0° C. The mixture was stirred at room temperature for 1 hr. Water was added to the mixture at room temperature, and the mixture was extracted with ethyl acetate. The organic layer was separated, washed with saturated brine, dried over anhydrous sodium sulfate, and concentrated under reduced pressure. The residue was purified by silica gel column chromatography (ethyl acetate/hexane) to give the title compound (108.1 mg).

$^1$H NMR (300 MHz, CDCl$_3$) δ 1.48-1.68 (6H, m), 1.85-2.19 (6H, m), 2.75-3.12 (4H, m), 3.13-3.89 (6H, m), 3.93-4.66 (3H, m), 4.87-5.16 (1H, m), 5.40 (1H, d, J=8.7 Hz), 6.66-6.83 (1H, m), 6.96 (1H, qd, J=9.1, 4.9 Hz).

The compounds of Examples 33-339 and 341-372 were produced according to the aforementioned production methods, a method shown in the Examples, or a method analogous thereto. The Example compounds produced are shown in the following Tables. In the Tables, MS shows measured values.

TABLE 1-1

| Ex. No. | IUPAC name | Structure | MS |
|---|---|---|---|
| 1 | N-(cis-2-(((cis-4-isopropylcyclohexyl)oxy)methyl)-piperidin-3-yl)methanesulfonamide | 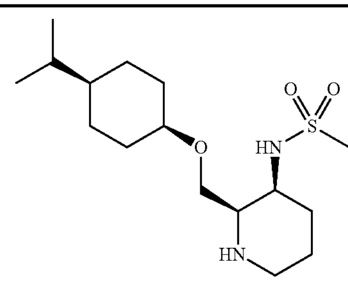 | 333.2 |
| 2 | (2R,3S)-N-ethyl-2-(((cis-4-isopropylcyclohexyl)oxy)methyl)-3-((methylsulfonyl)amino)piperidine-1-carboxamide | 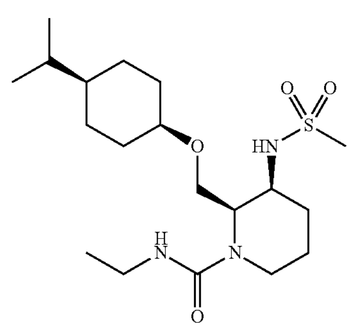 [SMILES: CCNC(=O)N1CCC[C@H](NS(C)(=O)=O)[C@@H]1CO[C@H]1CC[C@@H](C(C)C)CC1] | 404.2 |

TABLE 1-1-continued

| Ex. No. | IUPAC name | Structure | MS |
|---|---|---|---|
| 3 | N-((2R,3S)-2-(((cis-4-phenylcyclohexyl)oxy)methyl)-piperidin-3-yl)methanesulfonamide | 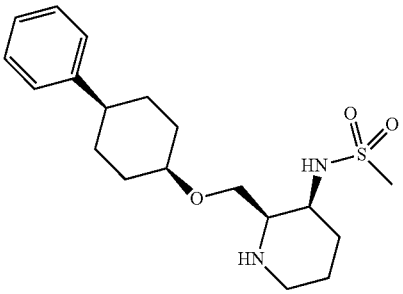 [SMILES: CS(=O)(=O)N[C@H]1CCCN[C@H]1CO[C@H]1CC[C@@H](c2ccccc2)CC1] | 367.1 |
| 4 | N-((2R,3S)-1-acetyl-2-(((cis-4-phenylcyclohexyl)oxy)methyl)-piperidin-3-yl)methanesulfonamide | 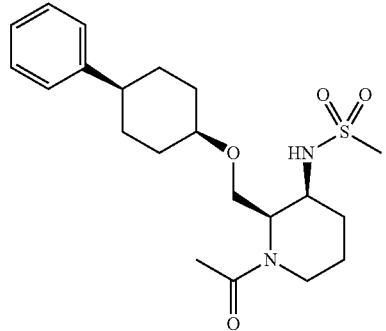 | 409.2 |
| 5 | methyl (2R,3S)-3-((methylsulfonyl)amino)-2-(((cis-4-phenylcyclohexyl)oxy)methyl)-piperidine-1-carboxylate | 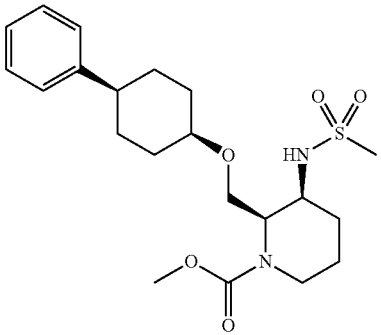 [SMILES: COC(=O)N1CCC[C@H](NS(C)(=O)=O)[C@@H]1CO[C@H]1CC[C@@H](c2ccccc2)CC1] | 425.1 |
| 6 | N-(cis-2-(((cis-4-(3,5-difluorophenyl)cyclohexyl)oxy)-methyl)piperidin-3-yl)methanesulfonamide acetate | 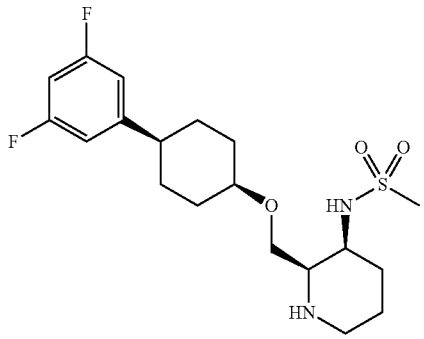 [SMILES: CS(=O)(=O)N[C@H]1CCCN[C@H]1CO[C@H]1CC[C@@H](c2cc(F)cc(F)c2)CC1] | 403.2 |

TABLE 1-2

| Ex. No. | IUPAC name | Structure | MS |
|---|---|---|---|
| 7 | N-((2R,3S)-2-(((cis-4-(3,5-difluorophenyl)cyclohexyl)oxy)-methyl)piperidin-3-yl)methanesulfonamide | 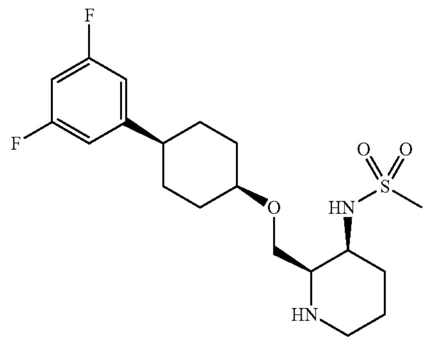 [SMILES: CS(=O)(=O)N[C@H]1CCCN[C@H]1CO[C@H]1CC[C@@H](c2cc(F)cc(F)c2)CC1] | 403.2 |
| 8 | N-((2R,3S)-1-acetyl-2-(((cis-4-(3,5-difluorophenyl)cyclohexyl)oxy)-methyl)piperidin-3-yl)methanesulfonamide | 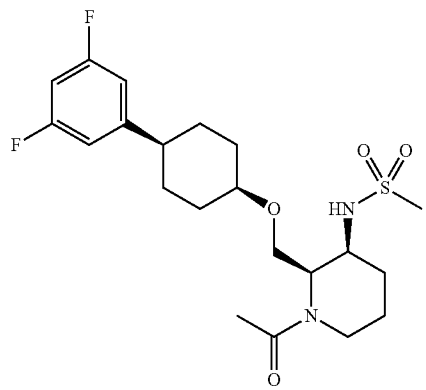 [SMILES: CC(=O)N1CCC[C@H](NS(C)(=O)=O)[C@@H]1CO[C@H]1CC[C@@H](c2cc(F)cc(F)c2)CC1] | 445.3 |
| 9 | N-(cis-2-(((cis-4-(2,5-difluorophenyl)cyclohexyl)oxy)-methyl)piperidin-3-yl)methanesulfonamide | 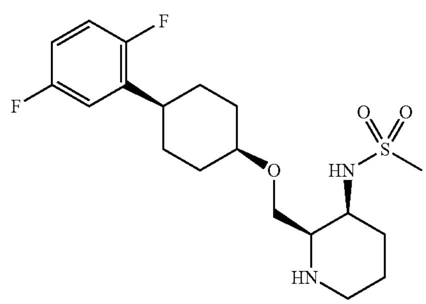 [SMILES: CS(=O)(=O)N[C@H]1CCCN[C@H]1CO[C@H]1CC[C@@H](c2cc(F)ccc2F)CC1] | 403.2 |
| 10 | N-((2R,3S)-2-(((cis-4-(2,5-difluorophenyl)cyclohexyl)oxy)-methyl)piperidin-3-yl)methanesulfonamide | 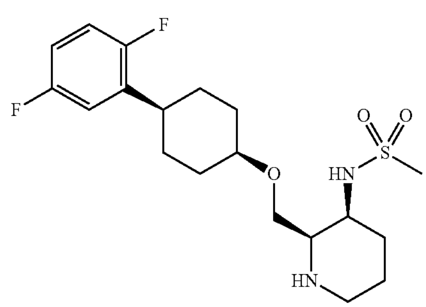 [SMILES: CS(=O)(=O)N[C@H]1CCCN[C@H]1CO[C@H]1CC[C@@H](c2cc(F)ccc2F)CC1] | 403.2 |

TABLE 1-2-continued

| Ex. No. | IUPAC name | Structure | MS |
|---|---|---|---|
| 11 | methyl (2R,3S)-2-(((cis-4-(2,5-difluorophenyl)cyclohexyl)oxy)-methyl)-3-((methylsulfonyl)amino)piperidine-1-carboxylate | 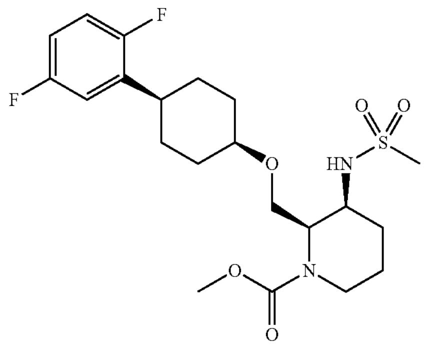 [SMILES: COC(=O)N1CCC[C@H](NS(C)(=O)=O)[C@@H]1CO[C@H]1CC[C@@H](c2cc(F)ccc2F)CC1] | 461.2 |
| 12 | N-(cis-2-(((cis-4-(2,6-difluorophenyl)cyclohexyl)oxy)-methyl)piperidin-3-yl)sulfonamide | 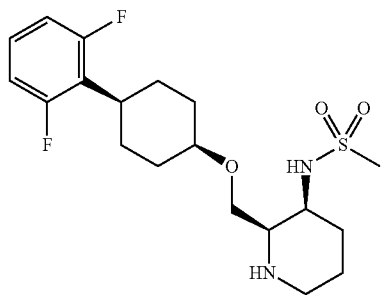 [SMILES: CS(=O)(=O)N[C@H]1CCCN[C@H]1CO[C@H]1CC[C@@H](c2c(F)cccc2F)CC1] | 403.2 |

TABLE 1-3

| Ex. No. | IUPAC name | Structure | MS |
|---|---|---|---|
| 13 | N-((2R,3S)-2-(((cis-4-(2,6-difluorophenyl)cyclohexyl)oxy)-methyl)piperidin-3-yl)methanesulfonamide | 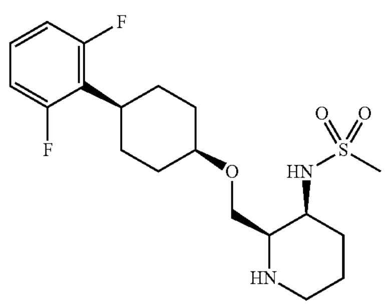 [SMILES: CS(=O)(=O)N[C@H]1CCCN[C@H]1CO[C@H]1CC[C@@H](c2c(F)cccc2F)CC1] | 403.2 |
| 14 | N-((2R,3S)-1-acetyl-2-(((cis-4-(2,6-difluorophenyl)cyclohexyl)oxy)-methyl)piperidin-3-yl)methanesulfonamide | 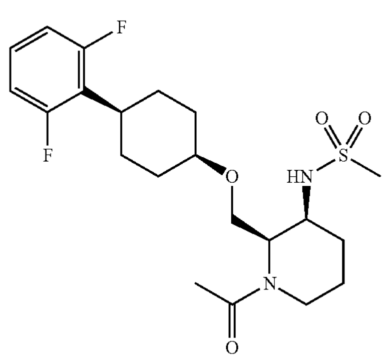 [SMILES: CC(=O)N1CCC[C@H](NS(C)(=O)=O)[C@@H]1CO[C@H]1CC[C@@H](c2c(F)cccc2F)CC1] | 445.2 |

TABLE 1-3-continued

| Ex. No. | IUPAC name | Structure | MS |
|---|---|---|---|
| 15 | N-((2R,3S)-2-(((cis-4-(3-fluorophenyl)cyclohexyl)oxy)-methyl)piperidin-3-yl)methanesulfonamide | 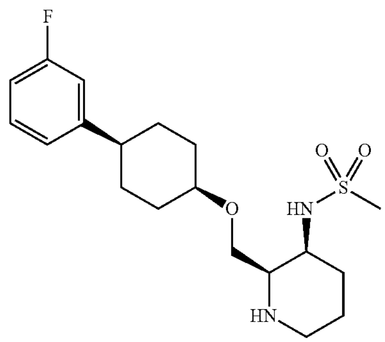 [SMILES: CS(=O)(=O)N[C@H]1CCCN[C@H]1CO[C@H]1CC[C@@H](c2cccc(F)c2)CC1] | 385.1 |
| 16 | N-((2R,3S)-1-(cyclopropylcarbonyl)-2-(((cis-4-(3-fluorophenyl)cyclohexyl)oxy)-methyl)piperidin-3-yl)methanesulfonamide | 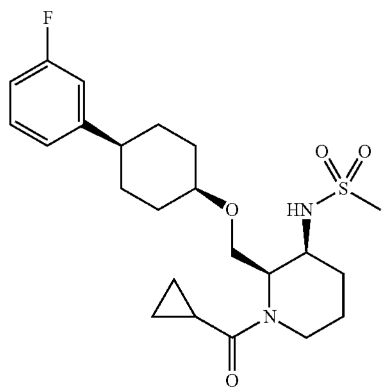 [SMILES: CS(=O)(=O)N[C@H]1CCCN(C(=O)C2CC2)[C@H]1CO[C@H]1CC[C@@H](c2cccc(F)c2)CC1] | 453.2 |
| 17 | N-(cis-2-(((cis-4-(2,3-difluorophenyl)cyclohexyl)oxy)-methyl)piperidin-3-yl)methanesulfonamide | 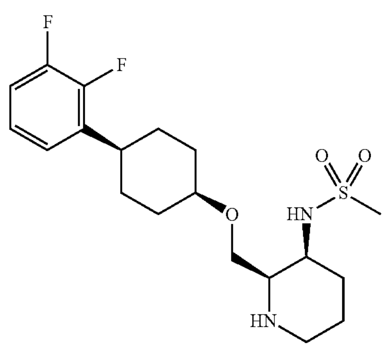 [SMILES: CS(=O)(=O)N[C@H]1CCCN[C@H]1CO[C@H]1CC[C@@H](c2cccc(F)c2F)CC1] | 403.1 |
| 18 | N-((2R,3S)-2-(((cis-4-(2,3-difluorophenyl)cyclohexyl)oxy)-methyl)piperidin-3-yl)methanesulfonamide | 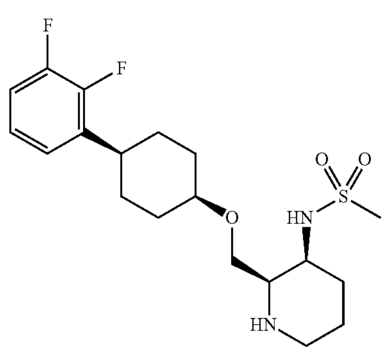 [SMILES: CS(=O)(=O)N[C@H]1CCCN[C@H]1CO[C@H]1CC[C@@H](c2cccc(F)c2F)CC1] | 403.2 |

TABLE 1-4

| Ex. No. | IUPAC name | Structure | MS |
|---|---|---|---|
| 19 | N-((2R,3S)-1-acetyl-2-(((cis-4-(2,3-difluorophenyl)cyclohexyl)oxy)-methyl)piperidin-3-yl)methanesulfonamide | 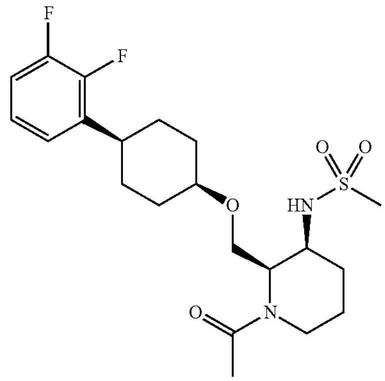 [SMILES: CC(=O)N1CCC[C@H](NS(C)(=O)=O)[C@@H]1CO[C@H]1CC[C@@H](c2cccc(F)c2F)CC1] | 445.2 |
| 20 | methyl (2R,3S)-2-(((cis-4-(2,3-difluorophenyl)cyclohexyl)oxy)-methyl)-3-((methylsulfonyl)amino)piperidine-1-carboxylate | 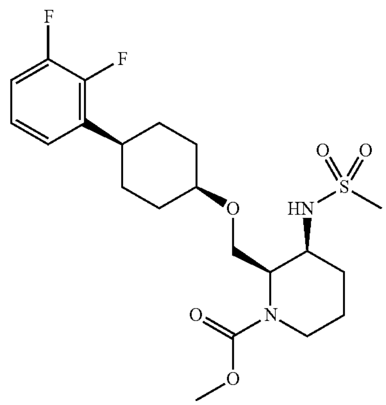 [SMILES: COC(=O)N1CCC[C@H](NS(C)(=O)=O)[C@@H]1CO[C@H]1CC[C@@H](c2cccc(F)c2F)CC1] | 459.2 |
| 21 | N-((2R,3S)-2-(((cis-4-(2,3,6-trifluorophenyl)cyclohexyl)oxy)-methyl)piperidin-3-yl)methanesulfonamide | 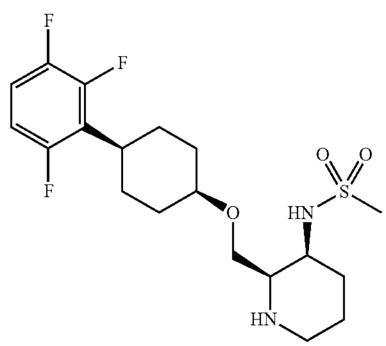 [SMILES: CS(=O)(=O)N[C@H]1CCCN[C@H]1CO[C@H]1CC[C@@H](c2c(F)ccc(F)c2F)CC1] | 421.1 |
| 22 | N-((2R,3S)-1-acetyl-2-(((cis-4-(2,3,6-trifluorophenyl)cyclohexyl)oxy)-methyl)piperidin-3-yl)methanesulfonamide | 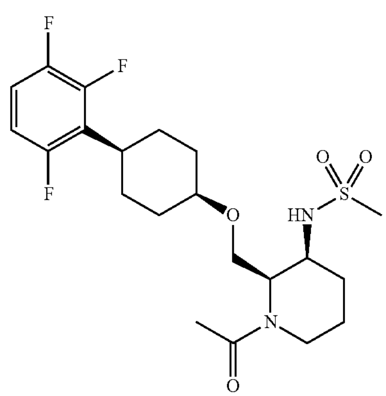 [SMILES: CC(=O)N1CCC[C@H](NS(C)(=O)=O)[C@@H]1CO[C@H]1CC[C@@H](c2c(F)ccc(F)c2F)CC1] | 463.2 |

TABLE 1-4-continued

| Ex. No. | IUPAC name | Structure | MS |
|---|---|---|---|
| 23 | N-((2R,3S)-2-(((cis-4-(2-(trifluoromethyl)phenyl)-cyclohexyl)oxy)methyl)piperidin-3-yl)methanesulfonamide | 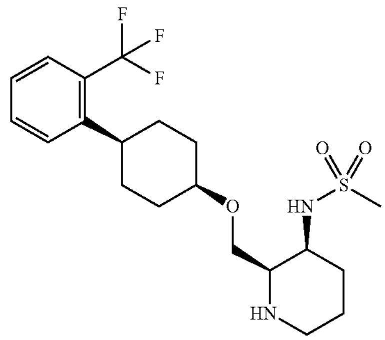 [SMILES: CS(=O)(=O)N[C@H]1CCCN[C@H]1CO[C@H]1CC[C@@H](c2ccccc2C(F)(F)F)CC1] | 435.1 |
| 24 | N-((2R,3S)-1-acetyl-2-(((cis-4-(2-(trifluoromethyl)phenyl)-cyclohexyl)oxy)methyl)piperidin-3-yl)methanesulfonamide | 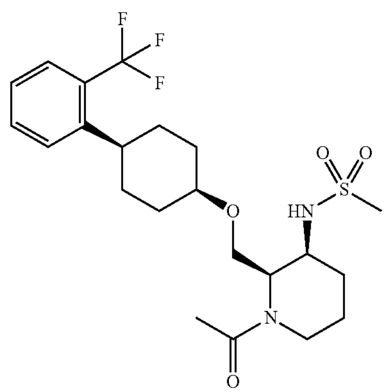 [SMILES: CC(=O)N1CCC[C@H](NS(C)(=O)=O)[C@@H]1CO[C@H]1CC[C@@H](c2ccccc2C(F)(F)F)CC1] | 477.2 |

TABLE 1-5

| Ex. No. | IUPAC name | Structure | MS |
|---|---|---|---|
| 25 | N-((2R,3S)-2-(((cis-4-(2,3-difluorophenyl)cyclohexyl)oxy)-methyl)-1-glycoloylpiperidin-3-yl)methanesulfonamide | 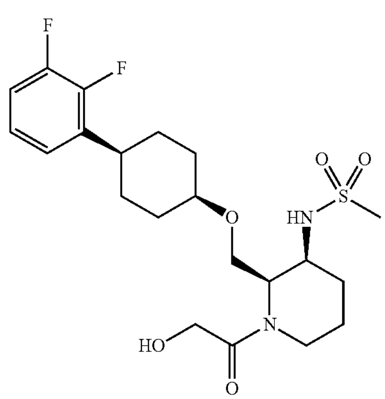 [SMILES: CS(=O)(=O)N[C@H]1CCCN(C(=O)CO)[C@H]1CO[C@H]1CC[C@@H](c2cccc(F)c2F)CC1] | 461.2 |

TABLE 1-5-continued

| Ex. No. | IUPAC name | Structure | MS |
|---|---|---|---|
| 26 | N-(cis-2-(((cis-4-(2-methoxyphenyl)cyclohexyl)oxy)-methyl)piperidin-3-yl) methanesulfonamide | 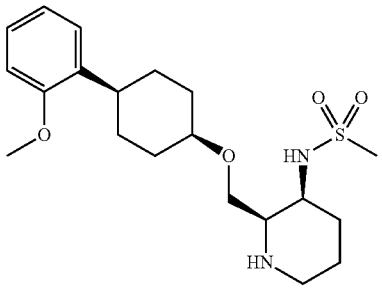 [SMILES: COc1ccccc1[C@H]1CC[C@@H](OC[C@@H]2NCCC[C@@H]2NS(C)(=O)=O)CC1] | 397.2 |
| 27 | N-((2R,3S)-2-(((cis-4-(2-methoxyphenyl)cyclohexyl)oxy)-methyl)piperidin-3-yl)methanesulfonamide | 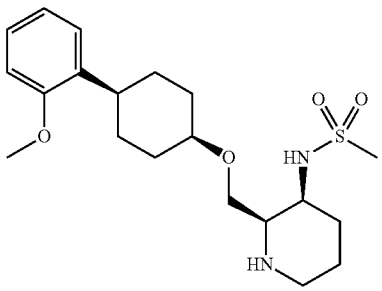 [SMILES: COc1ccccc1[C@H]1CC[C@@H](OC[C@@H]2NCCC[C@@H]2NS(C)(=O)=O)CC1] | 397.2 |
| 28 | N-((2R,3S)-1-(cyclopropylcarbonyl)-2-(((cis-4-(2-methoxyphenyl)cyclohexyl)oxy)-methyl)piperidin-3-yl]methanesulfonamide | 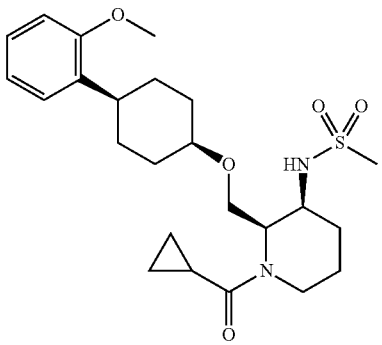 [SMILES: COc1ccccc1[C@H]1CC[C@@H](OC[C@H]2[C@@H](NS(C)(=O)=O)CCCN2C(=O)C2CC2)CC1] | 465.2 |
| 29 | isopropyl cis-3-((dimethylsulfamoyl)amino)-2-(((1-(pyrimidin-2-yl)piperidin-4-yl)oxy)methyl)piperidine-1-carboxylate | 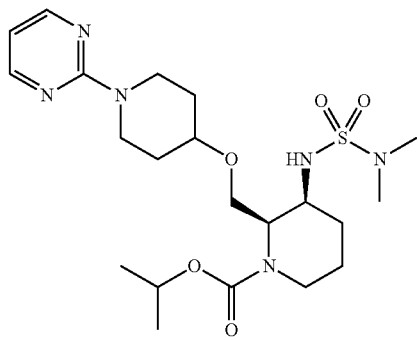 [SMILES: CC(C)OC(=O)N1CCC[C@H](NS(=O)(=O)N(C)C)[C@@H]1COC1CCN(c2ncccn2)CC1] | 485.2 |

TABLE 1-5-continued

| Ex. No. | IUPAC name | Structure | MS |
|---|---|---|---|
| 30 | (2R,3S)-N-ethyl-3-((methylsulfonyl)amino)-2-(((cis-4-phenylcyclohexyl)oxy)methyl)-piperidine-1-carboxamide | 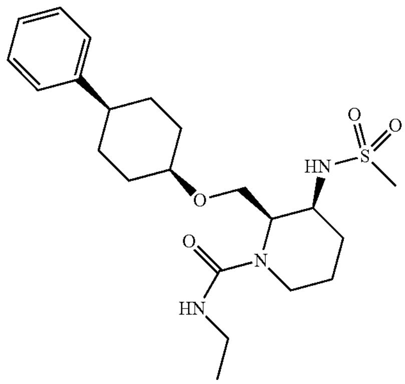 [SMILES: CCNC(=O)N1CCC[C@H](NS(C)(=O)=O)[C@@H]1CO[C@H]1CC[C@@H](c2ccccc2)CC1] | 438.3 |

TABLE 1-6

| Ex. No. | IUPAC name | Structure | MS |
|---|---|---|---|
| 31 | N-((2R,3S)-1-(cyclopropylcarbonyl)-2-(((cis-4-phenylcyclohexyl)oxy)methyl)-piperidin-3-yl)methanesulfonamide | 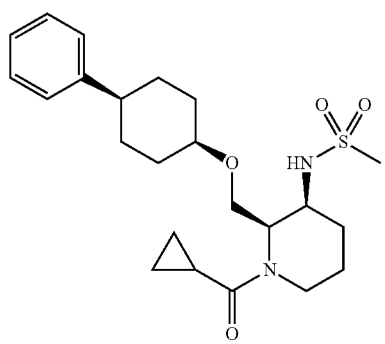 [SMILES: CS(=O)(=O)N[C@H]1CCCN(C(=O)C2CC2)[C@H]1CO[C@H]1CC[C@@H](c2ccccc2)CC1] | 435.2 |
| 32 | methyl (2R,3S)-3-((methylsulfonyl)amino)-2-(((cis-4-(2-(trifluoromethyl)phenyl)-cyclohexyl)oxy)methyl)piperidine-1-carboxylate | 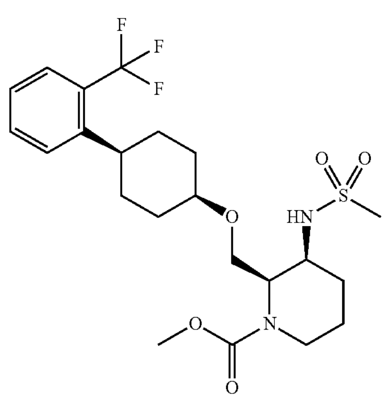 [SMILES: COC(=O)N1CCC[C@H](NS(C)(=O)=O)[C@@H]1CO[C@H]1CC[C@@H](c2ccccc2C(F)(F)F)CC1] | 493.2 |

TABLE 1-6-continued

| Ex. No. | IUPAC name | Structure | MS |
|---|---|---|---|
| 33 | N-((2R,3S)-1-acetyl-2-(((cis-4-isopropylcyclohexyl)oxy)methyl)-piperidin-3-yl)ethanesulfonamide | 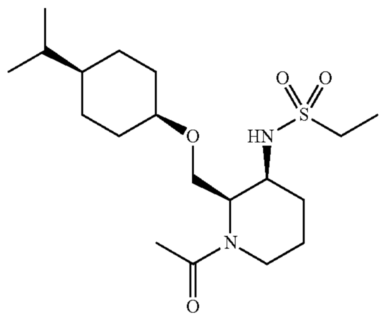 [SMILES: CCS(=O)(=O)N[C@H]1CCCN(C(C)=O)[C@H]1CO[C@H]1CC[C@@H](C(C)C)CC1] | 389.2 |
| 34 | N-(cis-1-benzoyl-2-(((cis-4-methylcyclohexyl)oxy)methyl)-piperidin-3-yl)ethanesulfonamide | 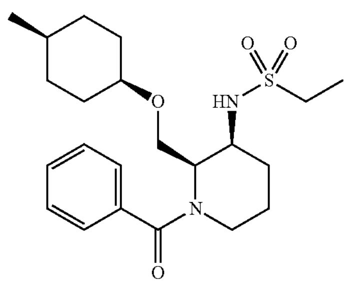 [SMILES: CCS(=O)(=O)N[C@H]1CCCN(C(=O)c2ccccc2)[C@H]1CO[C@H]1CC[C@@H](C)CC1] | 423.2 |
| 35 | N-(cis-1-butyryl-2-(((cis-4-isopropylcyclohexyl)oxy)methyl)-piperidin-3-yl)methanesulfonamide | 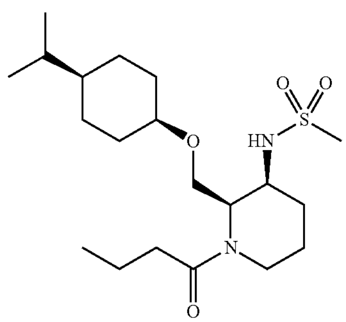 [SMILES: CCCC(=O)N1CCC[C@H](NS(C)(=O)=O)[C@@H]1CO[C@H]1CC[C@@H](C(C)C)CC1] | 403.2 |
| 36 | N-(cis-2-(((cis-4-isopropylcyclohexyl)oxy)methyl)-1-(methylsulfonyl)piperidin-3-yl)methanesulfonamide | 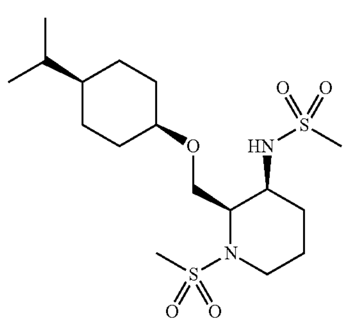 [SMILES: CC(C)[C@H]1CC[C@@H](OC[C@H]2[C@@H](NS(C)(=O)=O)CCCN2S(C)(=O)=O)CC1] | 409.2 |

TABLE 1-7

| Ex. No. | IUPAC name | Structure | MS |
|---|---|---|---|
| 37 | cis-3-((ethylsulfonyl)amino)-2-(((cis-4-methylcyclohexyl)oxy)methyl)-N-phenylpiperidine-1-carboxamide | 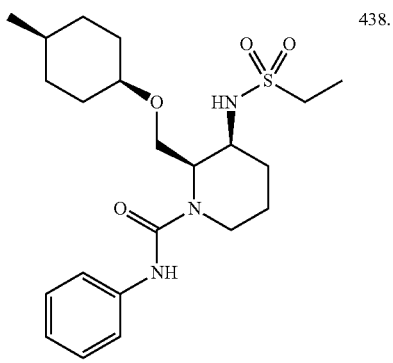 | 438.1 |
| 38 | N-(cis-2-(((cis-4-isopropylcyclohexyl)oxy)methyl)-1-(morpholin-4-ylcarbonyl)piperidin-3-yl)methanesulfonamide | 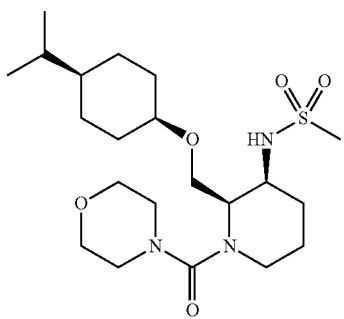 | 446.2 |
| 39 | N-(cis-2-(((cis-4-isopropylcyclohexyl)oxy)methyl)-1-(pyrrolidin-1-ylcarbonyl)piperidin-3-yl)methanesulfonamide | 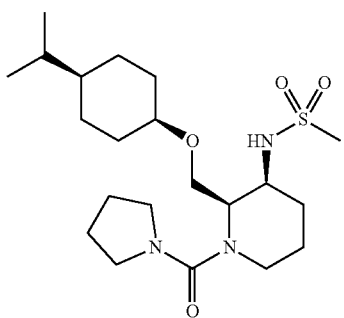 [SMILES: CC(C)[C@H]1CC[C@@H](OC[C@H]2[C@@H](NS(C)(=O)=O)CCCN2C(=O)N2CCCC2)CC1] | 430.2 |
| 40 | cis-2-(((cis-4-isopropylcyclohexyl)oxy)methyl)-N,N-dimethyl-3-((methylsulfonyl)amino)piperidine-1-carboxamide | 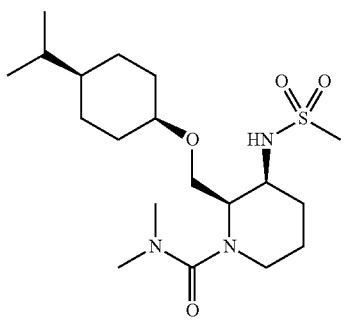 [SMILES: CC(C)[C@H]1CC[C@@H](OC[C@H]2[C@@H](NS(C)(=O)=O)CCCN2C(=O)N(C)C)CC1] | 404.2 |

TABLE 1-7-continued

| Ex. No. | IUPAC name | Structure | MS |
|---|---|---|---|
| 41 | benzyl cis-2-(((cis-4-isopropylcyclohexyl)oxy)methyl)-3-((methylsulfonyl)amino)piperidine-1-carboxylate | 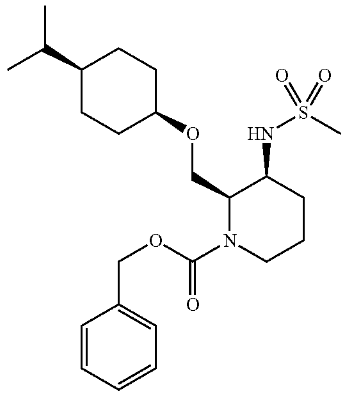 [SMILES: CC(C)[C@H]1CC[C@@H](OC[C@H]2[C@@H](NS(C)(=O)=O)CCCN2C(=O)OCc2ccccc2)CC1] | 465.1 |
| 42 | ethyl cis-2-(((cis-4-isopropylcyclohexyl)oxy)methyl)-3-((methylsulfonyl)amino)piperidine-1-carboxylate | 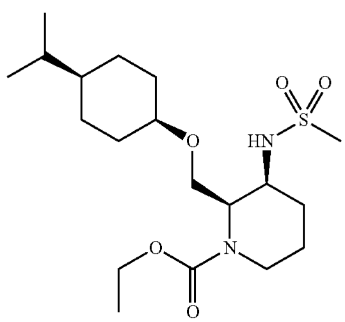 [SMILES: CCOC(=O)N1CCC[C@H](NS(C)(=O)=O)[C@@H]1CO[C@H]1CC[C@@H](C(C)C)CC1] | 403.2 |

TABLE 1-8

| Ex. No. | IUPAC name | Structure | MS |
|---|---|---|---|
| 43 | phenyl cis-2- (((cis-4-isopropylcyclohexyl)oxy)methyl)-3-((methylsulfonyl)amino)piperidine-1-carboxylate | 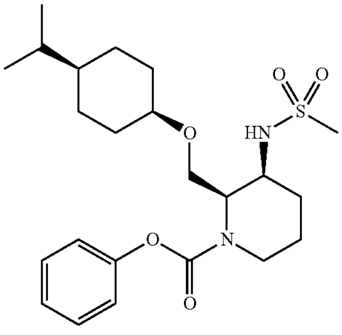 [SMILES: CC(C)[C@H]1CC[C@@H](OC[C@H]2[C@@H](NS(C)(=O)=O)CCCN2C(=O)Oc2ccccc2)CC1] | 453.2 |

TABLE 1-8-continued

| Ex. No. | IUPAC name | MS |
|---|---|---|
| 44 | N-(cis-2-(((cis-4-isopropylcyclohexyl)oxy)methyl)-1-(phenoxyacetyl)piperidin-3-yl)methanesulfonamide | 467.2 |
| 45 | N-(cis-2-(((cis-4-isopropylcyclohexyl)oxy)methyl)-1-(methoxyacetyl)piperidin-3-yl)methanesulfonamide | 405.2 |
| 46 | N-(cis-1-(2-furoyl)-2-(((cis-4-isopropylcyclohexyl)oxy)methyl)-piperidin-3-yl)methanesulfonamide | 427.2 |
| 47 | 2-(cis-2-(((cis-4-isopropylcyclohexyl)oxy)methyl)-3-((methylsulfonyl)amino)piperidin-1-yl)-2-oxoethyl acetate | 431.1 |

TABLE 1-8-continued

| Ex. No. | IUPAC name | Structure | MS |
|---|---|---|---|
| 48 | N-(cis-2-(((cis-4-isopropylcyclohexyl)oxy)methyl)-1-(1,2-oxazol-5-ylcarbonyl)piperidin-3-yl) methanesulfonamide | 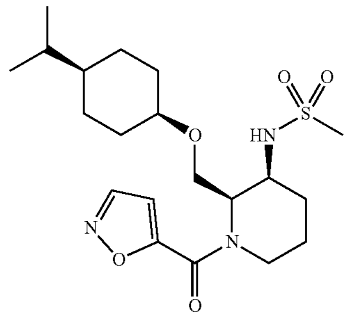 [SMILES: CC(C)[C@H]1CC[C@@H](OC[C@H]2[C@@H](NS(C)(=O)=O)CCCN2C(=O)c2ccno2)CC1] | 426.2 |

TABLE 1-9

| Ex. No. | IUPAC name | Structure | MS |
|---|---|---|---|
| 49 | N-(cis-1-(4-fluorobenzoyl)-2-(((cis-4-isopropylcyclohexyl)oxy)methyl)-piperidin-3-yl)methanesulfonamide | 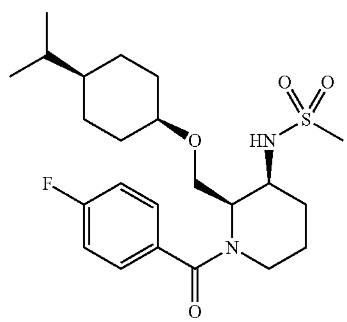 [SMILES: CC(C)[C@H]1CC[C@@H](OC[C@H]2[C@@H](NS(C)(=O)=O)CCCN2C(=O)c2ccc(F)cc2)CC1] | 453.1 |
| 50 | N-(cis-1-(4-chlorobenzoyl)-2-(((cis-4-isopropylcyclohexyl)oxy)methyl)-piperidin-3-yl)methanesulfonamide | 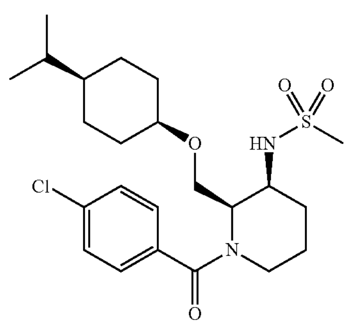 [SMILES: CC(C)[C@H]1CC[C@@H](OC[C@H]2[C@@H](NS(C)(=O)=O)CCCN2C(=O)c2ccc(Cl)cc2)CC1] | 469.1 |
| 51 | N-(cis-1-(biphenyl-4-ylcarbonyl)-2-(((cis-4-isopropylcyclohexyl)oxy)methyl)-piperidin-3-yl)methanesulfonamide | 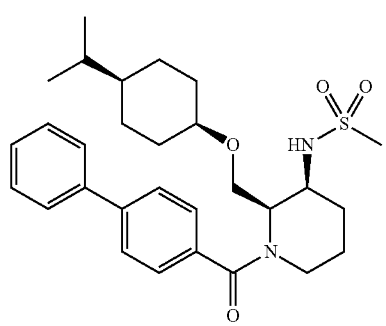 [SMILES: CC(C)[C@H]1CC[C@@H](OC[C@H]2[C@@H](NS(C)(=O)=O)CCCN2C(=O)c2ccc(-c3ccccc3)cc2)CC1] | 513.2 |

TABLE 1-9-continued

| Ex. No. | IUPAC name | Structure | MS |
|---|---|---|---|
| 52 | N-(cis-1-(2,2,3,3,4,4,4-heptafluorobutanoyl)-2-(((cis-4-isopropylcyclohexyl)oxy)methyl)-piperidin-3-yl)methanesulfonamide | 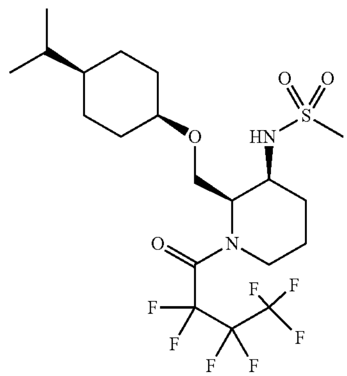 [SMILES: CC(C)[C@H]1CC[C@@H](OC[C@H]2[C@@H](NS(C)(=O)=O)CCCN2C(=O)C(F)(F)C(F)(F)C(F)(F)F)CC1] | 527.1 |
| 53 | N-(cis-1-(2,2-dimethylpropanoyl)-2-(((cis-4-isopropylcyclohexyl)oxy)methyl)-piperidin-3-yl)methanesulfonamide | 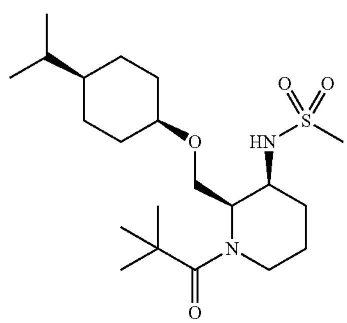 [SMILES: CC(C)[C@H]1CC[C@@H](OC[C@H]2[C@@H](NS(C)(=O)=O)CCCN2C(=O)C(C)(C)C)CC1] | 415.1 |
| 54 | N-(cis-2-(((cis-4-isopropylcyclohexyl)oxy)methyl)-(3-phenylpropanoyl)piperidin-3-yl)methanesulfonamide | 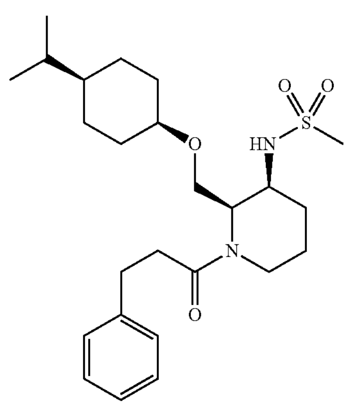 [SMILES: CC(C)[C@H]1CC[C@@H](OC[C@H]2[C@@H](NS(C)(=O)=O)CCCN2C(=O)CCc2ccccc2)CC1] | 465.2 |

TABLE 1-10

| Ex. No. | IUPAC name | Structure | MS |
|---|---|---|---|
| 55 | methyl4-(cis-2-(((cis-4-isopropylcyclohexyl)oxy)methyl)-3-((methylsulfonyl)amino)piperidin-1-yl)-4-oxobutanoate | 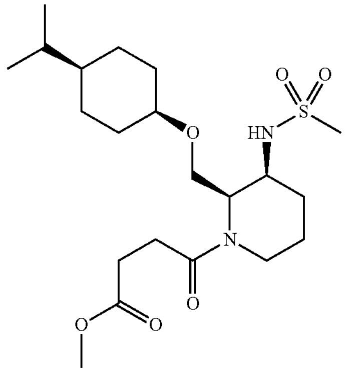 [SMILES: COC(=O)CCC(=O)N1CCC[C@H](NS(C)(=O)=O)[C@@H]1CO[C@H]1CC[C@@H](C(C)C)CC1] | 447.2 |
| 56 | N-(cis-2-(((cis-4-isopropylcyclohexyl)oxy)methyl)-1-(2-thienylcarbonyl)piperidin-3-yl)methanesulfonamide | 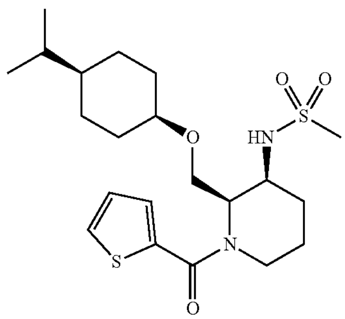 [SMILES: CC(C)[C@H]1CC[C@@H](OC[C@H]2[C@@H](NS(C)(=O)=O)CCCN2C(=O)c2cccs2)CC1] | 441.1 |
| 57 | N-(cis-2-(((cis-4-isopropylcyclohexyl)oxy)methyl)-1-(pyridin-3-ylcarbonyl)piperidin-3-yl)methanesulfonamide | 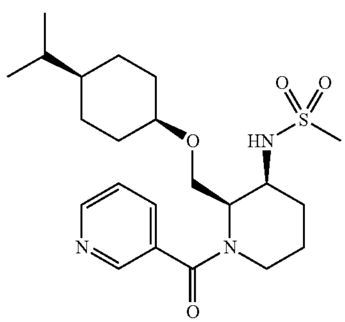 [SMILES: CC(C)[C@H]1CC[C@@H](OC[C@H]2[C@@H](NS(C)(=O)=O)CCCN2C(=O)c2cccnc2)CC1] | 438.2 |
| 58 | N-(cis-1-isonicotinoyl-2-(((cis-4-isopropylcyclohexyl)oxy)methyl)-piperidin-3-yl)methanesulfonamide | 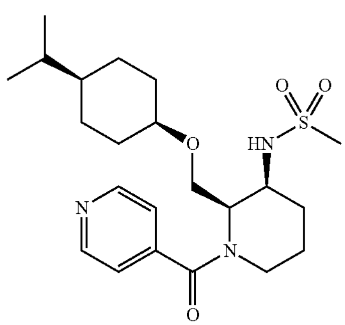 [SMILES: CC(C)[C@H]1CC[C@@H](OC[C@H]2[C@@H](NS(C)(=O)=O)CCCN2C(=O)c2ccncc2)CC1] | 438.1 |

TABLE 1-10-continued

| Ex. No. | IUPAC name | Structure | MS |
|---|---|---|---|
| 59 | N-(cis-2-(((cis-4-isopropylcyclohexyl)oxy)methyl)-1-((1-methyl-1H-pyrazol-4-yl)carbonyl)piperidin-3-yl)methanesulfonamide | 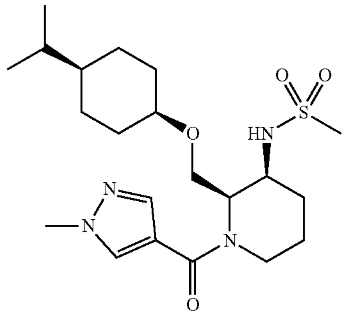 [SMILES: CC(C)[C@H]1CC[C@@H](OC[C@H]2[C@@H](NS(C)(=O)=O)CCCN2C(=O)c2cnn(C)c2)CC1] | 441.3 |
| 60 | N-(cis-2-(((cis-4-isopropylcyclohexyl)oxy)methyl)-1-(tetrahydro-2H-pyran-4-ylcarbonyl)piperidin-3-yl)methanesulfonamide | 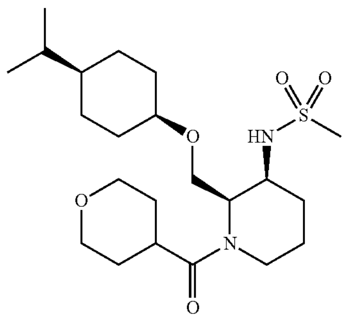 [SMILES: CC(C)[C@H]1CC[C@@H](OC[C@H]2[C@@H](NS(C)(=O)=O)CCCN2C(=O)C2CCOCC2)CC1] | 445.3 |

TABLE 1-11

| Ex. No. | IUPAC name | Structure | MS |
|---|---|---|---|
| 61 | cis-2-(((cis-4-isopropylcyclohexyl)oxy)methyl)-N,N-dimethyl-3-((methylsulfonyl)amino)piperidine-1-sulfonamide | 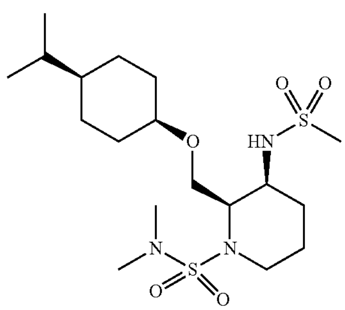 [SMILES: CC(C)[C@H]1CC[C@@H](OC[C@H]2[C@@H](NS(C)(=O)=O)CCCN2S(=O)(=O)N(C)C)CC1] | 438.1 |
| 62 | N-(cis-1-(cyclopropylsulfonyl)-2-(((cis-4-isopropylcyclohexyl)oxy)methyl)-piperidin-3-yl)methanesulfonamide | 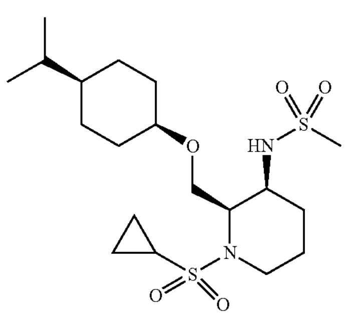 [SMILES: CC(C)[C@H]1CC[C@@H](OC[C@H]2[C@@H](NS(C)(=O)=O)CCCN2S(=O)(=O)C2CC2)CC1] | 435.1 |

TABLE 1-11-continued

| Ex. No. | IUPAC name | MS |
|---|---|---|
| 63 | N-(cis-2-(((cis-4-isopropylcyclohexyl)oxy)methyl)-1-(2-thienylsulfonyl)piperidin-3-yl)methanesulfonamide | 477 |
| 64 | N-(cis-1-((4-chlorophenyl)sulfonyl)-2-(((cis-4-isopropylcyclohexyl)oxy)methyl)-piperidin-3-yl)methanesulfonamide | 505.1 |
| 65 | N-(cis-1-((1,2-dimethyl-1H-imidazol-4-yl)sulfonyl)-2-(((cis-4-isopropylcyclohexyl)oxy)methyl)-piperidin-3-yl)methanesulfonamide | 491.2 |
| 66 | N-(cis-2-(((cis-4-isopropylcyclohexyl)oxy)methyl)-1-(pyridin-3-ylsulfonyl)piperidin-3-yl)methanesulfonamide | 474.2 |

TABLE 1-12

| Ex. No. | IUPAC name | Structure | MS |
|---|---|---|---|
| 67 | N-(cis-2-(((cis-4-isopropylcyclohexyl)oxy)methyl)-1-((1-methyl-1H-pyrazol-4-yl)sulfonyl)piperidin-3-yl)methanesulfonamide | 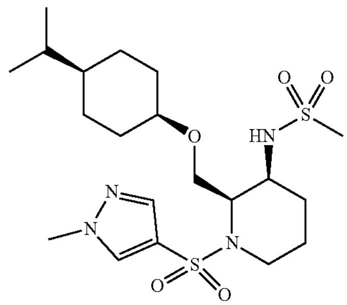 [SMILES: CC(C)[C@H]1CC[C@@H](OC[C@H]2[C@@H](NS(C)(=O)=O)CCCN2S(=O)(=O)c2cnn(C)c2)CC1] | 475.1 |
| 68 | N-(cis-1-(3,4-dihydro-2H-chromen-6-ylsulfonyl)-2-(((cis-4-isopropylcyclohexyl)oxy)methyl)-piperidin-3-yl)methanesulfonamide | 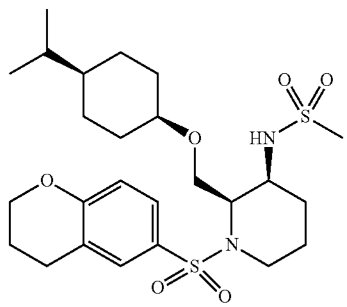 [SMILES: CC(C)[C@H]1CC[C@@H](OC[C@H]2[C@@H](NS(C)(=O)=O)CCCN2S(=O)(=O)c2ccc3c(c2)CCCO3)CC1] | 527.2 |
| 69 | N-((2R,3S)-2-(((cis-4-isopropylcyclohexyl)oxy)methyl)-piperidin-3-yl)methanesulfonamide ((2S,3S)-2,3-bis((4-methylbenzoyl)oxy)succinate | 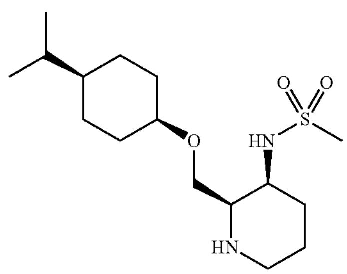 [SMILES: CC(C)[C@H]1CC[C@@H](OC[C@@H]2NCCC[C@@H]2NS(C)(=O)=O)CC1] | 333.1 |
| 70 | N-((2R,3S)-1-acetyl-2-(((cis-4-isopropylcyclohexyl)oxy)methyl)-piperidin-3-yl)methanesulfonamide | 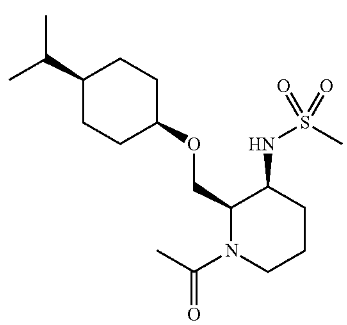 [SMILES: CC(=O)N1CCC[C@H](NS(C)(=O)=O)[C@@H]1CO[C@H]1CC[C@@H](C(C)C)CC1] | 375.1 |
| 71 | N-(cis-1-acetyl-2-(((1s,4s)-1,1'-bi(cyclohexyl)-4-yloxy)methyl)piperidin-3-yl)methanesulfonamide | 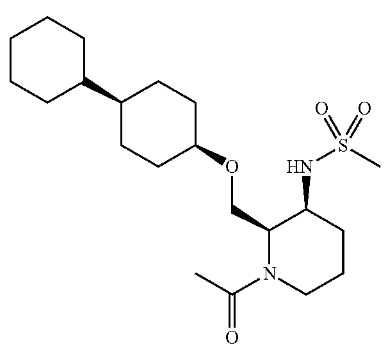 [SMILES: CC(=O)N1CCC[C@H](NS(C)(=O)=O)[C@@H]1CO[C@H]1CC[C@@H](C2CCCCC2)CC1] | 415.1 |

TABLE 1-12-continued

| Ex. No. | IUPAC name | Structure | MS |
|---|---|---|---|
| 72 | N-(cis-1-(3-hydroxypropanoyl)-2-(((cis-4-isopropylcyclohexyl)oxy)methyl)-piperidin-3-yl)methanesulfonamide | 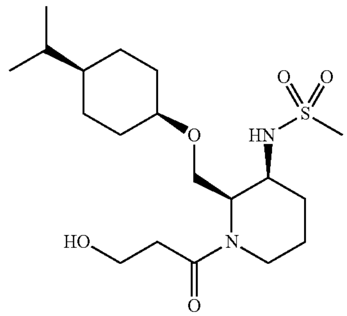 [SMILES: CC(C)[C@H]1CC[C@@H](OC[C@H]2[C@@H](NS(C)(=O)=O)CCCN2C(=O)CCO)CC1] | 405.2 |

TABLE 1-13

| Ex. No. | IUPAC name | Structure | MS |
|---|---|---|---|
| 73 | N-(cis-1-(3-hydroxy-3-methylbutanoyl)-2-(((cis-4-isopropylcyclohexyl)oxy)methyl)-piperidin-3-yl)methanesulfonamide | 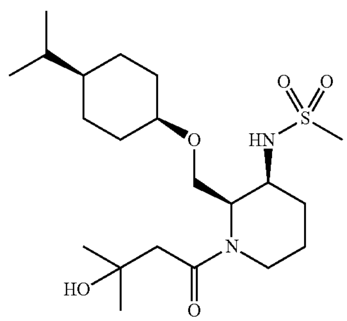 [SMILES: CC(C)[C@H]1CC[C@@H](OC[C@H]2[C@@H](NS(C)(=O)=O)CCCN2C(=O)CC(C)(C)O)CC1] | 433.1 |
| 74 | N-(cis-2-(((cis-4-isopropylcyclohexyl)oxy)methyl)-1-(3-(methylsulfonyl)-propanoyl)piperidin-3-yl)methanesulfonamide | 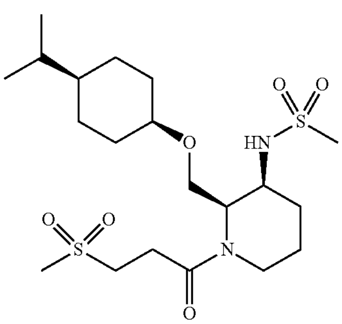 [SMILES: CC(C)[C@H]1CC[C@@H](OC[C@H]2[C@@H](NS(C)(=O)=O)CCCN2C(=O)CCS(C)(=O)=O)CC1] | 467.2 |
| 75 | N-(cis-2-(((cis-4-isopropylcyclohexyl)oxy)methyl)-1-(4-oxopentanoyl)piperidin-3-yl)methanesulfonamide | 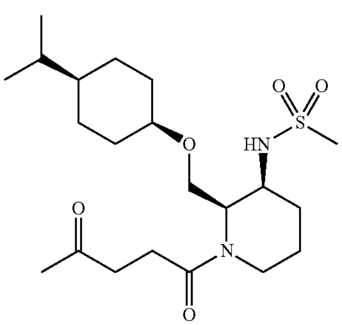 [SMILES: CC(=O)CCC(=O)N1CCC[C@H](NS(C)(=O)=O)[C@@H]1CO[C@H]1CC[C@@H](C(C)C)CC1] | 429.1 |

TABLE 1-13-continued

| Ex. No. | IUPAC name | Structure | MS |
|---|---|---|---|
| 76 | N-(cis-1-acetyl-2-(((cis-4-isopropylcyclohexyl)oxy)methyl)-piperidin-3-yl)propane-2-sulfonamide | 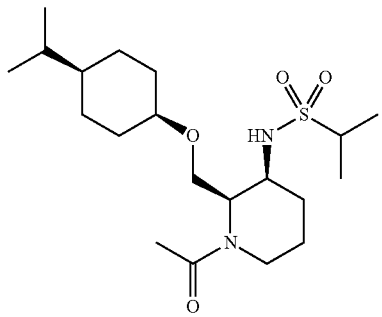 [SMILES: CC(=O)N1CCC[C@H](NS(=O)(=O)C(C)C)[C@@H]1CO[C@H]1CC[C@@H](C(C)C)CC1] | 403.1 |
| 77 | N-(cis-1-acetyl-2-(((cis-4-isopropylcyclohexyl)oxy)methyl)-piperidin-3-yl)propane-1-sulfonamide | 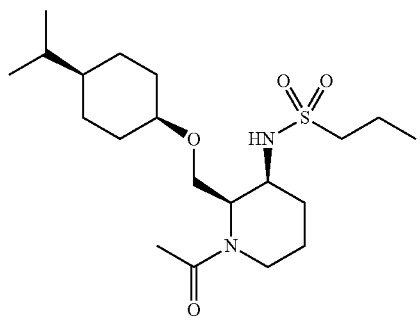 [SMILES: CCCS(=O)(=O)N[C@H]1CCCN(C(C)=O)[C@H]1CO[C@H]1CC[C@@H](C(C)C)CC1] | 403.2 |
| 78 | N'-(cis-1-acetyl-2-(((cis-4-isopropylcyclohexyl)oxy)methyl)-piperidin-3-yl)-N,N-dimethylsulfuric diamide | 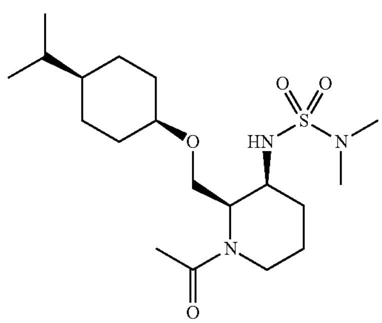 [SMILES: CC(=O)N1CCC[C@H](NS(=O)(=O)N(C)C)[C@@H]1CO[C@H]1CC[C@@H](C(C)C)CC1] | 404.2 |

TABLE 1-14

| Ex. No. | IUPAC name | Structure | MS |
|---|---|---|---|
| 79 | N-(cis-1-acetyl-2-(((cis-4-isopropylcyclohexyl)oxy)methyl)-piperidin-3-yl)-N'-ethylsulfuric diamide | 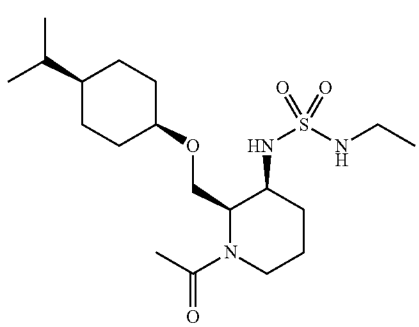 [SMILES: CCNS(=O)(=O)N[C@H]1CCCN(C(C)=O)[C@H]1CO[C@H]1CC[C@@H](C(C)C)CC1] | 404.2 |

TABLE 1-14-continued

| Ex. No. | IUPAC name | Structure | MS |
|---|---|---|---|
| 80 | N-(cis-1-acetyl-2-(((cis-4-isopropylcyclohexyl)oxy)methyl)-piperidin-3-yl)-1,1,1-trifluoromethanesulfonamide | 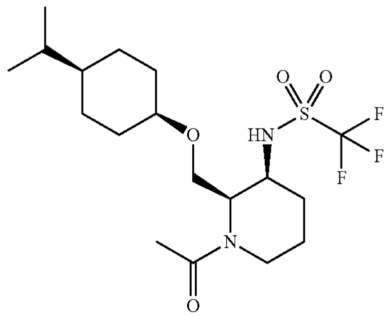 [SMILES: CC(=O)N1CCC[C@H](NS(=O)(=O)C(F)(F)F)[C@@H]1CO[C@H]1CC[C@@H](C(C)C)CC1] | 429.2 |
| 81 | N-(cis-1-acetyl-2-(((cis-4-isopropylcyclohexyl)oxy)methyl)-piperidin-3-yl)-2-methylpropane-1-sulfonamide | 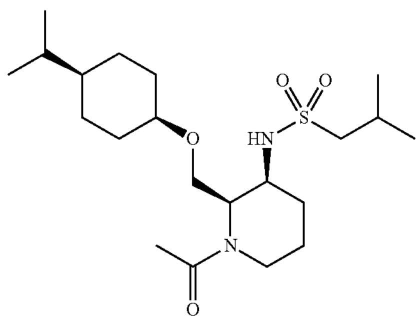 [SMILES: CC(=O)N1CCC[C@H](NS(=O)(=O)CC(C)C)[C@@H]1CO[C@H]1CC[C@@H](C(C)C)CC1] | 417.2 |
| 82 | N-(cis-1-acetyl-2-(((cis-4-isopropylcyclohexyl)oxy)methyl)-piperidin-3-yl)-1-phenylmethanesulfonamide | 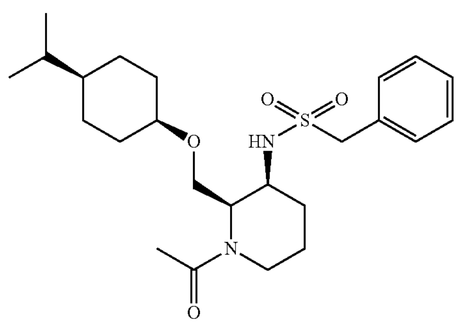 [SMILES: CC(=O)N1CCC[C@H](NS(=O)(=O)Cc2ccccc2)[C@@H]1CO[C@H]1CC[C@@H](C(C)C)CC1] | 451.2 |
| 83 | N-(2-(cis-2-(((cis-4-isopropylcyclohexyl)oxy)methyl)-3-((methylsulfonyl)amino)piperidin-1-yl)-2-oxoethyl)acetamide | 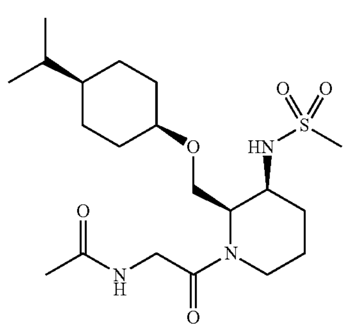 [SMILES: CC(=O)NCC(=O)N1CCC[C@H](NS(C)(=O)=O)[C@@H]1CO[C@H]1CC[C@@H](C(C)C)CC1] | 432.1 |

TABLE 1-14-continued

| Ex. No. | IUPAC name | Structure | MS |
|---|---|---|---|
| 84 | N-((2R,3S)-2-(((cis-4-isopropylcyclohexyl)oxy)methyl)-1-(((1-methyl-1H-pyrazol-3-yl)oxy)acetyl)piperidin-3-yl)methanesulfonamide | 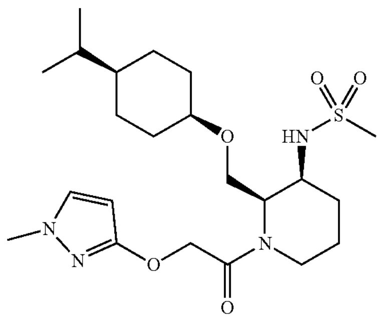 | 471.2 |

TABLE 1-15

| Ex. No. | IUPAC name | Structure | MS |
|---|---|---|---|
| 85 | N-(cis-1-(N,N-dimethyl-beta-alanyl)-2-(((cis-4-isopropylcyclohexyl)oxy)methyl)-piperidin-3-yl)methanesulfonamide | 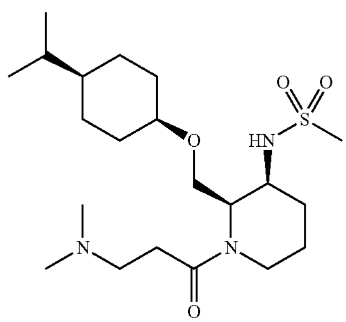 [SMILES: CC(C)[C@H]1CC[C@@H](OC[C@H]2[C@@H](NS(C)(=O)=O)CCCN2C(=O)CCN(C)C)CC1] | 430.2 |
| 86 | tert-butyl 3-((cis-2-(((cis-4-isopropylcyclohexyl)oxy)methyl)-3-((methylsulfonyl)amino)piperidin-1-yl)carbonyl)azetidine-1-carboxylate | 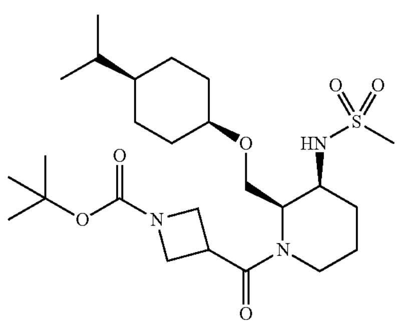 [SMILES: CC(C)[C@H]1CC[C@@H](OC[C@H]2[C@@H](NS(C)(=O)=O)CCCN2C(=O)C2CN(C(=O)OC(C)(C)C)C2)CC1] | 514.1 |
| 87 | N-(cis-2-(((cis-4-isopropylcyclohexyl)oxy)methyl)-1-(5-oxoprolyl)piperidin-3-yl)methanesulfonamide | 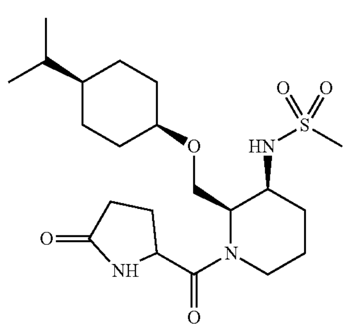 [SMILES: CC(C)[C@H]1CC[C@@H](OC[C@H]2[C@@H](NS(C)(=O)=O)CCCN2C(=O)C2CCC(=O)N2)CC1] | 444.2 |

TABLE 1-15-continued

| Ex. No. | IUPAC name | Structure | MS |
|---|---|---|---|
| 88 | N-(cis-1-(azetidin-3-ylcarbonyl)-2-(((cis-4-isopropylcyclohexyl)oxy)methyl)-piperidin-3-yl)methanesulfonamide | 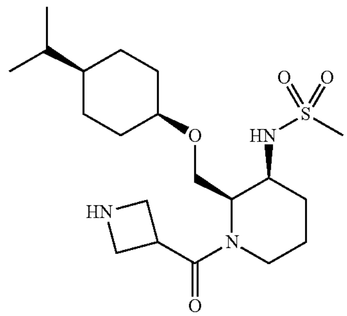 [SMILES: CC(C)[C@H]1CC[C@@H](OC[C@H]2[C@@H](NS(C)(=O)=O)CCCN2C(=O)C2CNC2)CC1] | 416.2 |
| 89 | N-(cis-1-((l-acetylazetidin-3-yl)carbonyl)-2-(((cis-4-isopropylcyclohexyl)oxy)methyl)-piperidin-3-yl)methanesulfonamide | 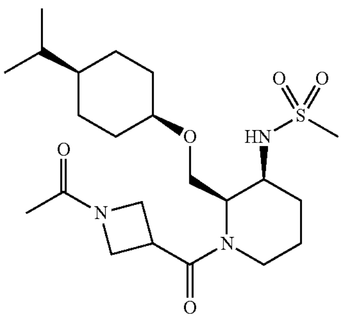 [SMILES: CC(=O)N1CC(C(=O)N2CCC[C@H](NS(C)(=O)=O)[C@@H]2CO[C@H]2CC[C@@H](C(C)C)CC2)C1] | 458.2 |
| 90 | N-(cis-2-(((cis-4-isopropylcyclohexyl)oxy)methyl)-((1-(methylsulfonyl)azetidin-3-yl)carbonyl)piperidin-3-yl)methanesulfonamide | 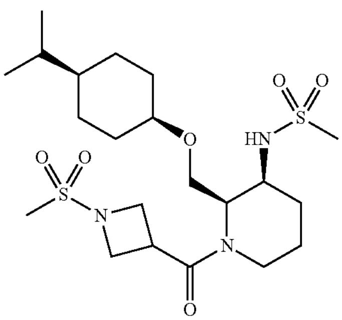 [SMILES: CC(C)[C@H]1CC[C@@H](OC[C@H]2[C@@H](NS(C)(=O)=O)CCCN2C(=O)C2CN(S(C)(=O)=O)C2)CC1] | 494.2 |

TABLE 1-16

| Ex. No. | IUPAC name | Structure | MS |
|---|---|---|---|
| 91 | N-((2R,3S)-2-(((cis-4-isopropylcyclohexyl)oxy)methyl)-1-((3-oxocyclobutyl)carbonyl)piperidin-3-yl)methanesulfonamide | 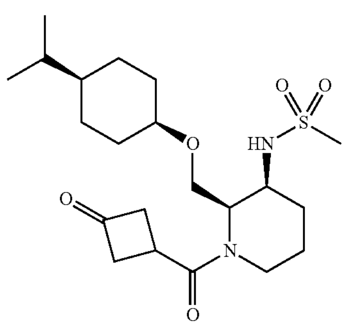 [SMILES: CC(C)[C@H]1CC[C@@H](OC[C@H]2[C@@H](NS(C)(=O)=O)CCCN2C(=O)C2CC(=O)C2)CC1] | 427.1 |

TABLE 1-16-continued

| Ex. No. | IUPAC name | Structure | MS |
|---|---|---|---|
| 92 | N-((2R,3S)-1-((3-hydroxycyclobutyl)carbonyl)-2-(((cis-4-isopropylcyclohexyl)oxy)methyl)-piperidin-3-yl)methanesulfonamide | 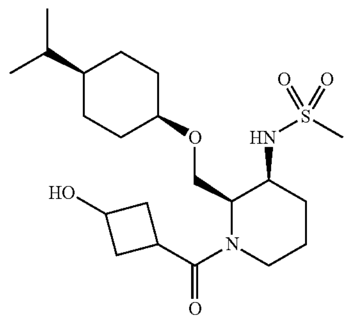 [SMILES: CC(C)[C@H]1CC[C@@H](OC[C@H]2[C@@H](NS(C)(=O)=O)CCCN2C(=O)C2CC(O)C2)CC1] | 431.2 |
| 93 | N-(cis-2-(((cis-4-isopropylcyclohexyl)oxy)methyl)-1-((6-oxopyrimidin-1(6H)-yl)acetyl)piperidin-3-yl)methanesulfonamide | 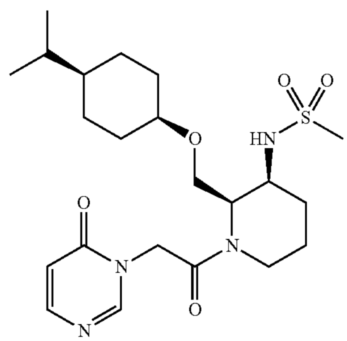 [SMILES: CC(C)[C@H]1CC[C@@H](OC[C@H]2[C@@H](NS(C)(=O)=O)CCCN2C(=O)Cn2cnccc2=O)CC1] | 467 |
| 94 | N-(cis-2-(((cis-4-isopropylcyclohexyl)oxy)methyl)-1-((4-oxopyridazin-1(4H)-yl)acetyl)piperidin-3-yl)methanesulfonamide | 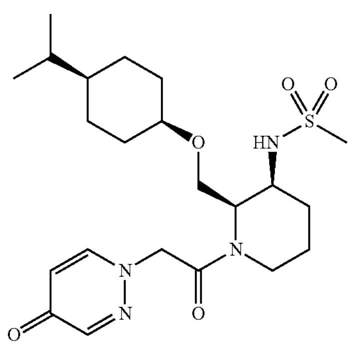 [SMILES: CC(C)[C@H]1CC[C@@H](OC[C@H]2[C@@H](NS(C)(=O)=O)CCCN2C(=O)Cn2ccc(=O)cn2)CC1] | 469.2 |
| 95 | N-(cis-1-acetyl-2-(((cis-4-(2-fluoropropan-2-yl)cyclohexyl)oxy)methyl)piperidin-3-yl)methanesulfonamide | 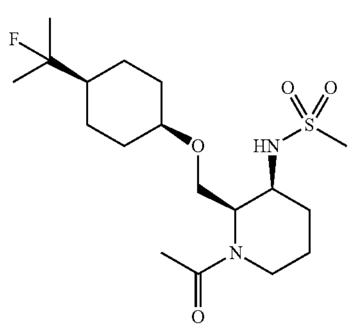 [SMILES: CC(=O)N1CCC[C@H](NS(C)(=O)=O)[C@@H]1CO[C@H]1CC[C@@H](C(C)(C)F)CC1] | 391 |

TABLE 1-16-continued

| Ex. No. | IUPAC name | Structure | MS |
|---|---|---|---|
| 96 | cis-2-(((cis-4-isopropylcyclohexyl)oxy)methyl)-N-(2-methoxyethyl)-3-((methylsulfonyl)amino)piperidine-1-carboxamide | 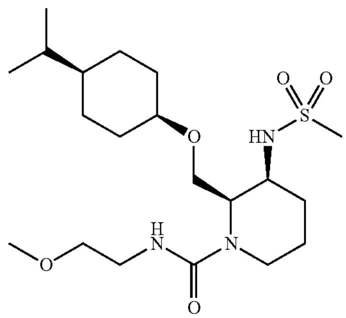 [SMILES: COCCNC(=O)N1CCC[C@H](NS(C)(=O)=O)[C@@H]1CO[C@H]1CC[C@@H](C(C)C)CC1] | 434.2 |

TABLE 1-17

| Ex. No. | IUPAC name | Structure | MS |
|---|---|---|---|
| 97 | cis-N-(2-hydroxyethyl) -2-(((cis-4 isopropylcyclohexyl)oxy)methyl)-3 ((methylsulfonyl)amino)piperidine 1-carboxamide | 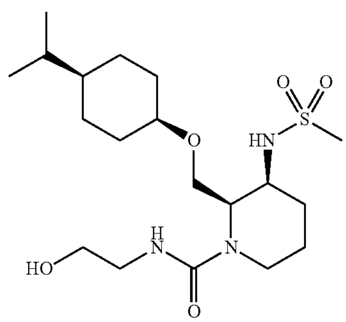 [SMILES: CC(C)[C@H]1CC[C@@H](OC[C@H]2[C@@H](NS(C)(=O)=O)CCCN2C(=O)NCCO)CC1] | 420.2 |
| 98 | cis-2-(((cis-4-isopropylcyclohexyl)oxy)methyl)-3-((methylsulfonyl)amino)-N-(2,2,2-trifluoroethyl)piperidine-l-carboxamide | 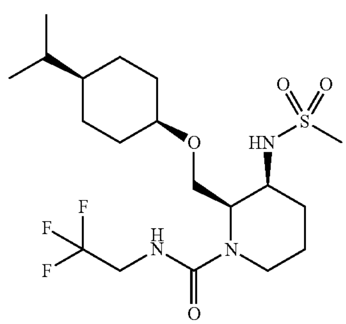 [SMILES: CC(C)[C@H]1CC[C@@H](OC[C@H]2[C@@H](NS(C)(=O)=O)CCCN2C(=O)NCC(F)(F)F)CC1] | 456 |
| 99 | cis-N-cyclopropyl-2-(((cis-4-isopropylcyclohexyl)oxy)methyl)-3-((methylsulfonyl)amino)piperidine 1-carboxamide | 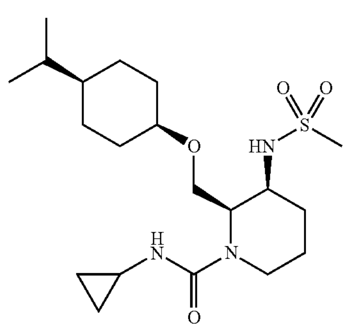 [SMILES: CC(C)[C@H]1CC[C@@H](OC[C@H]2[C@@H](NS(C)(=O)=O)CCCN2C(=O)NC2CC2)CC1] | 416.2 |

TABLE 1-17-continued

| Ex. No. | IUPAC name | Structure | MS |
|---|---|---|---|
| 100 | cis-2-((icis-4-isopropylcyclohexyl)oxy)methyl)-3-((methylsulfonyl)amino)-N-propylpiperidine-1-carboxamide | 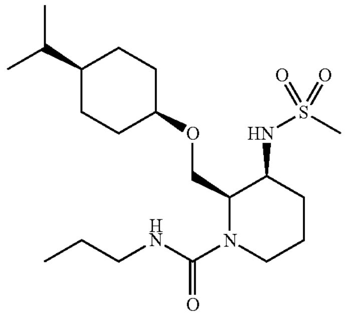 [SMILES: CCCNC(=O)N1CCC[C@H](NS(C)(=O)=O)[C@@H]1CO[C@H]1CC[C@@H](C(C)C)CC1] | 418.2 |
| 101 | cis-N-isopropyl-2-(((cis-4-isopropylcyclohexyl)oxy)methyl)-3((methylsulfonyl)amino)piperidine 1-carboxamide | 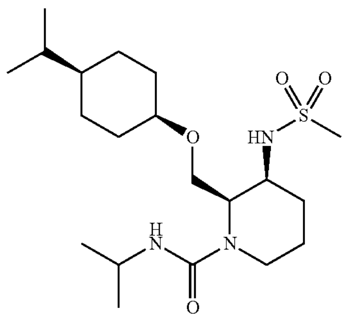 [SMILES: CC(C)NC(=O)N1CCC[C@H](NS(C)(=O)=O)[C@@H]1CO[C@H]1CC[C@@H](C(C)C)CC1] | 418.2 |
| 102 | (2R,3S)-2-(((cis-4-isopropylcyclohexyl)oxy)methyl)-N-methyl-3-((methylsulfonyl)amino)piperidin 1-carboxamide | 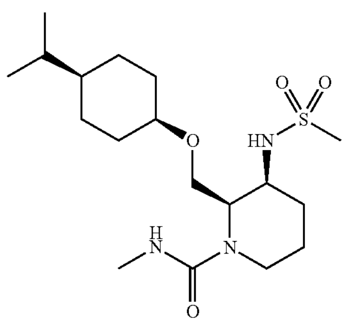 [SMILES: CNC(=O)N1CCC[C@H](NS(C)(=O)=O)[C@@H]1CO[C@H]1CC[C@@H](C(C)C)CC1] | 390.2 |

TABLE 1-18

| Ex. No. | IUPAC name | Structure | MS |
|---|---|---|---|
| 103 | N-(cis-1-acetyl-2-(((cis-4-isopropyl(1,2,3,4,5,6-d6)cyclohexyl)oxy)methyl)piperidin-3-yl)methanesulfonamide | 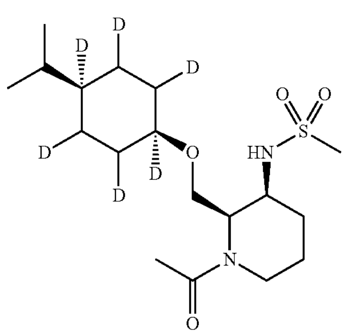 [SMILES: [2H]C1C([2H])[C@]([2H])(C(C)C)C([2H])C([2H])[C@]1([2H])OC[C@H]1[C@@H](NS(C)(=O)=O)CCCN1C(C)=O] | 381.2 |

TABLE 1-18-continued

| Ex. No. | IUPAC name | Structure | MS |
|---|---|---|---|
| 104 | cis-N-ethyl-2-(((cis-4-isopropyl(1,2,3,4,5,6-d6)cyclohexyl)oxy)methyl)-3-((methylsulfonyl)amino)piperidine-1-carboxamide | 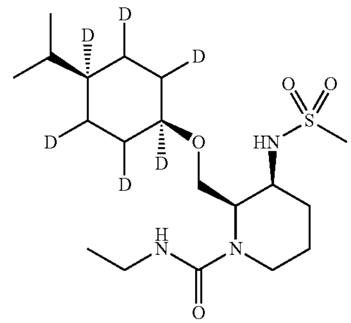 [SMILES: [2H]C1C([2H])[C@]([2H])(C(C)C)C([2H])C([2H])[C@]1([2H])OC[C@H]1[C@@H](NS(C)(=O)=O)CCCN1C(=O)NCC] | 410.3 |
| 105 | cis-2-(((4-((tert-butyl(dimethyl)silyl)oxy)-cyclohexyl)oxy)methyl)-N-ethyl-3-((methylsulfonyl)amino)piperidine-1-carboxamide | 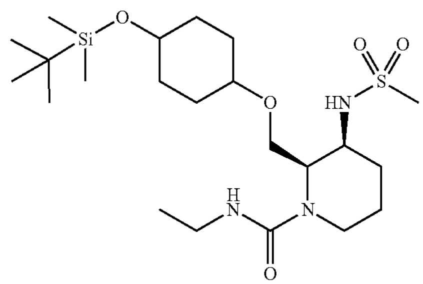 [SMILES: CCNC(=O)N1CCC[C@H](NS(C)(=O)=O)[C@@H]1COC1CCC(O[Si](C)(C)C(C)(C)C)CC1] | 492.3 |
| 106 | N-(cis-1-acetyl-2-(((cis-4-(trifluoromethyl)cyclohexyl)oxy)-methyl)piperidin-3-yl)methanesulfonamide | 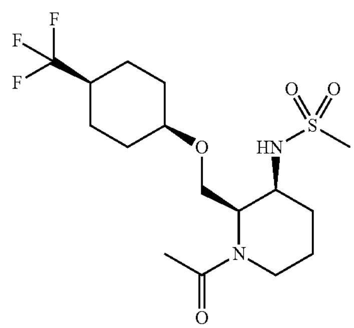 [SMILES: CC(=O)N1CCC[C@H](NS(C)(=O)=O)[C@@H]1CO[C@H]1CC[C@@H](C(F)(F)F)CC1] | 400.9 |
| 107 | cis-N-ethyl-3-((methylsulfonyl)amino)-2-(((cis-4-(trifluoromethyl)cyclohexyl)oxy)-methyl)piperidine-1-carboxamide | 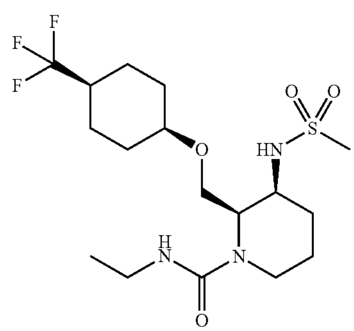 [SMILES: CCNC(=O)N1CCC[C@H](NS(C)(=O)=O)[C@@H]1CO[C@H]1CC[C@@H](C(F)(F)F)CC1] | 430 |
| 108 | cis-2-(((4,4-difluorocyclohexyl)oxy)methyl)-N-ethyl-3-((methylsulfonyl)amino)piperidine-1-carboxamide | 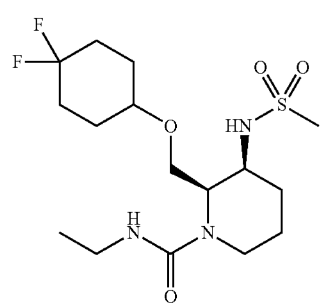 [SMILES: CCNC(=O)N1CCC[C@H](NS(C)(=O)=O)[C@@H]1COC1CCC(F)(F)CC1] | 398.1 |

TABLE 1-19

| Ex. No. | IUPAC name | Structure | MS |
|---|---|---|---|
| 109 | N,N-dimethyl-N'-(cis-2-(((cis-4-phenylcyclohexyl)oxy)methyl)-piperidin-3-yl)sulfuric diamide | 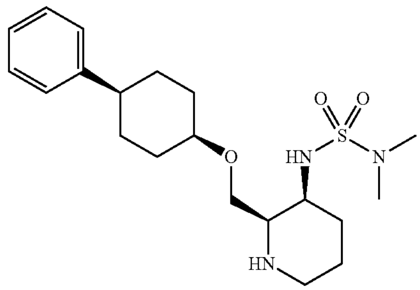 [SMILES: CN(C)S(=O)(=O)N[C@H]1CCCN[C@H]1CO[C@H]1CC[C@@H](c2ccccc2)CC1] | 396.2 |
| 110 | N-(cis-2-(((cis-4-(4-fluorophenyl)cyclohexyl)oxy)-methyl)piperidin-3-yl)methanesulfonamide | 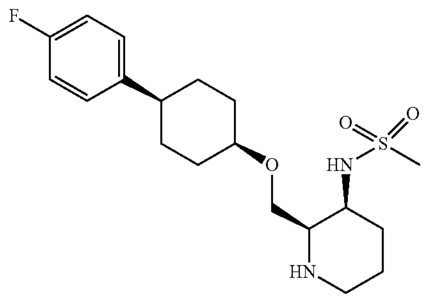 [SMILES: CS(=O)(=O)N[C@H]1CCCN[C@H]1CO[C@H]1CC[C@@H](c2ccc(F)cc2)CC1] | 385 |
| 111 | N'-(cis-1-acetyl-2-(((cis-4-phenylcyclohexyl)oxy)methyl)-piperidin-3-yl)-N,N-dimethylsulfuric diamide | 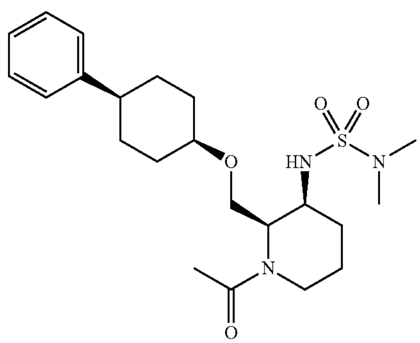 [SMILES: CC(=O)N1CCC[C@H](NS(=O)(=O)N(C)C)[C@@H]1CO[C@H]1CC[C@@H](c2ccccc2)CC1] | 438.1 |
| 112 | N-(cis-1-acetyl-2-(((cis-4-(4-fluorophenyl)cyclohexyl)oxy)-methyl)piperidin-3-yl)methanesulfonamide | 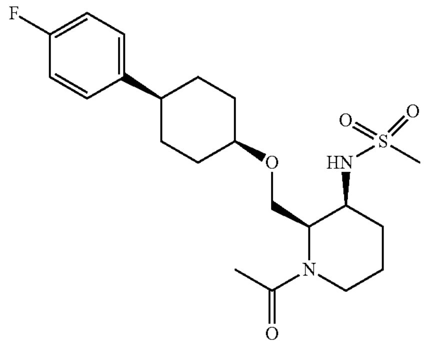 [SMILES: CC(=O)N1CCC[C@H](NS(C)(=O)=O)[C@@H]1CO[C@H]1CC[C@@H](c2ccc(F)cc2)CC1] | 427.1 |

TABLE 1-19-continued

| Ex. No. | IUPAC name | Structure | MS |
|---|---|---|---|
| 113 | cis-N-ethyl-3-((methylsulfonyl)amino)-2-(((cis-3-phenylcyclobutyl)oxy)methyl)-piperidine-1-carboxamide | 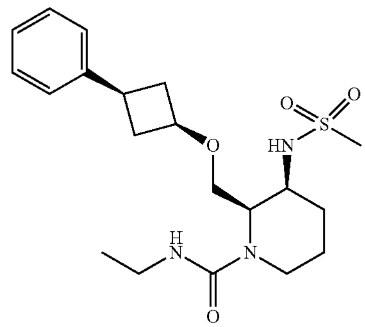 [SMILES: CCNC(=O)N1CCC[C@H](NS(C)(=O)=O)[C@@H]1CO[C@H]1C[C@@H](c2ccccc2)C1] | 410.1 |
| 114 | N-(cis-1-acetyl-2-(((cis-3-phenylcyclobutyl)oxy)methyl)-piperidin-3-yl)methanesulfonamide | 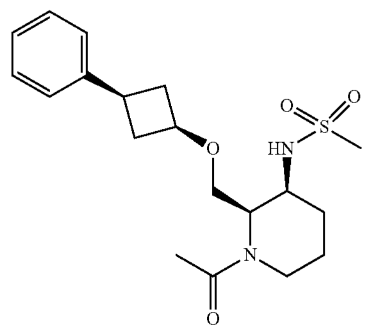 [SMILES: CC(=O)N1CCC[C@H](NS(C)(=O)=O)[C@@H]1CO[C@H]1C[C@@H](c2ccccc2)C1] | 381 |

TABLE 1-20

| Ex. No. | IUPAC name | Structure | MS |
|---|---|---|---|
| 115 | N-(cis-2-(((cis-4-(2-fluorophenyl)cyclohexyl)oxy)-methyl)piperidin-3-yl)methanesulfonamide | 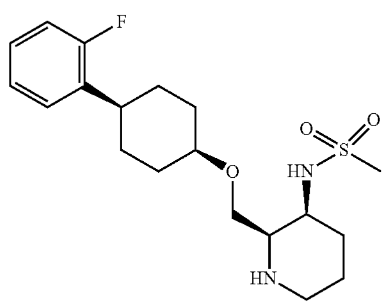 [SMILES: CS(=O)(=O)N[C@H]1CCCN[C@H]1CO[C@H]1CC[C@@H](c2ccccc2F)CC1] | 385 |
| 116 | N-(cis-1-acetyl-2-(((1-(pyridin-2-yl)piperidin-4-yl)oxy)methyl)piperidin-3-yl)methanesulfonamide | 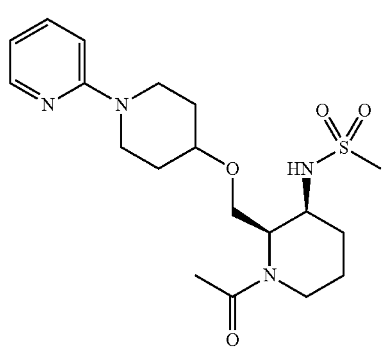 [SMILES: CC(=O)N1CCC[C@H](NS(C)(=O)=O)[C@@H]1COC1CCN(c2ccccn2)CC1] | 411.1 |

TABLE 1-20-continued

| Ex. No. | IUPAC name | Structure | MS |
|---|---|---|---|
| 117 | cis-N-ethyl-2-(((cis-4-(2-fluorophenyl)cyclohexyl)oxy)-methyl)-3-((methylsulfonyl)amino)piperidine-1-carboxamide | 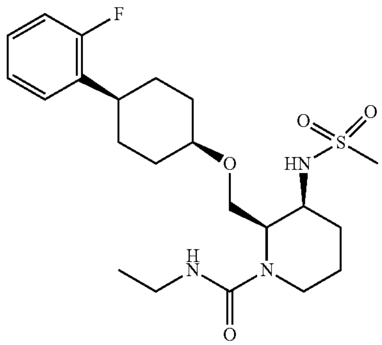 [SMILES: CCNC(=O)N1CCC[C@H](NS(C)(=O)=O)[C@@H]1CO[C@H]1CC[C@@H](c2ccccc2F)CC1] | 456.1 |
| 118 | cis-N-ethyl-3-((methylsulfonyl)amino)-2-(((1-(pyrimidin-2-yl)piperidin-4-yl)oxy)methyl)piperidine-1-carboxamide | 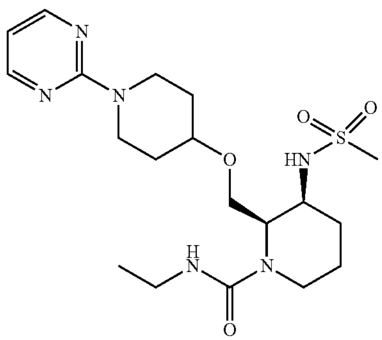 [SMILES: CCNC(=O)N1CCC[C@H](NS(C)(=O)=O)[C@@H]1COC1CCN(c2ncccn2)CC1] | 441.1 |
| 119 | N-(cis-1-(methoxyacetyl)-2-(((cis-4-phenylcyclohexyl)oxy)methyl)-piperidin-3-yl)methanesulfonamide | 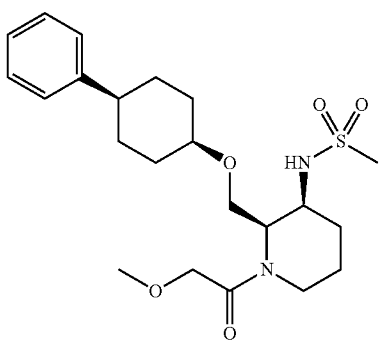 [SMILES: COCC(=O)N1CCC[C@H](NS(C)(=O)=O)[C@@H]1CO[C@H]1CC[C@@H](c2ccccc2)CC1] | 439.1 |
| 120 | N-(cis-1-(oxetan-3-ylcarbonyl)-2-(((cis-4-phenylcyclohexyl)oxy)methyl)-piperidin-3-yl)methanesulfonamide | 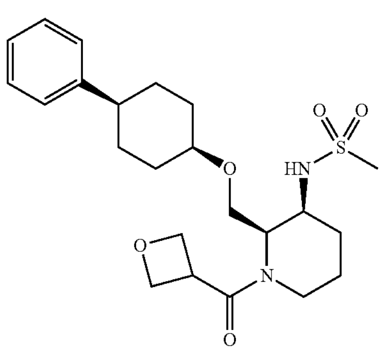 [SMILES: CS(=O)(=O)N[C@H]1CCCN(C(=O)C2COC2)[C@H]1CO[C@H]1CC[C@@H](c2ccccc2)CC1] | 451 |

TABLE 1-21

| Ex. No. | IUPAC name | Structure | MS |
|---|---|---|---|
| 121 | N-(cis-2-(((cis-4-phenylcyclohexyl)oxy)methyl)-1-(tetrahydro-2H-pyran-4-ylcarbonyl)piperidin-3-yl)methanesulfonamide | 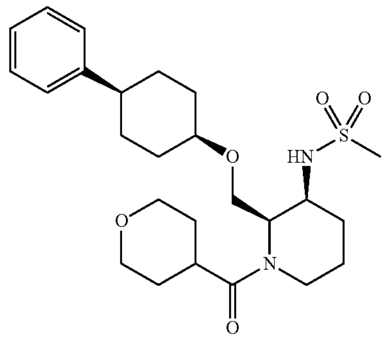 [SMILES: CS(=O)(=O)N[C@H]1CCCN(C(=O)C2CCOCC2)[C@H]1CO[C@H]1CC[C@@H](c2ccccc2)CC1] | 479.1 |
| 122 | N-(cis-2-(((cis-4-methylcyclohexyl)oxy)methyl)-piperidin-3-yl)methanesulfonamide | 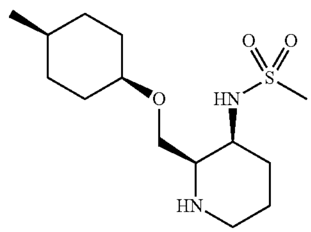 | 305.1 |
| 123 | cis-N-ethyl-3-((methylsulfonyl)amino)-2-(((1-phenylpiperidin-4-yl)oxy)methyl)piperidine-1-carboxamide | 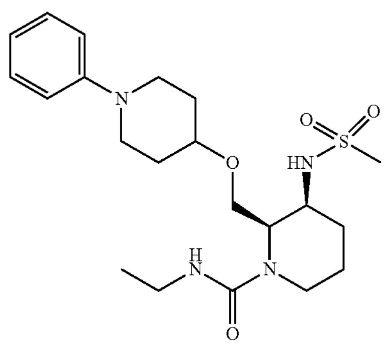 [SMILES: CCNC(=O)N1CCC[C@H](NS(C)(=O)=O)[C@@H]1COC1CCN(c2ccccc2)CC1] | 439.1 |
| 124 | N-(cis-2-(((cis-4-(1-methyl-1H-pyrazol-4-yl)cyclohexyl)oxy)methyl)piperidin-3-yl)methanesulfonamide | 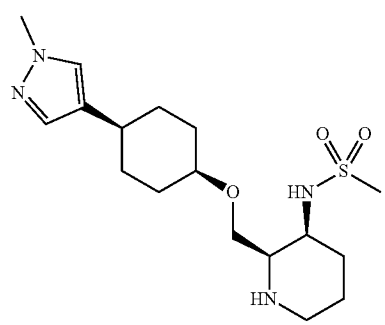 [SMILES: Cn1cc([C@H]2CC[C@@H](OC[C@@H]3NCCC[C@@H]3NS(C)(=O)=O)CC2)cn1] | 371.1 |
| 125 | N-(cis-1-acetyl-2-(((4-methoxycyclohexyl)oxy)methyl)-piperidin-3-yl)methanesulfonamide | 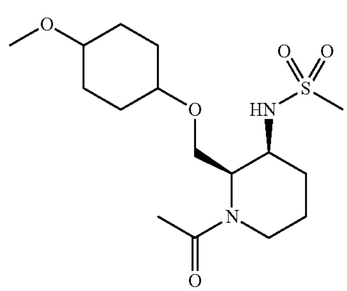 | 363.1 |

TABLE 1-21-continued

| Ex. No. | IUPAC name | Structure | MS |
|---|---|---|---|
| 126 | cis-N-ethyl-2-(((4-methoxycyclohexyl)oxy)methyl)-3-((methylsulfonyl)amino)piperidine-1-carboxamide | 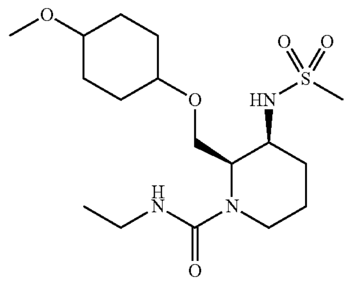 | 392.1 |

TABLE 1-22

| Ex. No. | IUPAC name | Structure | MS |
|---|---|---|---|
| 127 | N-(cis-1-acetyl-2-(((4-(1H-pyrazol-1-yl)cyclohexyl)oxy)methyl)piperidin-3-yl)methanesulfonamide | 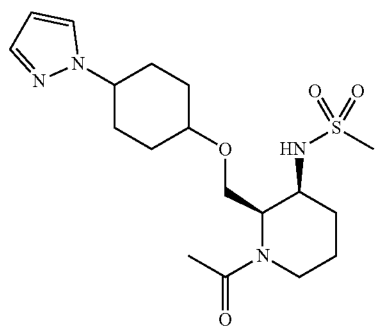 [SMILES: CC(=O)N1CCC[C@H](NS(C)(=O)=O)[C@@H]1COC1CCC(n2cccn2)CC1] | 399 |
| 128 | N-(cis-1-acetyl-2-(((cis-4-methylcyclohexyl)oxy)methyl)-piperidin-3-yl)methanesulfonamide | 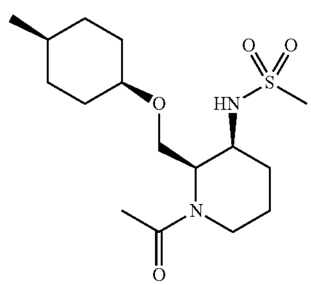 | 347.1 |
| 129 | cis-N-ethyl-2-(((cis-4-methylcyclohexyl)oxy)methyl)-3-((methylsulfonyl)amino)piperidine-1-carboxamide | 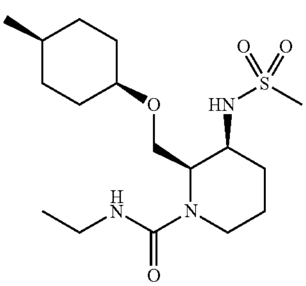 | 376.1 |

TABLE 1-22-continued

| Ex. No. | IUPAC name | Structure | MS |
|---|---|---|---|
| 130 | cis-N-ethyl-3-((methylsulfonyl)amino)-2-(((trans-3-phenylcyclobutyl)oxy)methyl)-piperidine-1-carboxamide | 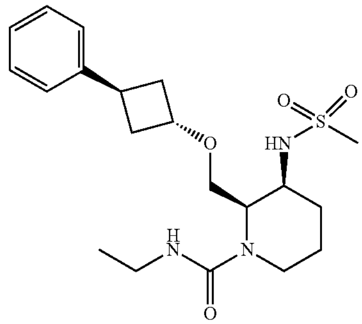 [SMILES: CCNC(=O)N1CCC[C@H](NS(C)(=O)=O)[C@@H]1CO[C@H]1C[C@H](c2ccccc2)C1] | 410.1 |
| 131 | N-(cis-1-acetyl-2-(((trans-3-phenylcyclobutyl)oxy)methyl)-piperidin-3-yl)methanesulfonamide | 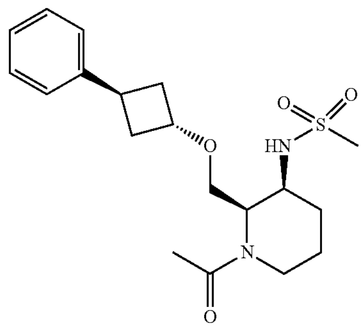 [SMILES: CC(=O)N1CCC[C@H](NS(C)(=O)=O)[C@@H]1CO[C@H]1C[C@H](c2ccccc2)C1] | 381.1 |
| 132 | N-(cis-1-acetyl-2-(((cis-2-phenyl-1,3-dioxan-5-yl)oxy)methyl)piperidin-3-yl)methanesulfonamide | 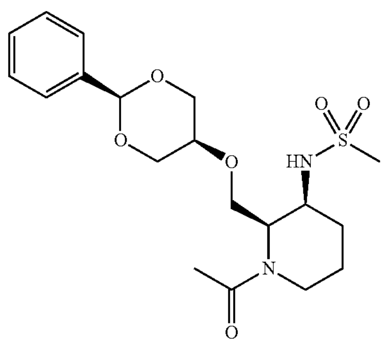 [SMILES: CC(=O)N1CCC[C@H](NS(C)(=O)=O)[C@@H]1CO[C@H]1CO[C@@H](c2ccccc2)OC1] | 413.1 |

TABLE 1-23

| Ex. No. | IUPAC name | Structure | MS |
|---|---|---|---|
| 133 | N-(cis-1-(N,N-dimethylglycyl)-2-(((cis-4-phenylcyclohexyl)oxy)methyl)-piperidin-3-yl)methanesulfonamide | 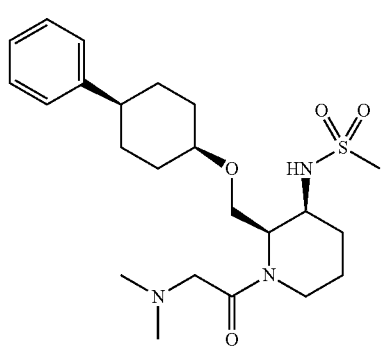 | 452.2 |

TABLE 1-23-continued

| Ex. No. | IUPAC name | Structure | MS |
|---|---|---|---|
| 134 | N-(cis-1-acetyl-2-(((cis-4-(1-methyl-1H-pyrazol-4-yl)cyclohexyl)oxy)methyl)piperidin-3-yl)methanesulfonamide | 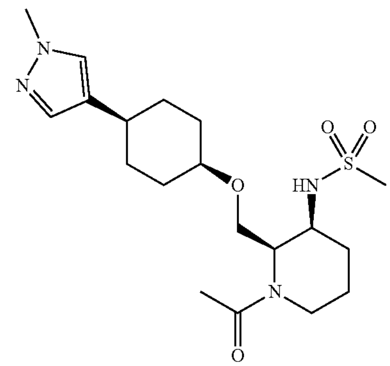 [SMILES: CC(=O)N1CCC[C@H](NS(C)(=O)=O)[C@@H]1CO[C@H]1CC[C@@H](c2cnn(C)c2)CC1] | 413.1 |
| 135 | N-(cis-2-(((cis-4-(3,4-difluorophenyl)cyclohexyl)oxy)-methyl)piperidin-3-yl)methanesulfonamide | 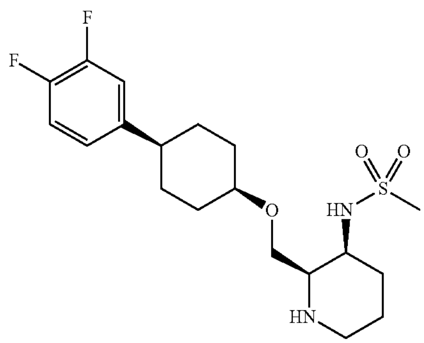 [SMILES: CS(=O)(=O)N[C@H]1CCCN[C@H]1CO[C@H]1CC[C@@H](c2ccc(F)c(F)c2)CC1] | 403.2 |
| 136 | cis-2-(((cis-4-(2,3-difluorophenyl)cyclohexyl)oxy)-methyl)-N-ethyl-3-((methylsulfonyl)amino)piperidine-1-carboxamide | 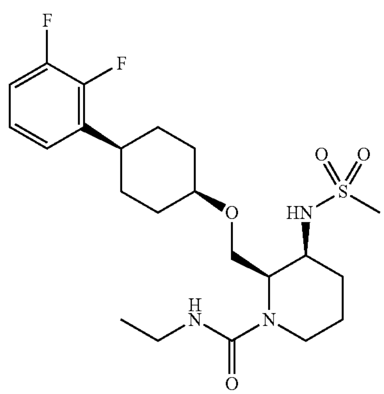 | 474.1 |
| 137 | cis-N-ethyl-2-(((cis-4-(1-methyl-1H-pyrazol-4-yl)cyclohexyl)oxy)methyl)-3-((methylsulfonyl)amino)piperidine-1-carboxamide | 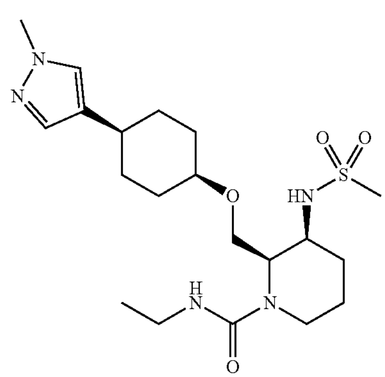 [SMILES: CCNC(=O)N1CCC[C@H](NS(C)(=O)=O)[C@@H]1CO[C@H]1CC[C@@H](c2cnn(C)c2)CC1] | 442.1 |

TABLE 1-23-continued

| Ex. No. | IUPAC name | Structure | MS |
|---|---|---|---|
| 138 | N-(cis-2-(((cis-4-phenylcyclohexyl)oxy)methyl)-1-(1H-pyrazol-1-ylacetyl)piperidin-3-yl)methanesulfonamide | 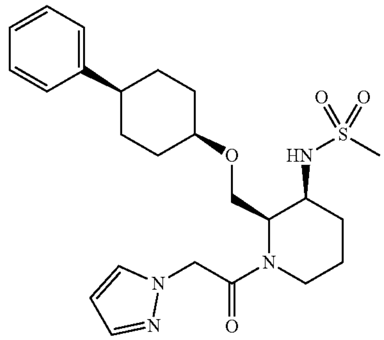 [SMILES: CS(=O)(=O)N[C@H]1CCCN(C(=O)Cn2cccn2)[C@H]1CO[C@H]1CC[C@@H](c2ccccc2)CC1] | 475.1 |

TABLE 1-24

| Ex. No. | IUPAC name | Structure | MS |
|---|---|---|---|
| 139 | N-(cis-1-(difluoroacetyl)-2-(((cis-4-phenylcyclohexyl)oxy)methyl)-piperidin-3-yl)methanesulfonamide | 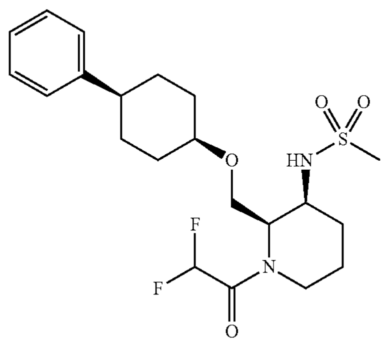 | 443.2 |
| 140 | cis-N-ethyl-3-((methylsulfonyl)amino)-2-(((cis-2-phenyl-1,3-dioxan-5-yl)oxy)methyl)piperidine-1-carboxamide | 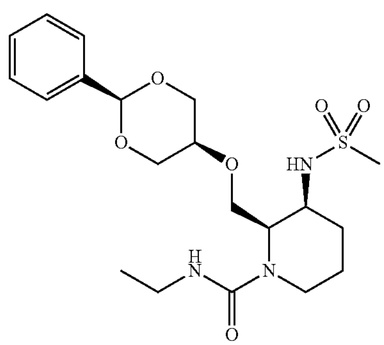 [SMILES: CCNC(=O)N1CCC[C@H](NS(C)(=O)=O)[C@@H]1CO[C@H]1CO[C@@H](c2ccccc2)OC1] | 442.1 |
| 141 | N-(cis-1-acetyl-2-(((cis-4-(3,4-difluorophenyl)cyclohexyl)oxy)methyl)piperidin-3-yl)methanesulfonamide | 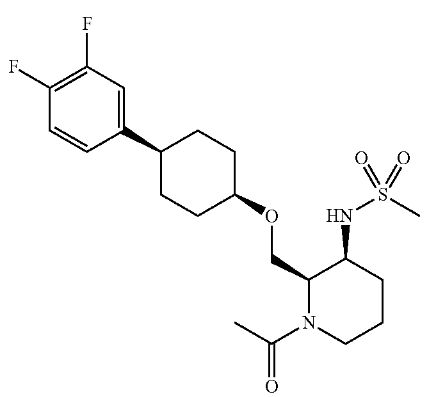 [SMILES: CC(=O)N1CCC[C@H](NS(C)(=O)=O)[C@@H]1CO[C@H]1CC[C@@H](c2ccc(F)c(F)c2)CC1] | 445.1 |

TABLE 1-24-continued

| Ex. No. | IUPAC name | Structure | MS |
|---|---|---|---|
| 142 | N-(cis-2-(((cis-4-(2,4-difluorophenyl)cyclohexyl)oxy)-methyl)piperidin-3-yl)methanesulfonamide | 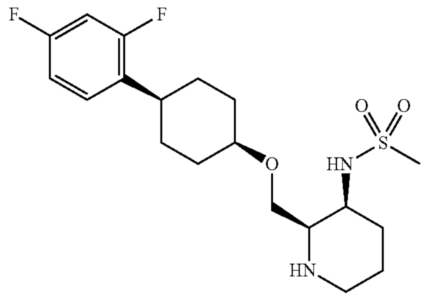 [SMILES: CS(=O)(=O)N[C@H]1CCCN[C@H]1CO[C@H]1CC[C@@H](c2ccc(F)cc2F)CC1] | 403 |
| 143 | N-(cis-2-(((cis-4-(1-methyl-1H-pyrazol-3-yl)cyclohexyl)oxy)methyl)piperidin-3-yl)methanesulfonamide | 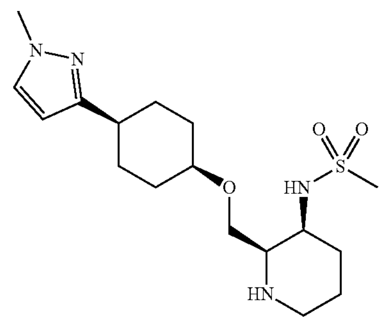 [SMILES: Cn1ccc([C@H]2CC[C@@H](OC[C@@H]3NCCC[C@@H]3NS(C)(=O)=O)CC2)n1] | 369 |
| 144 | cis-2-(((cis-4-(3,4-difluorophenyl)cyclohexyl)oxy)-methyl)-N-ethyl-3-((methylsulfonyl)amino)piperidine-1-carboxamide | 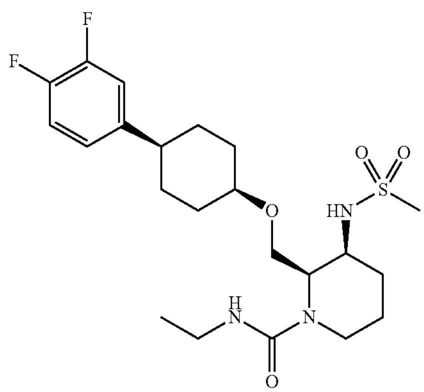 [SMILES: CCNC(=O)N1CCC[C@H](NS(C)(=O)=O)[C@@H]1CO[C@H]1CC[C@@H](c2ccc(F)c(F)c2)CC1] | 474.1 |

TABLE 1-25

| Ex. No. | IUPAC name | Structure | MS |
|---|---|---|---|
| 145 | N-(cis-1-acetyl-2-(((cis-4-(2,4-difluorophenyl)cyclohexyl)oxy)-methyl)piperidin-3-yl)methanesulfonamide | 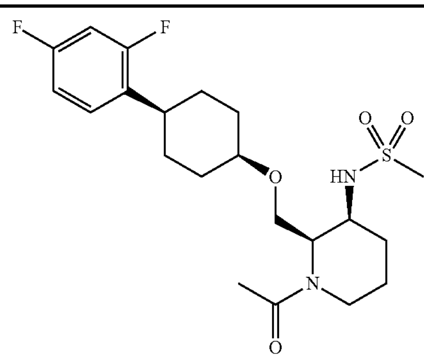 | 445.2 |

TABLE 1-25-continued

| Ex. No. | IUPAC name | Structure | MS |
|---|---|---|---|
| 146 | cis-2-(((cis-4-(2,4-difluorophenyl)cyclohexyl)oxy)-methyl)-N-ethyl-3-((methylsulfonyl)amino)piperidine-1-carboxamide | 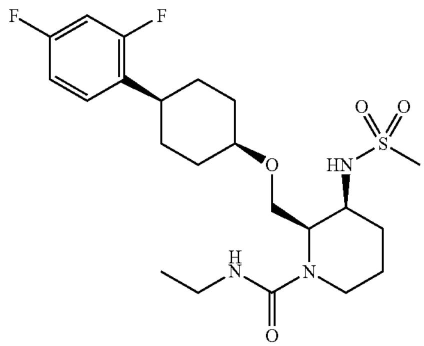 [SMILES: CCNC(=O)N1CCC[C@H](NS(C)(=O)=O)[C@@H]1CO[C@H]1CC[C@@H](c2ccc(F)cc2F)CC1] | 474.1 |
| 147 | N-((2R,3S)-1-acetyl-2-(((cis-4-(3-fluorophenyl)cyclohexyl)oxy)-methyl)piperidin-3-yl)methanesulfonamide | 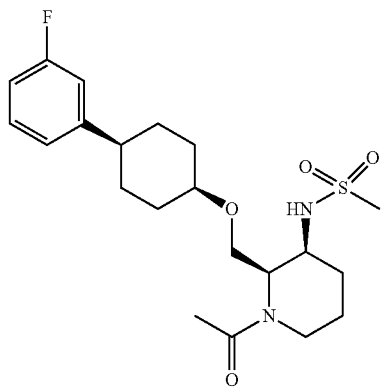 [SMILES: CC(=O)N1CCC[C@H](NS(C)(=O)=O)[C@@H]1CO[C@H]1CC[C@@H](c2cccc(F)c2)CC1] | 427.2 |
| 148 | (2R,3S)-N-ethyl-2-(((cis-4-(3-fluorophenyl)cyclohexyl)oxy)-methyl)-3-((methylsulfonyl)amino)piperidine-1-carboxamide | 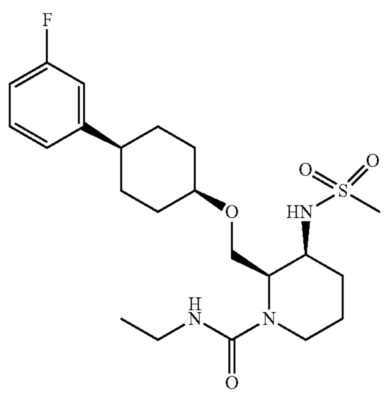 [SMILES: CCNC(=O)N1CCC[C@H](NS(C)(=O)=O)[C@@H]1CO[C@H]1CC[C@@H](c2cccc(F)c2)CC1] | 456 |
| 149 | N-(cis-2-(((cis-4-phenylcyclohexyl)oxy)methyl)-1-((3S)-tetrahydrofuran-3-ylcarbonyl)piperidin-3-yl)methanesulfonamide | 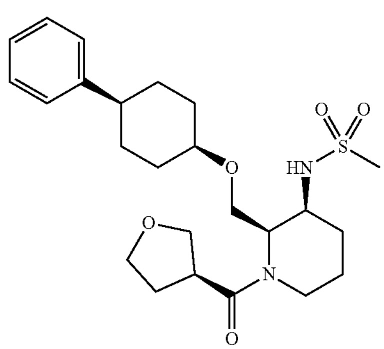 [SMILES: CS(=O)(=O)N[C@H]1CCCN(C(=O)[C@H]2CCOC2)[C@H]1CO[C@H]1CC[C@@H](c2ccccc2)CC1] | 465.1 |

TABLE 1-25-continued

| Ex. No. | IUPAC name | Structure | MS |
|---|---|---|---|
| 150 | N-(cis-2-(((cis-4-phenylcyclohexyl)oxy)methyl)-1-((3R)-tetrahydrofuran-3-ylcarbonyl)piperidin-3-yl)methanesulfonamide | 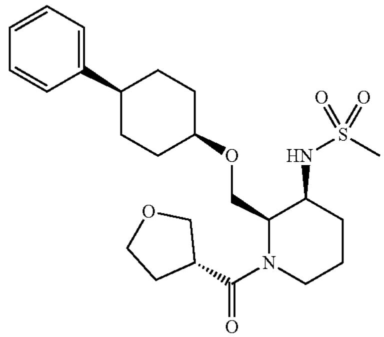 [SMILES: CS(=O)(=O)N[C@H]1CCCN(C(=O)[C@@H]2CCOC2)[C@H]1CO[C@H]1CC[C@@H](c2ccccc2)CC1] | 465.1 |

TABLE 1-26

| Ex. No. | IUPAC name | Structure | MS |
|---|---|---|---|
| 151 | methyl cis-3-((methylsulfonyl)amino)-2-(((1-(pyrimidin-2-yl)piperidin-4-yl)oxy)methyl)piperidine-1-carboxylate | 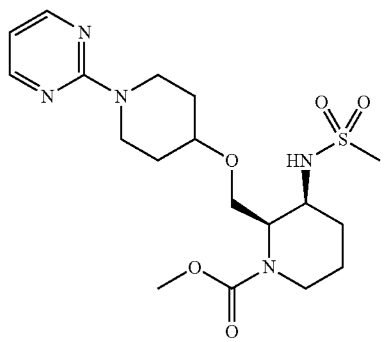 | 428.1 |
| 152 | N-(cis-1-(methylsulfonyl)-2-(((cis-4-phenylcyclohexyl)oxy)methyl)-piperidin-3-yl)methanesulfonamide | 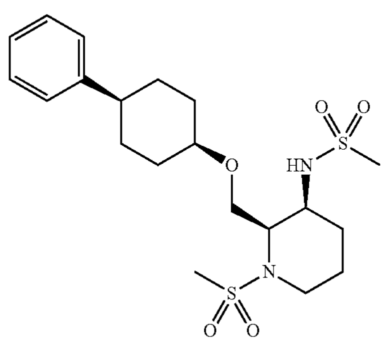 [SMILES: CS(=O)(=O)N[C@H]1CCCN(S(C)(=O)=O)[C@H]1CO[C@H]1CC[C@@H](c2ccccc2)CC1] | 443.1 |
| 153 | N-(cis-1-acetyl-2-(((4-(cyclopropylmethoxy)cyclohexyl)-oxy)methyl)piperidin-3-yl)methanesulfonamide | 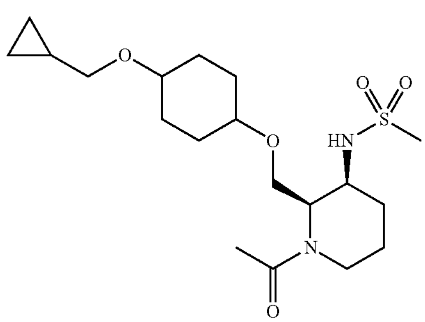 [SMILES: CC(=O)N1CCC[C@H](NS(C)(=O)=O)[C@@H]1COC1CCC(OCC2CC2)CC1] | 403.2 |

TABLE 1-26-continued

| Ex. No. | IUPAC name | Structure | MS |
|---|---|---|---|
| 154 | methyl cis-2-(((cis-4-(1-methyl-1H-pyrazol-3-yl)cyclohexyl)oxy)methyl)-3-((methylsulfonyl)amino)piperidine-1-carboxylate | 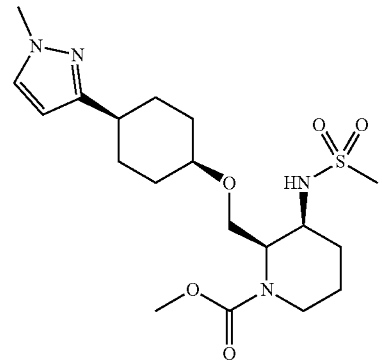 [SMILES: COC(=O)N1CCC[C@H](NS(C)(=O)=O)[C@@H]1CO[C@H]1CC[C@@H](c2ccn(C)n2)CC1] | 429.3 |
| 155 | tert-butyl cis-3-((methylsulfonyl)amino)-2-(((cis-4-phenylcyclohexyl)oxy)methyl)-piperidine-1-carboxylate | 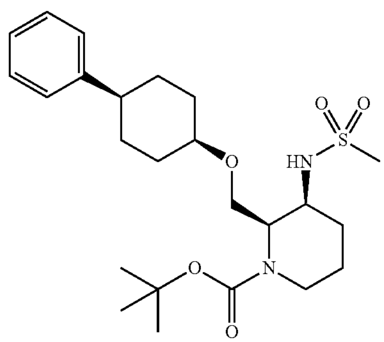 [SMILES: CC(C)(C)OC(=O)N1CCC[C@H](NS(C)(=O)=O)[C@@H]1CO[C@H]1CC[C@@H](c2ccccc2)CC1] | 465.2 |
| 156 | N-methyl-N-(2-(cis-3-((methylsulfonyl)amino)-2-(((cis-4-phenylcyclohexyl)oxy)methyl)-piperidin-1-yl)-2-oxoethyl)acetamide | 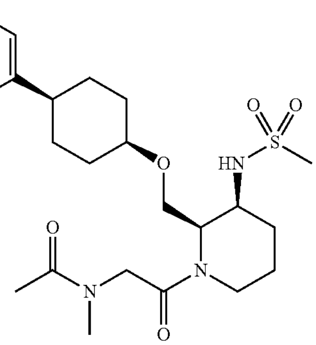 | 480.3 |

TABLE 1-27

| Ex. No. | IUPAC name | Structure | MS |
|---|---|---|---|
| 157 | N-(cis-2-(((cis-4-phenylcyclohexyl)oxy)methyl)-1-(1,3-thiazol-2-ylacetyl)piperidin-3-yl)methanesulfonamide | 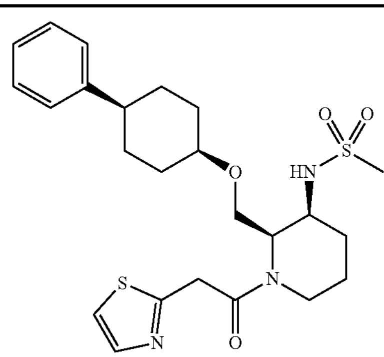 | 492.2 |

TABLE 1-27-continued

| Ex. No. | IUPAC name | Structure | MS |
|---|---|---|---|
| 158 | N-(cis-1-acetyl-2-(((cis-4-(1-methyl-1H-pyrazol-3-yl)cyclohexyl)oxy)methyl)piperidin-3-yl)methanesulfonamide | 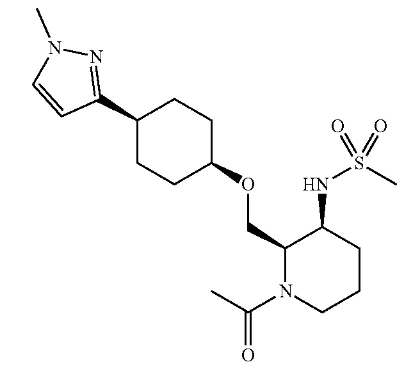 [SMILES: CC(=O)N1CCC[C@H](NS(C)(=O)=O)[C@@H]1CO[C@H]1CC[C@@H](c2ccn(C)n2)CC1] | 413.2 |
| 159 | cis-N-ethyl-2-(((cis-4-(1-methyl-1H-pyrazol-3-yl)cyclohexyl)oxy)methyl)-3-((methylsulfonyl)amino)piperidine-1-carboxamide | 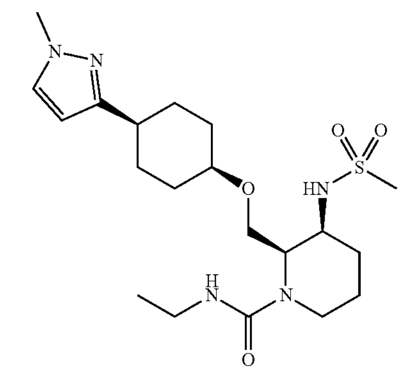 [SMILES: CCNC(=O)N1CCC[C@H](NS(C)(=O)=O)[C@@H]1CO[C@H]1CC[C@@H](c2ccn(C)n2)CC1] | 442.2 |
| 160 | methyl cis-2-(((1-(3-fluorophenyl)piperidin-4-yl)oxy)methyl)-3-((methylsulfonyl)amino)piperidine-1-carboxylate | 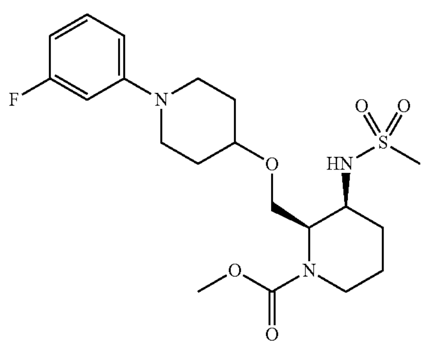 [SMILES: COC(=O)N1CCC[C@H](NS(C)(=O)=O)[C@@H]1COC1CCN(c2cccc(F)c2)CC1] | 444.2 |
| 161 | methyl cis-2-(((1-(4-fluorophenyl)piperidin-4-yl)oxy)methyl)-3-((methylsulfonyl)amino)piperidine-1-carboxylate | 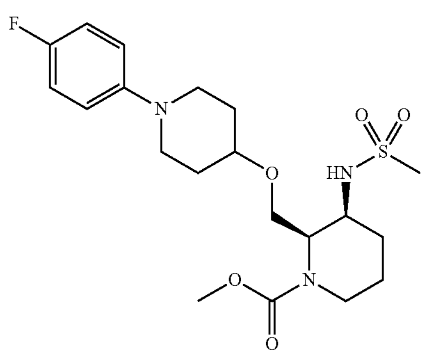 [SMILES: COC(=O)N1CCC[C@H](NS(C)(=O)=O)[C@@H]1COC1CCN(c2ccc(F)cc2)CC1] | 444.2 |

TABLE 1-27-continued

| Ex. No. | IUPAC name | Structure | MS |
|---|---|---|---|
| 162 | methyl cis-2-(((1-(2-fluorophenyl)piperidin-4-yl)oxy)methyl)-3-((methylsulfonyl)amino)piperidine-1-carboxylate | 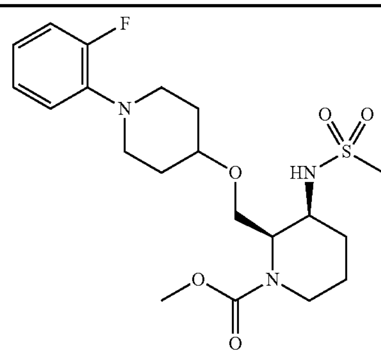 | 444.2 |

TABLE 1-28

| Ex. No. | IUPAC name | Structure | MS |
|---|---|---|---|
| 163 | methyl cis-2-(((1-(3,5-difluorophenyl)piperidin-4-yl)oxy)methyl)-3-((methylsulfonyl)amino)piperidine-1-carboxylate | 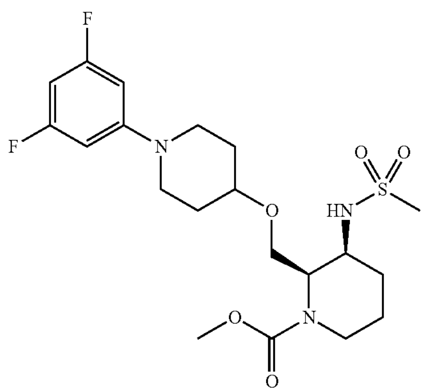 [SMILES: COC(=O)N1CCC[C@H](NS(C)(=O)=O)[C@@H]1COC1CCN(c2cc(F)cc(F)c2)CC1] | 462.2 |
| 164 | methyl cis-2-(((1-(2-methoxyphenyl)piperidin-4-yl)oxy)methyl)-3-((methylsulfonyl)amino)piperidine-1-carboxylate | 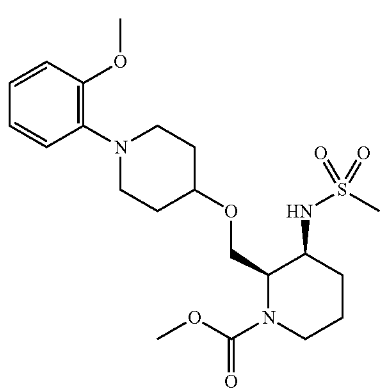 [SMILES: COC(=O)N1CCC[C@H](NS(C)(=O)=O)[C@@H]1COC1CCN(c2ccccc2OC)CC1] | 456.1 |

TABLE 1-28-continued

| Ex. No. | IUPAC name | Structure | MS |
|---|---|---|---|
| 165 | methyl cis-3-((methylsulfonyl)amino)-2-(((1-(2-(trifluoromethyl)phenyl)piperidin-4-yl)oxy)methyl)piperidine-1-carboxylate | 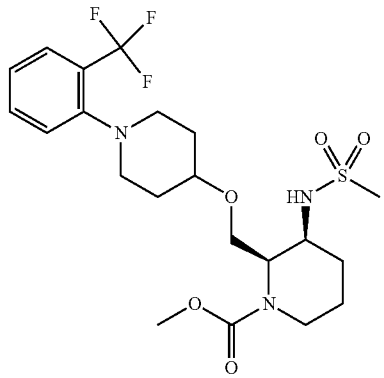 [SMILES: COC(=O)N1CCC[C@H](NS(C)(=O)=O)[C@@H]1COC1CCN(c2ccccc2C(F)(F)F)CC1] | 494.2 |
| 166 | methyl cis-2-(((1-(3-chlorophenyl)piperidin-4-yl)oxy)methyl)-3-((methylsulfonyl)amino)piperidine-1-carboxylate | 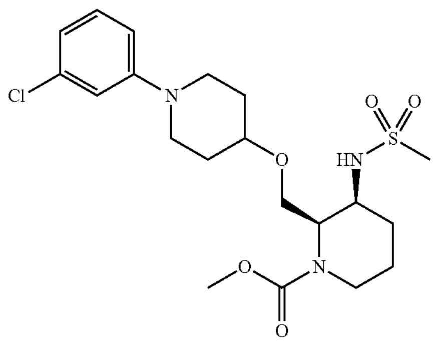 [SMILES: COC(=O)N1CCC[C@H](NS(C)(=O)=O)[C@@H]1COC1CCN(c2cccc(Cl)c2)CC1] | 460.3 |
| 167 | methyl cis-2-(((1-(2-chlorophenyl)piperidin-4-yl)oxy)methyl)-3-((methylsulfonyl)amino)piperidine-1-carboxylate | 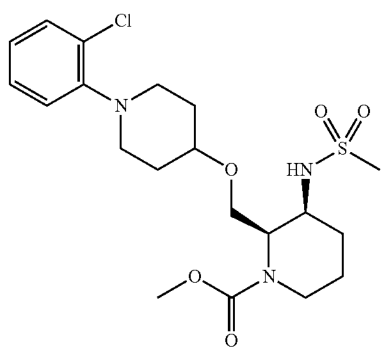 [SMILES: COC(=O)N1CCC[C@H](NS(C)(=O)=O)[C@@H]1COC1CCN(c2ccccc2Cl)CC1] | 460.2 |
| 168 | methyl cis-3-((methylsulfonyl)amino)-2-(((1-(pyridin-2-yl)piperidin-4-yl)oxy)methyl)piperidine-1-carboxylate | 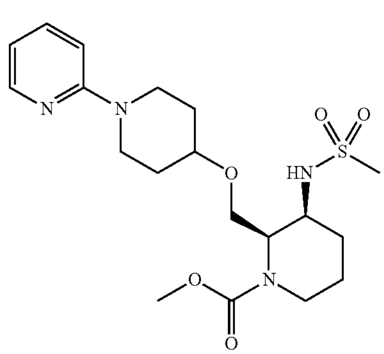 [SMILES: COC(=O)N1CCC[C@H](NS(C)(=O)=O)[C@@H]1COC1CCN(c2ccccn2)CC1] | 427.2 |

TABLE 1-29

| Ex. No. | IUPAC name | Structure | MS |
|---|---|---|---|
| 169 | methyl cis-3-((methylsulfonyl)amino)-2-(((1-(1,3-thiazol-2-yl)piperidin-4-yl)oxy)methyl)piperidine-1-carboxylate | 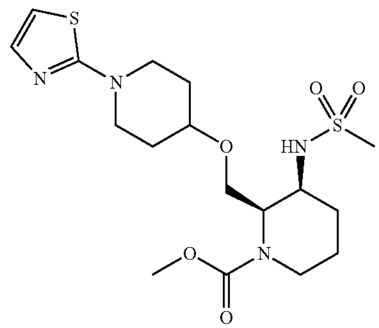 [SMILES: COC(=O)N1CCC[C@H](NS(C)(=O)=O)[C@@H]1COC1CCN(c2nccs2)CC1] | 433.1 |
| 170 | methyl cis-3-((methylsulfonyl)amino)-2-(((1-(1,3-thiazol-4-yl)piperidin-4-yl)oxy)methyl)piperidine-1-carboxylate | 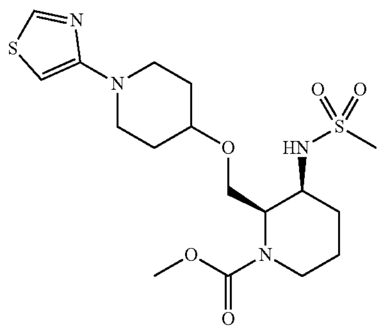 [SMILES: COC(=O)N1CCC[C@H](NS(C)(=O)=O)[C@@H]1COC1CCN(c2cscn2)CC1] | 433.1 |
| 171 | methyl cis-2-(((1-(4-methylpyrimidin-2-yl)piperidin-4-yl)oxy)methyl)-3-((methylsulfonyl)amino)piperidine-1-carboxylate hydrochloride | 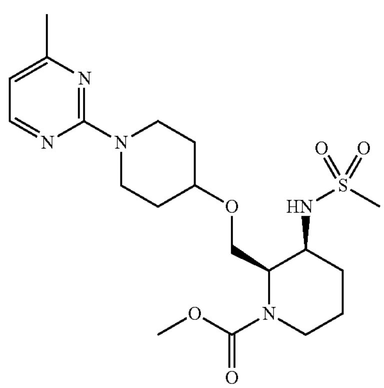 [SMILES: COC(=O)N1CCC[C@H](NS(C)(=O)=O)[C@@H]1COC1CCN(c2nccc(C)n2)CC1] | 442.2 |
| 172 | methyl cis-2-(((1-(5-methylpyrimidin-2-yl)piperidin-4-yl)oxy)methyl)-3-((methylsulfonyl)amino)piperidine-1-carboxylate hydrochloride | 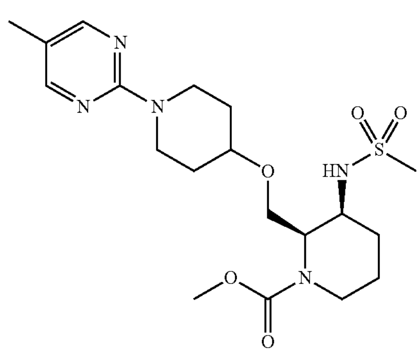 | 442.2 |

TABLE 1-29-continued

| Ex. No. | IUPAC name | Structure | MS |
|---|---|---|---|
| 173 | methyl cis-2-(((1-(4-methoxypyrimidin-2-yl)piperidin-4-yl)oxy)methyl)-3-((methylsulfonyl)amino)piperidine-1-carboxylate hydrochloride | 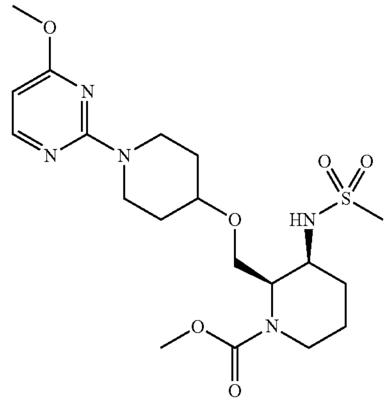 [SMILES: COC(=O)N1CCC[C@H](NS(C)(=O)=O)[C@@H]1COC1CCN(c2nccc(OC)n2)CC1] | 458.2 |
| 174 | methyl cis-3-((methylsulfonyl)amino)-2-(((1-(pyrimidin-2-yl)pyrrolidin-3-yl)oxy)methyl)piperidine-1-carboxylate | 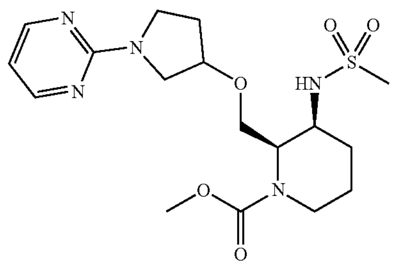 [SMILES: COC(=O)N1CCC[C@H](NS(C)(=O)=O)[C@@H]1COC1CCN(c2ncccn2)C1] | 414.2 |

TABLE 1-30

| Ex. No. | IUPAC name | Structure | MS |
|---|---|---|---|
| 175 | N-(cis-1-acetyl-2-(((4-(difluoromethyl)cyclohexyl)oxy)methyl)piperidin-3-yl)methanesulfonamide | 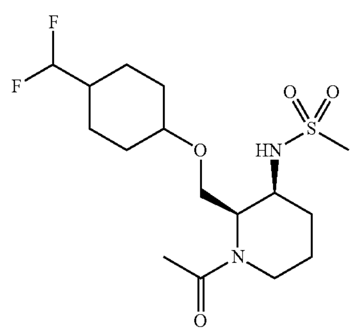 [SMILES: CC(=O)N1CCC[C@H](NS(C)(=O)=O)[C@@H]1COC1CCC(C(F)F)CC1] | 383.1 |
| 176 | N-(cis-1-((1-hydroxycyclopropyl)carbonyl)-2-(((cis-4-phenylcyclohexyl)oxy)methyl)-piperidin-3-yl)methanesulfonamide | 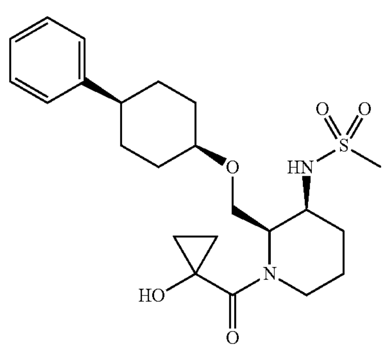 [SMILES: CS(=O)(=O)N[C@H]1CCCN(C(=O)C2(O)CC2)[C@H]1CO[C@H]1CC[C@@H](c2ccccc2)CC1] | 451.1 |

TABLE 1-30-continued

| Ex. No. | IUPAC name | Structure | MS |
|---|---|---|---|
| 177 | N-(cis-2-(((cis-4-phenylcyclohexyl)oxy)methyl)-1-pyruvoylpiperidin-3-yl)methanesulfonamide | 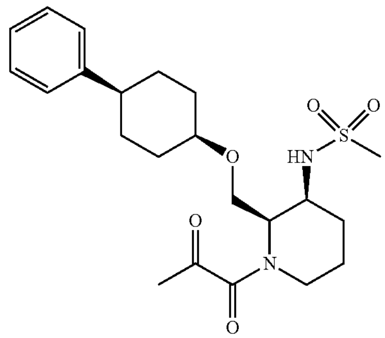 [SMILES: CC(=O)C(=O)N1CCC[C@H](NS(C)(=O)=O)[C@@H]1CO[C@H]1CC[C@@H](c2ccccc2)CC1] | 435.1 |
| 178 | methyl cis-2-(((4-methyl-1-(pyrimidin-2-yl)piperidin-4-yl)oxy)methyl)-3-((methylsulfonyl)amino)piperidine-1-carboxylate hydrochloride | 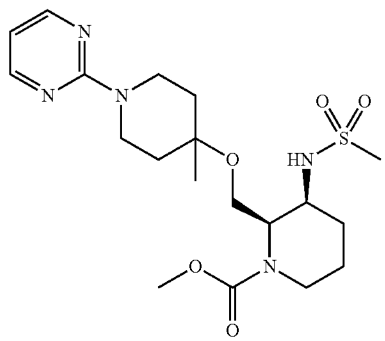 [SMILES: COC(=O)N1CCC[C@H](NS(C)(=O)=O)[C@@H]1COC1(C)CCN(c2ncccn2)CC1] | 442.2 |
| 179 | cis-N-(cyanomethyl)-3-((methylsulfonyl)amino)-2-(((cis-4-phenylcyclohexyl)oxy)methyl)-piperidine-1-carboxamide | 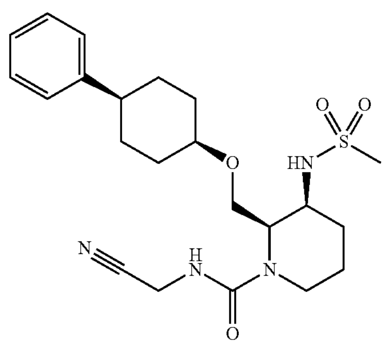 [SMILES: CS(=O)(=O)N[C@H]1CCCN(C(=O)NCC#N)[C@H]1CO[C@H]1CC[C@@H](c2ccccc2)CC1] | 447.1 |
| 180 | N-((2R,3S)-1-(cyanoacetyl)-2-(((cis-4-phenylcyclohexyl)oxy)methyl)-piperidin-3-yl)methanesulfonamide | 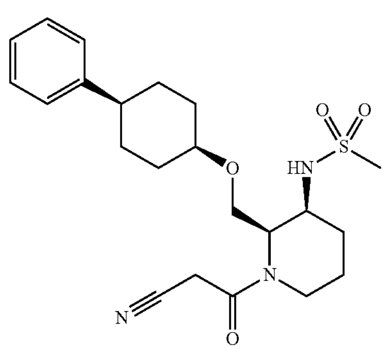 [SMILES: CS(=O)(=O)N[C@H]1CCCN(C(=O)CC#N)[C@H]1CO[C@H]1CC[C@@H](c2ccccc2)CC1] | 432.1 |

TABLE 1-31

| Ex. No. | IUPAC name | Structure | MS |
|---|---|---|---|
| 181 | N-((2R,3S)-1-((methylsulfonyl)acetyl)-2-(((cis-4-phenylcyclohexyl)oxy)methyl)-piperidin-3-yl)methanesulfonamide | 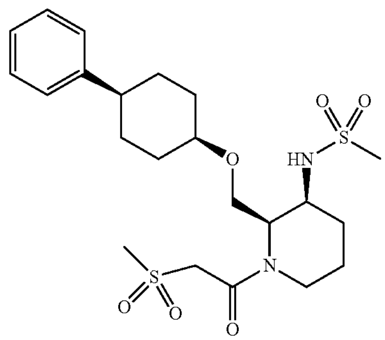 [SMILES: CS(=O)(=O)CC(=O)N1CCC[C@H](NS(C)(=O)=O)[C@@H]1CO[C@H]1CC[C@@H](c2ccccc2)CC1] | 485.1 |
| 182 | N-((2R,3S)-2-(((cis-4-phenylcyclohexyl)oxy)methyl)-1-propionylpiperidin-3-yl)methanesulfonamide | 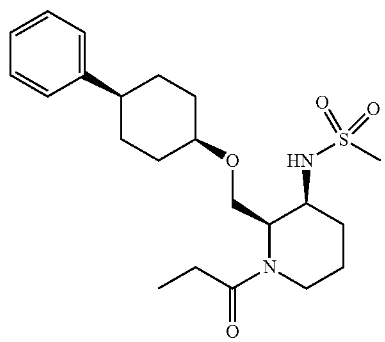 [SMILES: CCC(=O)N1CCC[C@H](NS(C)(=O)=O)[C@@H]1CO[C@H]1CC[C@@H](c2ccccc2)CC1] | 423.2 |
| 183 | N-((2R,3S)-1-(((2R)-5-oxotetrahydrofuran-2-yl)carbonyl)-2-(((cis-4-phenylcyclohexyl)oxy)methyl)-piperidin-3-yl)methanesulfonamide | 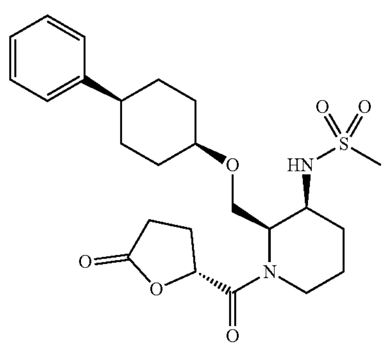 [SMILES: CS(=O)(=O)N[C@H]1CCCN(C(=O)[C@H]2CCC(=O)O2)[C@H]1CO[C@H]1CC[C@@H](c2ccccc2)CC1] | 479.2 |
| 184 | N-((2R,3S)-1-(((2S)-5-oxotetrahydrofuran-2-yl)carbonyl)-2-(((cis-4-phenylcyclohexyl)oxy)methyl)-piperidin-3-yl)methanesulfonamide | 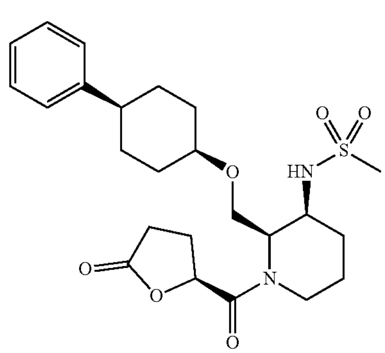 [SMILES: CS(=O)(=O)N[C@H]1CCCN(C(=O)[C@@H]2CCC(=O)O2)[C@H]1CO[C@H]1CC[C@@H](c2ccccc2)CC1] | 479.2 |

TABLE 1-31-continued

| Ex. No. | IUPAC name | Structure | MS |
|---|---|---|---|
| 185 | N-((2R,3S)-1-glycoloyl-2-(((cis-4-phenylcyclohexyl)oxy)methyl)-piperidin-3-yl)methanesulfonamide | 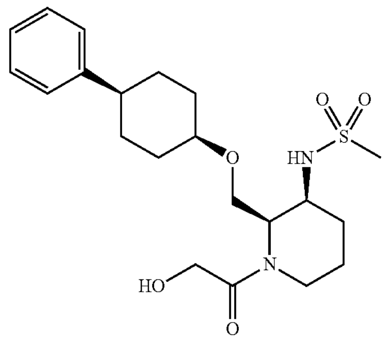 [SMILES: CS(=O)(=O)N[C@H]1CCCN(C(=O)CO)[C@H]1CO[C@H]1CC[C@@H](c2ccccc2)CC1] | 425.1 |
| 186 | methyl cis-2-(((1-(2,6-dichlorophenyl)piperidin-4-yl)oxy)methyl)-3-((methylsulfonyl)amino)piperidine-1-carboxylate | 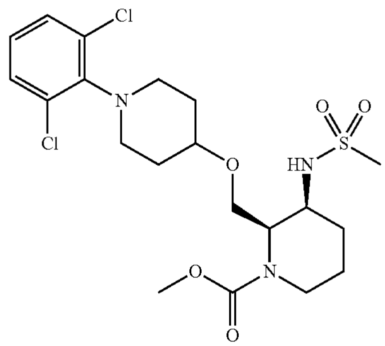 [SMILES: COC(=O)N1CCC[C@H](NS(C)(=O)=O)[C@@H]1COC1CCN(c2c(Cl)cccc2Cl)CC1] | 494 |

TABLE 1-32

| Ex. No. | IUPAC name | Structure | MS |
|---|---|---|---|
| 187 | N-((2R,3S)-1-((1-cyanocyclopropyl)carbonyl)-2-(((cis-4-phenylcyclohexyl)oxy)methyl)-piperidin-3-yl)methanesulfonamide | 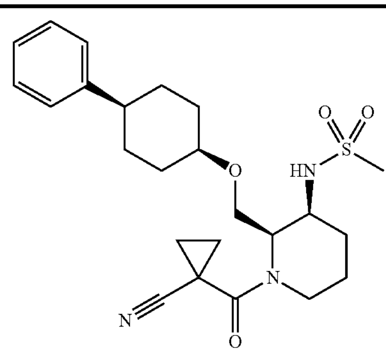 | 460.3 |
| 188 | N-((2R,3S)-1-((2S)-2-hydroxypropanoyl)-2-(((cis-4-phenylcyclohexyl)oxy)methyl)-piperidin-3-yl)methanesulfonamide | 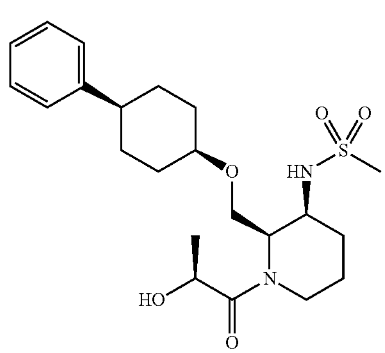 [SMILES: C[C@H](O)C(=O)N1CCC[C@H](NS(C)(=O)=O)[C@@H]1CO[C@H]1CC[C@@H](c2ccccc2)CC1] | 439.2 |

TABLE 1-32-continued

| Ex. No. | IUPAC name | Structure | MS |
|---|---|---|---|
| 189 | N-(cis-1-(2-hydroxy-2-methylpropanoyl)-2-(((cis-4-phenylcyclohexyl)oxy)methyl)-piperidin-3-yl)methanesulfonamide | 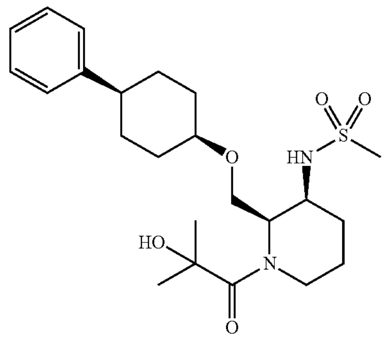 [SMILES: CC(C)(O)C(=O)N1CCC[C@H](NS(C)(=O)=O)[C@@H]1CO[C@H]1CC[C@@H](c2ccccc2)CC1] | 453.2 |
| 190 | methyl cis-2-(((1-(3-chloropyridin-2-yl)piperidin-4-yl)oxy)methyl)-3-((methylsulfonyl)amino)piperidine-1-carboxylate | 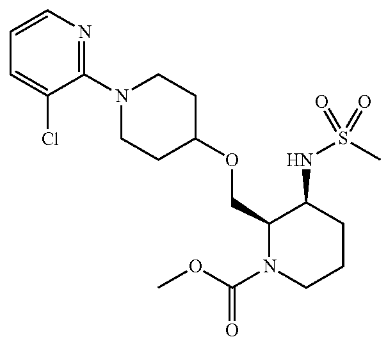 [SMILES: COC(=O)N1CCC[C@H](NS(C)(=O)=O)[C@@H]1COC1CCN(c2ncccc2Cl)CC1] | 461.2 |
| 191 | methyl-d3 (2R,3S)-3-((methylsulfonyl)amino)-2-(((cis-4-phenylcyclohexyl)oxy)methyl)-piperidine-1-carboxylate | 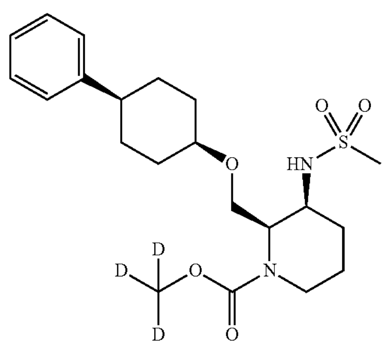 [SMILES: [2H]C([2H])([2H])OC(=O)N1CCC[C@H](NS(C)(=O)=O)[C@@H]1CO[C@H]1CC[C@@H](c2ccccc2)CC1] | 428.3 |
| 192 | cis-N-ethyl-2-(((cis-3-(4-methylphenyl)cyclobutyl)oxy)methyl)-3-((methylsulfonyl)amino)piperidine-1-carboxamide | 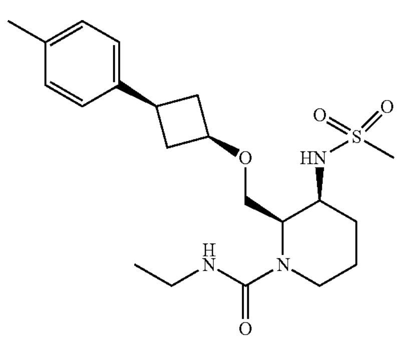 | 424.2 |

TABLE 1-33

| Ex. No. | IUPAC name | Structure | MS |
|---|---|---|---|
| 193 | N-(cis-1-(cyclopropylcarbonyl)-2-(((cis-3-phenylcyclobutyl)oxy)methyl)-piperidin-3-yl)methanesulfonamide | 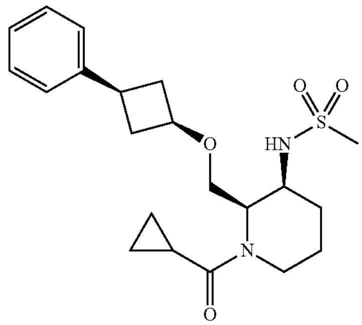 [SMILES: CS(=O)(=O)N[C@H]1CCCN(C(=O)C2CC2)[C@H]1CO[C@H]1C[C@@H](c2ccccc2)C1] | 407.2 |
| 194 | methyl cis-3-((methylsulfonyl)amino)-2-(((cis-3-phenylcyclobutyl)oxy)methyl)-piperidine-1-carboxylate | 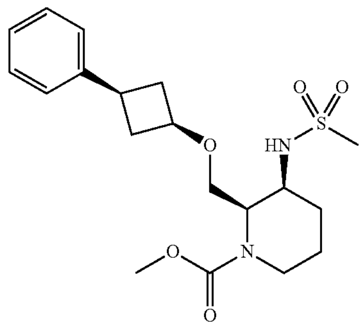 [SMILES: COC(=O)N1CCC[C@H](NS(C)(=O)=O)[C@@H]1CO[C@H]1C[C@@H](c2ccccc2)C1] | 395.1 |
| 195 | cis-N-ethyl-2-(((1-(2-fluorophenyl)piperidin-4-yl)oxy)methyl)-3-((methylsulfonyl)amino)piperidine-1-carboxamide | 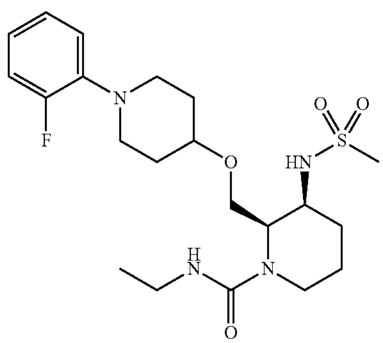 [SMILES: CCNC(=O)N1CCC[C@H](NS(C)(=O)=O)[C@@H]1COC1CCN(c2ccccc2F)CC1] | 457.2 |
| 196 | N-(cis-1-(cyclopropylcarbonyl)-2-(((1-(pyrimidin-2-yl)piperidin-4-yl)oxy)methyl)piperidin-3-yl)methanesulfonamide | 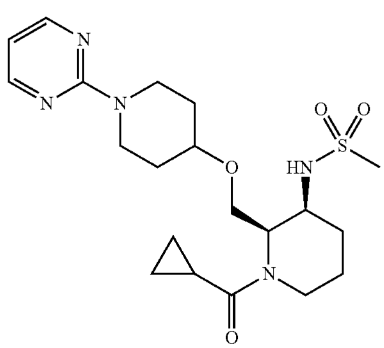 | 438.2 |

TABLE 1-33-continued

| Ex. No. | IUPAC name | Structure | MS |
|---|---|---|---|
| 197 | N-(cis-1-(cyclopropylcarbonyl)-2-(((cis-4-methylcyclohexyl)oxy)methyl)-piperidin-3-yl)methanesulfonamide | 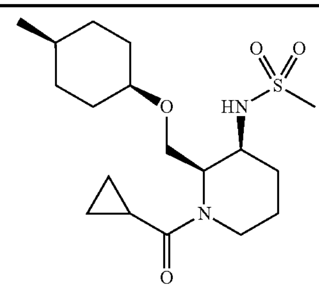 | 371.2 |
| 198 | N-(cis-1-acetyl-2-(((cis-4-(2,5-difluorophenyl)cyclohexyl)oxy)-methyl)piperidin-3-yl)methanesulfonamide | 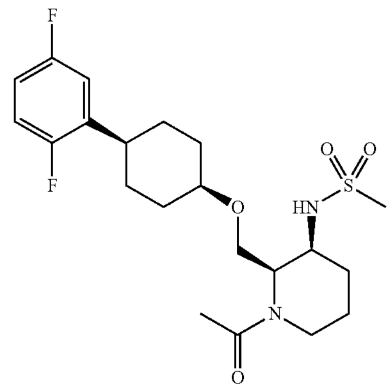 [SMILES: CC(=O)N1CCC[C@H](NS(C)(=O)=O)[C@@H]1CO[C@H]1CC[C@@H](c2cc(F)ccc2F)CC1] | 445.3 |

TABLE 1-34

| Ex. No. | IUPAC name | Structure | MS |
|---|---|---|---|
| 199 | methyl cis-3-((methylsulfonyl)amino)-2-(((1-phenylpiperidin-4-yl)oxy)methyl)piperidine-1-carboxylate | 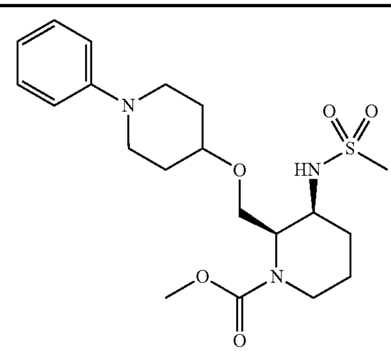 | 426.2 |
| 200 | methyl (2R,3S)-2-(((cis-4-(3-fluorophenyl)cyclohexyl)oxy)-methyl)-3-((methylsulfonyl)amino)piperidine-1-carboxylate | 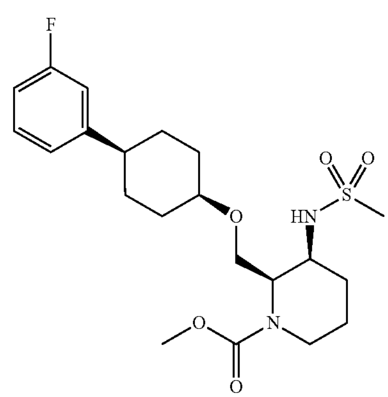 [SMILES: COC(=O)N1CCC[C@H](NS(C)(=O)=O)[C@@H]1CO[C@H]1CC[C@@H](c2cccc(F)c2)CC1] | 441 |

TABLE 1-34-continued

| Ex. No. | IUPAC name | Structure | MS |
|---|---|---|---|
| 201 | N-(cis-2-(((1-(2-chlorophenyl)piperidin-4-yl)oxy)methyl)-1-(cyclopropylcarbonyl)piperidin-3-yl)methanesulfonamide | 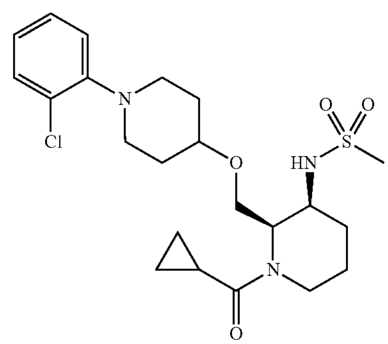 | 470.3 |
| 202 | N-(cis-1-(cyclopropylcarbonyl)-2-(((1-(5-fluoropyrimidin-2-yl)piperidin-4-yl)oxy)methyl)piperidin-3-yl)methanesulfonamide | 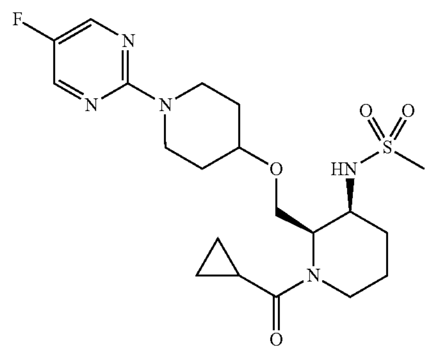 [SMILES: CS(=O)(=O)N[C@H]1CCCN(C(=O)C2CC2)[C@H]1COC1CCN(c2ncc(F)cn2)CC1] | 456.2 |
| 203 | methyl cis-2-(((cis-3-(4-methylphenyl)cyclobutyl)oxy)methyl)-3-((methylsulfonyl)amino)piperidine-1-carboxylate | 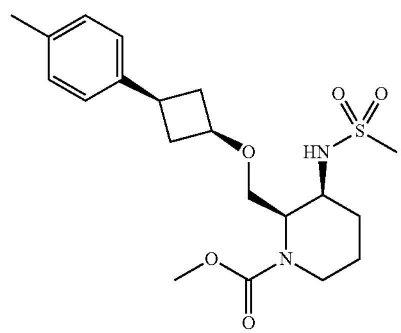 | 409.1 |
| 204 | N-(cis-1-acetyl-2-(((cis-4-(3-(trifluoromethyl)phenyl)cyclohexyl)oxy)methyl)piperidin-3-yl)methanesulfonamide | 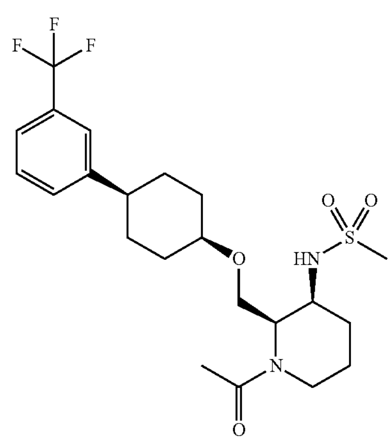 [SMILES: CC(=O)N1CCC[C@H](NS(C)(=O)=O)[C@@H]1CO[C@H]1CC[C@@H](c2cccc(C(F)(F)F)c2)CC1] | 477.2 |

TABLE 1-35

| Ex. No. | IUPAC name | Structure | MS |
|---|---|---|---|
| 205 | N-(cis-2-(((cis-4-(3-(trifluoromethyl)phenyl)-cyclohexyl)oxy)methyl)piperidin-3-yl)methanesulfonamide | 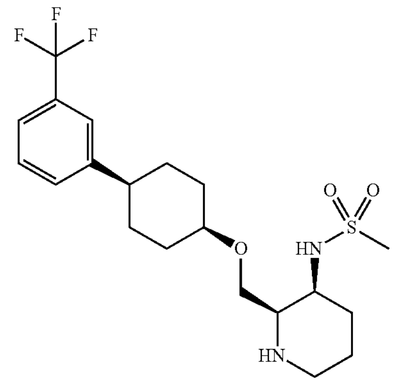 [SMILES: CS(=O)(=O)N[C@H]1CCCN[C@H]1CO[C@H]1CC[C@@H](c2cccc(C(F)(F)F)c2)CC1] | 435.2 |
| 206 | N-(cis-1-acetyl-2-(((cis-3-(4-methylphenyl)cyclobutyl)oxy)-methyl)piperidin-3-yl)methanesulfonamide | 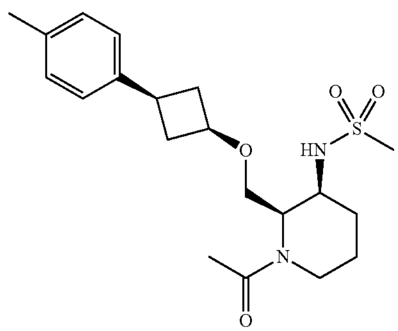 | 395.3 |
| 207 | cis-N-ethyl-3-((methylsulfonyl)amino)-2-(((cis-4-(3-(trifluoromethyl)phenyl)-cyclohexyl)oxy)methyl)piperidine-1-carboxamide | 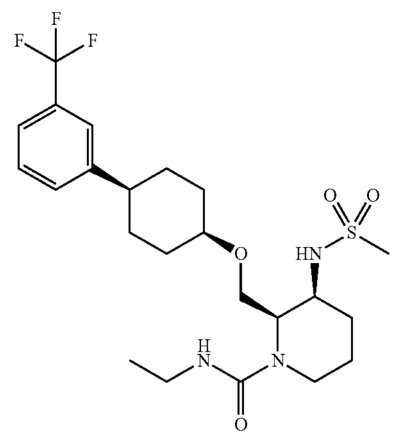 [SMILES: CCNC(=O)N1CCC[C@H](NS(C)(=O)=O)[C@@H]1CO[C@H]1CC[C@@H](c2cccc(C(F)(F)F)c2)CC1] | 506.2 |
| 208 | N-(cis-1-(cyclohexylcarbonyl)-2-(((1-(pyrimidin-2-yl)piperidin-4-yl)oxy)methyl)piperidin-3-yl)methanesulfonamide | 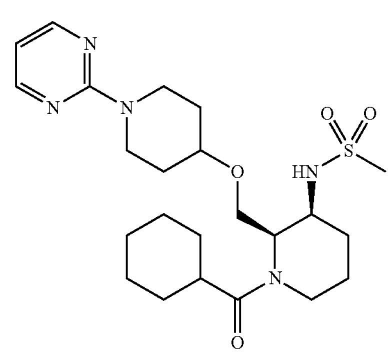 [SMILES: CS(=O)(=O)N[C@H]1CCCN(C(=O)C2CCCCC2)[C@H]1COC1CCN(c2ncccn2)CC1] | 480.3 |

TABLE 1-35-continued

| Ex. No. | IUPAC name | Structure | MS |
|---|---|---|---|
| 209 | N-(cis-2-(((1-(2-chloro-3-fluorophenyl)piperidin-4-yl)oxy)methyl)-1-(cyclopropylcarbonyl)piperidin-3-yl)methanesulfonamide | 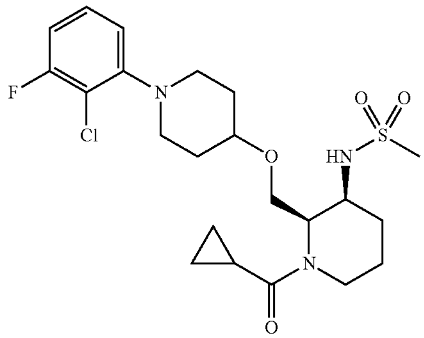 [SMILES: CS(=O)(=O)N[C@H]1CCCN(C(=O)C2CC2)[C@H]1COC1CCN(c2cccc(F)c2Cl)CC1] | 488.1 |
| 210 | N-(cis-1-((4,4-dimethylcyclohexyl)carbonyl)-2-(((1-(pyrimidin-2-yl)piperidin-4-yl)oxy)methyl)piperidin-3-yl)methanesulfonamide | 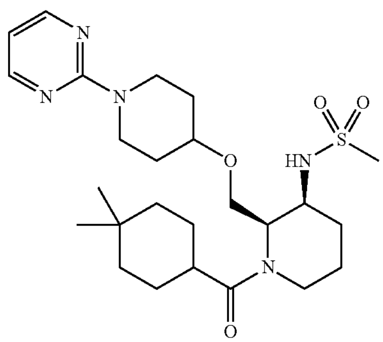 [SMILES: CC1(C)CCC(C(=O)N2CCC[C@H](NS(C)(=O)=O)[C@@H]2COC2CCN(c3ncccn3)CC2)CC1] | 508.3 |

TABLE 1-36

| Ex. No. | IUPAC name | Structure | MS |
|---|---|---|---|
| 211 | N-(cis-1-(cyclopropylcarbonyl)-2-(((3,3-difluoro-1-(pyrimidin-2-yl)piperidin-4-yl)oxy)methyl)piperidin-3-yl)methanesulfonamide | 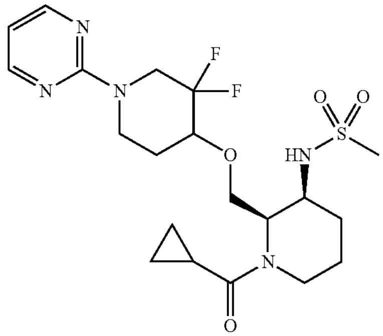 [SMILES: CS(=O)(=O)N[C@H]1CCCN(C(=O)C2CC2)[C@H]1COC1CCN(c2ncccn2)CC1(F)F] | 474.2 |

TABLE 1-36-continued

| Ex. No. | IUPAC name | Structure | MS |
|---|---|---|---|
| 212 | N-(cis-2-(((1-(2-chloro-5-fluorophenyl)piperidin-4-yl)oxy)methyl)-1-(cyclopropylcarbonyl)piperidin-3-yl)methanesulfonamide | 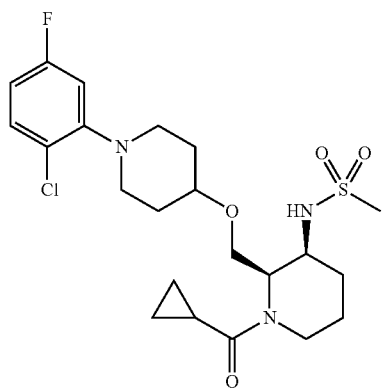 [SMILES: CS(=O)(=O)N[C@H]1CCCN(C(=O)C2CC2)[C@H]1COC1CCN(c2cc(F)ccc2Cl)CC1] | 488.1 |
| 213 | N-((2R,3S)-1-(cyclopropylcarbonyl)-2-(((cis-4-(2,6-difluorophenyl)cyclohexyl)oxy)-methyl)piperidin-3-yl)methanesulfonamide | 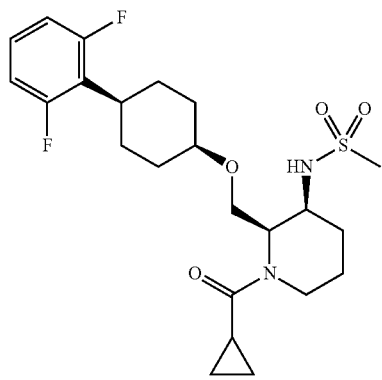 [SMILES: CS(=O)(=O)N[C@H]1CCCN(C(=O)C2CC2)[C@H]1CO[C@H]1CC[C@@H](c2c(F)cccc2F)CC1] | 471.2 |
| 214 | N-((2R,3S)-1-(cyclopropylcarbonyl)-2-(((cis-4-(2,5-difluorophenyl)cyclohexyl)oxy)methyl)piperidin-3-yl)methanesulfonamide | 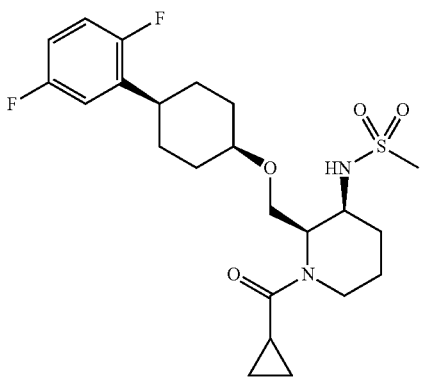 [SMILES: CS(=O)(=O)N[C@H]1CCCN(C(=O)C2CC2)[C@H]1CO[C@H]1CC[C@@H](c2cc(F)ccc2F)CC1] | 471.2 |
| 215 | methyl (2R,3S)-2-(((cis-4-(2,6-difluorophenyl)cyclohexyl)oxy)-methyl)-3-((methylsulfonyl)amino)piperidine-1-carboxylate | 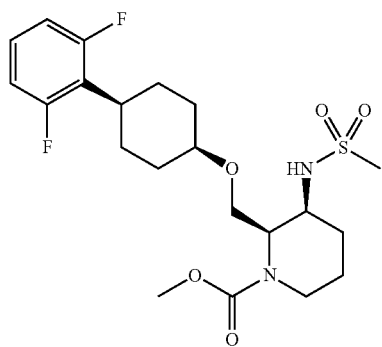 [SMILES: COC(=O)N1CCC[C@H](NS(C)(=O)=O)[C@@H]1CO[C@H]1CC[C@@H](c2c(F)cccc2F)CC1] | 461.3 |

TABLE 1-36-continued

| Ex. No. | IUPAC name | Structure | MS |
|---|---|---|---|
| 216 | N-(cis-1-acetyl-2-(((4-fluoro-4-(3-fluorophenyl)cyclohexyl)oxy)-methyl)piperidin-3-yl)methanesulfonamide | 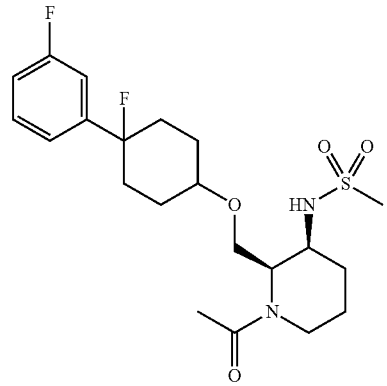 [SMILES: CC(=O)N1CCC[C@H](NS(C)(=O)=O)[C@@H]1COC1CCC(F)(c2cccc(F)c2)CC1] | 445.2 |

TABLE 1-37

| Ex. No. | IUPAC name | Structure | MS |
|---|---|---|---|
| 217 | N-((2R,3S)-1-acetyl-2-(((cis-4-(2,5-difluorophenyl)cyclohexyl)oxy)-methyl)piperidin-3-yl)methanesulfonamide | 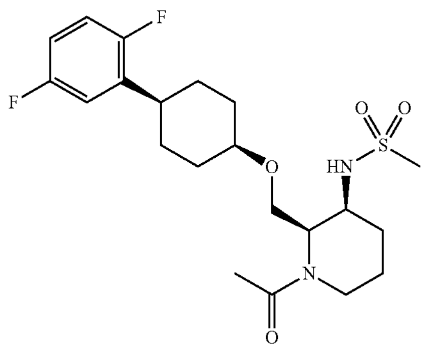 [SMILES: CC(=O)N1CCC[C@H](NS(C)(=O)=O)[C@@H]1CO[C@H]1CC[C@@H](c2cc(F)ccc2F)CC1] | 445.2 |
| 218 | N-(cis-2-(((1-(2-fluorophenyl)piperidin-4-yl)oxy)methyl)-1-glycoloylpiperidin-3-yl)methanesulfonamide | 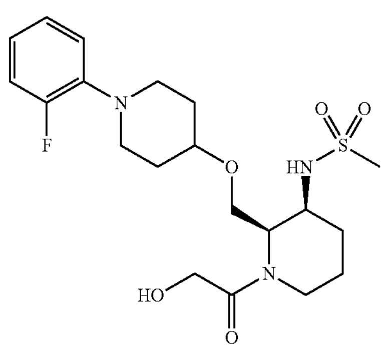 [SMILES: CS(=O)(=O)N[C@H]1CCCN(C(=O)CO)[C@H]1COC1CCN(c2ccccc2F)CC1] | 444.2 |

TABLE 1-37-continued

| Ex. No. | IUPAC name | Structure | MS |
|---|---|---|---|
| 219 | N-(cis-2-(((1-(2-fluorophenyl)piperidin-4-yl)oxy)methyl)-1-propionylpiperidin-3-yl)methanesulfonamide | 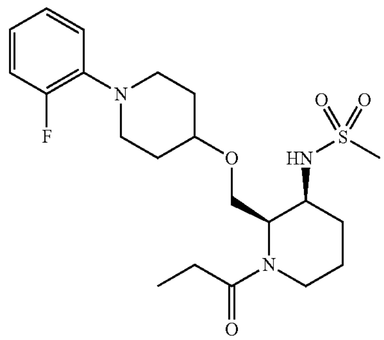 [SMILES: CCC(=O)N1CCC[C@H](NS(C)(=O)=O)[C@@H]1COC1CCN(c2ccccc2F)CC1] | 442.2 |
| 220 | N-(cis-1-((1-fluorocyclopropyl)carbonyl)-2-(((1-(2-fluorophenyl)piperidin-4-yl)oxy)methyl)piperidin-3-yl)methanesulfonamide | 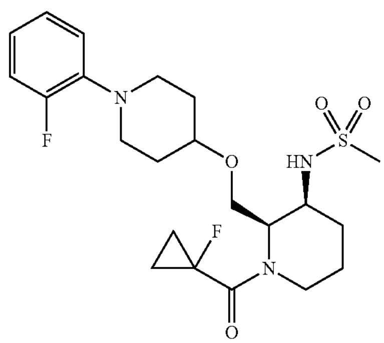 [SMILES: CS(=O)(=O)N[C@H]1CCCN(C(=O)C2(F)CC2)[C@H]1COC1CCN(c2ccccc2F)CC1] | 472.2 |
| 221 | N-(cis-1-(((1S,2S)-2-fluorocyclopropyl)carbonyl)-2-(((1-(2-fluorophenyl)piperidin-4-yl)oxy)methyl)piperidin-3-yl)methanesulfonamide | 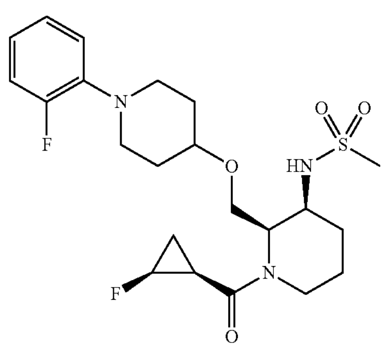 [SMILES: CS(=O)(=O)N[C@H]1CCCN(C(=O)[C@@H]2C[C@@H]2F)[C@H]1COC1CCN(c2ccccc2F)CC1] | 472.2 |
| 222 | N-(cis-1-(((1R,2S)-2-fluorocyclopropyl)carbonyl)-2-(((1-(2-fluorophenyl)piperidin-4-yl)oxy)methyl)piperidin-3-yl)methanesulfonamide | 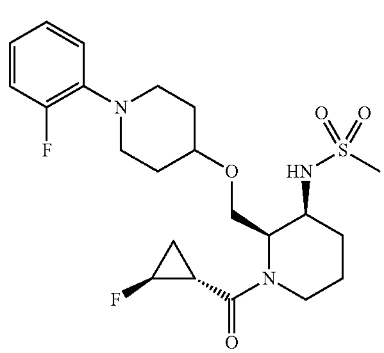 [SMILES: CS(=O)(=O)N[C@H]1CCCN(C(=O)[C@H]2C[C@@H]2F)[C@H]1COC1CCN(c2ccccc2F)CC1] | 472.2 |

TABLE 1-38

| Ex. No. | IUPAC name | Structure | MS |
|---|---|---|---|
| 223 | N-(cis-1-(cyclobutylcarbonyl)-2-(((1-(2-fluorophenyl)piperidin-4-yl)oxy)methyl)piperidin-3-yl)methanesulfonamide | 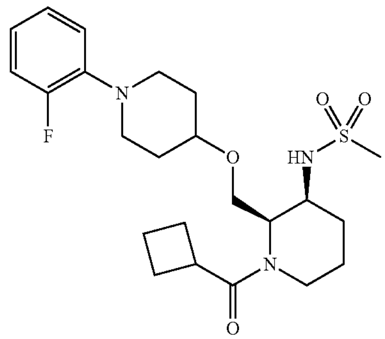 [SMILES: CS(=O)(=O)N[C@H]1CCCN(C(=O)C2CCC2)[C@H]1COC1CCN(c2ccccc2F)CC1] | 468.2 |
| 224 | N-(cis-2-(((1-(2-fluorophenyl)piperidin-4-yl)oxy)methyl)-1-isobutyrylpiperidin-3-yl)methanesulfonamide | 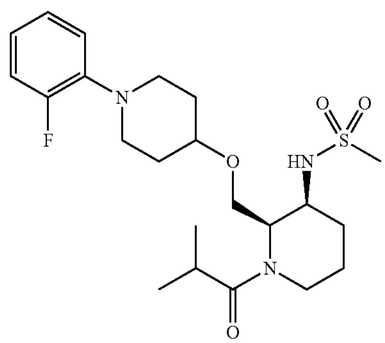 [SMILES: CC(C)C(=O)N1CCC[C@H](NS(C)(=O)=O)[C@@H]1COC1CCN(c2ccccc2F)CC1] | 456.3 |
| 225 | N-(cis-1-((2,2-difluorocyclopropyl)carbonyl)-2-(((1-(2-fluorophenyl)piperidin-4-yl)oxy)methyl)piperidin-3-yl)methanesulfonamide | 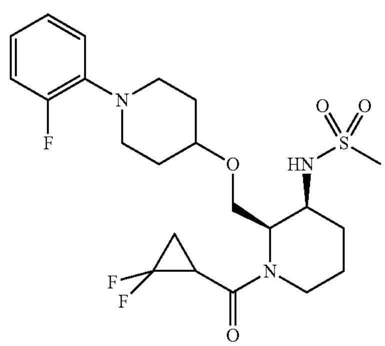 [SMILES: CS(=O)(=O)N[C@H]1CCCN(C(=O)C2CC2(F)F)[C@H]1COC1CCN(c2ccccc2F)CC1] | 490.2 |
| 226 | N-(cis-1-(cyclopropylacetyl)-2-(((1-(2-fluorophenyl)piperidin-4-yl)oxy)methyl)piperidin-3-yl)methanesulfonamide | 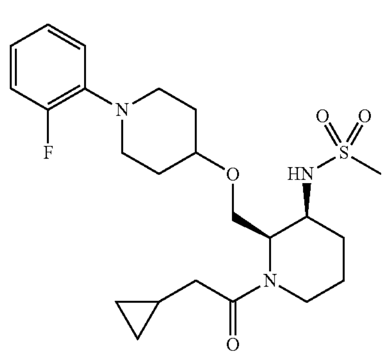 [SMILES: CS(=O)(=O)N[C@H]1CCCN(C(=O)CC2CC2)[C@H]1COC1CCN(c2ccccc2F)CC1] | 468.2 |

TABLE 1-38-continued

| Ex. No. | IUPAC name | Structure | MS |
|---|---|---|---|
| 227 | N-(cis-1-butyryl-2-(((1-(2-fluorophenyl)piperidin-4-yl)oxy)methyl)piperidin-3-yl)methanesulfonamide | 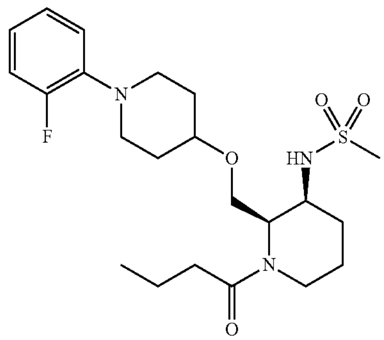 [SMILES: CCCC(=O)N1CCC[C@H](NS(C)(=O)=O)[C@@H]1COC1CCN(c2ccccc2F)CC1] | 456.2 |
| 228 | ethyl cis-2-(((1-(2-fluorophenyl)piperidin-4-yl)oxy)methyl)-3-((methylsulfonyl)amino)piperidine-1-carboxylate | 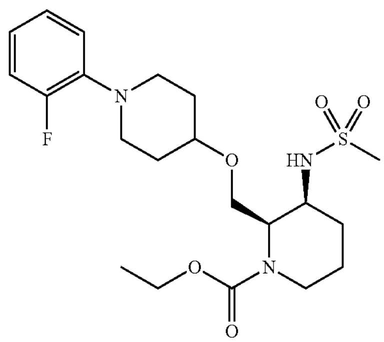 [SMILES: CCOC(=O)N1CCC[C@H](NS(C)(=O)=O)[C@@H]1COC1CCN(c2ccccc2F)CC1] | 458.2 |

TABLE 1-39

| Ex. No. | IUPAC name | Structure | MS |
|---|---|---|---|
| 229 | N-(cis-1-(cyclopentylcarbonyl)-2-(((1-(2-fluorophenyl)piperidin-4-yl)oxy)methyl)piperidin-3-yl)methanesulfonamide | 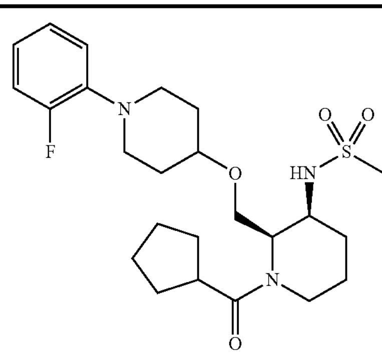 | 482.2 |
| 230 | N-(cis-2-(((1-(2-fluorophenyl)piperidin-4-yl)oxy)methyl)-1-(3-methylbutanoyl)piperidin-3-yl)methanesulfonamide | 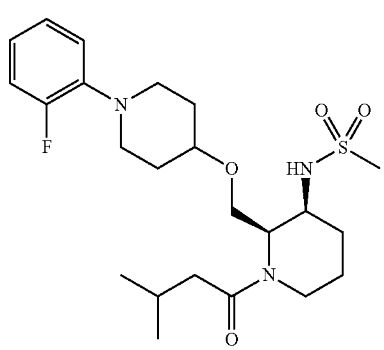 [SMILES: CC(C)CC(=O)N1CCC[C@H](NS(C)(=O)=O)[C@@H]1COC1CCN(c2ccccc2F)CC1] | 470.2 |

TABLE 1-39-continued

| Ex. No. | IUPAC name | Structure | MS |
|---|---|---|---|
| 231 | N-(cis-2-(((1-(2-fluorophenyl)piperidin-4-yl)oxy)methyl)-1-(tetrahydro-2H-pyran-4-ylcarbonyl)piperidin-3-yl)methanesulfonamide | 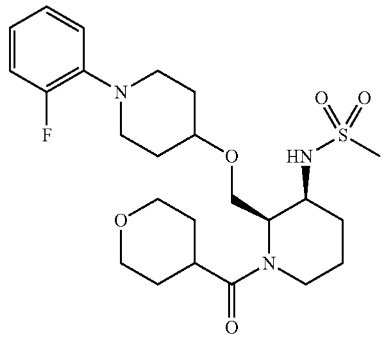 [SMILES: CS(=O)(=O)N[C@H]1CCCN(C(=O)C2CCOCC2)[C@H]1COC1CCN(c2ccccc2F)CC1] | 498.2 |
| 232 | N-(cis-2-(((1-(2-fluorophenyl)piperidin-4-yl)oxy)methyl)-1-(3-hydroxypropanoyl)piperidin-3-yl)methanesulfonamide | 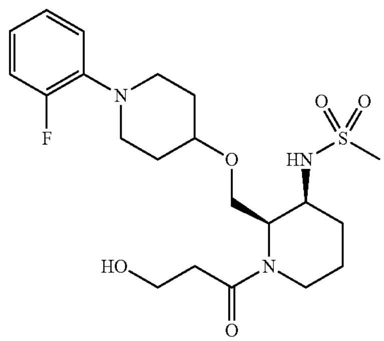 [SMILES: CS(=O)(=O)N[C@H]1CCCN(C(=O)CCO)[C@H]1COC1CCN(c2ccccc2F)CC1] | 458.2 |
| 233 | N-(cis-2-(((1-(2-fluorophenyl)piperidin-4-yl)oxy)methyl)-1-((3-oxocyclobutyl)carbonyl)piperidin-3-yl)methanesulfonamide | 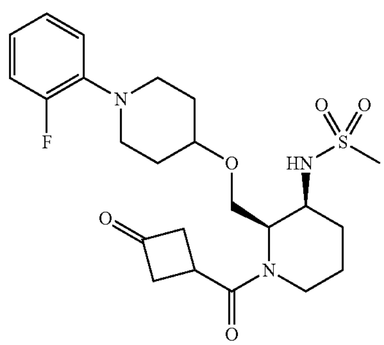 [SMILES: CS(=O)(=O)N[C@H]1CCCN(C(=O)C2CC(=O)C2)[C@H]1COC1CCN(c2ccccc2F)CC1] | 482.2 |
| 234 | N-(cis-1-(3,3-dimethylbutanoyl)-2-(((1-(2-fluorophenyl)piperidin-4-yl)oxy)methyl)piperidin-3-yl)methanesulfonamide | 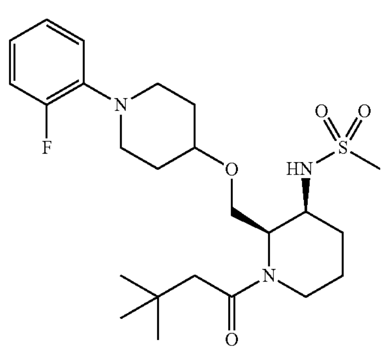 [SMILES: CC(C)(C)CC(=O)N1CCC[C@H](NS(C)(=O)=O)[C@@H]1COC1CCN(c2ccccc2F)CC1] | 484.3 |

TABLE 1-40

| Ex. No. | IUPAC name | Structure | MS |
|---|---|---|---|
| 235 | N-(cis-2-(((1-(2-fluorophenyl)piperidin-4-yl)oxy)methyl)-1-(oxetan-3-ylcarbonyl)piperidin-3-yl)methanesulfonamide | 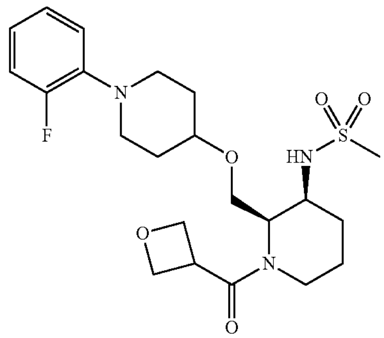 [SMILES: CS(=O)(=O)N[C@H]1CCCN(C(=O)C2COC2)[C@H]1COC1CCN(c2ccccc2F)CC1] | 470.2 |
| 236 | N-(cis-1-(cyclohexylcarbonyl)-2-(((1-(2-fluorophenyl)piperidin-4-yl)oxy)methyl)piperidin-3-yl)methanesulfonamide | 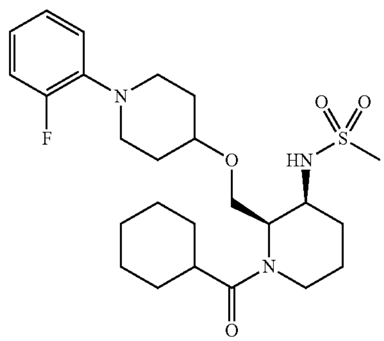 [SMILES: CS(=O)(=O)N[C@H]1CCCN(C(=O)C2CCCCC2)[C@H]1COC1CCN(c2ccccc2F)CC1] | 496.3 |
| 237 | isopropyl cis-2-(((1-(2-fluorophenyl)piperidin-4-yl)oxy)methyl)-3-((methylsulfonyl)amino)piperidine-1-carboxylate | 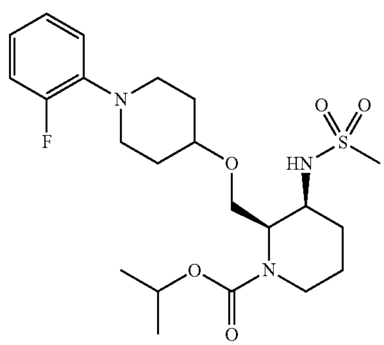 [SMILES: CC(C)OC(=O)N1CCC[C@H](NS(C)(=O)=O)[C@@H]1COC1CCN(c2ccccc2F)CC1] | 472.2 |
| 238 | N-(cis-1-((4,4-difluorocyclohexyl)carbonyl)-2-(((1-(2-fluorophenyl)piperidin-4-yl)oxy)methyl)piperidin-3-yl)methanesulfonamide | 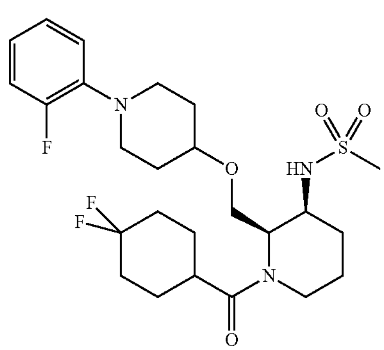 [SMILES: CS(=O)(=O)N[C@H]1CCCN(C(=O)C2CCC(F)(F)CC2)[C@H]1COC1CCN(c2ccccc2F)CC1] | 532.3 |

TABLE 1-40-continued

| Ex. No. | IUPAC name | Structure | MS |
|---|---|---|---|
| 239 | N-((2R,3S)-2-(((cis-4-(2,3,5-trifluorophenyl)cyclohexyl)oxy)methyl)piperidin-3-yl)methanesulfonamide | 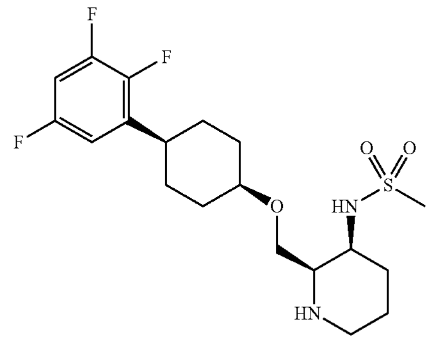 [SMILES: CS(=O)(=O)N[C@H]1CCCN[C@H]1CO[C@H]1CC[C@@H](c2cc(F)cc(F)c2F)CC1] | 421.2 |
| 240 | N-((2R,3S)-1-acetyl-2-(((cis-4-(2-fluorophenyl)cclohexyl)oxy)methyl)piperidin-3-yl)methanesulfonamide | 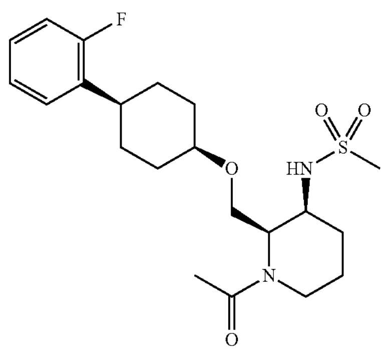 [SMILES: CC(=O)N1CCC[C@H](NS(C)(=O)=O)[C@@H]1CO[C@H]1CC[C@@H](c2ccccc2F)CC1] | 427.1 |

TABLE 1-41

| Ex. No. | IUPAC name | Structure | MS |
|---|---|---|---|
| 241 | methyl (2R,3S)-2-(((cis-4-(3,5-difluorophenyl)cyclohexyl)oxy)methyl)-3-((methylsulfonyl)amino)piperidine-1-carboxylate | 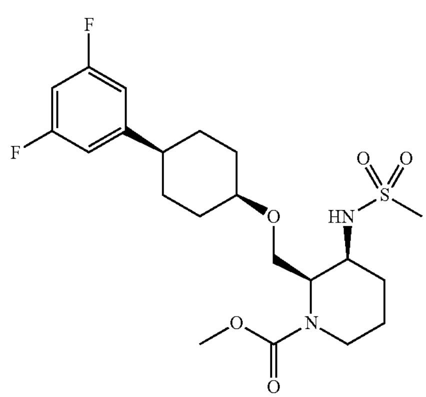 [SMILES: COC(=O)N1CCC[C@H](NS(C)(=O)=O)[C@@H]1CO[C@H]1CC[C@@H](c2cc(F)cc(F)c2)CC1] | 459.1 |

TABLE 1-41-continued

| Ex. No. | IUPAC name | Structure | MS |
|---|---|---|---|
| 242 | N-((2R,3S)-1-(cyclopropylcarbonyl)-2-(((cis-4-(3,5-difluorophenyl)cyclohexyl)oxy)-methyl)piperidin-3-yl)methanesulfonamide | 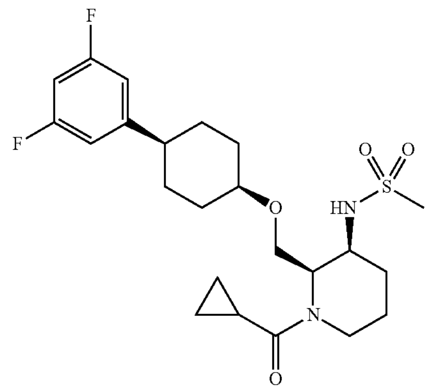 [SMILES: CS(=O)(=O)N[C@H]1CCCN(C(=O)C2CC2)[C@H]1CO[C@H]1CC[C@@H](c2cc(F)cc(F)c2)CC1] | 469.1 |
| 243 | N-((2R,3S)-1-acetyl-2-(((cis-4-(2,3,5-trifluorophenyl)cyclohexyl)oxy)-methyl)piperidin-3-yl)methanesulfonamide | 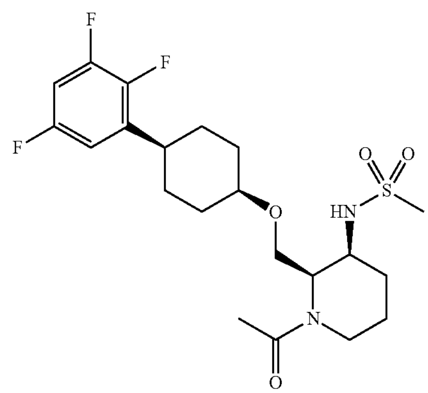 [SMILES: CC(=O)N1CCC[C@H](NS(C)(=O)=O)[C@@H]1CO[C@H]1CC[C@@H](c2cc(F)cc(F)c2F)CC1] | 463.1 |
| 244 | methyl (2R,3S)-3-((methylsulfonyl)amino)-2-(((cis-4-(2,3,5-trifluorophenyl)cyclohexyl)oxy)-methyl)piperidine-1-carboxylate | 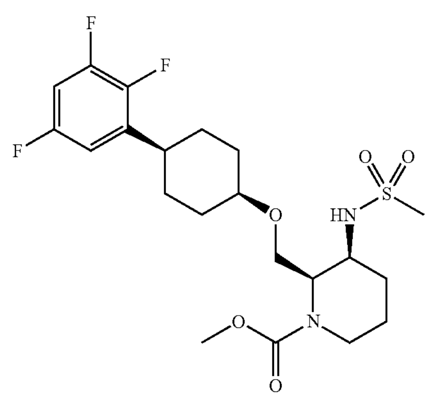 [SMILES: COC(=O)N1CCC[C@H](NS(C)(=O)=O)[C@@H]1CO[C@H]1CC[C@@H](c2cc(F)cc(F)c2F)CC1] | 477.1 |
| 245 | N-((2R,3S)-1-(cyclopropylcarbonyl)-2-(((cis-4-(2,3,5-trifluorophenyl)cyclohexyl)oxy)-methyl)piperidin-3-yl)methanesulfonamide | 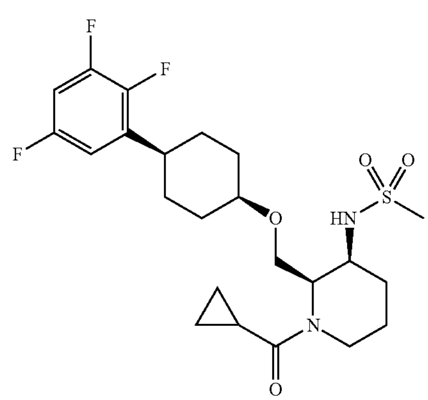 [SMILES: CS(=O)(=O)N[C@H]1CCCN(C(=O)C2CC2)[C@H]1CO[C@H]1CC[C@@H](c2cc(F)cc(F)c2F)CC1] | 489.1 |

TABLE 1-41-continued

| Ex. No. | IUPAC name | Structure | MS |
|---|---|---|---|
| 246 | N-((2R,3S)-1-(cyclopropylcarbonyl)-2-(((1-(2-fluorophenyl)piperidin-4-yl)oxy)methyl)piperidin-3-yl)methanesulfonamide | 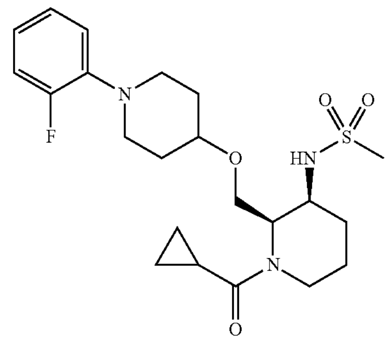 [SMILES: CS(=O)(=O)N[C@H]1CCCN(C(=O)C2CC2)[C@H]1COC1CCN(c2ccccc2F)CC1] | 454.2 |

TABLE 1-42

| Ex. No. | IUPAC name | Structure | MS |
|---|---|---|---|
| 247 | N-(cis-1-(cyclopropylcarbonyl)-2-(((1-phenylpiperidin-4-yl)oxy)methyl)piperidin-3-yl)methanesulfonamide | 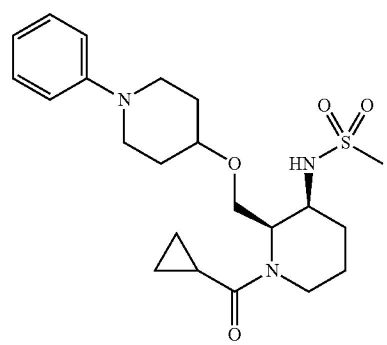 [SMILES: CS(=O)(=O)N[C@H]1CCCN(C(=O)C2CC2)[C@H]1COC1CCN(c2ccccc2)CC1] | 436.2 |
| 248 | cis-N-ethyl-3-((methylsulfonyl)amino)-2-(((cis-3-(4-(trifluoromethyl)phenyl)-cyclobutyl)oxy)methyl)piperidine-1-carboxamide | 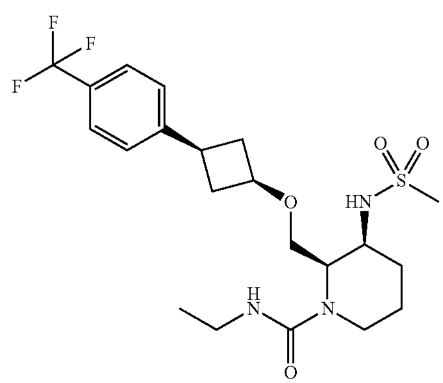 [SMILES: CCNC(=O)N1CCC[C@H](NS(C)(=O)=O)[C@@H]1CO[C@H]1C[C@@H](c2ccc(C(F)(F)F)cc2)C1] | 478.2 |

TABLE 1-42-continued

| Ex. No. | IUPAC name | Structure | MS |
|---|---|---|---|
| 249 | cis-N-ethyl-3-((methylsulfonyl)amino)-2-(((cis-4-(2-(trifluoromethyl)phenyl)-cyclohexyl)oxy)methyl)piperidine-1-carboxamide | 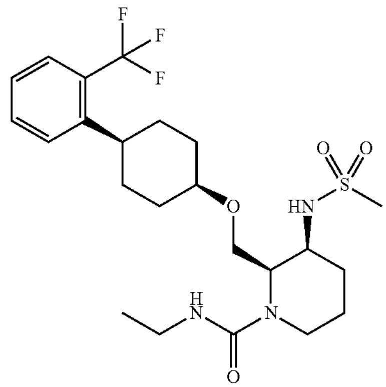 [SMILES: CCNC(=O)N1CCC[C@H](NS(C)(=O)=O)[C@@H]1CO[C@H]1CC[C@@H](c2ccccc2C(F)(F)F)CC1] | 506.2 |
| 250 | N-((2R,3S)-1-(cyclopropylcarbonyl)-2-(((cis-4-(2,3-difluorophenyl)cyclohexyl)oxy)-methyl)piperidin-3-yl)methanesulfonamide | 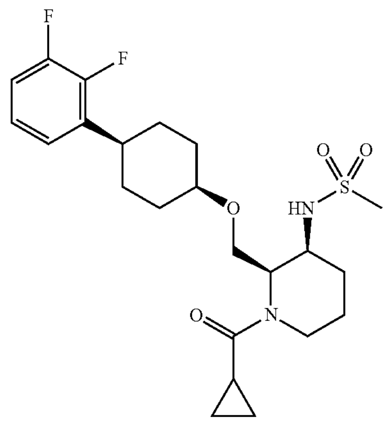 [SMILES: CS(=O)(=O)N[C@H]1CCCN(C(=O)C2CC2)[C@H]1CO[C@H]1CC[C@@H](c2cccc(F)c2F)CC1] | 471.2 |
| 251 | N-(cis-1-(cyclopropylcarbonyl)-2-(((4-(pyridin-2-yl)cyclohexyl)oxy)methyl)piperidin-3-yl)methanesulfonamide | 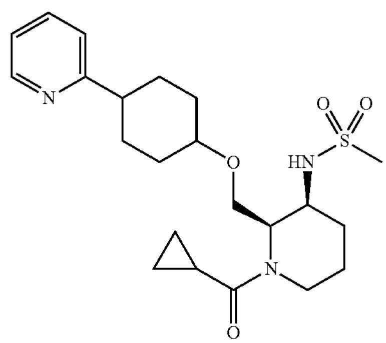 [SMILES: CS(=O)(=O)N[C@H]1CCCN(C(=O)C2CC2)[C@H]1COC1CCC(c2ccccn2)CC1] | 436.2 |
| 252 | N-(cis-1-acetyl-2-(((cis-4-(3-cyanophenyl)cyclohexyl)oxy)methyl)-piperidin-3-yl)methanesulfonamide | 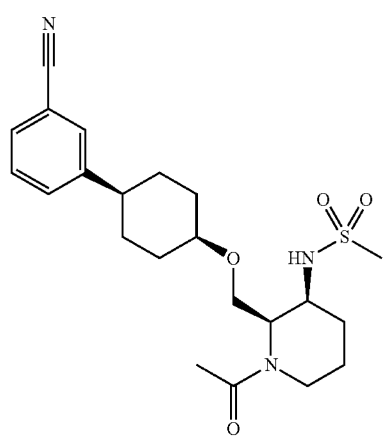 [SMILES: CC(=O)N1CCC[C@H](NS(C)(=O)=O)[C@@H]1CO[C@H]1CC[C@@H](c2cccc(C#N)c2)CC1] | 434.1 |

TABLE 1-43

| Ex. No. | IUPAC name | Structure | MS |
|---|---|---|---|
| 253 | N-(cis-2-(((cis-4-(3-cyanophenyl)cyclohexyl)oxy)methyl)-piperidin-3-yl)methanesulfonamide | 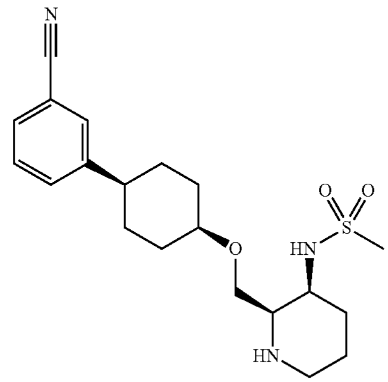 [SMILES: CS(=O)(=O)N[C@H]1CCCN[C@H]1CO[C@H]1CC[C@@H](c2cccc(C#N)c2)CC1] | 392.2 |
| 254 | cis-2-(((cis-4-(3-cyanophenyl)cyclohexyl)oxy)methyl)-N-ethyl-3-((methylsulfonyl)amino)piperidine-1-carboxamide | 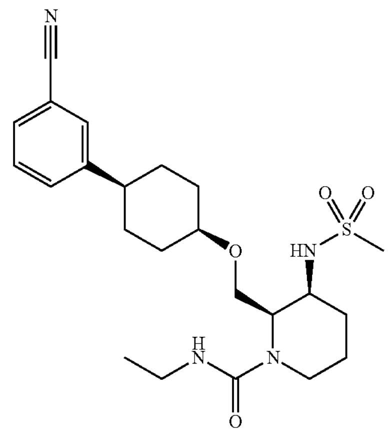 [SMILES: CCNC(=O)N1CCC[C@H](NS(C)(=O)=O)[C@@H]1CO[C@H]1CC[C@@H](c2cccc(C#N)c2)CC1] | 463.2 |
| 255 | isopropyl cis-3-((methylsulfonyl)amino)-2-(((1-(pyrimidin-2-yl)piperidin-4-yl)oxy)methyl)piperidine-1-carboxylate | 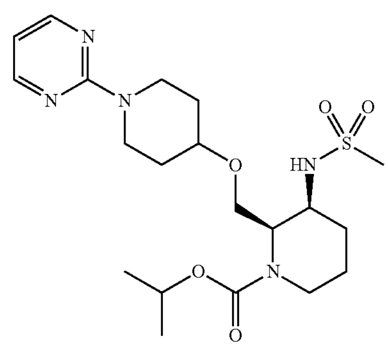 [SMILES: CC(C)OC(=O)N1CCC[C@H](NS(C)(=O)=O)[C@@H]1COC1CCN(c2ncccn2)CC1] | 456.2 |
| 256 | isopropyl cis-3-((methylsulfonyl)amino)-2-(((1-(quinazolin-2-yl)piperidin-4-yl)oxy)methyl)piperidine-1-carboxylate | 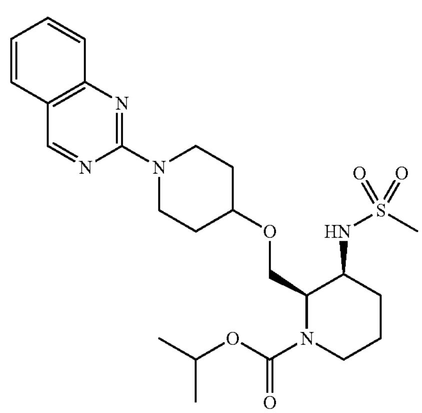 [SMILES: CC(C)OC(=O)N1CCC[C@H](NS(C)(=O)=O)[C@@H]1COC1CCN(c2ncc3ccccc3n2)CC1] | 506.2 |

TABLE 1-43-continued

| Ex. No. | IUPAC name | Structure | MS |
|---|---|---|---|
| 257 | methyl (2R,3S)-3-((methylsulfonyl)amino)-2-(((cis-4-(2,3,6-trifluorophenyl)cyclohexyl)oxy)-methyl)piperidine-1-carboxylate | 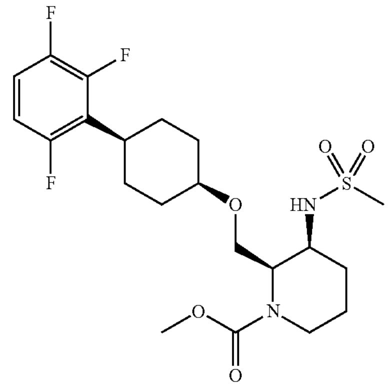 [SMILES: COC(=O)N1CCC[C@H](NS(C)(=O)=O)[C@@H]1CO[C@H]1CC[C@@H](c2c(F)ccc(F)c2F)CC1] | 477.1 |
| 258 | N-((2R,3S)-1-(cyclopropylcarbonyl)-2-(((cis-4-(2,3,6-trifluorophenyl)cyclohexyl)oxy)-methyl)piperidin-3-yl)methanesulfonamide | 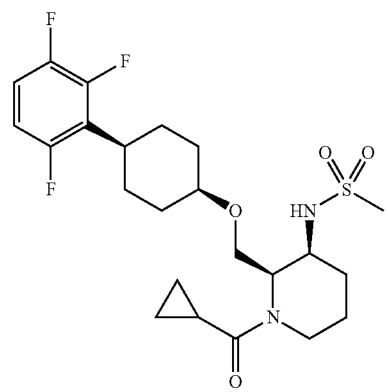 [SMILES: CS(=O)(=O)N[C@H]1CCCN(C(=O)C2CC2)[C@H]1CO[C@H]1CC[C@@H](c2c(F)ccc(F)c2F)CC1] | 489.1 |

TABLE 1-44

| Ex. No. | IUPAC name | Structure | MS |
|---|---|---|---|
| 259 | isopropyl cis-2-(((1-(1,3-benzothiazol-2-yl)piperidin-4-yl)oxy)methyl)-3-((methylsulfonyl)amino)piperidine-1-carboxylate | 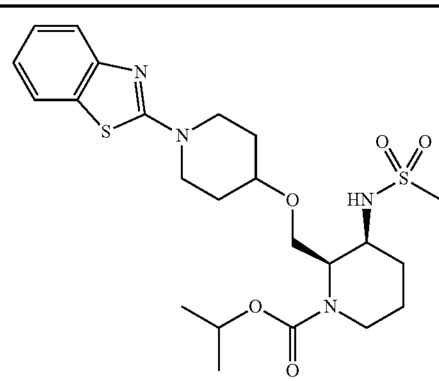 | 511.2 |

TABLE 1-44-continued

| Ex. No. | IUPAC name | Structure | MS |
|---|---|---|---|
| 260 | N-((2R,3S)-2-(((cis-4-(2-fluorophenyl)cyclohexyl)oxy)methyl)piperidin-3-yl)methanesulfonamide | 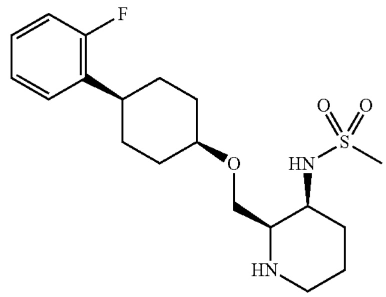 [SMILES: CS(=O)(=O)N[C@H]1CCCN[C@H]1CO[C@H]1CC[C@@H](c2ccccc2F)CC1] | 385.1 |
| 261 | isopropyl cis-2-(((1-(isoquinolin-1-yl)piperidin-4-yl)oxy)methyl)-3-((methylsulfonyl)amino)piperidine-1-carboxylate | 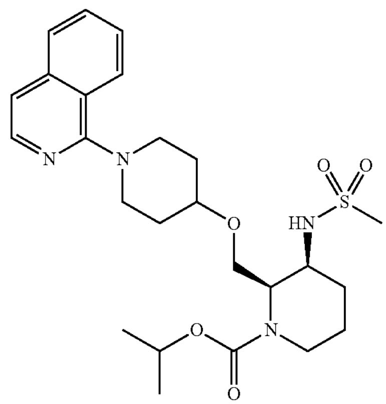 [SMILES: CC(C)OC(=O)N1CCC[C@H](NS(C)(=O)=O)[C@@H]1COC1CCN(c2nccc3ccccc23)CC1] | 505.2 |
| 262 | N-(cis-2-(((cis-4-(2-cyanophenyl)cyclohexyl)oxy)methyl)piperidin-3-yl)methanesulfonamide | 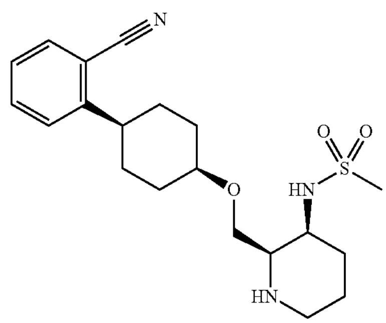 [SMILES: CS(=O)(=O)N[C@H]1CCCN[C@H]1CO[C@H]1CC[C@@H](c2ccccc2C#N)CC1] | 392.2 |
| 263 | cis-2-(((cis-4-(2-cyanophenyl)cyclohexyl)oxy)methyl)-N-ethyl-3-((methylsulfonyl)amino)piperidine-1-carboxamide | 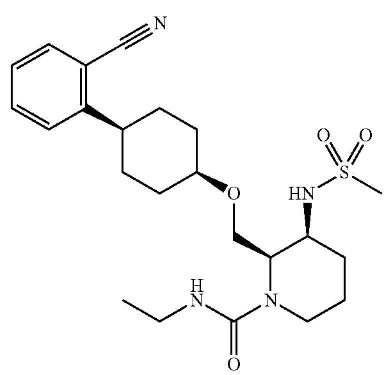 [SMILES: CCNC(=O)N1CCC[C@H](NS(C)(=O)=O)[C@@H]1CO[C@H]1CC[C@@H](c2ccccc2C#N)CC1] | 463.1 |

TABLE 1-44-continued

| Ex. No. | IUPAC name | Structure | MS |
|---|---|---|---|
| 264 | isopropyl (2R,3S)-2-(((cis-4-(3-fluorophenyl)cyclohexyl)oxy)methyl)-3-((methylsulfonyl)amino)piperidine-1-carboxylate | 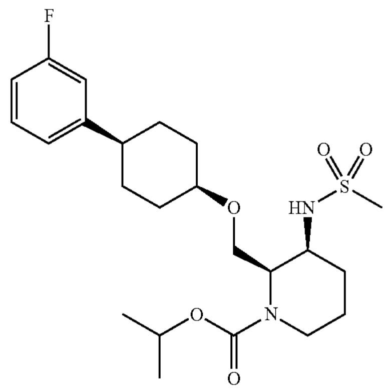 [SMILES: CC(C)OC(=O)N1CCC[C@H](NS(C)(=O)=O)[C@@H]1CO[C@H]1CC[C@@H](c2cccc(F)c2)CC1] | 471.2 |

TABLE 1-45

| Ex. No. | IUPAC name | Structure | MS |
|---|---|---|---|
| 265 | methyl cis-2-(((cis-4-(2-cyanophenyl)cyclohexyl)oxy)methyl)-3-((methylsulfonyl)amino)piperidine-1-carboxylate | 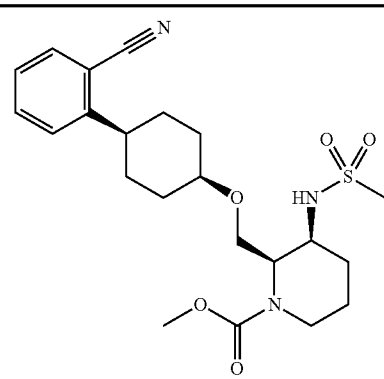 | 450.1 |
| 266 | cis-2-(((cis-3-benzylcyclobutyl)oxy)methyl)-N-ethyl-3-((methylsulfonyl)amino)piperidine-1-carboxamide | 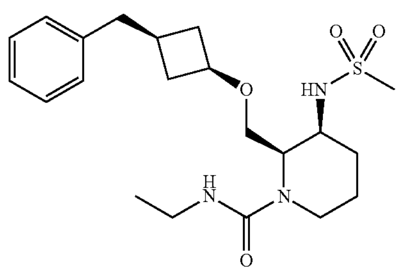 [SMILES: CCNC(=O)N1CCC[C@H](NS(C)(=O)=O)[C@@H]1CO[C@H]1C[C@@H](Cc2ccccc2)C1] | 424.2 |
| 267 | methyl (2R,3S)-2-(((cis-4-(2-fluorophenyl)cyclohexyl)oxy)methyl)-3-((methylsulfonyl)amino)piperidine-1-carboxylate | 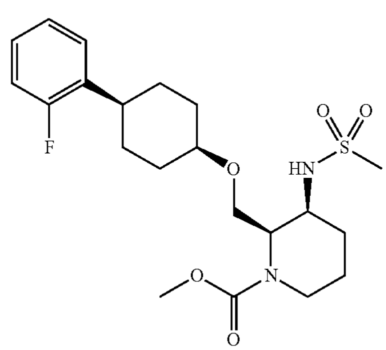 [SMILES: COC(=O)N1CCC[C@H](NS(C)(=O)=O)[C@@H]1CO[C@H]1CC[C@@H](c2ccccc2F)CC1] | 443.3 |

TABLE 1-45-continued

| Ex. No. | IUPAC name | Structure | MS |
|---|---|---|---|
| 268 | N-((2R,3S)-1-(cyclopropylcarbonyl)-2-(((cis-4-(2-fluorophenyl)cyclohexyl)oxy)-methyl)piperidin-3-yl)methanesulfonamide | 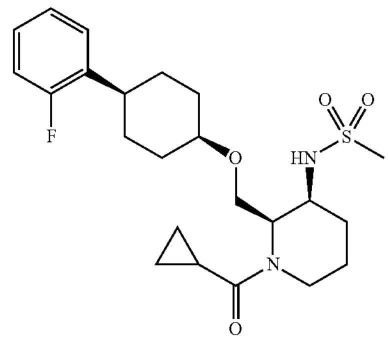 [SMILES: CS(=O)(=O)N[C@H]1CCCN(C(=O)C2CC2)[C@H]1CO[C@H]1CC[C@@H](c2ccccc2F)CC1] | 453.2 |
| 269 | N-(cis-2-(((cis-4-(3-methoxyphenyl)cyclohexyl)oxy)-methyl)piperidin-3-yl)methanesulfonamide | 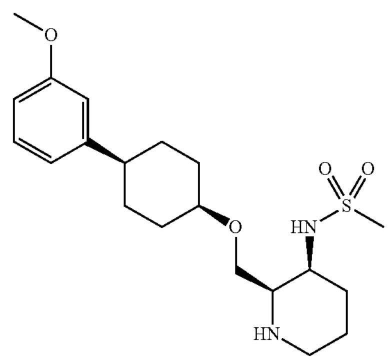 [SMILES: COc1cccc([C@H]2CC[C@@H](OC[C@@H]3NCCC[C@@H]3NS(C)(=O)=O)CC2)c1] | 397.2 |
| 270 | methyl cis-2-(((cis-4-(3-methoxyphenyl)cyclohexyl)oxy)-methyl)-3-((methylsulfonyl)amino)piperidine-1-carboxylate | 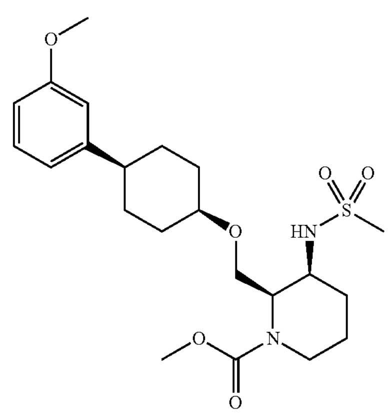 [SMILES: COC(=O)N1CCC[C@H](NS(C)(=O)=O)[C@@H]1CO[C@H]1CC[C@@H](c2cccc(OC)c2)CC1] | 455.2 |

TABLE 1-46

| Ex. No. | IUPAC name | Structure | MS |
|---|---|---|---|
| 271 | N-(cis-1-acetyl-2-(((cis-4-(3-methoxyphenyl)cyclohexyl)oxy)-methyl)piperidin-3-yl)methanesulfonamide | 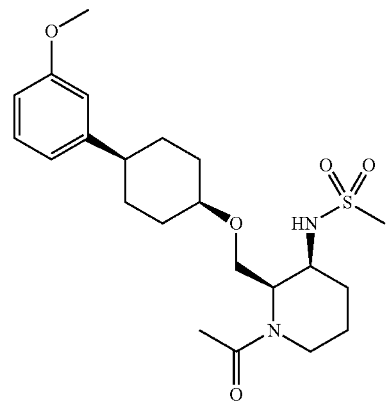 [SMILES: COc1cccc([C@H]2CC[C@@H](OC[C@H]3[C@@H](NS(C)(=O)=O)CCCN3C(C)=O)CC2)c1] | 439.2 |
| 272 | cyclopropyl (2R,3S)-2-(((cis-4-(3-fluorophenyl)cyclohexyl)oxy)-methyl)-3-((methylsulfonyl)amino)piperidine-1-carboxylate | 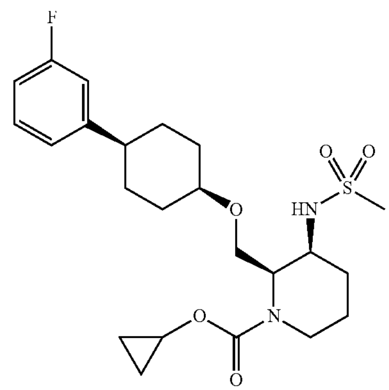 [SMILES: CS(=O)(=O)N[C@H]1CCCN(C(=O)OC2CC2)[C@H]1CO[C@H]1CC[C@@H](c2cccc(F)c2)CC1] | 469.2 |
| 273 | methyl cis-3-((methylsulfonyl)amino)-2-(((3-phenoxycyclopentyl)oxy)methyl)-piperidine-1-carboxylate | 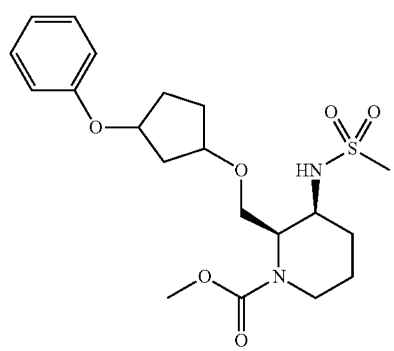 [SMILES: COC(=O)N1CCC[C@H](NS(C)(=O)=O)[C@@H]1COC1CCC(Oc2ccccc2)C1] | 427.1 |
| 274 | methyl cis-3-((methylsulfonyl)amino)-2-((((1r,4r)-3H-spiro[2-benzofuran-1,1'-cyclohexan]-4'-yloxy)methyl)piperidine-1-carboxylate | 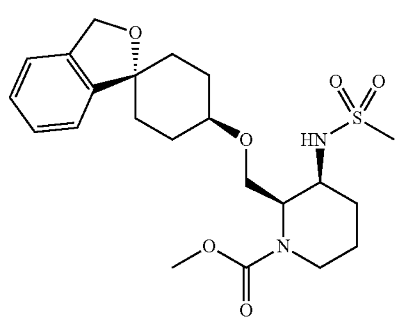 [SMILES: COC(=O)N1CCC[C@H](NS(C)(=O)=O)[C@@H]1CO[C@H]1CC[C@@]2(CC1)OCc1ccccc12] | 453.1 |

TABLE 1-46-continued

| Ex. No. | IUPAC name | Structure | MS |
|---|---|---|---|
| 275 | methyl cis-3-((methylsulfonyl)amino)-2-(((1s,4's)-3H-spiro[2-benzofuran-1,1'-cyclohexan]-4'-yloxy)methyl)piperidine-1-carboxylate | 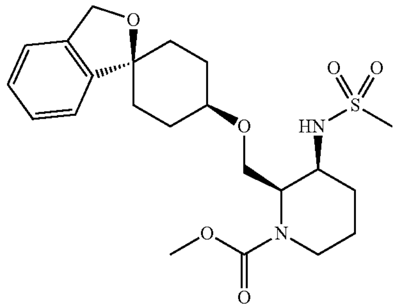 [SMILES: COC(=O)N1CCC[C@H](NS(C)(=O)=O)[C@@H]1CO[C@H]1CC[C@]2(CC1)OCc1ccccc12] | 453.1 |
| 276 | 2,2,2-trifluoroethyl (2R,3S)-2-(((cis-4-(3-fluorophenyl)cyclohexyl)oxy)-methyl)-3-((methylsulfonyl)amino)piperidine-1-carboxylate | 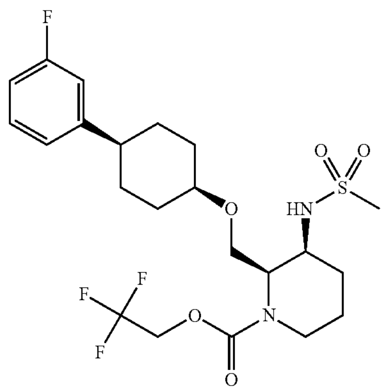 [SMILES: CS(=O)(=O)N[C@H]1CCCN(C(=O)OCC(F)(F)F)[C@H]1CO[C@H]1CC[C@@H](c2cccc(F)c2)CC1] | 509.2 |

TABLE 1-47

| Ex. No. | IUPAC name | Structure | MS |
|---|---|---|---|
| 277 | methyl (2R,3S)-2-(((cis-4-(2-methoxyphenyl)cyclohexyl)oxy)-methyl)-3-((methylsulfonyl)amino)piperidine-1-carboxylate | 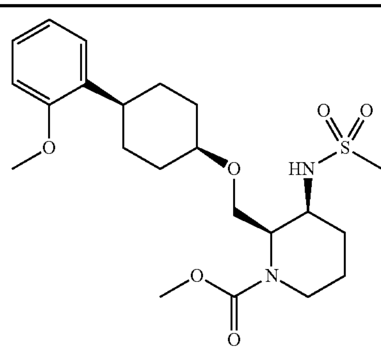 | 455.2 |
| 278 | N-(cis-1-acetyl-2-(((cis-4-(2-cyanophenyl)cyclohexyl)oxy)methyl)-piperidin-3-yl)methanesulfonamide | 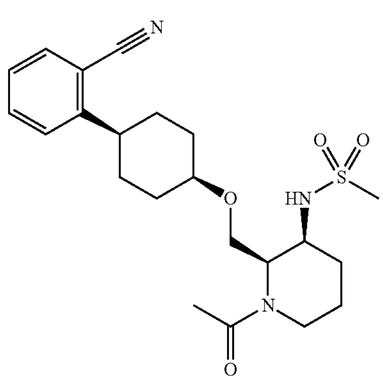 [SMILES: CC(=O)N1CCC[C@H](NS(C)(=O)=O)[C@@H]1CO[C@H]1CC[C@@H](c2ccccc2C#N)CC1] | 434.1 |

TABLE 1-47-continued

| Ex. No. | IUPAC name | Structure | MS |
|---|---|---|---|
| 279 | N-(cis-1-(cyclopropylcarbonyl)-2-(((cis-4-phenylcyclohexyl)oxy)methyl)-piperidin-3-yl)ethanesulfonamide | 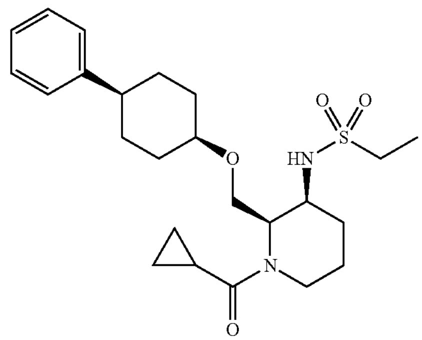 [SMILES: CCS(=O)(=O)N[C@H]1CCCN(C(=O)C2CC2)[C@H]1CO[C@H]1CC[C@@H](c2ccccc2)CC1] | 449.2 |
| 280 | methyl cis-3-((methylsulfonyl)amino)-2-(((trans-3-phenoxycyclobutyl)oxy)methyl)-piperidine-1-carboxylate | 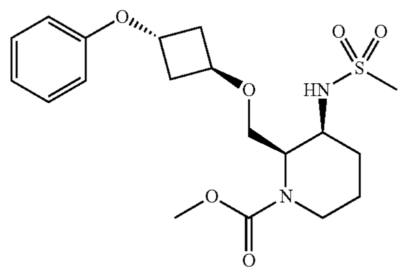 [SMILES: COC(=O)N1CCC[C@H](NS(C)(=O)=O)[C@@H]1CO[C@H]1C[C@H](Oc2ccccc2)C1] | 411.1 |
| 281 | cis-N-ethyl-3-((methylsulfonyl)amino)-2-(((trans-3-phenoxycyclobutyl)oxy)methyl)-piperidine-1-carboxamide | 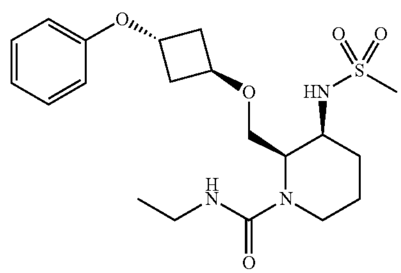 [SMILES: CCNC(=O)N1CCC[C@H](NS(C)(=O)=O)[C@@H]1CO[C@H]1C[C@H](Oc2ccccc2)C1] | 426.1 |
| 282 | (2R,3S)-N-ethyl-3-((methylsulfonyl)amino)-2-(((cis-4-(2-(trifluoromethyl)phenyl)-cyclohexyl)oxy)methyl)piperidine-1-carboxamide | 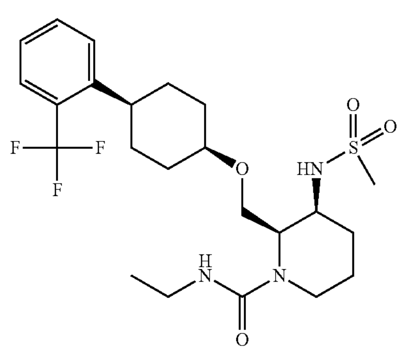 [SMILES: CCNC(=O)N1CCC[C@H](NS(C)(=O)=O)[C@@H]1CO[C@H]1CC[C@@H](c2ccccc2C(F)(F)F)CC1] | 506.2 |

TABLE 1-48

| Ex. No. | IUPAC name | Structure | MS |
|---|---|---|---|
| 283 | N-((2R,3S)-1-glycoloyl-2-(((cis-4-(2-(trifluoromethyl)phenyl)-cyclohexyl)oxy)methyl)piperidin-3-yl)methanesulfonamide | 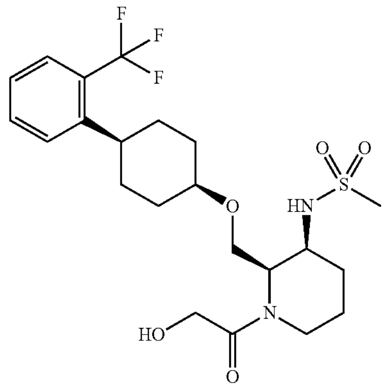 [SMILES: CS(=O)(=O)N[C@H]1CCCN(C(=O)CO)[C@H]1CO[C@H]1CC[C@@H](c2ccccc2C(F)(F)F)CC1] | 493.2 |
| 284 | 1-methylcyclopropyl cis-3-((methylsulfonyl)amino)-2-(((1-(pyrimidin-2-yl)piperidin-4-yl)oxy)methyl)piperidine-1-carboxylate | 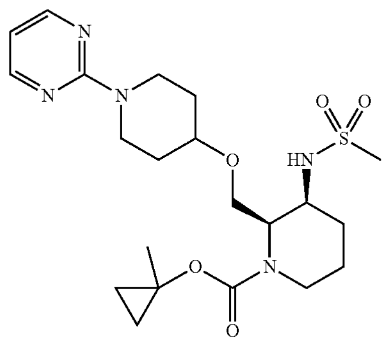 [SMILES: CC1(OC(=O)N2CCC[C@H](NS(C)(=O)=O)[C@@H]2COC2CCN(c3ncccn3)CC2)CC1] | 468.2 |
| 285 | cis-2-(((trans-3-benzylcyclobutyl)oxy)methyl)-N-ethyl-3-((methylsulfonyl)amino)piperidine-1-carboxamide | 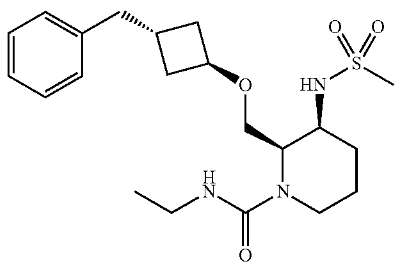 [SMILES: CCNC(=O)N1CCC[C@H](NS(C)(=O)=O)[C@@H]1CO[C@H]1C[C@H](Cc2ccccc2)C1] | 424.2 |
| 286 | 2,2,2-trifluoroethyl cis-3-((methylsulfonyl)amino)-2-(((1-(pyrimidin-2-yl)piperidin-4-yl)oxy)methyl)piperidine-1-carboxylate | 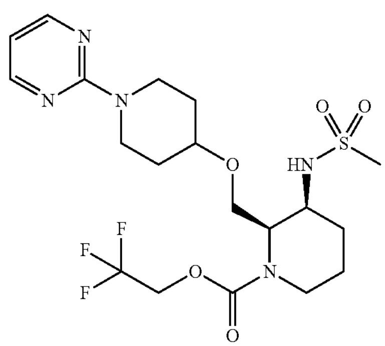 [SMILES: CS(=O)(=O)N[C@H]1CCCN(C(=O)OCC(F)(F)F)[C@H]1COC1CCN(c2ncccn2)CC1] | 496.1 |

TABLE 1-48-continued

| Ex. No. | IUPAC name | Structure | MS |
|---|---|---|---|
| 287 | cyclopropyl cis-3-((methylsulfonyl)amino)-2-(((1-(pyrimidin-2-yl)piperidin-4-yl)oxy)methyl)piperidine-1-carboxylate | 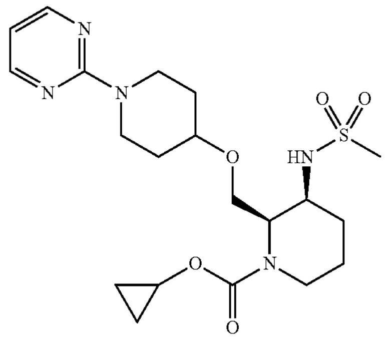 [SMILES: CS(=O)(=O)N[C@H]1CCCN(C(=O)OC2CC2)[C@H]1COC1CCN(c2ncccn2)CC1] | 454.2 |
| 288 | 2,2,2-trifluoroethyl cis-2-(((1-(2-fluorophenyl)piperidin-4-yl)oxy)methyl)-3-((methylsulfonyl)amino)piperidine-1-carboxylate | 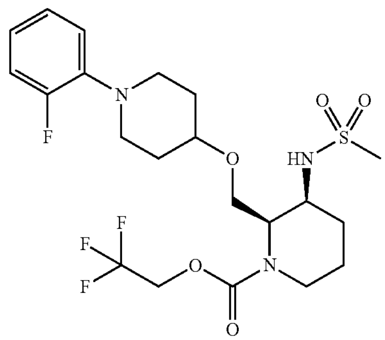 [SMILES: CS(=O)(=O)N[C@H]1CCCN(C(=O)OCC(F)(F)F)[C@H]1COC1CCN(c2ccccc2F)CC1] | 512.2 |

TABLE 1-49

| Ex. No. | IUPAC name | Structure | MS |
|---|---|---|---|
| 289 | 2,2,2-trifluoroethyl cis-3-((methylsulfonyl)amino)-2-(((1-phenylpiperidin-4-yl)oxy)methyl)piperidine-1-carboxylate | 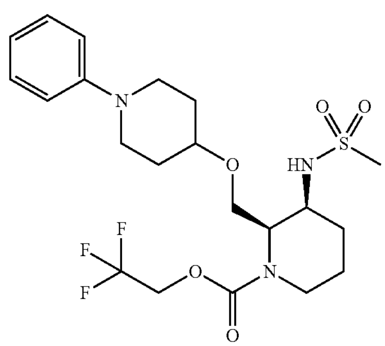 [SMILES: CS(=O)(=O)N[C@H]1CCCN(C(=O)OCC(F)(F)F)[C@H]1COC1CCN(c2ccccc2)CC1] | 494.2 |
| 290 | cyclopropyl cis-2-(((1-(2-fluorophenyl)piperidin-4-yl)oxy)methyl)-3-((methylsulfonyl)amino)piperidine-1-carboxylate | 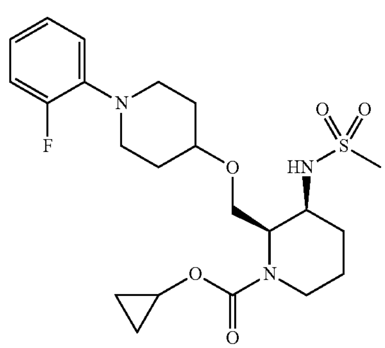 [SMILES: CS(=O)(=O)N[C@H]1CCCN(C(=O)OC2CC2)[C@H]1COC1CCN(c2ccccc2F)CC1] | 470.2 |

TABLE 1-49-continued

| Ex. No. | IUPAC name | Structure | MS |
|---|---|---|---|
| 291 | N-((2R,3S)-1-acetyl-2-(((cis-4-(2-methoxyphenyl)cyclohexyl)oxy)-methyl)piperidin-3-yl)methanesulfonamide | 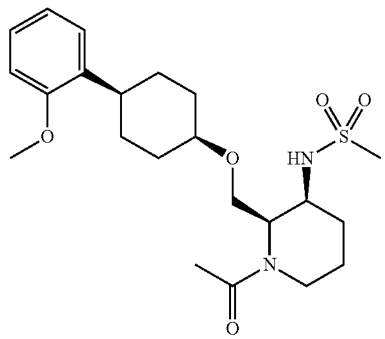 [SMILES: COc1ccccc1[C@H]1CC[C@@H](OC[C@H]2[C@@H](NS(C)(=O)=O)CCCN2C(C)=O)CC1] | 439.2 |
| 292 | N-(cis-2-(((cis-4-(2-(trifluoromethoxy)phenyl)-cyclohexyl)oxy)methyl)piperidin-3-yl)methanesulfonamide | 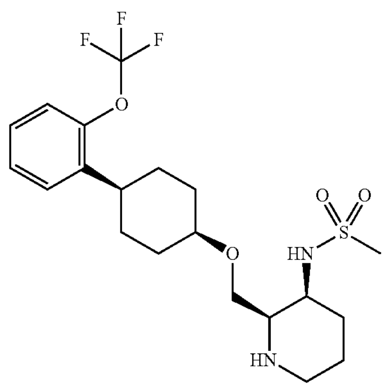 [SMILES: CS(=O)(=O)N[C@H]1CCCN[C@H]1CO[C@H]1CC[C@@H](c2ccccc2OC(F)(F)F)CC1] | 451.1 |
| 293 | N-(cis-1-acetyl-2-(((cis-4-(2-(trifluoromethoxy)phenyl)-cyclohexyl)oxy)methyl)piperidin-3-yl)methanesulfonamide | 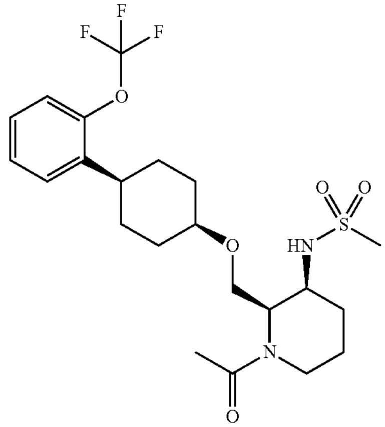 [SMILES: CC(=O)N1CCC[C@H](NS(C)(=O)=O)[C@@H]1CO[C@H]1CC[C@@H](c2ccccc2OC(F)(F)F)CC1] | 493.2 |

TABLE 1-49-continued

| Ex. No. | IUPAC name | Structure | MS |
|---|---|---|---|
| 294 | N-(cis-1-(cyclopropylcarbonyl)-2-(((cis-4-(2-(trifluoromethoxy)phenyl)-cyclohexyl)oxy)methyl)piperidin-3-yl)methanesulfonamide | 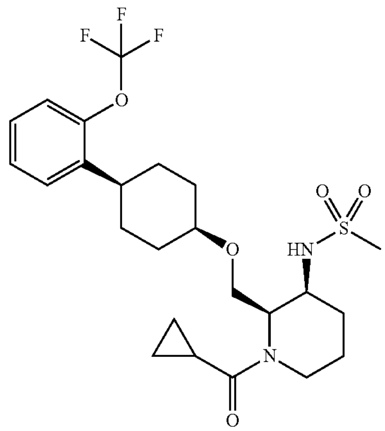 [SMILES: CS(=O)(=O)N[C@H]1CCCN(C(=O)C2CC2)[C@H]1CO[C@H]1CC[C@@H](c2ccccc2OC(F)(F)F)CC1] | 519.2 |

TABLE 1-50

| Ex. No. | IUPAC name | Structure | MS |
|---|---|---|---|
| 295 | cis-N-ethyl-3-((methylsulfonyl)amino)-2-(((cis-4-(2-(trifluoromethoxy)phenyl)-cyclohexyl)oxy)methyl)piperidine-1-carboxamide | 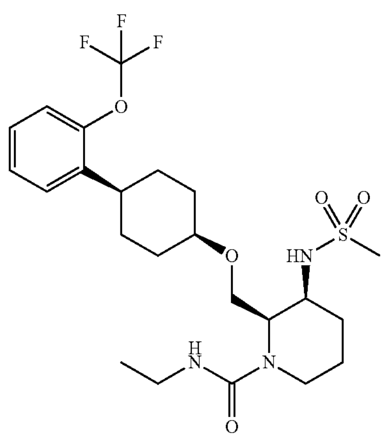 [SMILES: CCNC(=O)N1CCC[C@H](NS(C)(=O)=O)[C@@H]1CO[C@H]1CC[C@@H](c2ccccc2OC(F)(F)F)CC1] | 522.2 |
| 296 | N-(cis-2-(((cis-4-(3-(trifluoromethoxy)phenyl)-cyclohexyl)oxy)methyl)piperidin-3-yl)methanesulfonamide | 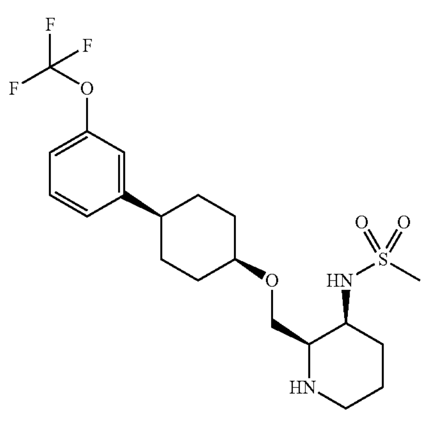 [SMILES: CS(=O)(=O)N[C@H]1CCCN[C@H]1CO[C@H]1CC[C@@H](c2cccc(OC(F)(F)F)c2)CC1] | 451.1 |

TABLE 1-50-continued

| Ex. No. | IUPAC name | Structure | MS |
|---|---|---|---|
| 297 | N-(cis-1-acetyl-2-(((cis-4-(3-(trifluoromethoxy)phenyl)cyclohexyl)oxy)methyl)piperidin-3-yl)methanesulfonamide | 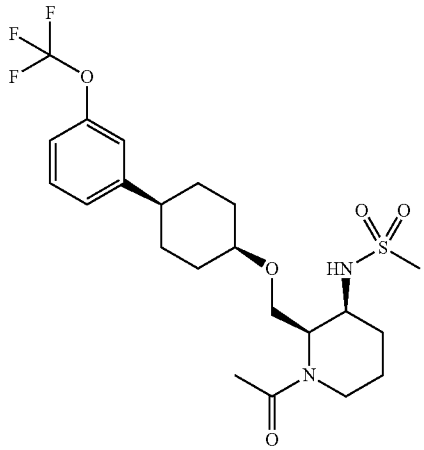 [SMILES: CC(=O)N1CCC[C@H](NS(C)(=O)=O)[C@@H]1CO[C@H]1CC[C@@H](c2cccc(OC(F)(F)F)c2)CC1] | 493.2 |
| 298 | methyl cis-3-((methylsulfonyl)amino)-2-(((cis-4-(3-(trifluoromethoxy)phenyl)cyclohexyl)oxy)methyl)piperidine-1-carboxylate | 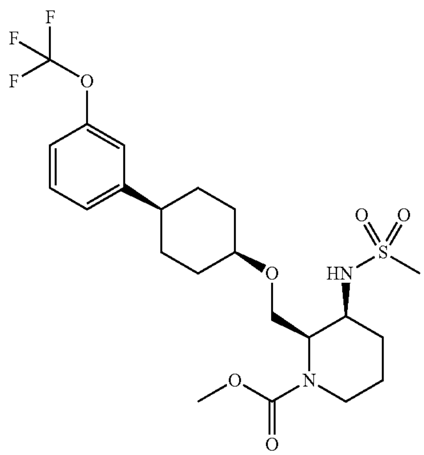 [SMILES: COC(=O)N1CCC[C@H](NS(C)(=O)=O)[C@@H]1CO[C@H]1CC[C@@H](c2cccc(OC(F)(F)F)c2)CC1] | 507.2 |
| 299 | N-(cis-1-(cyclopropylcarbonyl)-2-(((cis-4-(3-(trifluoromethoxy)phenyl)cyclohexyl)oxy)methyl)piperidin-3-yl)methanesulfonamide | 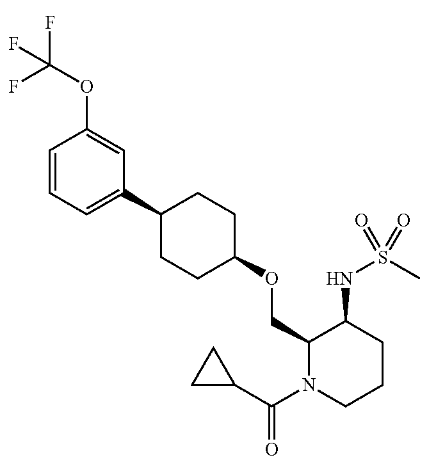 [SMILES: CS(=O)(=O)N[C@H]1CCCN(C(=O)C2CC2)[C@H]1CO[C@H]1CC[C@@H](c2cccc(OC(F)(F)F)c2)CC1] | 519.1 |

TABLE 1-50-continued

| Ex. No. | IUPAC name | Structure | MS |
|---|---|---|---|
| 300 | cis-N-ethyl-3-((methylsulfonyl)amino)-2-(((cis-4-(3-(trifluoromethoxy)phenyl)cyclohexyl)oxy)methyl)piperidine-1-carboxamide | 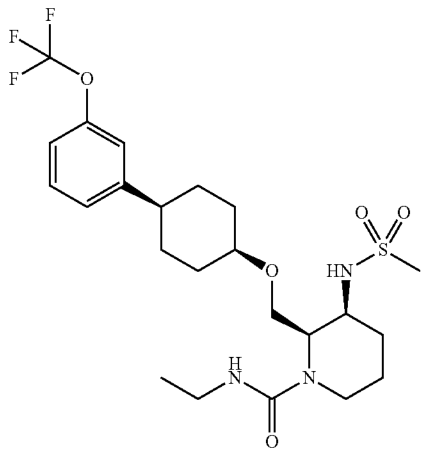 [SMILES: CCNC(=O)N1CCC[C@H](NS(C)(=O)=O)[C@@H]1CO[C@H]1CC[C@@H](c2cccc(OC(F)(F)F)c2)CC1] | 522.2 |

TABLE 1-51

| Ex. No. | IUPAC name | Structure | MS |
|---|---|---|---|
| 301 | methyl cis-3-((ethylsulfonyl)amino)-2-(((cis-4-phenylcyclohexyl)oxy)methyl)-piperidine-1-carboxylate | 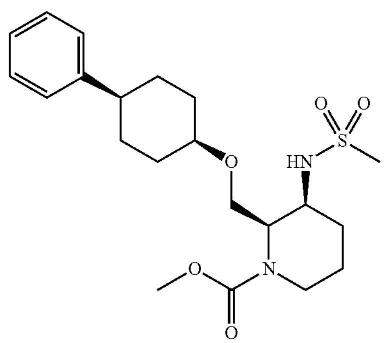 [SMILES: COC(=O)N1CCC[C@H](NS(C)(=O)=O)[C@@H]1CO[C@H]1CC[C@@H](c2ccccc2)CC1] | 439.2 |
| 302 | methyl cis-3-((methylsulfonyl)amino)-2-(((3-phenoxycyclopentyl)oxy)methyl)-piperidine-1-carboxylate | 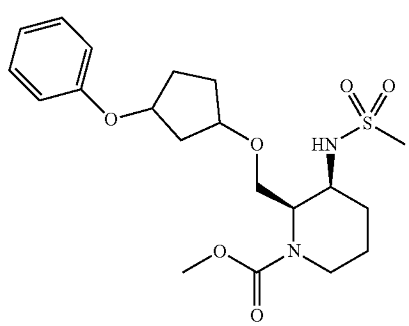 [SMILES: COC(=O)N1CCC[C@H](NS(C)(=O)=O)[C@@H]1COC1CCC(Oc2ccccc2)C1] | 427.2 |

TABLE 1-51-continued

| Ex. No. | IUPAC name | Structure | MS |
|---|---|---|---|
| 303 | ethyl (2R,3S)-3-((methylsulfonyl)amino)-2-(((cis-4-phenylcyclohexyl)oxy)methyl)-piperidine-1-carboxylate | 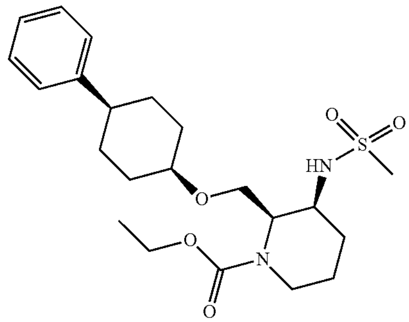 [SMILES: CCOC(=O)N1CCC[C@H](NS(C)(=O)=O)[C@@H]1CO[C@H]1CC[C@@H](c2ccccc2)CC1] | 439.2 |
| 304 | N-((2R,3S)-1-(cyclopropylcarbonyl)-2-(((cis-4-(3-methoxyphenyl)cyclohexyl)oxy)-methyl)piperidin-3-yl)methanesulfonamide | 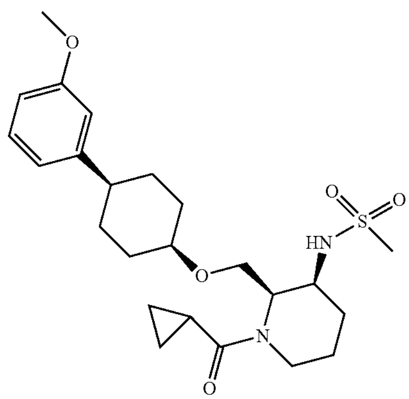 [SMILES: COc1cccc([C@H]2CC[C@@H](OC[C@H]3[C@@H](NS(C)(=O)=O)CCCN3C(=O)C3CC3)CC2)c1] | 465.2 |
| 305 | 2,2,2-trifluoroethyl (2R,3S)-3-((methylsulfonyl)amino)-2-(((1-(pyrimidin-2-yl)piperidin-4-yl)oxy)methyl)piperidine-1-carboxylate | 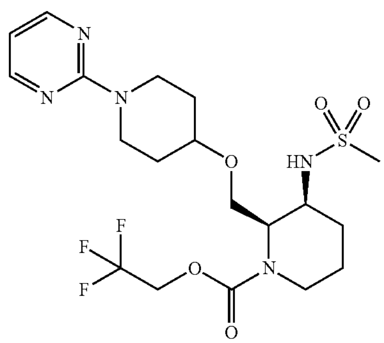 [SMILES: CS(=O)(=O)N[C@H]1CCCN(C(=O)OCC(F)(F)F)[C@H]1COC1CCN(c2ncccn2)CC1] | 496.2 |
| 306 | N-((2R,3S)-2-(((cis-4-phenylcyclohexyl)oxy)methyl)-1-(3,3,3-trifluoropropanoyl)piperidin-3-yl)methanesulfonamide | 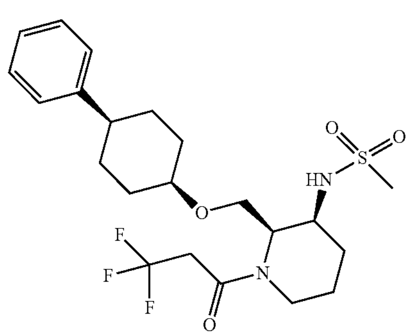 [SMILES: CS(=O)(=O)N[C@H]1CCCN(C(=O)CC(F)(F)F)[C@H]1CO[C@H]1CC[C@@H](c2ccccc2)CC1] | 477.2 |

TABLE 1-52

| Ex. No. | IUPAC name | Structure | MS |
|---|---|---|---|
| 307 | isopropyl cis-3-((methylsulfonyl)amino)-2-(((cis-3-phenylcyclobutyl)oxy)methyl)-piperidine-1-carboxylate | 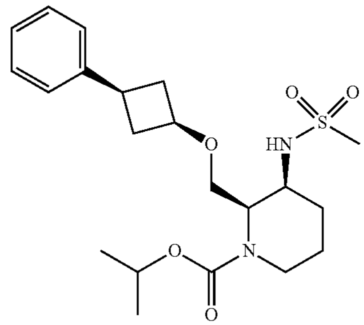 [SMILES: CC(C)OC(=O)N1CCC[C@H](NS(C)(=O)=O)[C@@H]1CO[C@H]1C[C@@H](c2ccccc2)C1] | 425.2 |
| 308 | N-(cis-1-(cyclopropylacetyl)-2-(((cis-3-phenylcyclobutyl)oxy)methyl)-piperidin-3-yl)methanesulfonamide | 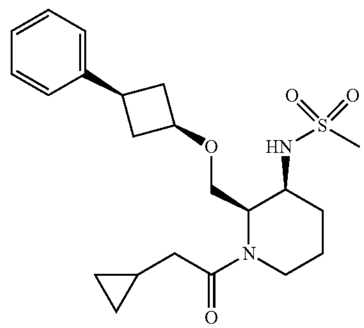 [SMILES: CS(=O)(=O)N[C@H]1CCCN(C(=O)CC2CC2)[C@H]1CO[C@H]1C[C@@H](c2ccccc2)C1] | 421.2 |
| 309 | methyl (2R,3S)-3-((dimethylsulfamoyl)amino)-2-(((cis-4-phenylcyclohexyl)oxy)methyl)-piperidine-1-carboxylate | 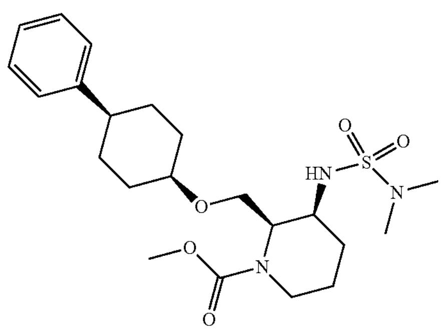 [SMILES: COC(=O)N1CCC[C@H](NS(=O)(=O)N(C)C)[C@@H]1CO[C@H]1CC[C@@H](c2ccccc2)CC1] | 454.2 |
| 310 | N'-((2R,3S)-1-(cyclopropylcarbonyl)-2-(((cis-4-phenylcyclohexyl)oxy)methyl)-piperidin-3-yl)-N,N-dimethylsulfuric diamide | 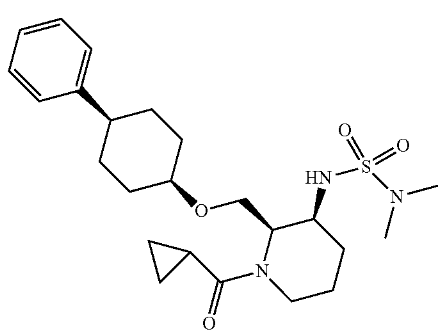 [SMILES: CN(C)S(=O)(=O)N[C@H]1CCCN(C(=O)C2CC2)[C@H]1CO[C@H]1CC[C@@H](c2ccccc2)CC1] | 464.2 |

TABLE 1-52-continued

| Ex. No. | IUPAC name | Structure | MS |
|---|---|---|---|
| 311 | N-(cis-2-(((cis-4-(2-ethylphenyl)cyclohexyl)oxy)methyl)-piperidin-3-yl)methanesulfonamide | 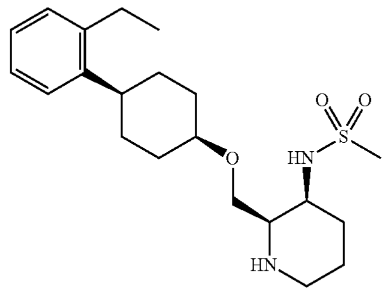 [SMILES: CCc1ccccc1[C@H]1CC[C@@H](OC[C@@H]2NCCC[C@@H]2NS(C)(=O)=O)CC1] | 395.3 |
| 312 | N-((2R,3S)-1-acetyl-2-(((cis-4-(2-ethylphenyl)cyclohexyl)oxy)methyl)-piperidin-3-yl)methanesulfonamide | 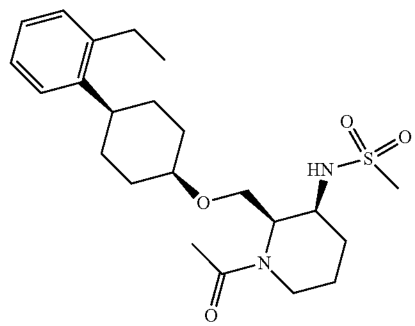 [SMILES: CCc1ccccc1[C@H]1CC[C@@H](OC[C@H]2[C@@H](NS(C)(=O)=O)CCCN2C(C)=O)CC1] | 437.2 |

TABLE 1-53

| Ex. No. | IUPAC name | Structure | MS |
|---|---|---|---|
| 313 | 1,1,1-trifluoropropan-2-yl cis-3-((methylsulfonyl)amino)-2-(((1-(pyrimidin-2-yl)piperidin-4-yl)oxy)methyl)piperidine-1-carboxylate | 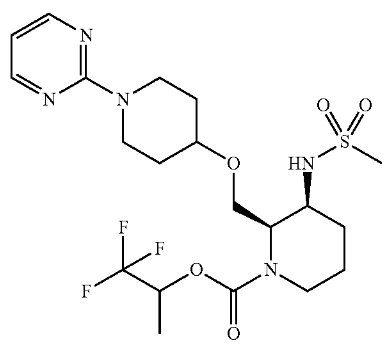 [SMILES: CC(OC(=O)N1CCC[C@H](NS(C)(=O)=O)[C@@H]1COC1CCN(c2ncccn2)CC1)C(F)(F)F] | 510.1 |
| 314 | 1,1,1,3,3,3-hexafluoropropan-2-yl cis-3-((methylsulfonyl)amino)-2-(((1-(pyrimidin-2-yl)piperidin-4-yl)oxy)methyl)piperidine-1-carboxylate | 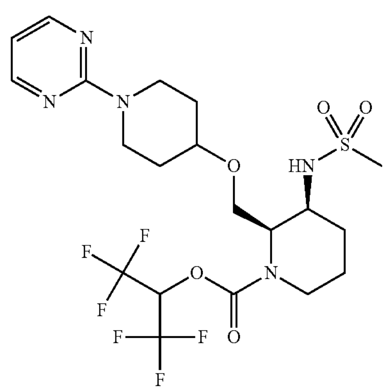 [SMILES: CS(=O)(=O)N[C@H]1CCCN(C(=O)OC(C(F)(F)F)C(F)(F)F)[C@H]1COC1CCN(c2ncccn2)CC1] | 564.1 |

TABLE 1-53-continued

| Ex. No. | IUPAC name | Structure | MS |
|---|---|---|---|
| 315 | 2,2,2-trifluoroethyl cis-3-((dimethylsulfamoyl)amino)-2-(((1-(pyrimidin-2-yl)piperidin-4-yl)oxy)methyl)piperidine-1-carboxylate | 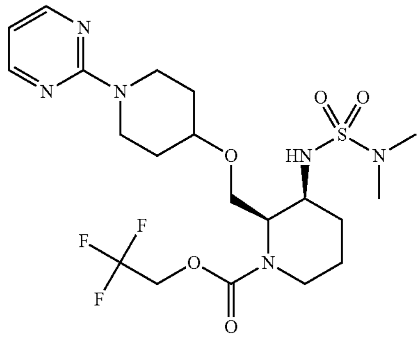 [SMILES: CN(C)S(=O)(=O)N[C@H]1CCCN(C(=O)OCC(F)(F)F)[C@H]1COC1CCN(c2ncccn2)CC1] | 525.2 |
| 316 | 1,1,1-trifluoropropan-2-yl cis-3-((dimethylsulfamoyl)amino)-2-(((1-(pyrimidin-2-yl)piperidin-4-yl)oxy)methyl)piperidine-1-carboxylate | 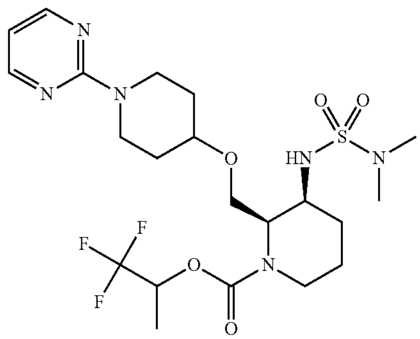 [SMILES: CC(OC(=O)N1CCC[C@H](NS(=O)(=O)N(C)C)[C@@H]1COC1CCN(c2ncccn2)CC1)C(F)(F)F] | 539.2 |
| 317 | cis-N-ethyl-3-((methylsulfonyl)amino)-2-(((cis-3-phenoxycyclobutyl)oxy)methyl)-piperidine-1-carboxamide | 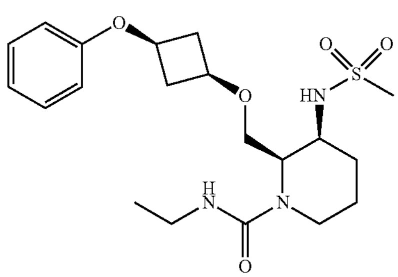 [SMILES: CCNC(=O)N1CCC[C@H](NS(C)(=O)=O)[C@@H]1CO[C@H]1C[C@@H](Oc2ccccc2)C1] | 426.1 |
| 318 | N-((2R,3S)-2-(((cis-4-(2-methylphenyl)cyclohexyl)oxy)-methyl)piperidin-3-yl)methanesulfonamide | 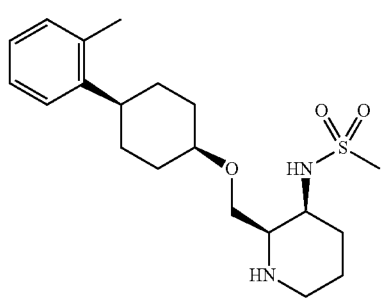 [SMILES: Cc1ccccc1[C@H]1CC[C@@H](OC[C@@H]2NCCC[C@@H]2NS(C)(=O)=O)CC1] | 381.2 |

TABLE 1-54

| Ex. No. | IUPAC name | Structure | MS |
|---|---|---|---|
| 319 | N-((2R,3S)-1-acetyl-2-(((cis-4-(2-methylphenyl)cyclohexyl)oxy)-methyl)piperidin-3-yl)methanesulfonamide | 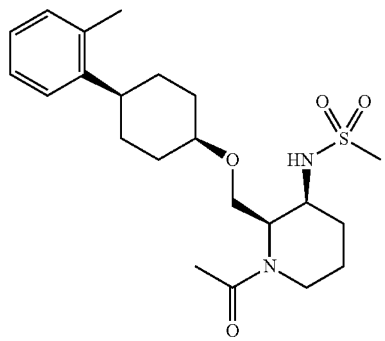 [SMILES: CC(=O)N1CCC[C@H](NS(C)(=O)=O)[C@@H]1CO[C@H]1CC[C@@H](c2ccccc2C)CC1] | 423.2 |
| 320 | N-((2R,3S)-2-(((cis-4-(2-(difluoromethyl)phenyl)cyclohexyl)-oxy)methyl)piperidin-3-yl)methanesulfonamide | 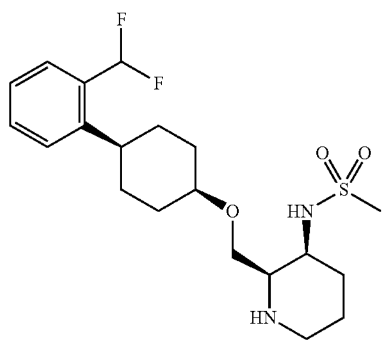 [SMILES: CS(=O)(=O)N[C@H]1CCCN[C@H]1CO[C@H]1CC[C@@H](c2ccccc2C(F)F)CC1] | 417.1 |
| 321 | N-(cis-1-acetyl-2-(((cis-4-(2,6-dimethylphenyl)cyclohexyl)oxy)-methyl)piperidin-3-yl)methanesulfonamide | 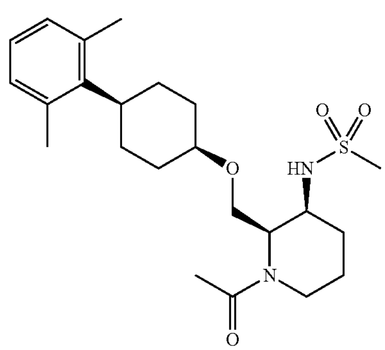 [SMILES: CC(=O)N1CCC[C@H](NS(C)(=O)=O)[C@@H]1CO[C@H]1CC[C@@H](c2c(C)cccc2C)CC1] | 437.2 |
| 322 | methyl cis-2-(((cis-4-(2-(difluoromethyl)phenyl)cyclohexyl)-oxy)methyl)-3-((methylsulfonyl)amino)piperidine-1-carboxylate | 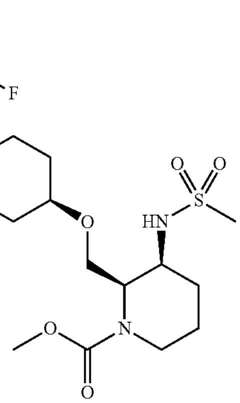 | 473.1 |

TABLE 1-54-continued

| Ex. No. | IUPAC name | Structure | MS |
|---|---|---|---|
| 323 | N-((2R,3S)-1-acetyl-2-(((cis-4-(2-(difluoromethyl)phenyl)cyclohexyl)-oxy)methyl)piperidin-3-yl)methanesulfonamide | 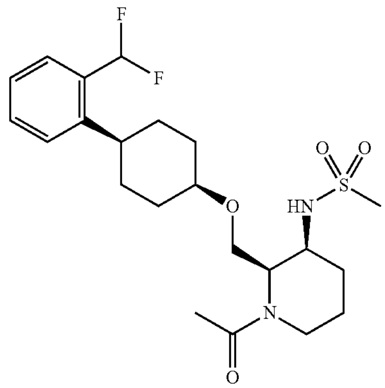 [SMILES: CC(=O)N1CCC[C@H](NS(C)(=O)=O)[C@@H]1CO[C@H]1CC[C@@H](c2ccccc2C(F)F)CC1] | 459.2 |
| 324 | methyl (2R,3S)-2-(((cis-4-(2-(difluoromethyl)phenyl)cyclohexyl)-oxy)methyl)-3-((methylsulfonyl)amino)piperidine-1-carboxylate | 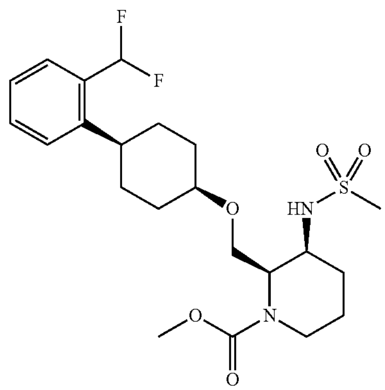 [SMILES: COC(=O)N1CCC[C@H](NS(C)(=O)=O)[C@@H]1CO[C@H]1CC[C@@H](c2ccccc2C(F)F)CC1] | 473.1 |

TABLE 1-55

| Ex. No. | IUPAC name | Structure | MS |
|---|---|---|---|
| 325 | N-(cis-2-(((4-(3,5-difluorophenyl)-4-fluorocyclohexyl)oxy)methyl)-piperidin-3-yl)methanesulfonamide | 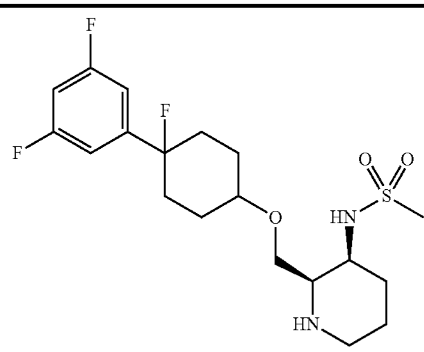 | 421.2 |
| 326 | N-(cis-2-(((cis-4-(pyrimidin-2-yl)cyclohexyl)oxy)methyl)piperidin-3-yl)methanesulfonamide | 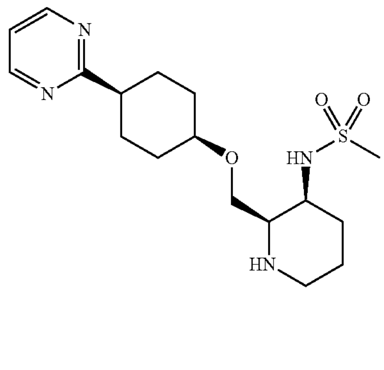 [SMILES: CS(=O)(=O)N[C@H]1CCCN[C@H]1CO[C@H]1CC[C@@H](c2ncccn2)CC1] | 369.1 |

TABLE 1-55-continued

| Ex. No. | IUPAC name | Structure | MS |
|---|---|---|---|
| 327 | N-(cis-1-(cyclopropylcarbonyl)-2-(((4-(3,5-difluorophenyl)-4-fluorocyclohexyl)oxy)methyl)-piperidin-3-yl)methanesulfonamide | 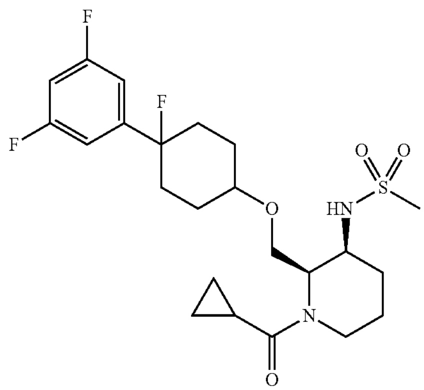 [SMILES: CS(=O)(=O)N[C@H]1CCCN(C(=O)C2CC2)[C@H]1COC1CCC(F)(c2cc(F)cc(F)c2)CC1] | 489.2 |
| 328 | N-(cis-1-(cyclopropylcarbonyl)-2-(((cis-4-(pyrimidin-2-yl)cyclohexyl)oxy)methyl)piperidin-3-yl)methanesulfonamide | 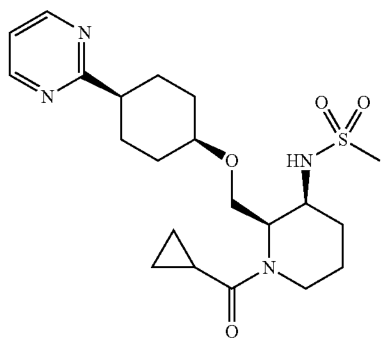 [SMILES: CS(=O)(=O)N[C@H]1CCCN(C(=O)C2CC2)[C@H]1CO[C@H]1CC[C@@H](c2ncccn2)CC1] | 437.2 |
| 329 | isopropyl cis-2-(((cis-2-methyl-1-(pyrimidin-2-yl)piperidin-4-yl)oxy)methyl)-3-((methylsulfonyl)amino)piperidine-1-carboxylate | 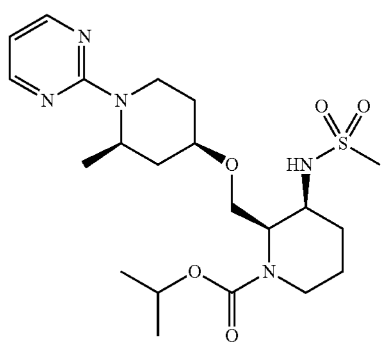 [SMILES: CC(C)OC(=O)N1CCC[C@H](NS(C)(=O)=O)[C@@H]1CO[C@@H]1CCN(c2ncccn2)[C@H](C)C1] | 470.2 |
| 330 | isopropyl cis-2-(((trans-2-methyl-1-(pyrimidin-2-yl)piperidin-4-yl)oxy)methyl)-3-((methylsulfonyl)amino)piperidine-1-carboxylate | 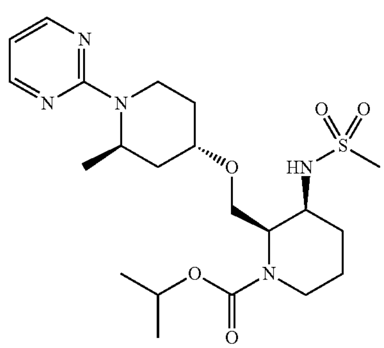 [SMILES: CC(C)OC(=O)N1CCC[C@H](NS(C)(=O)=O)[C@@H]1CO[C@H]1CCN(c2ncccn2)[C@H](C)C1] | 470.2 |

TABLE 1-56

| Ex. No. | IUPAC name | Structure | MS |
|---|---|---|---|
| 331 | methyl cis-2-(((trans-4-hydroxy-4-phenylcyclohexyl)oxy)methyl)-3-((methylsulfonyl)amino)piperidine-1-carboxylate | 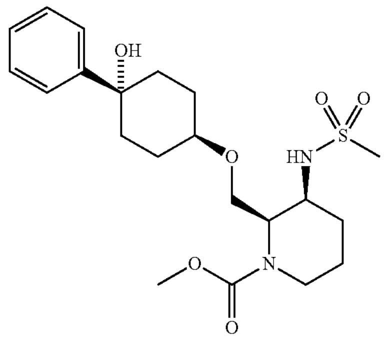 [SMILES: COC(=O)N1CCC[C@H](NS(C)(=O)=O)[C@@H]1CO[C@H]1CC[C@@](O)(c2ccccc2)CC1] | 439.1 |
| 332 | N-(cis-2-(((cis-4-(2-chlorophenyl)cyclohexyl)oxy)methyl)piperidin-3-yl)methanesulfonamide | 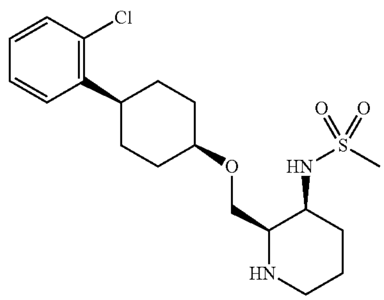 [SMILES: CS(=O)(=O)N[C@H]1CCCN[C@H]1CO[C@H]1CC[C@@H](c2ccccc2Cl)CC1] | 401.1 |
| 333 | N-((2R,3S)-2-(((cis-4-phenylcyclohexyl)oxy)methyl)-piperidin-3-yl)methanesulfonamide (s)-mandelate | 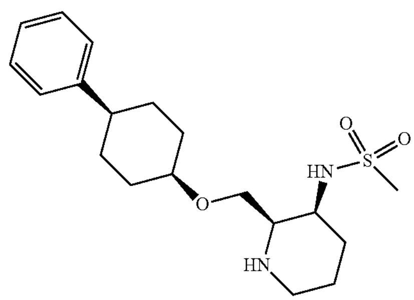 [SMILES: CS(=O)(=O)N[C@H]1CCCN[C@H]1CO[C@H]1CC[C@@H](c2ccccc2)CC1] | 367.2 |
| 334 | N-(cis-1-acetyl-2-(((cis-4-(2-chlorophenyl)cyclohexyl)oxy)methyl)piperidin-3-yl)methanesulfonamide | 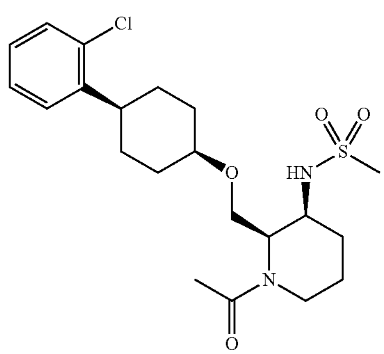 [SMILES: CC(=O)N1CCC[C@H](NS(C)(=O)=O)[C@@H]1CO[C@H]1CC[C@@H](c2ccccc2Cl)CC1] | 443.2 |

TABLE 1-56-continued

| Ex. No. | IUPAC name | Structure | MS |
|---|---|---|---|
| 335 | methyl cis-2-(((cis-4-(2-chlorophenyl)cyclohexyl)oxy)methyl)-3-((methylsulfonyl)amino)piperidine-1-carboxylate | 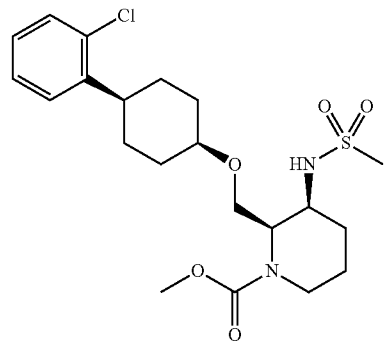 [SMILES: COC(=O)N1CCC[C@H](NS(C)(=O)=O)[C@@H]1CO[C@H]1CC[C@@H](c2ccccc2Cl)CC1] | 459.2 |
| 336 | N-(cis-2-(((3-phenylcyclopentyl)oxy)methyl)-piperidin-3-yl)methanesulfonamide | 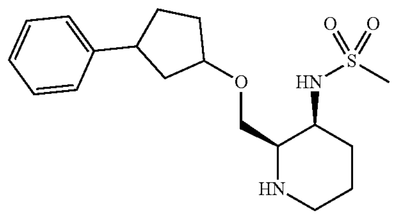 [SMILES: CS(=O)(=O)N[C@H]1CCCN[C@H]1COC1CCC(c2ccccc2)C1] | 353.2 |

TABLE 1-57

| Ex. No. | IUPAC name | Structure | MS |
|---|---|---|---|
| 337 | N-(cis-1-acetyl-2-(((3-phenylcyclopentyl)oxy)methyl)-piperidin-3-yl)methanesulfonamide | 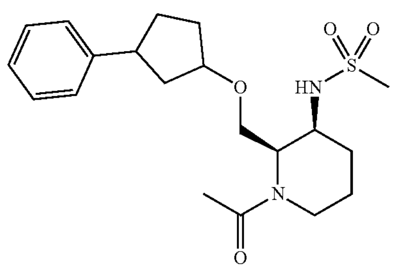 [SMILES: CC(=O)N1CCC[C@H](NS(C)(=O)=O)[C@@H]1COC1CCC(c2ccccc2)C1] | 395.3 |
| 338 | methyl cis-3-((methylsulfonyl)amino)-2-(((3-phenylcyclopentyl)oxy)methyl)-piperidine-1-carboxylate | 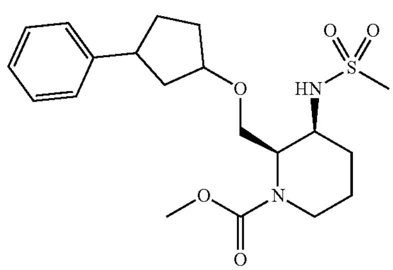 [SMILES: COC(=O)N1CCC[C@H](NS(C)(=O)=O)[C@@H]1COC1CCC(c2ccccc2)C1] | 411.2 |
| 339 | cis-N-ethyl-3-((methylsulfonyl)amino)-2-(((3-phenylcyclopentyl)oxy)methyl)-piperidine-1-carboxamide | 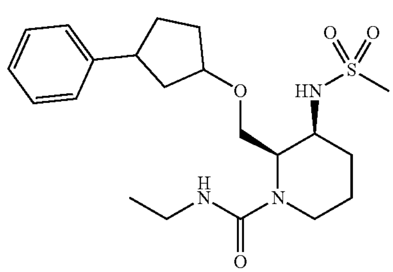 [SMILES: CCNC(=O)N1CCC[C@H](NS(C)(=O)=O)[C@@H]1COC1CCC(c2ccccc2)C1] | 424.1 |

TABLE 1-57-continued

| Ex. No. | IUPAC name | Structure | MS |
|---|---|---|---|
| 340 | N-((2R,3S)-1-glycoloyl-2-(((cis-4-(2,3,6-trifluorophenyl)cyclohexyl)oxy)-methyl)piperidin-3-yl)methanesulfonamide | 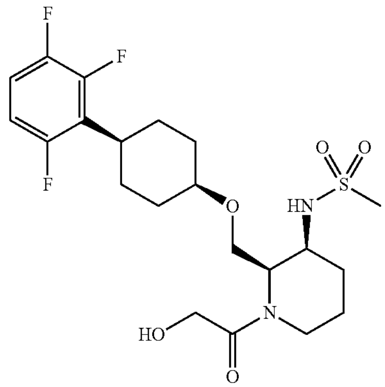 [SMILES: CS(=O)(=O)N[C@H]1CCCN(C(=O)CO)[C@H]1CO[C@H]1CC[C@@H](c2c(F)ccc(F)c2F)CC1] | 479.2 |
| 341 | isopropyl cis-2-(((trans-3-fluoro-1-(pyrimidin-2-yl)piperidin-4-yl)oxy)methyl)-3-((methylsulfonyl)amino)piperidine-1-carboxylate | 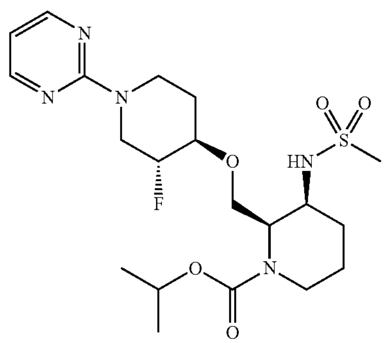 [SMILES: CC(C)OC(=O)N1CCC[C@H](NS(C)(=O)=O)[C@@H]1CO[C@@H]1CCN(c2ncccn2)C[C@H]1F] | 474.2 |
| 342 | isopropyl cis-2-(((cis-3-fluoro-1-(pyrimidin-2-yl)piperidin-4-yl)oxy)methyl)-3-((methylsulfonyl)amino)piperidine-1-carboxylate | 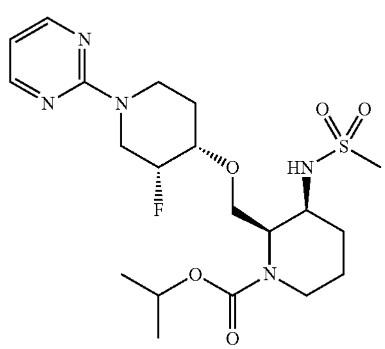 [SMILES: CC(C)OC(=O)N1CCC[C@H](NS(C)(=O)=O)[C@@H]1CO[C@H]1CCN(c2ncccn2)C[C@H]1F] | 474.2 |

TABLE 1-58

| Ex. No. | IUPAC name | Structure | MS |
|---|---|---|---|
| 343 | methyl cis-2-(((cis-4-(3-hydroxyphenyl)cyclohexyl)oxy)methyl)-3-((methylsulfonyl)amino)piperidine-1-carboxylate | 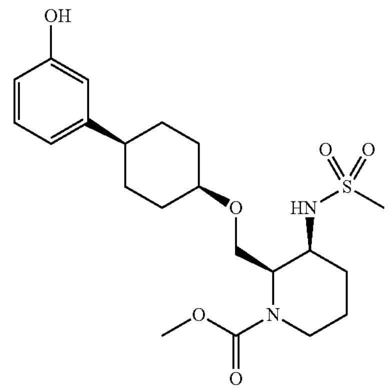 [SMILES: COC(=O)N1CCC[C@H](NS(C)(=O)=O)[C@@H]1CO[C@H]1CC[C@@H](c2cccc(O)c2)CC1] | 441.2 |
| 344 | methyl cis-2-(((cis-4-(4-methoxyphenyl)cyclohexyl)oxy)methyl)-3-((methylsulfonyl)amino)piperidine-1-carboxylate | 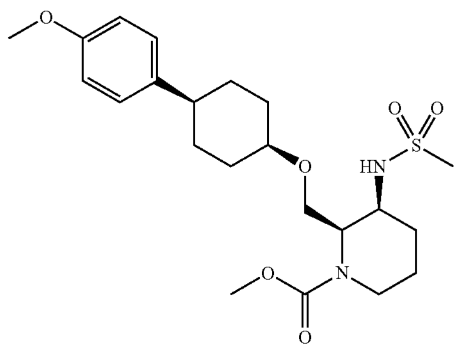 | 455.2 |
| 345 | methyl cis-2-(((cis-4-(4-hydroxyphenyl)cyclohexyl)oxy)methyl)-3-((methylsulfonyl)amino)piperidine-1-carboxylate | 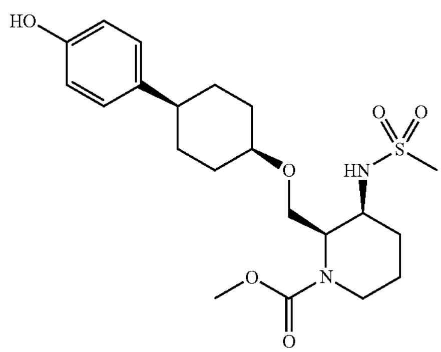 [SMILES: COC(=O)N1CCC[C@H](NS(C)(=O)=O)[C@@H]1CO[C@H]1CC[C@@H](c2ccc(O)cc2)CC1] | 439.0 |
| 346 | methyl cis-2-(((4-hydroxy-4-(2-methoxyphenyl)cyclohexyl)oxy)methyl)-3-((methylsulfonyl)amino)piperidine-1-carboxylate | 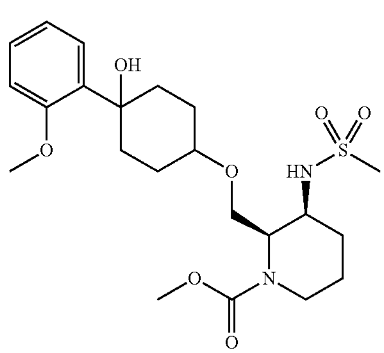 [SMILES: COC(=O)N1CCC[C@H](NS(C)(=O)=O)[C@@H]1COC1CCC(O)(c2ccccc2OC)CC1] | 469.1 |

TABLE 1-58-continued

| Ex. No. | IUPAC name | Structure | MS |
|---|---|---|---|
| 347 | methyl cis-2-(((cis-4-(2-hydroxyphenyl)cyclohexyl)oxy)methyl)-3-((methylsulfonyl)amino)piperidine-1-carboxylate | 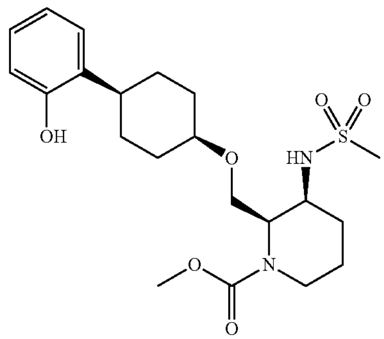 [SMILES: COC(=O)N1CCC[C@H](NS(C)(=O)=O)[C@@H]1CO[C@H]1CC[C@@H](c2ccccc2O)CC1] | 439.2 |
| 348 | methyl (2R,3S)-2-(((cis-4-(4-hydroxyphenyl)cyclohexyl)oxy)methyl)-3-((methylsulfonyl)amino)piperidine-1-carboxylate | 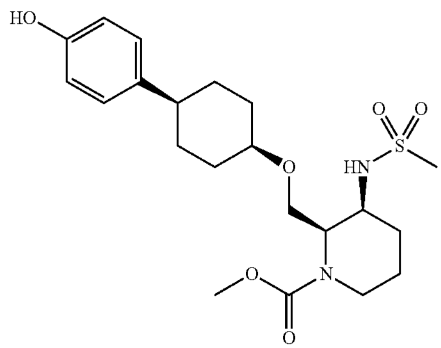 [SMILES: COC(=O)N1CCC[C@H](NS(C)(=O)=O)[C@@H]1CO[C@H]1CC[C@@H](c2ccc(O)cc2)CC1] | 439.1 |

TABLE 1-59

| Ex. No. | ICIPAC name | Structure | MS |
|---|---|---|---|
| 349 | methyl cis-2-((1,4-dioxaspiro[4.5]dec-8-yloxy)methyl)-3-((methylsulfonyl)amino)piperidine-1-carboxylate | 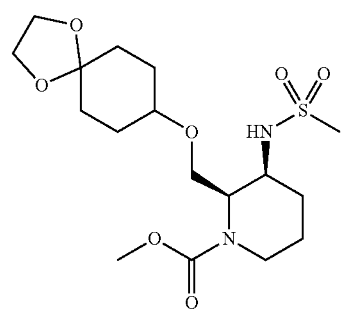 [SMILES: COC(=O)N1CCC[C@H](NS(C)(=O)=O)[C@@H]1COC1CCC2(CC1)OCCO2] | 405.1 |
| 350 | cis-N-ethyl-3-((methylsulfonyl)amino)-2-((((1S,2S)-2-phenoxycyclopentyl)oxy)methyl)-piperidine-1-carboxamide | 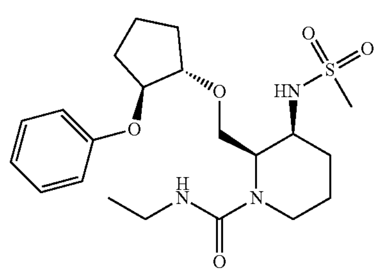 [SMILES: CCNC(=O)N1CCC[C@H](NS(C)(=O)=O)[C@@H]1CO[C@H]1CCC[C@@H]1Oc1ccccc1] | 438.0 |

TABLE 1-59-continued

| Ex. No. | ICIPAC name | Structure | MS |
|---|---|---|---|
| 351 | cis-2-((((3S)-1-benzoylpyrrolidin-3-yl)oxy)methyl)-N-ethyl-3-((methylsulfonyl)amino)piperidine-1-carboxamide | 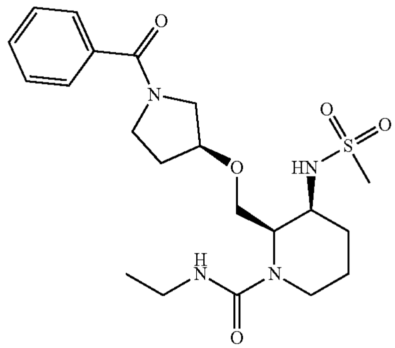 [SMILES: CCNC(=O)N1CCC[C@H](NS(C)(=O)=O)[C@@H]1CO[C@H]1CCN(C(=O)c2ccccc2)C1] | 453.3 |
| 352 | cis-2-((((3R)-1-benzoylpyrrolidin-3-yl)oxy)methyl)-N-ethyl-3-((methylsulfonyl)amino)piperidine-1-carboxamide | 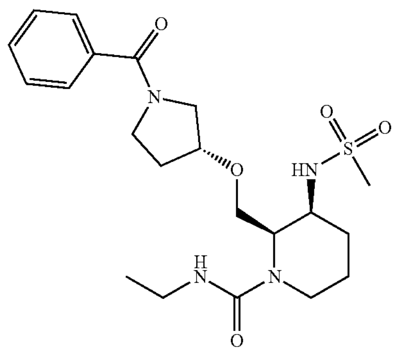 [SMILES: CCNC(=O)N1CCC[C@H](NS(C)(=O)=O)[C@@H]1CO[C@@H]1CCN(C(=O)c2ccccc2)C1] | 451.0 |
| 353 | N-(cis-2-(((cis-4-phenylcyclohexyl)oxy)methyl)-piperidin-3-yl)cyclopropanesulfonamide | 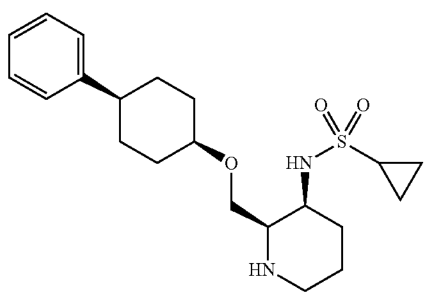 [SMILES: O=S(=O)(N[C@H]1CCCN[C@H]1CO[C@H]1CC[C@@H](c2ccccc2)CC1)C1CC1] | 393.2 |
| 354 | N-(cis-1-acetyl-2-(((cis-4-phenylcyclohexyl)oxy)methyl)-piperidin-3-yl)cyclopropanesulfonamide | 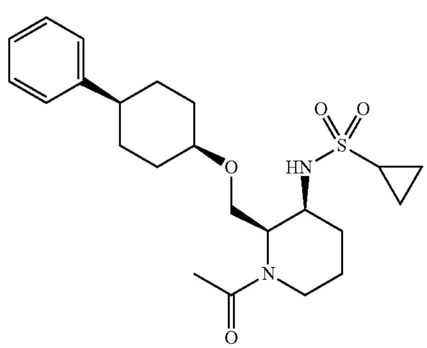 [SMILES: CC(=O)N1CCC[C@H](NS(=O)(=O)C2CC2)[C@@H]1CO[C@H]1CC[C@@H](c2ccccc2)CC1] | 435.1 |

TABLE 1-60

| Ex. No. | IUPAC name | Structure | MS |
|---|---|---|---|
| 355 | cis-3-((cyclopropylsulfonyl)amino)-N-ethyl-2-(((cis-4-phenylcyclohexyl)oxy)methyl)-piperidine-1-carboxamide | 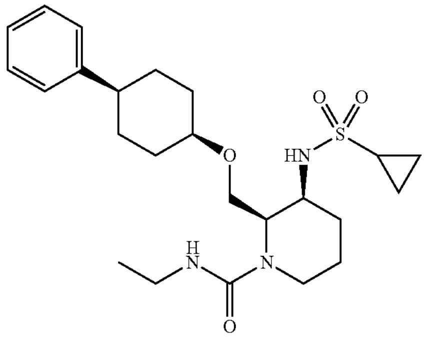 [SMILES: CCNC(=O)N1CCC[C@H](NS(=O)(=O)C2CC2)[C@@H]1CO[C@H]1CC[C@@H](c2ccccc2)CC1] | 464.1 |
| 356 | isopropyl cis-3-((cyclopropylsulfonyl)amino)-2-(((1-(pyrimidin-2-yl)piperidin-4-yl)oxy)methyl)piperidine-1-carboxylate | 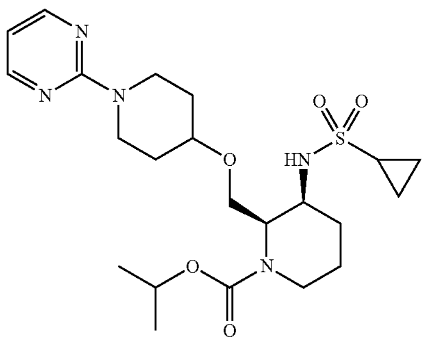 [SMILES: CC(C)OC(=O)N1CCC[C@H](NS(=O)(=O)C2CC2)[C@@H]1COC1CCN(c2ncccn2)CC1] | 482.2 |
| 357 | N-(cis-1-acetyl-2-(((cis-4-isopropylcyclohexyl)oxy)methyl)-piperidin-3-yl)cyclopropanesulfonamide | 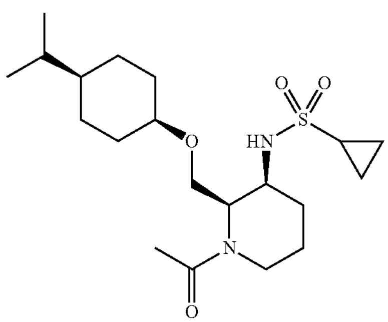 [SMILES: CC(=O)N1CCC[C@H](NS(=O)(=O)C2CC2)[C@@H]1CO[C@H]1CC[C@@H](C(C)C)CC1] | 401.1 |
| 358 | N-(cis-1-acetyl-2-(((cis-4-isopropylcyclohexyl)oxy)methyl)-piperidin-3-yl)cyclohexanesulfonamide | 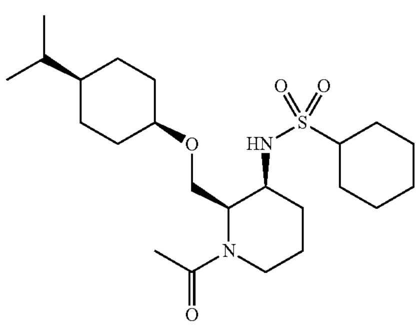 [SMILES: CC(=O)N1CCC[C@H](NS(=O)(=O)C2CCCCC2)[C@@H]1CO[C@H]1CC[C@@H](C(C)C)CC1] | 443.2 |

TABLE 1-60-continued

| Ex. No. | IUPAC name | Structure | MS |
|---|---|---|---|
| 359 | cis-3-((cyclopropylsulfonyl)amino)-N-methyl-2-(((cis-4-phenylcyclohexyl)oxy)methyl)-piperidine-1-carboxamide | 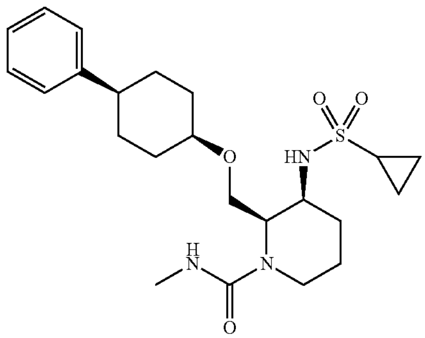 [SMILES: CNC(=O)N1CCC[C@H](NS(=O)(=O)C2CC2)[C@@H]1CO[C@H]1CC[C@@H](c2ccccc2)CC1] | 450.1 |
| 360 | 2,2,2-trifluoroethyl cis-3-((cyclopropylsulfonyl)amino)-2-(((1-(pyrimidin-2-yl)piperidin-4-yl)oxy)methyl)piperidine-1-carboxylate | 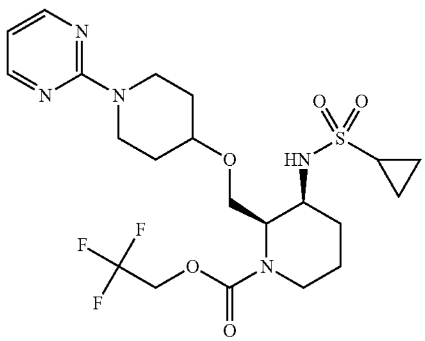 [SMILES: O=C(OCC(F)(F)F)N1CCC[C@H](NS(=O)(=O)C2CC2)[C@@H]1COC1CCN(c2ncccn2)CC1] | 522.2 |

TABLE 1-61

| Ex. No. | IUPAC name | Structure | MS |
|---|---|---|---|
| 361 | 1,1,1,3,3,3-hexafluoropropan-2-yl cis-3-((cyclopropylsulfonyl)amino)-2-(((1-(pyrimidin-2-yl)piperidin-4-yl)oxy)methyl)piperidine-1-carboxylate | 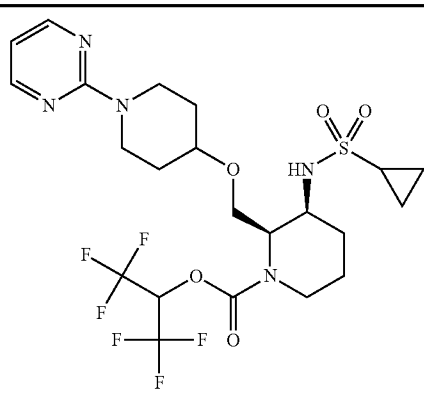 | 590.2 |
| 362 | 1,1,1-trifluoropropan-2-yl cis-3-((cyclopropylsulfonyl)amino)-2-(((1-(pyrimidin-2-yl)piperidin-4-yl)oxy)methyl)piperidine-1-carboxylate | 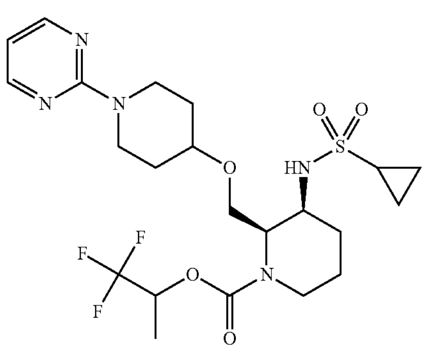 [SMILES: CC(OC(=O)N1CCC[C@H](NS(=O)(=O)C2CC2)[C@@H]1COC1CCN(c2ncccn2)CC1)C(F)(F)F] | 536.3 |

TABLE 1-61-continued

| Ex. No. | IUPAC name | Structure | MS |
|---|---|---|---|
| 363 | N-(1-acetyl-2-(((cis-4-isopropylcyclohexyl)oxy)methyl)-(2,3,4,5,6-d5)piperidin-3-yl)methanesulfonamide | 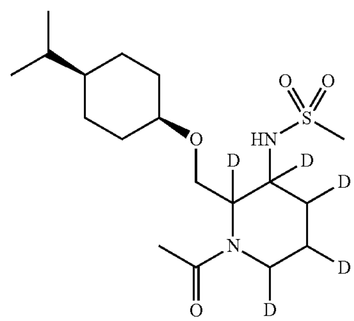 [SMILES: [2H]C1C([2H])N(C(C)=O)C([2H])(CO[C@H]2CC[C@@H](C(C)C)CC2)C([2H])(NS(C)(=O)=O)C1[2H]] | 380.2 |
| 364 | ethyl 3-((ethylsulfonyl)amino)-2-(((cis-4-isopropylcyclohexyl)oxy)methyl)-piperidine-1-carboxylate | 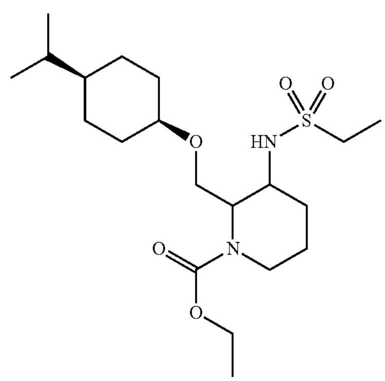 [SMILES: CCOC(=O)N1CCCC(NS(=O)(=O)CC)C1CO[C@H]1CC[C@@H](C(C)C)CC1] | 417.2 |
| 365 | ethyl 3-((ethylsulfonyl)amino)-2-(((cis-4-methylcyclohexyl)oxy)methyl)-piperidine-1-carboxylate | 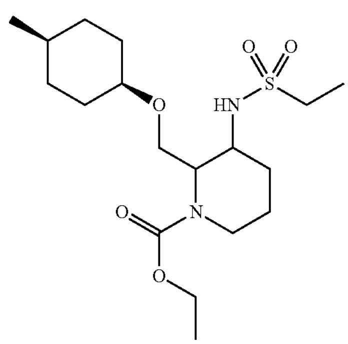 [SMILES: CCOC(=O)N1CCCC(NS(=O)(=O)CC)C1CO[C@H]1CC[C@@H](C)CC1] | 391.2 |
| 366 | N-(1-acetyl-2-(((cis-4-tert-butylcyclohexyl)oxy)methyl)-piperidin-3-yl)ethanesulfonamide | 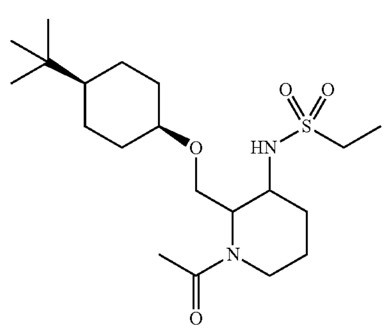 [SMILES: CCS(=O)(=O)NC1CCCN(C(C)=O)C1CO[C@H]1CC[C@@H](C(C)(C)C)CC1] | 403.1 |

TABLE 1-62

| Ex. No. | IUPAC name | Structure | MS |
|---|---|---|---|
| 367 | N-(2-(((cis-4-isopropyl-cyclohexyl)oxy)methyl)-1-(tetrahydrofuran-3-ylcarbonyl)piperidin-3-yl)methanesulfonamide | 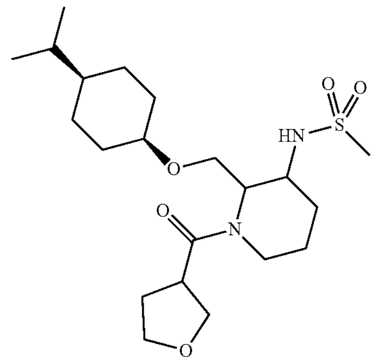 [SMILES: CC(C)[C@H]1CC[C@@H](OCC2C(NS(C)(=O)=O)CCCN2C(=O)C2CCOC2)CC1] | 431.2 |
| 368 | N-(2-(((cis-4-isopropylcyclohexyl)oxy)methyl)-1-(oxetan-3-ylcarbonyl)piperidin-3-yl)methanesulfonamide | 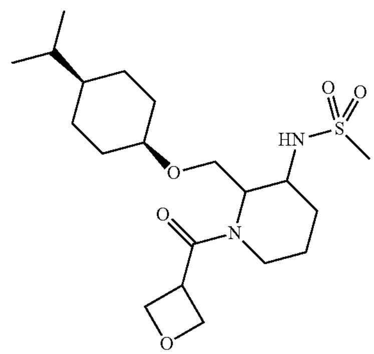 [SMILES: CC(C)[C@H]1CC[C@@H](OCC2C(NS(C)(=O)=O)CCCN2C(=O)C2COC2)CC1] | 417.1 |
| 369 | N-ethyl-2-(((cis-4-isopropylcyclohexyl)oxy)methyl)-3-((methylsulfonyl)amino)piperidine-1-carboxamide | 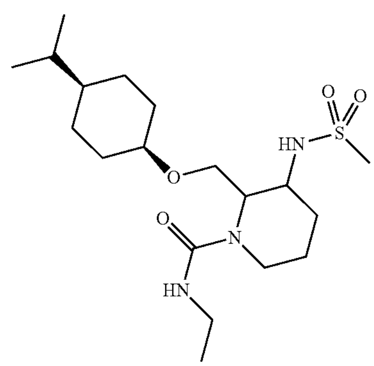 [SMILES: CCNC(=O)N1CCCC(NS(C)(=O)=O)C1CO[C@H]1CC[C@@H](C(C)C)CC1] | 404.2 |
| 370 | N-ethyl-3-((methylsulfonyl)amino)-2-(((cis-4-phenylcyclohexyl)oxy)methyl)-piperidine-1-carboxamide | 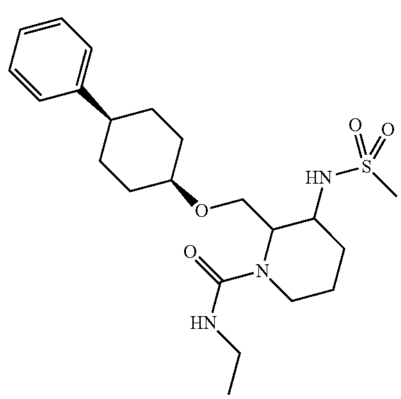 [SMILES: CCNC(=O)N1CCCC(NS(C)(=O)=O)C1CO[C@H]1CC[C@@H](c2ccccc2)CC1] | 438.2 |

TABLE 1-62-continued

| Ex. No. | IUPAC name | Structure | MS |
|---|---|---|---|
| 371 | trans-N-ethyl-2-(((cis-4-(3-fluorophenyl)cyclohexyl)oxy)-methyl)-3-((methylsulfonyl)amino)piperidine-1-carboxamide | 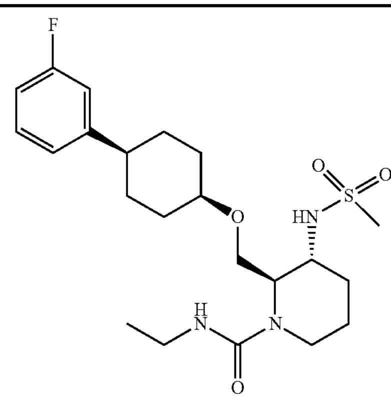 | 456.0 |
| 372 | trans-N-ethyl-2-(((cis-4-(2-fluorophenyl)cyclohexyl)oxy)-methyl)-3-((methylsulfonyl)amino)piperidine-1-carboxamide | 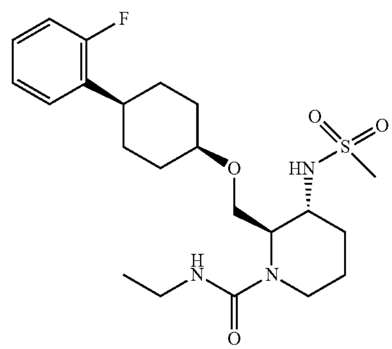 [SMILES: CCNC(=O)N1CCC[C@@H](NS(C)(=O)=O)[C@@H]1CO[C@H]1CC[C@@H](c2ccccc2F)CC1] | 456.1 |

Experimental Example 1

Obtainment of Cell Stably Expressing Human Orexin Type 2 Receptor

To obtain a cell clone stably expressing human orexin type 2 receptor, human orexin type 2 receptor cDNA was inserted into pcDNA3.1(+) plasmid vector (Invitrogen), and a plasmid DNA for expression of human orexin type 2 receptor (pcDNA3.1(+)/hOX2R) was cloned. The plasmid DNA was introduced into CHO-dhfr cell by an electroporation method, and human orexin type 2 receptor expressing clone cells were obtained by limiting dilution method by using G418 drug resistance as a selection marker.

Experimental Example 2-1

Measurement of Orexin Type 2 Receptor Agonist Activity

Chinese hamster ovary (CHO) dhfr-cells forcibly expressing human orexin type 2 receptor (hOX2R) were seeded in each well of Black clear bottom plate (384 wells) (Becton, Dickinson and Company) by 10,000 cells, and cultured for 16 hr in an MEM-alpha (Nikken-Bio Co., Ltd.) medium containing 100 U/ml penicillin, 100 μg/ml streptomycin, 0.5 g/ml G418 (all above Invitrogen), and 10% fetal calf serum (Thermo), under the conditions of 37° C., 5% $CO_2$. After removal of the medium, 30 μL of assay buffer 1 (0.1% bovine serum albumin (Wako Pure Chemical Industries, Ltd.), 1.25 mM probenecid, 10% B2-Quencher, 2.5 μg/mL Fluo-4AM, 10 mM HEPES (DOJINDO)) was added, and the cells were incubated for 60 min under the conditions of 37° C., 5% $CO_2$. A test compound was dissolved in dimethyl sulfoxide to 10 mM, and then diluted with assay buffer 2 (20 mM HEPES, Hanks' balanced salt solution (Invitrogen), 0.1% bovine serum albumin). For the reaction, a test compound solution (10 μL) was added using Fluorescent Imaging Plate Reader TETRA (FLIPR TETRA; manufactured by Molecular Devices), a fluorescence value (excitation wavelength 488 nm, measurement wavelength 570 nm) of each well was measured every one second for 1 min, and the agonist activity was determined using the area of the fluorescence value as an indicator of intracellular $Ca^{2+}$ concentration. The agonist activity of the test compound was calculated assuming that the fluorescence value of the well added with only the dilution buffer was 0% and the fluorescence value of the well added with 10 nM human orexin B (PEPTIDE INSTITUTE, INC.) buffer was 100%. The agonist activity values $EC_{50}$ and Emax of each compound are shown below. As used herein, Emax indicates the value at 30 uM concentration when orexin B is converted to a full agonist (maximum value of agonist activity: 100%). As is clear from the results, the compound of the present invention was shown to have an agonist activity on hOX2R.

TABLE 2-1

| Ex. No. | $EC_{50}$ (nM) | Emax (%) |
|---|---|---|
| 2 | 1.9 | 99 |
| 3 | 540 | 96 |
| 4 | 44 | 106 |
| 5 | 2.2 | 98 |
| 7 | 250 | 100 |

TABLE 2-1-continued

| Ex. No. | EC$_{50}$ (nM) | Emax (%) |
|---|---|---|
| 8 | 5.6 | 96 |
| 10 | 220 | 113 |
| 11 | 2.0 | 114 |
| 13 | 130 | 115 |
| 14 | 6.6 | 105 |
| 15 | 280 | 105 |
| 16 | 0.84 | 99 |
| 18 | 520 | 96 |
| 19 | 12 | 102 |
| 20 | 3.4 | 100 |
| 21 | 200 | 108 |
| 22 | 5.3 | 98 |
| 23 | 1200 | 90 |
| 24 | 21 | 102 |
| 25 | 7.9 | 94 |
| 27 | 310 | 108 |
| 28 | 2.7 | 96 |
| 29 | 17 | 104 |
| 30 | 0.11 | 113 |
| 31 | 0.66 | 95 |
| 32 | 15 | 102 |
| 33 | 68 | 98 |
| 35 | 93 | 99 |
| 36 | 880 | 74 |
| 37 | 880 | 97 |
| 39 | 940 | 93 |
| 40 | 720 | 91 |
| 42 | 210 | 97 |
| 43 | 1100 | 93 |
| 44 | 1300 | 96 |
| 45 | 330 | 100 |
| 47 | 60 | 101 |
| 53 | 980 | 96 |
| 54 | 4100 | 88 |
| 55 | 140 | 97 |
| 60 | 140 | 101 |
| 62 | 2300 | 93 |
| 65 | 1300 | 95 |
| 66 | 3800 | 87 |
| 67 | 910 | 93 |
| 70 | 97 | 98 |
| 71 | 4300 | 83 |
| 72 | 89 | 96 |
| 73 | 560 | 92 |
| 74 | 750 | 89 |
| 75 | 220 | 88 |
| 76 | 300 | 103 |
| 77 | 1000 | 91 |
| 78 | 63 | 91 |
| 79 | 330 | 85 |
| 80 | 660 | 98 |
| 84 | 840 | 98 |
| 87 | 4900 | 82 |
| 90 | 2800 | 74 |
| 91 | 39 | 89 |
| 92 | 370 | 92 |
| 93 | 2300 | 84 |
| 95 | 4300 | 89 |
| 96 | 26 | 95 |
| 97 | 4.5 | 108 |
| 98 | 2.9 | 107 |
| 99 | 13 | 112 |
| 100 | 2.2 | 112 |
| 101 | 2.3 | 115 |
| 102 | 1.2 | 101 |
| 103 | 170 | 98 |
| 104 | 2.2 | 100 |
| 106 | 4800 | 89 |
| 107 | 120 | 75 |
| 109 | 480 | 102 |
| 111 | 13 | 97 |
| 112 | 420 | 94 |
| 113 | 59 | 93 |
| 114 | 3500 | 79 |
| 115 | 770 | 97 |
| 117 | 0.12 | 91 |
| 118 | 4.6 | 105 |

TABLE 2-1-continued

| Ex. No. | EC$_{50}$ (nM) | Emax (%) |
|---|---|---|
| 119 | 30 | 107 |
| 120 | 61 | 96 |

TABLE 2-2

| Ex. No. | EC$_{50}$ (nM) | Emax (%) |
|---|---|---|
| 121 | 8.8 | 111 |
| 123 | 390 | 120 |
| 126 | 2600 | 85 |
| 128 | 2400 | 88 |
| 129 | 39 | 96 |
| 130 | 460 | 96 |
| 133 | 1000 | 97 |
| 136 | 0.22 | 102 |
| 137 | 240 | 101 |
| 138 | 22 | 94 |
| 139 | 31 | 103 |
| 140 | 390 | 92 |
| 141 | 460 | 95 |
| 142 | 4000 | 96 |
| 143 | 590 | 96 |
| 144 | 1.0 | 104 |
| 145 | 810 | 106 |
| 146 | 2.5 | 100 |
| 147 | 10 | 100 |
| 148 | 0.053 | 103 |
| 149 | 25 | 100 |
| 150 | 30 | 99 |
| 151 | 490 | 107 |
| 152 | 290 | 96 |
| 154 | 2400 | 94 |
| 155 | 1700 | 95 |
| 156 | 350 | 95 |
| 157 | 140 | 91 |
| 158 | 1600 | 83 |
| 159 | 140 | 96 |
| 165 | 3800 | 80 |
| 167 | 2400 | 83 |
| 176 | 45 | 98 |
| 177 | 190 | 96 |
| 179 | 0.31 | 100 |
| 180 | 17 | 106 |
| 181 | 240 | 89 |
| 182 | 2.3 | 92 |
| 183 | 40 | 94 |
| 184 | 9.3 | 93 |
| 185 | 21 | 98 |
| 186 | 3300 | 86 |
| 187 | 370 | 93 |
| 188 | 23 | 97 |
| 189 | 78 | 88 |
| 191 | 2.9 | 107 |
| 192 | 150 | 108 |
| 193 | 300 | 88 |
| 194 | 2400 | 81 |
| 195 | 250 | 102 |
| 196 | 30 | 104 |
| 197 | 100 | 90 |
| 198 | 56 | 92 |
| 200 | 22 | 95 |
| 201 | 2000 | 92 |
| 202 | 19 | 97 |
| 204 | 710 | 102 |
| 207 | 26 | 110 |
| 208 | 940 | 93 |
| 209 | 1900 | 89 |
| 210 | 3600 | 86 |
| 211 | 1100 | 94 |
| 212 | 2200 | 89 |
| 213 | 0.44 | 102 |
| 214 | 1.5 | 105 |
| 215 | 2.5 | 105 |
| 216 | 210 | 105 |
| 217 | 13 | 110 |

TABLE 2-2-continued

| Ex. No. | EC$_{50}$ (nM) | Emax (%) |
|---|---|---|
| 219 | 3000 | 91 |
| 221 | 1600 | 96 |
| 222 | 2100 | 102 |
| 223 | 1100 | 110 |
| 224 | 1700 | 90 |
| 225 | 1000 | 98 |
| 226 | 2200 | 86 |
| 227 | 2400 | 102 |
| 228 | 2100 | 89 |
| 229 | 1500 | 85 |
| 230 | 2600 | 80 |
| 233 | 5000 | 83 |
| 236 | 1800 | 86 |
| 237 | 490 | 90 |
| 238 | 2100 | 91 |
| 239 | 280 | 102 |

TABLE 2-3

| Ex. No. | EC$_{50}$ (nM) | Emax (%) |
|---|---|---|
| 240 | 24 | 107 |
| 241 | 1.2 | 97 |
| 242 | 0.88 | 99 |
| 243 | 17 | 97 |
| 244 | 2.6 | 97 |
| 245 | 2.0 | 97 |
| 246 | 730 | 113 |
| 247 | 960 | 102 |
| 249 | 0.61 | 99 |
| 250 | 1.7 | 105 |
| 251 | 240 | 98 |
| 252 | 2900 | 93 |
| 254 | 88 | 105 |
| 255 | 8.1 | 102 |
| 257 | 2.6 | 97 |
| 258 | 0.72 | 101 |
| 260 | 550 | 99 |
| 262 | 2500 | 94 |
| 263 | 57 | 88 |
| 264 | 21 | 91 |
| 265 | 2300 | 94 |
| 266 | 3700 | 95 |
| 267 | 3.4 | 94 |
| 268 | 1.5 | 103 |
| 269 | 3000 | 95 |
| 270 | 80 | 102 |
| 271 | 650 | 104 |
| 272 | 28 | 96 |
| 274 | 260 | 118 |
| 275 | 3100 | 87 |
| 276 | 110 | 95 |
| 277 | 2.9 | 95 |
| 279 | 5.2 | 97 |
| 281 | 3300 | 81 |
| 282 | 0.55 | 93 |
| 283 | 8.9 | 95 |
| 284 | 260 | 95 |
| 286 | 130 | 93 |
| 287 | 150 | 99 |
| 290 | 3300 | 79 |
| 291 | 26 | 98 |
| 293 | 540 | 78 |
| 294 | 130 | 95 |
| 295 | 4.2 | 93 |
| 297 | 2100 | 76 |
| 298 | 280 | 92 |
| 299 | 95 | 90 |
| 300 | 9.7 | 94 |
| 301 | 21 | 105 |
| 303 | 15 | 102 |
| 304 | 23 | 105 |
| 305 | 53 | 106 |
| 306 | 13 | 101 |
| 307 | 1600 | 98 |

TABLE 2-3-continued

| Ex. No. | EC$_{50}$ (nM) | Emax (%) |
|---|---|---|
| 308 | 590 | 109 |
| 309 | 3.1 | 106 |
| 310 | 2.2 | 101 |
| 311 | 3200 | 98 |
| 312 | 32 | 98 |
| 313 | 270 | 95 |
| 315 | 170 | 103 |
| 316 | 330 | 91 |
| 318 | 1100 | 99 |
| 319 | 29 | 106 |
| 320 | 2000 | 74 |
| 321 | 2200 | 37 |
| 322 | 25 | 71 |
| 323 | 96 | 95 |
| 324 | 8.0 | 95 |
| 325 | 5000 | 75 |
| 327 | 2600 | 86 |
| 328 | 7100 | 72 |
| 329 | 22 | 93 |
| 331 | 1500 | 98 |
| 332 | 610 | 93 |
| 333 | 340 | 87 |
| 334 | 27 | 93 |
| 335 | 6.1 | 101 |
| 337 | 2400 | 88 |
| 338 | 490 | 83 |
| 339 | 11 | 101 |
| 340 | 2.5 | 109 |
| 341 | 13 | 103 |
| 342 | 30 | 104 |

Experimental Example 2-2

Measurement of Orexin Type 2 Receptor Agonist Activity

CHO cells forcibly expressing human OX2 receptor were seeded in each well of 384 well black transparent bottom plate (BD Falcon) at 7,500 cells/well, and cultured for one day in a 5% CO$_2$ incubator at 37° C. After removal of the medium in the cell plate, assay buffer A containing a calcium indicator (HBSS (Life Technologies), 20 mM HEPES (Life Technologies), 0.1% BSA (Wako Pure Chemical Industries, Ltd.), 2.5 μg/mL Fluo-4 AM (DOJINDO Chemical), 0.08% Pluronic F127 (DOJINDO Chemical), 1.25 mM probenecid (DOJINDO Chemical)) was added at 30 μL/well. The plate was stood for 30 min in a 5% CO$_2$ incubator at 37° C., and further stood at room temperature for 30 min. A test compound prepared by diluting with assay buffer B (HBSS, 20 mM HEPES, 0.1% BSA) was added at 10 μL/well, and the fluorescence value was measured by FDSSμCELL (Hamamatsu Photonics K.K.) every one sec for 1 min, and thereafter every two sec for 1 min 40 sec. The activity (%) of the test compound was calculated assuming that variation in the fluorescence value when DMSO was added instead of the test compound was 0% inhibition, and variation in the fluorescence value when OX-A was added at the final concentration of 10 nM was 100% inhibition.

TABLE 2-4

| Ex. No. | EC$_{50}$ (nM) | Emax (%) |
|---|---|---|
| 343 | 150 | 109 |
| 344 | 290 | 109 |
| 345 | 21 | 105 |
| 347 | 260 | 94 |
| 348 | 9.5 | 92 |
| 350 | 1600 | 116 |
| 353 | 1300 | 100 |
| 354 | 51 | 104 |
| 355 | 0.44 | 108 |
| 356 | 21 | 98 |
| 357 | 84 | 101 |
| 359 | 1.1 | 97 |
| 360 | 210 | 98 |
| 362 | 390 | 95 |

Experimental Example 3

Measurement of Locomotor Activity in Mice

Increased locomotor activity is one of the indexes of arousal action together with increase in wakefulness time, increase in body temperature, enhancement of cardiovascular system parameters and the like. In this Experimental Example, the arousal action effective for the treatment of narcolepsy was evaluated by measuring the locomotor activity of mouse. Male C57BL/6J mice (6-10 weeks old, Japan CLEA) were used for the measurement of locomotor activity (8 mice each group), infrared rays were irradiated from the top part of the cage, and a locomotor activity measuring device (MDC system—Neurosciences Idea) capable of quantifying the number of times the mice pass through the irradiated rays was used. To be specific, the mice were placed in the cage of the device and acclimatized for 4 hours or longer, and a test compound was intraperitoneally administered (dose: 30 mg/kg body weight). The locomotor activity was measured for 2 hr after the administration. In the test compound group, a solution obtained by dissolving the test compound in a solvent (composition: 10% DMSO, 10% Cremophor EL (trade name), 20% polyethylene glycol 400 (20% PEG400, 60% H$_2$O)) was administered to mice. On the other hand, in the control group, only the aforementioned solvent not containing the test compound was administered to mice.

The results are shown in Table 3 below.

TABLE 3

| test compound | control group | Example 2 | Example 5 | Example 340 |
|---|---|---|---|---|
| locomotor activity (counts) (mean ± S.E.M., n = 8) | 372.00 ± 24.23 | 817.00 ± 67.88 | 1175.25 ± 61.97 | 979.25 ± 109.96 |

As is clear from Table 3, the compound of the present invention enhanced the locomotor activity of mice.

That is, the compound of the present invention has a waking-up effect and was shown to be effective for the treatment of narcolepsy.

Formulation Example 1 (Production of Capsule)

| 1) compound of Example 1 | 30 mg |
|---|---|
| 2) crystalline cellulose | 10 mg |
| 3) lactose | 19 mg |
| 4) magnesium stearate | 1 mg |
| total | 60 mg |

1), 2), 3) and 4) are mixed and filled in a gelatin capsule.

Formulation Example 2 (Production of Tablet)

| 1) compound of Example 1 | 30 g |
|---|---|
| 2) lactose | 50 g |
| 3) cornstarch | 15 g |
| 4) calcium carboxymethylcellulose | 44 g |
| 5) magnesium stearate | 1 g |
| 1000 tablets | 140 g in total |

The total amount of 1), 2), 3) and 30 g of 4) are kneaded with water, vacuum dried and sieved. The sieved powder is mixed with 14 g of 4) and 1 g of 5), and the mixture is punched by a tableting machine. In this way, 1000 tablets containing 30 mg of the compound of Example 1 per tablet are obtained.

INDUSTRIAL APPLICABILITY

The compound of the present invention has an orexin type 2 receptor agonist activity, and is useful as a prophylactic or therapeutic agent for narcolepsy.

This application is based on patent application No. 2016-019834 filed in Japan, the contents of which are encompassed in full herein.

The invention claimed is:

1. A pharmaceutical composition comprising methyl (2R, 3S)-3-((methyl sulfonyl)amino)-2-(((cis-4-phenylcyclohexyl)oxy)methyl)piperidine-1-carboxylate or a salt thereof.

* * * * *